United States Patent
Murugesan et al.

(10) Patent No.: US 10,562,887 B2
(45) Date of Patent: Feb. 18, 2020

(54) TRIAZOLONES AND TETRAZOLONES AS INHIBITORS OF ROCK

(71) Applicant: BRISTOL-MYERS SQUIBB COMPANY, Princeton, NJ (US)

(72) Inventors: Natesan Murugesan, Princeton Junction, NJ (US); Peter W. Glunz, Yardley, PA (US); Mandar Shrikrishna Bodas, Bangalore (IN); Navnath Dnyanoba Yadav, Bangalore (IN); Venu Alla, Nellore District (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/098,978

(22) PCT Filed: May 26, 2017

(86) PCT No.: PCT/US2017/034613
§ 371 (c)(1),
(2) Date: Nov. 5, 2018

(87) PCT Pub. No.: WO2017/205709
PCT Pub. Date: Nov. 30, 2017

(65) Prior Publication Data
US 2019/0152956 A1 May 23, 2019

Related U.S. Application Data

(60) Provisional application No. 62/342,441, filed on May 27, 2016.

(51) Int. Cl.
| | | |
|---|---|---|
| C07D 403/10 | (2006.01) | |
| C07D 401/10 | (2006.01) | |
| C07D 403/14 | (2006.01) | |
| C07D 471/04 | (2006.01) | |
| C07D 487/04 | (2006.01) | |

(52) U.S. Cl.
CPC ......... C07D 403/10 (2013.01); C07D 401/10 (2013.01); C07D 403/14 (2013.01); C07D 471/04 (2013.01); C07D 487/04 (2013.01)

(58) Field of Classification Search
None
See application file for complete search history.

(56) References Cited

U.S. PATENT DOCUMENTS 5,977,149 A   11/1999 Brown et al.

FOREIGN PATENT DOCUMENTS

| | | |
|---|---|---|
| WO | WO1996025410 A1 | 8/1996 |
| WO | WO1996036615 A1 | 11/1996 |
| WO | WO2005112941 A3 | 11/2006 |
| WO | WO2014134391 A1 | 9/2014 |
| WO | WO2014113620 A3 | 10/2014 |
| WO | WO2015002915 A1 | 1/2015 |
| WO | WO2015002926 A1 | 1/2015 |
| WO | WO2016010950 A1 | 1/2016 |
| WO | WO2016028971 A1 | 2/2016 |
| WO | WO2016112236 A1 | 7/2016 |
| WO | WO2016144936 A1 | 9/2016 |
| WO | WO2017123860 A1 | 7/2017 |
| WO | WO2018009622 A1 | 1/2018 |
| WO | WO2018009625 A1 | 1/2018 |
| WO | WO2018009627 A1 | 1/2018 |
| WO | WO2018102325 A1 | 6/2018 |

Primary Examiner — Alicia L Otton
(74) Attorney, Agent, or Firm — Hong Liu

(57) ABSTRACT

The present invention provides compounds of Formula (I): or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

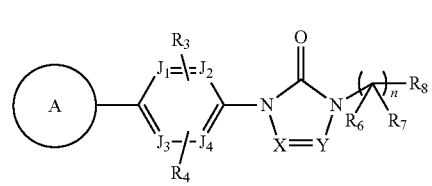

17 Claims, No Drawings

TRIAZOLONES AND TETRAZOLONES AS INHIBITORS OF ROCK

CROSS REFERENCE TO RELATED APPLICATIONS

This application is a 371 application of PCT/US2017/034613 filed May 26, 2017 which is entitled to priority pursuant to 35 U.S.C. § 119(e) to U.S. provisional patent application No. 62/342,441, filed on May 27, 2016, which is incorporated herein in its entirety.

FIELD OF THE INVENTION

The present invention relates to novel triazolone and tetrazolone derivatives, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as ACTIN® organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example, angiotensin II (Yamakawa, T. et al., *Hypertension*, 35:313-318 (2000)), urotensin II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. 1*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol. Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J. Mol.*

Sci., 13:8293-8307 (2012); Zhou, L. et al., *Am. J. Nephrol.*, 34:468-475 (2011)), as well as neurological disorders, such as spinal-cord injury, Alzheimer disease, multiple sclerosis, stroke and neuropathic pain (Mueller, B. K. et al., *Nat. Rev. Drug Disc.*, 4:387-398 (2005); Sun, X. et al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010 ~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2008/0275062 A1), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel triazolone and tetrazolone derivatives including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

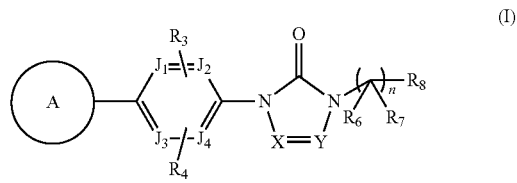

or stereoisomers, enantiomers, diastereoisomers, tautomers, pharmaceutically acceptable salts, solvates, or prodrugs thereof, wherein Ring A is independently selected from

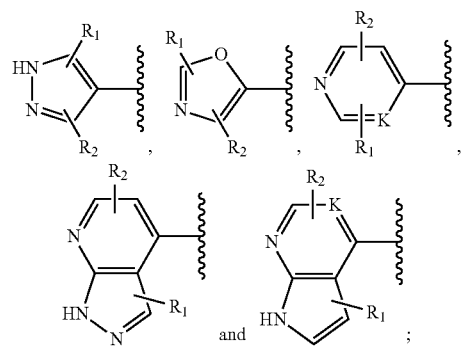

$J_1$, $J_2$, $J_3$, and $J_4$ are independently selected from N, $CR_3$, and $CR_4$; provided no more than two of $J_1$, $J_2$, $J_3$, and $J_4$ are N;

K, at each occurrence, is independently selected from N, $CR_1$, and $CR_2$;

X and Y are independently selected from N and $CR_5$; provided X and Y are not both $CR_5$;

$R_1$, at each occurrence, is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$, at each occurrence, is independently selected from H, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_3$ is independently selected from H, F, Cl, Br, CN, $C_{1-4}$ alkyl substituted with 0-3 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rCN$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, $OC_{1-4}$ alkyl substituted with 0-3 $R_e$, $NR_aR_a$, and $C_{1-4}$ alkyl substituted with 0-3 $R_e$;

$R_5$ is independently selected from H, $C_{1-4}$alkyl substituted with 0-4 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_6$ and $R_7$ are independently selected from H, $C_{1-4}$alkyl substituted with 0-4 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_8$ is independently selected from $C_{3-6}$ cycloalkyl, heterocyclyl, aryl and heteroaryl, each substituted with 0-5 $R_9$;

$R_9$, at each occurrence, is independently selected from F, Cl, Br, $C_{1-4}$alkyl, $C_{2-4}$alkenyl, $C_{2-4}$alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_r$ $OC(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, —$(CH_2)_r$-aryl, —$(CH_2)_r$-heteroaryl, F, Cl, Br, CN, $NO_2$, =O, $CO_2H$, —$(CH_2)_rOR_f$, $S(O)_pR_f$, $C(=O)NR_fR_f$, $NR_fC(=O)R_d$, $S(O)_pNR_fR_f$, $NR_fS(O)_pR_d$, $NR_fC(=O)OR_d$, $OC(=O)NR_fR_f$, and —$(CH_2)_rNR_fR_f$;

$R_f$, at each occurrence, is independently selected from H, F, Cl, Br, CN, OH, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4.

In another aspect, the present invention provides compounds of Formula (I) or stereoisomers, enantiomers, diastereoisomers, tautomers, pharmaceutically acceptable salts, solvates, or prodrugs thereof, wherein $R_1$, at each occurrence, is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$, at each occurrence, is independently selected from H, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rNR_aC(=O)OR_b$, —$(CH_2)_rOC(=O)NR_aR_a$, —$(CH_2)_rC(=O)OR_b$, —$(CH_2)_rNR_aS(O)_pNR_aR_a$, and —$(CH_2)_rNR_aS(O)_pR_c$;

$R_3$ is independently selected from H, F, Cl, Br, CN, $C_{1-4}$ alkyl substituted with 0-3 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, and $C_{1-4}$ alkyl substituted with 0-3 $R_e$;

$R_5$ is independently selected from H, $C_{1-4}$alkyl substituted with 0-4 $R_e$, —$(CH_2)_rOR_b$, —$(CH_2)_rNR_aR_a$, and —$(CH_2)_r$-heterocyclyl substituted with 0-3 $R_e$;

$R_6$ and $R_7$ are independently selected from H, $C_{1-4}$alkyl substituted with 0-4 $R_e$, —$(CH_2)_rOR_b$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rC(=O)OR_b$, $(CH_2)_r$—$C_{3-6}$ carbocyclyl substituted with 0-3 $R_e$, and —$(CH_2)_r$-heterocyclyl substituted with 0-3 $R_e$;

$R_8$ is independently selected from

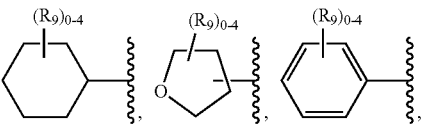

-continued

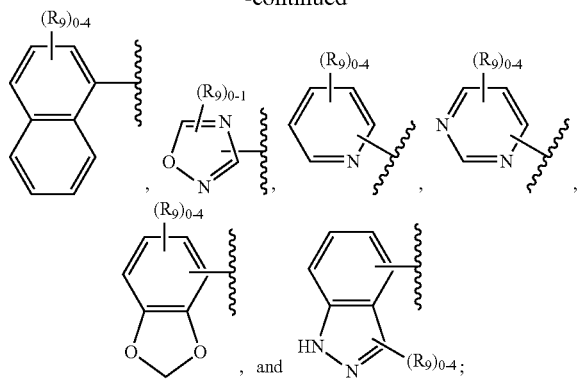

$R_9$, at each occurrence, is independently selected from F, Cl, Br, $C_{1-4}$alkyl, $C_{2-4}$alkenyl, $C_{2-4}$alkynyl, nitro, —(CHR$_d$)$_r$S(O)$_p$R$_e$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$, and other variables are as defined in Formula (I) above.

In another aspect, the present invention provides compounds of Formula (II):

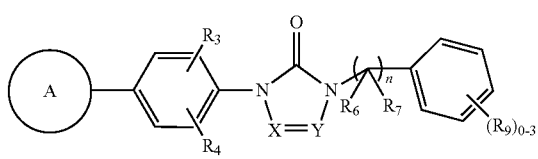

(II)

or stereoisomers, enantiomers, diastereoisomers, tautomers, pharmaceutically acceptable salts, solvates, or prodrugs thereof, wherein
Ring A is independently selected from

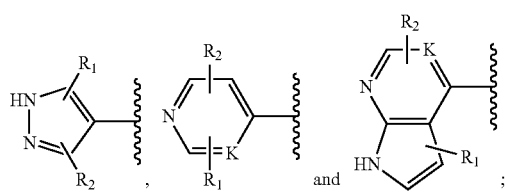

X and Y are independently selected from N and CR$_5$; provided X and Y are not both CR$_5$;
R$_1$, at each occurrence, is independently selected from H, F, Cl, Br, CN, NR$_a$R$_a$, and C$_{1-4}$alkyl substituted with 0-4 R$_e$;
R$_2$, at each occurrence, is independently selected from H, F, Cl, Br, OH, CN, NR$_a$R$_a$, and C$_{1-4}$alkyl substituted with 0-4 R$_e$;
R$_3$ is independently selected from H, F, Cl, Br, CN, C$_{1-4}$ alkyl substituted with 0-3 R$_e$, —(CH$_2$)$_r$OR$_b$, and —C$_{3-6}$ cycloalkyl;
R$_4$ is independently selected from H, F, Cl, Br, OH, CN, OC$_{1-4}$ alkyl substituted with 0-3 R$_e$, and C$_{1-4}$ alkyl substituted with 0-3 R$_e$;

R$_5$ is independently selected from H, C$_{1-4}$alkyl substituted with 0-4 R$_e$, —(CH$_2$)$_r$OR$_b$, —(CH$_2$)$_r$NR$_a$R$_a$, and —(CH$_2$)$_r$-heterocyclyl substituted with 0-3 R$_e$;
R$_6$ and R$_7$ are independently selected from H, C$_{1-4}$alkyl substituted with 0-4 R$_e$, —(CH$_2$)$_r$OR$_b$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$C(=O)OR$_b$, (CH$_2$)$_r$—C$_{3-6}$ carbocyclyl substituted with 0-3 R$_e$, and —(CH$_2$)$_r$-heterocyclyl substituted with 0-3 R$_e$;
R$_9$, at each occurrence, is independently selected from F, Cl, Br, C$_{1-4}$ alkyl, nitro, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —(CH$_2$)$_r$OC(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;
R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;
R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;
R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;
R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;
R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;
n is independently selected from 1 and 2;
p, at each occurrence, is independently selected from zero, 1, and 2; and
r, at each occurrence, is independently selected from zero, 1, 2, 3, and 4; and
In another aspect, the present invention provides compounds of Formula (III):

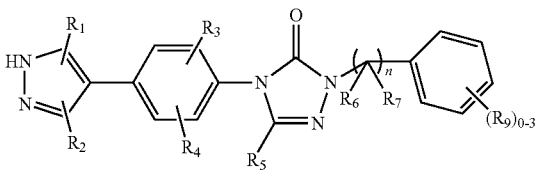

(III)

or stereoisomers, tautomers, pharmaceutically acceptable salts, solvates, or prodrugs thereof, wherein $R_1$ is independently selected from H, F, Cl, Br, CN, $NR_aR_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, —$(CH_2)_rOR_b$, and —$C_{3-6}$ cycloalkyl;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H and $C_{1-4}$alkyl substituted with 0-4 $R_e$;

$R_6$ is independently selected from H, $C_{1-4}$alkyl substituted with 0-4 $R_e$, —$CH_2OR_b$, —$C(=O)R_b$, $NR_aC(=O)R_b$, —$CH_2NR_aR_a$, —$C(=O)NR_aR_a$, —$_rC(=O)OR_b$, and heterocyclyl substituted with 0-3 $R_e$;

$R_7$ is independently selected from H and $C_{1-4}$alkyl;

$R_9$, at each occurrence, is independently selected from F, Cl, Br, $C_{1-4}$ alkyl, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (IV):

(IV)

or stereoisomers, tautomers, pharmaceutically acceptable salts, solvates, or prodrugs thereof, wherein $R_1$ is independently selected from H and $CF_3$;

$R_3$ is independently selected from H, CN, $C_{1-4}$ alkyl, —$OC_{1-3}$ alkyl, and —$C_{3-6}$ cycloalkyl;

$R_5$ is independently selected from H and $C_{1-4}$alkyl;

$R_7$ is independently selected from H and $C_{1-4}$alkyl;

$R_9$, at each occurrence, is independently selected from F, Cl, $C_{1-4}$ alkyl substituted with 0-3 $R_e$, —$OR_b$, CN, and heterocyclyl substituted with 0-3 $R_e$;

$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;

n is independently selected from 1 and 2; and r, at each occurrence, is independently selected from zero, 1, 2, and 3.

In another aspect, the present invention provides compounds of Formula (V):

(V)

or stereoisomers, tautomers, pharmaceutically acceptable salts, solvates, or prodrugs thereof, wherein $R_1$ is independently selected from H, F, Cl, Br, CN, $NR_aR_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, —$(CH_2)_rOR_b$, and —$C_{3-6}$ cycloalkyl;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, $C_{1-4}$alkyl substituted with 0-4 $R_e$, —$(CH_2)_rOR_b$, —$(CH_2)_rNR_aR_a$, and —$(CH_2)_r$-heterocyclyl substituted with 0-3 $R_e$;

$R_6$ is independently selected from H, $C_{1-4}$alkyl substituted with 0-4 $R_e$, —$CH_2OR_b$, —C(=O)$R_b$, $NR_aC(=O)R_b$, —$CH_2NR_aR_a$, —C(=O)$NR_aR_a$, —$_rC(=O)OR_b$, and heterocyclyl substituted with 0-3 $R_e$;

$R_7$ is independently selected from H and $C_{1-4}$alkyl;

$R_9$, at each occurrence, is independently selected from F, Cl, Br, $C_{1-4}$ alkyl, —(CH$_2$)$_r$OR$_b$, —(CH$_2$)$_r$CN, —(CH$_2$)$_r$N-R$_a$R$_a$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —(CH$_2$)$_r$OC(=O)R$_b$, —(CH$_2$)$_r$C(=O)NR$_a$R$_a$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$cycloalkyl substituted with 0-5 $R_e$, —(CH$_2$)$_r$-aryl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—C$_{3-6}$ cycloalkyl, —(CH$_2$)$_r$—C$_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (VI):

(VI)

or stereoisomers, tautomers, pharmaceutically acceptable salts, solvates, or prodrugs thereof, wherein $R_1$ is independently selected from H and $CF_3$;

$R_3$ is independently selected from H, CN, $C_{1-4}$ alkyl, —OC$_{1-3}$ alkyl, and —$C_{3-6}$ cycloalkyl;

$R_5$ is independently selected from H, $C_{1-4}$alkyl substituted with 0-4 $R_e$, —(CH$_2$)$_r$OR$_b$, —(CH$_2$)$_r$NR$_a$R$_a$;

$R_6$ is independently selected from H and $C_{1-4}$alkyl substituted with 0-3 $R_e$;

$R_7$ is independently selected from H and $C_{1-4}$alkyl;

$R_9$, at each occurrence, is independently selected from F, Cl, $C_{1-4}$ alkyl substituted with 0-3 $R_e$, —OR$_b$, CN, and heterocyclyl substituted with 0-3 $R_e$;

$R_a$, at each occurrence, is independently selected from H, $C_{1-6}$ alkyl substituted with 0-5 $R_e$, —(CH$_2$)$_r$—C$_{3-6}$ cycloalkyl substituted with 0-5 $R_e$, —(CH$_2$)$_r$-aryl substituted with 0-5 $R_e$, and —(CH$_2$)$_r$-heterocyclyl substituted with 0-5 $R_e$, or $R_a$ and $R_a$ together with the nitrogen atom to which they are both attached form a heterocyclic ring selected from $R_b$, at each occurrence, is independently selected from H, $C_{1-6}$ alkyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_e$, at each occurrence, is independently selected from $C_{1-6}$ alkyl substituted with 0-5 $R_f$, F, Cl, Br, CN, NO$_2$, =O, CO$_2$H, OH, and OC$_{1-4}$alkyl; and r, at each occurrence, is independently selected from zero, 1, 2, and 3.

In another aspect, the present invention provides compounds of Formula (VII):

(VII)

or stereoisomers, enantiomers, diastereoisomers, tautomers, pharmaceutically acceptable salts, solvates, or prodrugs thereof, wherein $R_1$ is independently selected from H, F, Cl, Br, CN, NR$_a$R$_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, —(CH$_2$)$_r$OR$_b$, and —$C_{3-6}$ cycloalkyl;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_6$ is independently selected from H, $C_{1-4}$alkyl substituted with 0-4 $R_e$, —$CH_2OR_b$, —C(=O)$R_b$, $NR_aC(=O)R_b$, —$CH_2NR_aR_a$, —C(=O)$NR_aR_a$, —$_rC(=O)OR_b$, and heterocyclyl substituted with 0-3 $R_e$;

$R_7$ is independently selected from H and $C_{1-4}$alkyl;

$R_9$, at each occurrence, is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (VIII):

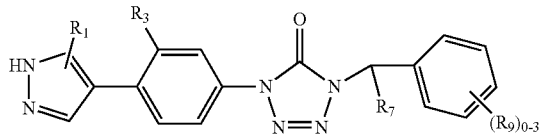

(VIII)

or stereoisomers, enantiomers, diastereoisomers, tautomers, pharmaceutically acceptable salts, solvates, or prodrugs thereof, wherein $R_1$ is independently selected from H and $CF_3$;

$R_3$ is independently selected from H, CN, $C_{1-4}$ alkyl, —$OC_{1-3}$ alkyl, and —$C_{3-6}$ cycloalkyl;

$R_5$ is independently selected from H, $C_{1-4}$alkyl substituted with 0-4 $R_e$, —$CH_2OR_b$, C(=O)$R_b$, and —C(=O)$OR_b$;

$R_7$ is independently selected from H and $C_{1-4}$alkyl;

$R_9$, at each occurrence, is independently selected from F, Cl, $C_{1-4}$ alkyl substituted with 0-3 $R_e$, —$OR_b$, CN, and heterocyclyl substituted with 0-3 $R_e$;

$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl; and r, at each occurrence, is independently selected from zero, 1, 2, and 3.

In another aspect, the present invention provides compounds of Formula (IX):

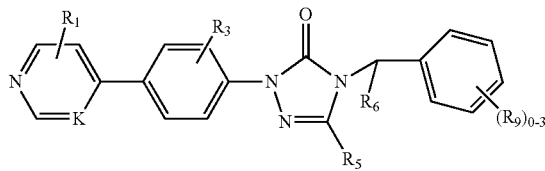

(IX)

or stereoisomers, enantiomers, diastereoisomers, tautomers, pharmaceutically acceptable salts, solvates, or prodrugs thereof, wherein K, at each occurrence, is independently selected from N and $CR_1$;

$R_1$ is independently selected from H, F, Cl, Br, CN, $NR_aR_a$, and $C_{1-4}$alkyl substituted with 0-4 $R_e$;

$R_3$ is independently selected from H, CN, $C_{1-4}$ alkyl substituted with 0-3 $R_e$, and —$OR_b$;

$R_5$ is independently selected from H, $C_{1-4}$alkyl substituted with 0-4 $R_e$, —$(CH_2)_rOR_b$, —$(CH_2)_rNR_aR_a$, and —$(CH_2)_r$-heterocyclyl substituted with 0-3 $R_e$;

$R_6$ is independently selected from H and $C_{1-4}$alkyl substituted with 0-4 $R_e$;

$R_9$, at each occurrence, is independently selected from F, Cl, Br, $C_{1-4}$ alkyl, nitro, —$S(O)_pR_c$, —$S(O)_pNR_aR_a$, —$OR_b$, CN, —$NR_aR_a$, —C(=O)$OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (X):

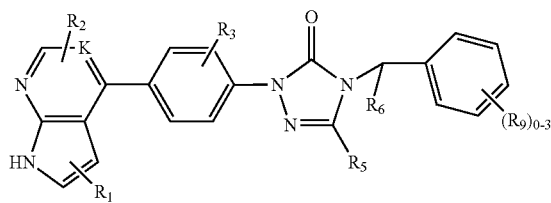

(X)

or stereoisomers, enantiomers, diastereoisomers, tautomers, pharmaceutically acceptable salts, solvates, or prodrugs thereof, wherein K is independently selected from N and CR$_2$;

R$_1$ at each occurrence, is independently selected from H, F, Cl, Br, CN, NR$_a$R$_a$, and C$_{1-4}$alkyl substituted with 0-4 R$_e$;

R$_2$ is independently selected from H and C$_{1-4}$alkyl substituted with 0-4 R$_e$;

R$_3$ is independently selected from H, CN, C$_{1-4}$ alkyl substituted with 0-3 R$_e$, and —OR$_b$;

R$_5$ is independently selected from H, C$_{1-4}$alkyl substituted with 0-4 R$_e$, —(CH$_2$)$_r$OR$_b$, —(CH$_2$)$_r$NR$_a$R$_a$, and —(CH$_2$)$_r$-heterocyclyl substituted with 0-3 R$_e$;

R$_6$ is independently selected from H and C$_{1-4}$alkyl substituted with 0-4 R$_e$;

R$_9$, at each occurrence, is independently selected from F, Cl, Br, C$_{1-4}$ alkyl, nitro, —S(O)$_p$R$_c$, —S(O)$_p$NR$_a$R$_a$, —OR$_b$, CN, —NR$_a$R$_a$, —C(=O)OR$_b$, —(CH$_2$)$_r$C(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, —(CH$_2$)$_r$—C$_{3-6}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (XI):

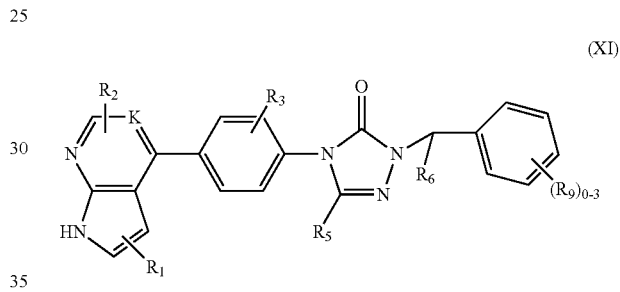

(XI)

or stereoisomers, enantiomers, diastereoisomers, tautomers, pharmaceutically acceptable salts, solvates, or prodrugs thereof, wherein K is independently selected from N and CR$_2$;

R$_1$, at each occurrence, is independently selected from H, F, Cl, Br, CN, NR$_a$R$_a$, and C$_{1-4}$alkyl substituted with 0-4 R$_e$;

R$_2$ is independently selected from H and C$_{1-4}$alkyl substituted with 0-4 R$_e$;

R$_3$ is independently selected from H, CN, C$_{1-4}$ alkyl substituted with 0-3 R$_e$, and —OR$_b$;

R$_5$ is independently selected from H, C$_{1-4}$alkyl substituted with 0-4 R$_e$, —(CH$_2$)$_r$OR$_b$, —(CH$_2$)$_r$NR$_a$R$_a$, and —(CH$_2$)$_r$-heterocyclyl substituted with 0-3 R$_e$; R$_6$ is independently selected from H, C$_{1-4}$alkyl substituted with 0-4 R$_e$, —(CH$_2$)$_r$OR$_b$, —(CH$_2$)$_r$C(=O)R$_b$, —(CH$_2$)$_r$NR$_a$C(=O)R$_b$, —(CH$_2$)$_r$C(=O)OR$_b$, and heterocyclyl substituted with 0-3 R$_e$;

R$_9$, at each occurrence, is independently selected from F, Cl, Br, C$_{1-4}$ alkyl, nitro, —S(O)$_p$R$_c$, —S(O)$_p$NR$_a$R$_a$, —OR$_b$, CN, —NR$_a$R$_a$, —C(=O)OR$_b$, —(CH$_2$)$_r$C(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, —(CH$_2$)$_r$—C$_{3-6}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—C$_{3-6}$ cycloalkyl, —(CH$_2$)$_r$—C$_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides a compound selected from any subset list of compounds exemplified in the present application.

In another aspect, the present invention provides a compound selected from 4-(4-(1H-pyrazol-4-yl)phenyl)-1-(3-fluorobenzyl)-1H-1,2,4-triazol-5(4H)-one;
4-(4-(1H-pyrazol-4-yl)phenyl)-1-benzyl-1H-1,2,4-triazol-5(4H)-one;
4-(4-(1H-pyrazol-4-yl)phenyl)-1-(3-methoxybenzyl)-1H-1,2,4-triazol-5(4H)-one;
4-(4-(1H-pyrazol-4-yl)phenyl)-1-(2,5-difluorobenzyl)-1H-1,2,4-triazol-5(4H)-one;
1-benzyl-4-(3-methoxy-4-(1H-pyrazol-4-yl)phenyl)-1H-1,2,4-triazol-5(4H)-one;
4-(3-methoxy-4-(1H-pyrazol-4-yl)phenyl)-1-(3-methoxybenzyl)-1H-1,2,4-triazol-5(4H)-one;
1-(3-fluorobenzyl)-4-(3-methoxy-4-(1H-pyrazol-4-yl)phenyl)-1H-1,2,4-triazol-5(4H)-one;
4-(3-methoxy-4-(1H-pyrazol-4-yl)phenyl)-1-(1-phenylethyl)-1H-1,2,4-triazol-5(4H)-one;
4-(3-methoxy-4-(1H-pyrazol-4-yl)phenyl)-1-phenethyl-1H-1,2,4-triazol-5(4H)-one;
1-benzyl-4-(2-methoxy-4-(1H-pyrazol-4-yl)phenyl)-1H-1,2,4-triazol-5(4H)-one;
4-(2-methoxy-4-(1H-pyrazol-4-yl)phenyl)-1-(3-methoxybenzyl)-1H-1,2,4-triazol-5(4H)-one;
1-(3-fluorobenzyl)-4-(2-methoxy-4-(1H-pyrazol-4-yl)phenyl)-1H-1,2,4-triazol-5(4H)-one;
1-(2,5-difluorobenzyl)-4-(2-methoxy-4-(1H-pyrazol-4-yl)phenyl)-1H-1,2,4-triazol-5(4H)-one;
4-(2-methoxy-4-(1H-pyrazol-4-yl)phenyl)-1-phenethyl-1H-1,2,4-triazol-5(4H)-one;
4-(4-(1H-pyrazol-4-yl)phenyl)-1-(1-phenylethyl)-1H-1,2,4-triazol-5(4H)-one;
1-(2,5-difluorobenzyl)-4-(2-methoxy-4-(1H-pyrazol-4-yl)phenyl)-1H-1,2,4-triazol-5(4H)-one;
1-(4-(1H-pyrazol-4-yl)phenyl)-4-benzyl-1H-1,2,4-triazol-5(4H)-one;
1-(4-(1H-pyrazol-4-yl)phenyl)-4-(3-methoxybenzyl)-1H-1,2,4-triazol-5(4H)-one;
1-(4-(1H-pyrazol-4-yl)phenyl)-4-(3-fluorobenzyl)-1H-1,2,4-triazol-5(4H)-one;
1-(4-(1H-pyrazol-4-yl)phenyl)-4-(2,5-difluorobenzyl)-1H-1,2,4-triazol-5(4H)-one;
1-(4-(1H-pyrazol-4-yl)phenyl)-4-(3-fluoro-5-methoxybenzyl)-1H-1,2,4-triazol-5(4H)-one;
1-(4-(1H-pyrazol-4-yl)phenyl)-4-(1-phenylethyl)-1H-1,2,4-triazol-5(4H)-one;
4-benzyl-1-(3-methoxy-4-(1H-pyrazol-4-yl)phenyl)-1H-1,2,4-triazol-5(4H)-one;
1-(3-methoxy-4-(1H-pyrazol-4-yl)phenyl)-4-(3-methoxybenzyl)-1H-1,2,4-triazol-5(4H)-one;
4-(2,5-difluorobenzyl)-1-(3-methoxy-4-(1H-pyrazol-4-yl)phenyl)-1H-1,2,4-triazol-5(4H)-one;
4-(3-fluoro-5-methoxybenzyl)-1-(3-methoxy-4-(1H-pyrazol-4-yl)phenyl)-1H-1,2,4-triazol-5(4H)-one;
1-(3-methoxy-4-(1H-pyrazol-4-yl)phenyl)-4-(1-phenylethyl)-1H-1,2,4-triazol-5(4H)-one;
1-(4-(1H-pyrazol-4-yl)phenyl)-4-(2-fluorobenzyl)-1H-1,2,4-triazol-5(4H)-one;
1-(4-(1H-pyrazol-4-yl)phenyl)-4-(2-chlorobenzyl)-1H-1,2,4-triazol-5(4H)-one;
4-(3-fluorobenzyl)-1-(3-methoxy-4-(1H-pyrazol-4-yl)phenyl)-1H-1,2,4-triazol-5(4H)-one;
4-(2-fluorobenzyl)-1-(3-methoxy-4-(1H-pyrazol-4-yl)phenyl)-1H-1,2,4-triazol-5(4H)-one;
4-(2-chlorobenzyl)-1-(3-methoxy-4-(1H-pyrazol-4-yl)phenyl)-1H-1,2,4-triazol-5(4H)-one;
1-(4-(1H-pyrazol-4-yl)phenyl)-4-(2,6-difluorobenzyl)-1H-1,2,4-triazol-5(4H)-one;
3-((1-(4-(1H-pyrazol-4-yl)phenyl)-5-oxo-1H-1,2,4-triazol-4(5H)-yl)methyl)benzonitrile;
3-((1-(3-methoxy-4-(1H-pyrazol-4-yl)phenyl)-5-oxo-1H-1,2,4-triazol-4(5H)-yl)methyl)benzonitrile;
4-(3,5-difluorobenzyl)-1-(3-methoxy-4-(1H-pyrazol-4-yl)phenyl)-1H-1,2,4-triazol-5(4H)-one;
4-(3-(difluoromethoxy)benzyl)-1-(3-methoxy-4-(1H-pyrazol-4-yl)phenyl)-1H-1,2,4-triazol-5(4H)-one;
4-(4-fluorobenzyl)-1-(3-methoxy-4-(1H-pyrazol-4-yl)phenyl)-1H-1,2,4-triazol-5(4H)-one;
4-(2,6-difluorobenzyl)-1-(3-methoxy-4-(1H-pyrazol-4-yl)phenyl)-1H-1,2,4-triazol-5(4H)-one;
1-(3-ethyl-4-(1H-pyrazol-4-yl)phenyl)-4-(3-fluoro-5-methoxybenzyl)-1H-1,2,4-triazol-5(4H)-one;
3-((1-(3-ethyl-4-(1H-pyrazol-4-yl)phenyl)-5-oxo-1H-1,2,4-triazol-4(5H)-yl)methyl)benzonitrile;
1-(3-ethyl-4-(1H-pyrazol-4-yl)phenyl)-4-(2-fluorobenzyl)-1H-1,2,4-triazol-5(4H)-one;
1-(3-ethyl-4-(1H-pyrazol-4-yl)phenyl)-4-(4-fluorobenzyl)-1H-1,2,4-triazol-5(4H)-one;
4-(3,5-difluorobenzyl)-1-(3-ethyl-4-(1H-pyrazol-4-yl)phenyl)-1H-1,2,4-triazol-5(4H)-one;
1-(3-ethyl-4-(1H-pyrazol-4-yl)phenyl)-4-(3-methoxybenzyl)-1H-1,2,4-triazol-5(4H)-one;
(difluoromethoxy)benzyl)-1-(3-ethyl-4-(1H-pyrazol-4-yl)phenyl)-1H-1,2,4-triazol-5(4H)-one;
1-(4-(1H-pyrazol-4-yl)phenyl)-4-(1-(3-methoxyphenyl)ethyl)-1H-1,2,4-triazol-5(4H)-one;
1-(4-(1H-pyrazol-4-yl)phenyl)-4-(3,5-dimethoxybenzyl)-1H-1,2,4-triazol-5(4H)-one;
4-[(4-fluoro-3-methoxyphenyl)methyl]-1-[4-(1H-pyrazol-4-yl)phenyl]-4,5-dihydro-1H-1,2,4-triazol-5-one;
1-(4-(1H-pyrazol-4-yl)phenyl)-4-(2-fluoro-3-methoxybenzyl)-1H-1,2,4-triazol-5(4H)-one;
1-(4-(1H-pyrazol-4-yl)phenyl)-4-(5-fluoro-2-methoxybenzyl)-1H-1,2,4-triazol-5(4H)-one;
1-(4-(1H-pyrazol-4-yl)phenyl)-4-(3-fluoro-4-methoxybenzyl)-1H-1,2,4-triazol-5(4H)-one;

4-benzyl-1-(3-ethyl-4-(1H-pyrazol-4-yl)phenyl)-1H-1,2,4-triazol-5(4H)-one
1-(3-ethyl-4-(1H-pyrazol-4-yl)phenyl)-4-(3-fluorobenzyl)-1H-1,2,4-triazol-5(4H)-one;
4-(2,6-difluorobenzyl)-1-(3-ethyl-4-(1H-pyrazol-4-yl)phenyl)-1H-1,2,4-triazol-5(4H)-one;
1-(3-ethyl-4-(1H-pyrazol-4-yl)phenyl)-4-(1-phenylethyl)-1H-1,2,4-triazol-5(4H)-one;
4-(4-(1H-pyrazol-4-yl)phenyl)-1-benzyl-3-methyl-1H-1,2,4-triazol-5(4H)-one;
1-benzyl-4-(3-methoxy-4-(1H-pyrazol-4-yl)phenyl)-3-methyl-1H-1,2,4-triazol-5(4H)-one;
4-(3-methoxy-4-(1H-pyrazol-4-yl)phenyl)-1-(3-methoxybenzyl)-3-methyl-1H-1,2,4-triazol-5(4H)-one;
4-(3-methoxy-4-(1H-pyrazol-4-yl)phenyl)-3-methyl-1-(1-phenylethyl)-1H-1,2,4-triazol-5(4H)-one;
1-benzyl-4-(2-methoxy-4-(1H-pyrazol-4-yl)phenyl)-3-methyl-1H-1,2,4-triazol-5(4H)-one;
4-(2-methoxy-4-(1H-pyrazol-4-yl)phenyl)-1-(3-methoxybenzyl)-3-methyl-1H-1,2,4-triazol-5(4H)-one;
1-(3-fluorobenzyl)-4-(3-methoxy-4-(1H-pyrazol-4-yl)phenyl)-3-methyl-1H-1,2,4-triazol-5(4H)-one;
4-(3-methoxy-4-(1H-pyrazol-4-yl)phenyl)-3-methyl-1-phenethyl-1H-1,2,4-triazol-5(4H)-one;
4-(4-(1H-pyrazol-4-yl)phenyl)-3-methyl-1-phenethyl-1H-1,2,4-triazol-5(4H)-one;
1-(2,5-difluorobenzyl)-4-(3-methoxy-4-(1H-pyrazol-4-yl)phenyl)-3-methyl-1H-1,2,4-triazol-5(4H)-one;
4-(4-(1H-pyrazol-4-yl)phenyl)-1-(3-methoxybenzyl)-3-methyl-1H-1,2,4-triazol-5(4H)-one;
4-(4-(1H-pyrazol-4-yl)phenyl)-1-(3-fluorobenzyl)-3-methyl-1H-1,2,4-triazol-5(4H)-one;
4-(4-(1H-pyrazol-4-yl)phenyl)-1-(2,5-difluorobenzyl)-3-methyl-1H-1,2,4-triazol-5(4H)-one;
4-(4-(1H-pyrazol-4-yl)phenyl)-1-(3-fluoro-5-methoxybenzyl)-3-methyl-1H-1,2,4-triazol-5(4H)-one;
4-(4-(1H-pyrazol-4-yl)phenyl)-3-methyl-1-(1-phenylethyl)-1H-1,2,4-triazol-5(4H)-one;
1-(3-fluorobenzyl)-4-(2-methoxy-4-(1H-pyrazol-4-yl)phenyl)-3-methyl-1H-1,2,4-triazol-5(4H)-one;
4-(2-methoxy-4-(1H-pyrazol-4-yl)phenyl)-3-methyl-1-(1-phenylethyl)-1H-1,2,4-triazol-5(4H)-one;
1-(3-fluoro-5-methoxybenzyl)-4-(2-methoxy-4-(1H-pyrazol-4-yl)phenyl)-3-methyl-1H-1,2,4-triazol-5(4H)-one;
4-(2-methoxy-4-(1H-pyrazol-4-yl)phenyl)-3-methyl-1-phenethyl-1H-1,2,4-triazol-5(4H)-one;
1-(2,5-difluorobenzyl)-4-(2-methoxy-4-(1H-pyrazol-4-yl)phenyl)-3-methyl-1H-1,2,4-triazol-5(4H)-one;
1-(4-(1H-pyrazol-4-yl)phenyl)-4-benzyl-3-methyl-1H-1,2,4-triazol-5(4H)-one;
1-(4-(1H-pyrazol-4-yl)phenyl)-4-(3-methoxybenzyl)-3-methyl-1H-1,2,4-triazol-5(4H)-one;
1-(4-(1H-pyrazol-4-yl)phenyl)-4-(3-fluorobenzyl)-3-methyl-1H-1,2,4-triazol-5(4H)-one;
1-(4-(1H-pyrazol-4-yl)phenyl)-4-(2,5-difluorobenzyl)-3-methyl-1H-1,2,4-triazol-5(4H)-one;
1-(4-(1H-pyrazol-4-yl)phenyl)-4-(3-fluoro-5-methoxybenzyl)-3-methyl-1H-1,2,4-triazol-5(4H)-one;
1-(4-(1H-pyrazol-4-yl)phenyl)-3-methyl-4-(1-phenylethyl)-1H-1,2,4-triazol-5(4H)-one;
1-(4-(1H-pyrazol-4-yl)phenyl)-3-methyl-4-phenethyl-1H-1,2,4-triazol-5(4H)-one;
1-(4-(1H-pyrazol-4-yl)phenyl)-4-(2-chlorobenzyl)-3-methyl-1H-1,2,4-triazol-5(4H)-one;
2-(4-(1H-pyrazol-4-yl)phenyl)-4-(2-fluorobenzyl)-5-methyl-2,4-dihydro-3H-1,2,4-triazol-3-one;
4-benzyl-1-(3-methoxy-4-(1H-pyrazol-4-yl)phenyl)-3-methyl-1H-1,2,4-triazol-5(4H)-one;
1-(3-methoxy-4-(1H-pyrazol-4-yl)phenyl)-4-(3-methoxybenzyl)-3-methyl-1H-1,2,4-triazol-5(4H)-one;
4-(3-fluorobenzyl)-1-(3-methoxy-4-(1H-pyrazol-4-yl)phenyl)-3-methyl-1H-1,2,4-triazol-5(4H)-one;
4-(2,5-difluorobenzyl)-1-(3-methoxy-4-(1H-pyrazol-4-yl)phenyl)-3-methyl-1H-1,2,4-triazol-5(4H)-one;
4-(3-fluoro-5-methoxybenzyl)-1-(3-methoxy-4-(1H-pyrazol-4-yl)phenyl)-3-methyl-1H-1,2,4-triazol-5(4H)-one;
1-(3-methoxy-4-(1H-pyrazol-4-yl)phenyl)-3-methyl-4-(1-phenylethyl)-1H-1,2,4-triazol-5(4H)-one;
1-(3-methoxy-4-(1H-pyrazol-4-yl)phenyl)-3-methyl-4-phenethyl-1H-1,2,4-triazol-5(4H)-one;
4-(2-fluorobenzyl)-1-(3-methoxy-4-(1H-pyrazol-4-yl)phenyl)-3-methyl-1H-1,2,4-triazol-5(4H)-one;
1-(4-(1H-pyrazol-4-yl)phenyl)-4-(3,5-difluorobenzyl)-3-methyl-1H-1,2,4-triazol-5(4H)-one;
3-((1-(3-methoxy-4-(1H-pyrazol-4-yl)phenyl)-3-methyl-5-oxo-1H-1,2,4-triazol-4(5H)-yl)methyl)benzonitrile;
4-(2,6-difluorobenzyl)-1-(3-methoxy-4-(1H-pyrazol-4-yl)phenyl)-3-methyl-1H-1,2,4-triazol-5(4H)-one;
4-(3,5-difluorobenzyl)-1-(3-methoxy-4-(1H-pyrazol-4-yl)phenyl)-3-methyl-1H-1,2,4-triazol-5(4H)-one;
4-(3-(difluoromethoxy)benzyl)-1-(3-methoxy-4-(1H-pyrazol-4-yl)phenyl)-3-methyl-1H-1,2,4-triazol-5(4H)-one;
4-(4-fluorobenzyl)-1-(3-methoxy-4-(1H-pyrazol-4-yl)phenyl)-3-methyl-1H-1,2,4-triazol-5(4H)-one;
1-(4-(1H-pyrazol-4-yl)phenyl)-4-(3-(difluoromethoxy)benzyl)-3-methyl-1H-1,2,4-triazol-5(4H)-one;
3-((1-(4-(1H-pyrazol-4-yl)phenyl)-3-methyl-5-oxo-1H-1,2,4-triazol-4(5H)-yl)methyl)benzonitrile;
1-(4-(1H-pyrazol-4-yl)phenyl)-4-(2,6-difluorobenzyl)-3-methyl-1H-1,2,4-triazol-5(4H)-one;
1-(3-ethyl-4-(1H-pyrazol-4-yl)phenyl)-4-(3-methoxybenzyl)-3-methyl-1H-1,2,4-triazol-5(4H)-one;
1-(3-ethyl-4-(1H-pyrazol-4-yl)phenyl)-4-(3-fluorobenzyl)-3-methyl-1H-1,2,4-triazol-5(4H)-one;
4-(2,5-difluorobenzyl)-1-(3-ethyl-4-(1H-pyrazol-4-yl)phenyl)-3-methyl-1H-1,2,4-triazol-5(4H)-one;
4-(3,5-difluorobenzyl)-1-(3-ethyl-4-(1H-pyrazol-4-yl)phenyl)-3-methyl-1H-1,2,4-triazol-5(4H)-one;
1-(3-ethyl-4-(1H-pyrazol-4-yl)phenyl)-3-methyl-4-(1-phenylethyl)-1H-1,2,4-triazol-5(4H)-one;
1-(3-ethyl-4-(1H-pyrazol-4-yl)phenyl)-3-methyl-4-phenethyl-1H-1,2,4-triazol-5(4H)-one;
3-((1-(3-ethyl-4-(1H-pyrazol-4-yl)phenyl)-3-methyl-5-oxo-1H-1,2,4-triazol-4(5H)-yl)methyl)benzonitrile;
4-(3-(difluoromethoxy)benzyl)-1-(3-ethyl-4-(1H-pyrazol-4-yl)phenyl)-3-methyl-1H-1,2,4-triazol-5(4H)-one;
1-(3-ethyl-4-(1H-pyrazol-4-yl)phenyl)-4-(2-fluorobenzyl)-3-methyl-1H-1,2,4-triazol-5(4H)-one;
1-(3-ethyl-4-(1H-pyrazol-4-yl)phenyl)-4-(4-fluorobenzyl)-3-methyl-1H-1,2,4-triazol-5(4H)-one;
1-(3-ethyl-4-(1H-pyrazol-4-yl)phenyl)-4-(3-fluoro-5-methoxybenzyl)-3-methyl-1H-1,2,4-triazol-5(4H)-one;
4-(2,6-difluorobenzyl)-1-(3-ethyl-4-(1H-pyrazol-4-yl)phenyl)-3-methyl-1H-1,2,4-triazol-5(4H)-one;
4-benzyl-1-(3-ethyl-4-(1H-pyrazol-4-yl)phenyl)-3-methyl-1H-1,2,4-triazol-5(4H)-one;
1-(4-(1H-pyrazol-4-yl)phenyl)-4-(1-(3-methoxyphenyl)ethyl)-3-methyl-1H-1,2,4-triazol-5(4H)-one;
1-(4-(1H-pyrazol-4-yl)phenyl)-4-(3,5-dimethoxybenzyl)-3-methyl-1H-1,2,4-triazol-5(4H)-one;
1-(4-(1H-pyrazol-4-yl)phenyl)-4-(4-fluoro-3-methoxybenzyl)-3-methyl-1H-1,2,4-triazol-5(4H)-one;

1-(4-(1H-pyrazol-4-yl)phenyl)-4-(2-fluoro-3-methoxybenzyl)-3-methyl-1H-1,2,4-triazol-5(4H)-one;
1-(4-(1H-pyrazol-4-yl)phenyl)-4-(5-fluoro-2-methoxybenzyl)-3-methyl-1H-1,2,4-triazol-5(4H)-one;
1-(4-(1H-pyrazol-4-yl)phenyl)-4-(3-fluoro-4-methoxybenzyl)-3-methyl-1H-1,2,4-triazol-5(4H)-one;
1-(4-(1H-pyrazol-4-yl)phenyl)-3-(hydroxymethyl)-4-(3-methoxybenzyl)-1H-1,2,4-triazol-5(4H)-one;
1-(4-(1H-pyrazol-4-yl)phenyl)-4-benzyl-3-(hydroxymethyl)-1H-1,2,4-triazol-5(4H)-one;
1-(4-(1H-pyrazol-4-yl)phenyl)-4-(3,5-dimethoxybenzyl)-3-(hydroxymethyl)-1H-1,2,4-triazol-5(4H)-one;
1-(4-(1H-pyrazol-4-yl)phenyl)-4-(3-fluorobenzyl)-3-(hydroxymethyl)-1H-1,2,4-triazol-5(4H)-one;
1-(4-(1H-pyrazol-4-yl)phenyl)-4-(2,5-difluorobenzyl)-3-(hydroxymethyl)-1H-1,2,4-triazol-5(4H)-one;
1-(4-(1H-pyrazol-4-yl)phenyl)-4-(3,5-difluorobenzyl)-3-(hydroxymethyl)-1H-1,2,4-triazol-5(4H)-one;
1-(4-(1H-pyrazol-4-yl)phenyl)-4-(3-(difluoromethoxy)benzyl)-3-(hydroxymethyl)-1H-1,2,4-triazol-5(4H)-one;
3-((1-(4-(1H-pyrazol-4-yl)phenyl)-3-(hydroxymethyl)-5-oxo-1H-1,2,4-triazol-4(5H)-yl)methyl)benzonitrile;
1-(4-(1H-pyrazol-4-yl)phenyl)-4-benzyl-3-(2-hydroxypropan-2-yl)-1H-1,2,4-triazol-5(4H)-one;
1-(4-(1H-pyrazol-4-yl)phenyl)-3-(2-hydroxypropan-2-yl)-4-(3-methoxybenzyl)-1H-1,2,4-triazol-5(4H)-one;
1-(4-(1H-pyrazol-4-yl)phenyl)-4-(3-fluorobenzyl)-3-(2-hydroxypropan-2-yl)-1H-1,2,4-triazol-5(4H)-one;
1-(4-(1H-pyrazol-4-yl)phenyl)-4-(2,5-difluorobenzyl)-3-(2-hydroxypropan-2-yl)-1H-1,2,4-triazol-5(4H)-one;
1-(4-(1H-pyrazol-4-yl)phenyl)-4-(3,5-difluorobenzyl)-3-(2-hydroxypropan-2-yl)-1H-1,2,4-triazol-5(4H)-one;
1-(4-(1H-pyrazol-4-yl)phenyl)-4-(2,6-difluorobenzyl)-3-(2-hydroxypropan-2-yl)-1H-1,2,4-triazol-5(4H)-one;
1-(4-(1H-pyrazol-4-yl)phenyl)-4-(3-(difluoromethoxy)benzyl)-3-(2-hydroxypropan-2-yl)-1H-1,2,4-triazol-5(4H)-one;
1-(4-(1H-pyrazol-4-yl)phenyl)-4-benzyl-3-(1-hydroxyethyl)-1H-1,2,4-triazol-5(4H)-one;
1-(4-(1H-pyrazol-4-yl)phenyl)-3-((dimethylamino)methyl)-4-(3-methoxybenzyl)-1H-1,2,4-triazol-5(4H)-one;
1-(4-(1H-pyrazol-4-yl)phenyl)-4-(3-methoxybenzyl)-3-(morpholinomethyl)-1H-1,2,4-triazol-5(4H)-one;
1-(4-(1H-pyrazol-4-yl)phenyl)-4-(3-fluoro-5-methoxybenzyl)-3-(hydroxymethyl)-1H-1,2,4-triazol-5(4H)-one;
1-(4-(1H-pyrazol-4-yl)phenyl)-4-(3-fluoro-5-methoxybenzyl)-3-(2-hydroxypropan-2-yl)-1H-1,2,4-triazol-5(4H)-one;
1-(4-(1H-pyrazol-4-yl)phenyl)-4-(3-methoxybenzyl)-3-(pyrrolidin-1-ylmethyl)-1H-1,2,4-triazol-5(4H)-one;
1-(4-(1H-pyrazol-4-yl)phenyl)-4-(3,5-dimethoxybenzyl)-3-(1-hydroxyethyl)-1H-1,2,4-triazol-5(4H)-one;
1-(4-(1H-pyrazol-4-yl)phenyl)-3-((dimethylamino)methyl)-4-(3-fluoro-5-methoxybenzyl)-1H-1,2,4-triazol-5(4H)-one;
1-(4-(1H-pyrazol-4-yl)phenyl)-4-(3-fluoro-5-methoxybenzyl)-3-(morpholinomethyl)-1H-1,2,4-triazol-5(4H)-one;
1-(4-(1H-pyrazol-4-yl)phenyl)-4-(3-fluoro-5-methoxybenzyl)-3-(pyrrolidin-1-ylmethyl)-1H-1,2,4-triazol-5(4H)-one;
1-(4-(1H-pyrazol-4-yl)phenyl)-4-(3-fluoro-5-methoxybenzyl)-3-(((2-hydroxyethyl)amino)methyl)-1H-1,2,4-triazol-5(4H)-one;
1-(4-(1H-pyrazol-4-yl)phenyl)-4-(3-fluoro-5-methoxybenzyl)-3-(piperazin-1-ylmethyl)-1H-1,2,4-triazol-5(4H)-one;
1-(4-(1H-pyrazol-4-yl)phenyl)-4-(3-fluoro-5-methoxybenzyl)-3-(((1-hydroxypropan-2-yl)amino)methyl)-1H-1,2,4-triazol-5(4H)-one;
1-(4-(1H-pyrazol-4-yl)phenyl)-4-(3-fluoro-5-methoxybenzyl)-3-((3-hydroxypyrrolidin-1-yl)methyl)-1H-1,2,4-triazol-5(4H)-one;
1-(4-(1H-pyrazol-4-yl)phenyl)-3-((3-hydroxypyrrolidin-1-yl)methyl)-4-(3-methoxybenzyl)-1H-1,2,4-triazol-5(4H)-one;
1-(4-(1H-pyrazol-4-yl)phenyl)-4-(5-fluoro-2-methoxybenzyl)-3-(hydroxymethyl)-1H-1,2,4-triazol-5(4H)-one;
1-(4-(1H-pyrazol-4-yl)phenyl)-4-(4-fluoro-3-methoxybenzyl)-3-(hydroxymethyl)-1H-1,2,4-triazol-5(4H)-one;
1-(4-(1H-pyrazol-4-yl)phenyl)-4-(3-fluoro-4-methoxybenzyl)-3-(hydroxymethyl)-1H-1,2,4-triazol-5(4H)-one;
1-(4-(1H-pyrazol-4-yl)phenyl)-4-(2-fluoro-3-methoxybenzyl)-3-(hydroxymethyl)-1H-1,2,4-triazol-5(4H)-one;
1-(4-(2-aminopyridin-4-yl)phenyl)-4-(3-methoxybenzyl)-3-methyl-1H-1,2,4-triazol-5(4H)-one;
1-(4-(2-aminopyridin-4-yl)phenyl)-4-(3-methoxybenzyl)-1H-1,2,4-triazol-5(4H)-one;
1-(4-(7H-pyrrolo[2,3-d]pyrimidin-4-yl)phenyl)-4-(3-methoxybenzyl)-1H-1,2,4-triazol-5(4H)-one;
1-(4-(7H-pyrrolo[2,3-d]pyrimidin-4-yl)phenyl)-4-(3-methoxybenzyl)-3-methyl-1H-1,2,4-triazol-5(4H)-one;
1-(4-(1H-pyrrolo[2,3-b]pyridin-4-yl)phenyl)-4-(3-methoxybenzyl)-3-methyl-1H-1,2,4-triazol-5(4H)-one;
1-(4-(2-aminopyrimidin-4-yl)phenyl)-4-(3-methoxybenzyl)-3-methyl-1H-1,2,4-triazol-5(4H)-one;
1-(4-(1H-pyrrolo[2,3-b]pyridin-4-yl)phenyl)-4-(3-methoxybenzyl)-1H-1,2,4-triazol-5(4H)-one;
1-(4-(2-aminopyrimidin-4-yl)phenyl)-4-(3-methoxybenzyl)-1H-1,2,4-triazol-5(4H)-one;
Preparation 1-(4-(1H-pyrazol-4-yl)phenyl)-4-(3-methoxybenzyl)-1H-tetrazol-5(4H)-one;
1-(4-(1H-pyrazol-4-yl)phenyl)-4-(3-fluorobenzyl)-1H-tetrazol-5(4H)-one;
1-(4-(1H-pyrazol-4-yl)phenyl)-4-(2,5-difluorobenzyl)-1H-tetrazol-5(4H)-one;
1-(4-(1H-pyrazol-4-yl)phenyl)-4-(3-fluoro-5-methoxybenzyl)-1H-tetrazol-5(4H)-one;
1-(4-(1H-pyrazol-4-yl)phenyl)-4-(1-phenylethyl)-1H-tetrazol-5(4H)-one;
1-(4-(1H-pyrazol-4-yl)phenyl)-4-(2-chlorobenzyl)-1H-tetrazol-5(4H)-one;
1-(4-(1H-pyrazol-4-yl)phenyl)-4-benzyl-1H-tetrazol-5(4H)-one;
1-benzyl-4-(3-methoxy-4-(1H-pyrazol-4-yl)phenyl)-1H-tetrazol-5(4H)-one;
1-(3-fluorobenzyl)-4-(3-methoxy-4-(1H-pyrazol-4-yl)phenyl)-1H-tetrazol-5(4H)-one;
1-(2,5-difluorobenzyl)-4-(3-methoxy-4-(1H-pyrazol-4-yl)phenyl)-1H-tetrazol-5(4H)-one;
1-(3-fluoro-5-methoxybenzyl)-4-(3-methoxy-4-(1H-pyrazol-4-yl)phenyl)-1H-tetrazol-5(4H)-one;
1-(2-fluorobenzyl)-4-(3-methoxy-4-(1H-pyrazol-4-yl)phenyl)-1H-tetrazol-5(4H)-one;
1-(2,6-difluorobenzyl)-4-(3-methoxy-4-(1H-pyrazol-4-yl)phenyl)-1H-tetrazol-5(4H)-one;
3-((4-(3-methoxy-4-(1H-pyrazol-4-yl)phenyl)-5-oxo-4,5-dihydro-1H-tetrazol-1-yl)methyl)benzonitrile;
1-(4-fluorobenzyl)-4-(3-methoxy-4-(1H-pyrazol-4-yl)phenyl)-1H-tetrazol-5(4H)-one;
1-(3-methoxy-4-(1H-pyrazol-4-yl)phenyl)-4-(3-methoxybenzyl)-1H-tetrazol-5(4H)-one;

In another embodiment, the compounds of the present invention have ROCK IC$_{50}$ values≤10 µM.

In another embodiment, the compounds of the present invention have ROCK $IC_{50}$ values≤1 µM.

In another embodiment, the compounds of the present invention have ROCK $IC_{50}$ values≤0.1 µM.

In another embodiment, the compounds of the present invention have ROCK $IC_{50}$ values≤0.05 µM.

In another embodiment, the compounds of the present invention have ROCK $IC_{50}$ values≤0.01 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example, trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle", "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydroquinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and S(O)$_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs", *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2H$" or "D". The term "deuterated" herein, by itself or used to modify a compound or group, refers to replacement of one or more hydrogen atom(s), which is attached to carbon(s), with a deuterium atom. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Me | Methyl |
| Et | Ethyl |
| Pr | Propyl |
| i-Pr | Isopropyl |
| Bu | Butyl |
| i-Bu | Isobutyl |
| t-Bu | tert-butyl |
| Ph | Phenyl |
| Bn | Benzyl |
| Boc | tert-butyloxycarbonyl |
| AcOH or HOAc | acetic acid |
| $AlCl_3$ | aluminum chloride |
| AIBN | Azobisisobutyronitrile |
| $BBr_3$ | boron tribromide |
| $BCl_3$ | boron trichloride |
| BEMP | 2-tert-butylimino-2-diethylamino-1,3-dimethylperhydro-1,3,2-diazaphosphorine |
| BOP reagent | benzotriazol-1-yloxytris(dimethylamino)phosphonium hexafluorophosphate |
| Burgess reagent | 1-methoxy-N-triethylammoniosulfonyl-methanimidate |
| CBz | Carbobenzyloxy |
| $CH_2Cl_2$ | Dichloromethane |
| $CH_3CN$ or ACN | Acetonitrile |
| $CDCl_3$ | deutero-chloroform |
| $CHCl_3$ | Chloroform |
| mCPBA or m-CPBA | meta-chloroperbenzoic acid |
| $Cs_2CO_3$ | cesium carbonate |
| $Cu(OAc)_2$ | copper (II) acetate |
| $Cy_2NMe$ | N-cyclohexyl-N-methylcyclohexanamine |
| DBU | 1,8-diazabicyclo[5.4.0]undec-7-ene |
| DCE | 1,2 dichloroethane |
| DCM | dichloromethane |
| DEA | diethylamine |
| Dess-Martin | 1,1,1-tris(acetyloxy)-1,1-dihydro-1,2-beniziodoxol-3-(1H)-one |
| DIC or DIPCDI | diisopropylcarbodiimide |
| DIEA, DIPEA or Hunig's base | diisopropylethylamine |
| DMAP | 4-dimethylaminopyridine |
| DME | 1,2-dimethoxyethane |
| DMF | dimethyl formamide |
| DMSO | dimethyl sulfoxide |
| cDNA | complementary DNA |
| Dppp | (R)-(+)-1,2-bis(diphenylphosphino)propane |
| DuPhos | (+)-1,2-bis((2S,5S)-2,5-diethylphospholano)benzene |
| EDC | N-(3-dimthylaminopropyl)-N'-ethylcarbodiimide |
| EDCI | N-(3-dimthylaminopropyl)-N'-ethylcarbodiimide hydrochloride |
| EDTA | ethylenediaminetetraacetic acid |
| (S,S)-EtDuPhosRh(I) | (+)-1,2-bis((2S,5S)-2,5-diethylphospholano)benzene(1,5-cyclooctadiene)rhodium(I) trifluoromethanesulfonate |
| $Et_3N$ or TEA | triethylamine |

-continued

| | |
|---|---|
| EtOAc | ethyl acetate |
| Et₂O | diethyl ether |
| EtOH | Ethanol |
| GMF | glass microfiber filter |
| Grubbs (II) | (1,3-bis(2,4,6-trimethylphenyl)-2-imidazolidinylidene)dichloro(phenylmethylene)(triycyclohexylphosphine)ruthenium |
| HCl | hydrochloric acid |
| HATU | O-(7-azabenzotriazol-1-yl)-N,N,N',N'-tetramethyluronium hexafluorophosphate |
| HEPES | 4-(2-hydroxyethyl)piperaxine-1-ethanesulfonic acid |
| Hex | Hexane |
| HOBt or HOBT | 1-hydroxybenzotriazole |
| H₂SO₄ | sulfuric acid |
| K₂CO₃ | potassium carbonate |
| KOAc | potassium acetate |
| K₃PO₄ | potassium phosphate |
| LAH | lithium aluminum hydride |
| LG | leaving group |
| LiOH | lithium hydroxide |
| MeOH | Methanol |
| MgSO₄ | magnesium sulfate |
| MsOH or MSA | methylsulfonic acid |
| NaCl | sodium chloride |
| NaH | sodium hydride |
| NaHCO₃ | sodium bicarbonate |
| Na₂CO₃ | sodium carbonate |
| NaOH | sodium hydroxide |
| Na₂SO₃ | sodium sulfite |
| Na₂SO₄ | sodium sulfate |
| NBS | N-bromosuccinimide |
| NCS | N-chlorosuccinimide |
| NH₃ | Ammonia |
| NH₄Cl | ammonium chloride |
| NH₄OH | ammonium hydroxide |
| OTf | triflate or trifluoromethanesulfonate |
| Pd₂(dba)₃ | tris(dibenzylideneacetone)dipalladium(0) |
| Pd(OAc)₂ | palladium(II) acetate |
| Pd/C | palladium on carbon |
| Pd(dppf)Cl₂ | [1,1'-bis(diphenylphosphino)-ferroceneldichloropalladium(II) |
| Ph₃PCl₂ | triphenylphosphine dichloride |
| PG | protecting group |
| POCl₃ | phosphorus oxychloride |
| i-PrOH or IPA | isopropanol |
| PS | polystyrene |
| PyBOP | benzotriazol-1-yl-oxytripyrrolidinophosphonium hexafluorophosphate |
| SEM-Cl | 2-(trimethysilyl)ethoxymethyl chloride |
| 2nd generation XPhos precatalyst | Chloro(2-dicyclohexylphosphino-2',4',6'-triisopropyl-1,1'biphenyl)[2-(2'-amino-1,1'-biphenyl)]palladium(II), THF adduct |
| SiO₂ | silica oxide |
| SnCl₂ | tin(II) chloride |
| TBAI | tetra-n-butylammonium iodide |
| TEA | triethylamine |
| TFA | trifluoroacetic acid |
| THF | tetrahydrofuran |
| TMSCHN₂ | trimethylsilyldiazomethane |
| T3P ® | propane phosphonic acid anhydride |
| TRIS | tris (hydroxymethyl) aminomethane |

The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL, assay containing 20 mM HEPES, pH 7.5, 20 mM MgCl₂, 0.015% Brij-35, 4 mM DTT, 5 μM ATP and 1.5 μM peptide substrate (FITC-AHA-AKRRRLSSLRA-OH). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the $IC_{50}$; i.e., the concentration of compound required to inhibit 50% of kinase activity.

Representative Examples were tested in the ROCK2 assay described above and found having ROCK2 inhibitory activity. Their ROCK2 inhibitory activity ($IC_{50}$ values) of ≤3 μM (3000 nM) was observed and shown in Table A below. The ranges of the ROCK2 $IC_{50}$ values are as follows: ROCK2 $IC_{50}$: ++++ (<5 nM) +++ (5-50 nM) ++ (50-250 nM) + (250-2000 nM)

TABLE A

| Example Number | ROCK2 $IC_{50}$ |
|---|---|
| 1 | ++ |
| 2 | ++ |
| 3 | ++ |
| 4 | + |
| 5 | ++ |
| 6 | +++ |
| 7 | ++ |
| 8 | + |
| 9 | ++ |
| 10 | + |
| 11 | ++ |
| 12 | ++ |
| 13 | + |
| 14 | ++ |
| 15 | + |
| 16 | ++ |
| 17 | +++ |
| 18 | ++++ |
| 19 | ++++ |
| 20 | +++ |
| 21 | ++++ |
| 22 | ++++ |
| 23 | ++++ |
| 24 | ++++ |
| 25 | +++ |
| 26 | ++++ |
| 27 | ++++ |
| 28 | +++ |
| 29 | +++ |
| 30 | ++++ |
| 31 | +++ |
| 32 | +++ |
| 33 | +++ |
| 34 | ++ |
| 35 | ++ |
| 36 | +++ |
| 37 | +++ |
| 38 | ++ |
| 39 | +++ |
| 40 | +++ |
| 41 | + |
| 42 | + |
| 43 | + |
| 44 | +++ |
| 45 | +++ |
| 46 | ++ |
| 47 | +++ |
| 48 | ++++ |
| 49 | + |
| 50 | ++++ |
| 51 | +++ |
| 52 | + |

TABLE A-continued

| Example Number | ROCK2 IC$_{50}$ |
|---|---|
| 53 | + |
| 54 | ++ |
| 55 | +++ |
| 57 | + |
| 58 | +++ |
| 59 | + |
| 60 | + |
| 61 | ++ |
| 62 | + |
| 63 | + |
| 64 | + |
| 65 | + |
| 66 | ++ |
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | ++ |
| 79 | +++ |
| 80 | ++++ |
| 81 | +++ |
| 82 | +++ |
| 83 | ++++ |
| 84 | ++ |
| 85 | ++ |
| 86 | +++ |
| 87 | +++ |
| 88 | ++++ |
| 89 | ++++ |
| 90 | ++++ |
| 91 | +++ |
| 92 | ++++ |
| 93 | +++ |
| 94 | +++ |
| 95 | +++ |
| 96 | +++ |
| 97 | ++ |
| 98 | +++ |
| 99 | +++ |
| 100 | +++ |
| 101 | +++ |
| 102 | ++ |
| 103 | + |
| 104 | ++ |
| 105 | +++ |
| 106 | +++ |
| 107 | ++ |
| 108 | +++ |
| 109 | + |
| 110 | + |
| 111 | + |
| 112 | ++ |
| 113 | ++ |
| 114 | + |
| 115 | +++ |
| 116 | + |
| 117 | +++ |
| 118 | +++ |
| 119 | +++ |
| 120 | + |
| 121 | ++++ |
| 122 | + |
| 123 | ++ |
| 124 | + |
| 125 | ++++ |
| 126 | +++ |
| 127 | ++ |
| 128 | +++ |
| 129 | +++ |
| 130 | +++ |
| 131 | +++ |
| 132 | ++ |
| 133 | +++ |
| 134 | ++++ |
| 135 | +++ |
| 136 | ++ |
| 137 | +++ |
| 138 | ++ |
| 139 | ++ |
| 140 | +++ |
| 141 | +++ |
| 142 | +++ |
| 143 | +++ |
| 144 | ++++ |
| 145 | +++ |
| 146 | +++ |
| 147 | ++ |
| 148 | +++ |
| 149 | +++ |
| 150 | +++ |
| 151 | +++ |
| 152 | +++ |
| 153 | +++ |
| 155 | +++ |
| 156 | +++ |
| 157 | ++ |
| 158 | +++ |
| 159 | + |
| 160 | + |
| 161 | ++ |
| 162 | +++ |
| 163 | ++ |
| 164 | + |
| 165 | +++ |
| 166 | +++ |
| 169 | ++++ |
| 170 | +++ |
| 172 | +++ |
| 173 | ++ |
| 174 | ++ |
| 175 | +++ |
| 176 | +++ |
| 177 | ++ |
| 178 | +++ |
| 179 | ++ |
| 180 | +++ |
| 181 | ++ |
| 182 | +++ |
| 183 | ++ |
| 184 | ++ |
| 185 | + |
| 186 | + |
| 187 | +++ |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example, as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, 4th Edition, Wiley-Interscience (2006)).

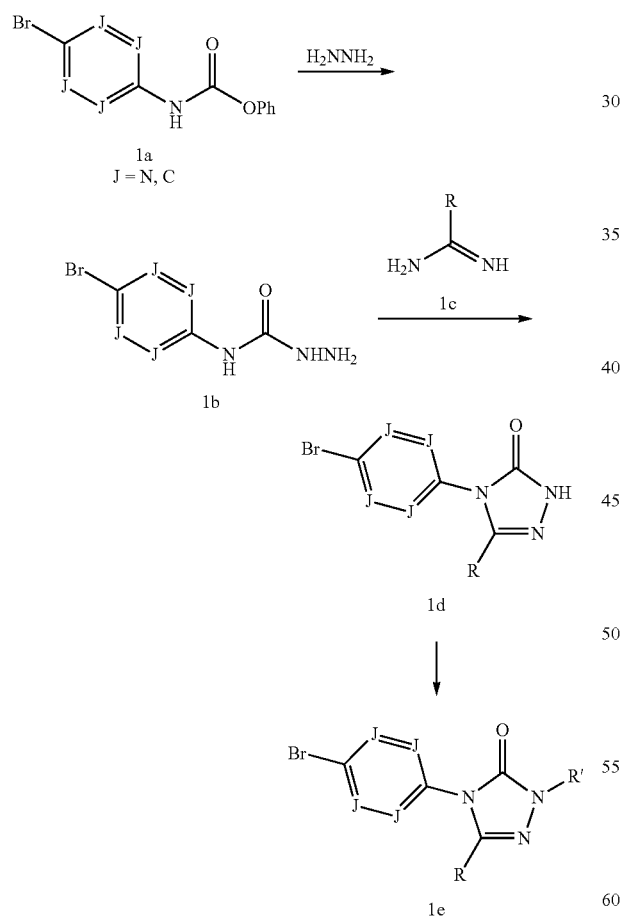

Scheme 1 shows the synthesis of compound 1e from phenylcarbamate 1a. Phenylcarbamate 1a is either commercially available or can be prepared by known methods. Treatment of 1a with hydrazine affords hydrazinecarboxamide 1b. Reaction of 1b with amidine 1c, either commercially available or prepared via known methods, affords triazolone 1 d. Treatment of intermediate 1d with a base, such as K$_2$CO$_3$ or NaH, followed by addition of an electrophile R'—X affords intermediate 1e. At this point, substituents R and R' may be further functionalized.

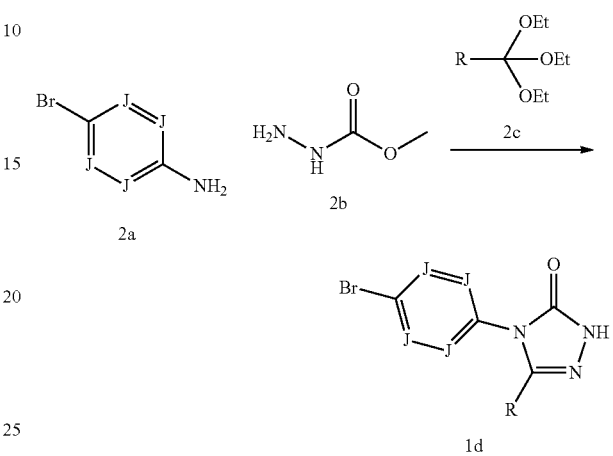

Scheme 2 shown an alternate synthesis of triazolone 1d. Triazolone 1d can be prepared from the reaction of aniline or heteroarylamine 2a, methyl hydrazinecarboxylate 2b and the appropriate triethoxyalkane (2c) in the presence of pTSA.

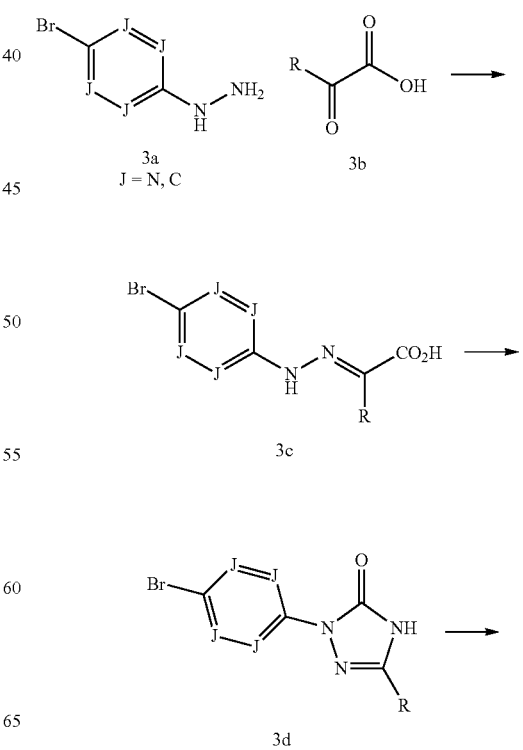

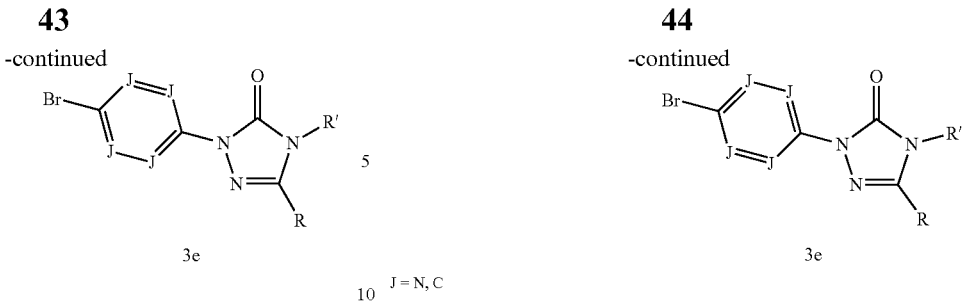

Scheme 3 depicts the synthesis of triazolone 3e from hydrazine 3a, which is either commercially available or can be prepared by known methods. Reaction of 3a with 2-oxoacetic acid 3b in the presence of acid, such as aqueous HCl, affords hydrazonoacetic acid 3c. Cyclization of intermediate 3c with diphenylphosphorylazide affords triazolone 3d. Treatment of intermediate 3d with a base, such as K$_2$CO$_3$ or NaH, followed by addition of an electrophile R′—X affords intermeidate 3e. At this point, substituents R and R′ may be further functionalized.

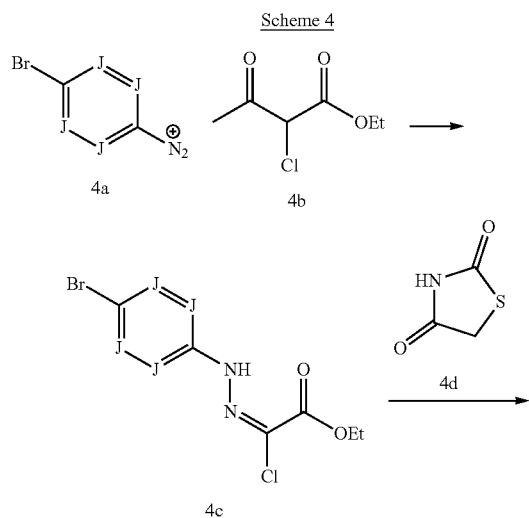

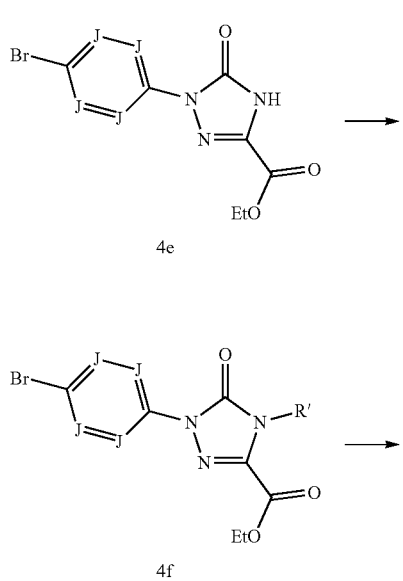

Scheme 4 depicts an alternate synthesis of triazolone 3e from aryldiazonium salt 4a and ethyl 2-chloro-3-oxobutanoate 4b. Reaction of 4a and 4b in the presence of sodium acetate affords hydrazone 4c. Treatment of 4c with thiazolidine-2,4-dione in the presence of a base such as KOH affords triazolone 4e. Treatment of intermediate 4e with a base, such as K$_2$CO$_3$ or NaH, followed by addition of an electrophile R′—X affords intermeidate 4f. At this point, the ester group may be functionalized to compound 3e in multiple ways, but not limited to the following. For instance, 4f may be reduced to the alcohol, hydrolysis to the acid (with optional further elaboration such as amide formation), reaction with a Grignard reagent to afford the tertiary alcohol, or reduction to the aldehyde followed by reductive amination to afford the amine. In addition, at this point, substituents R and R′ may be further functionalized.

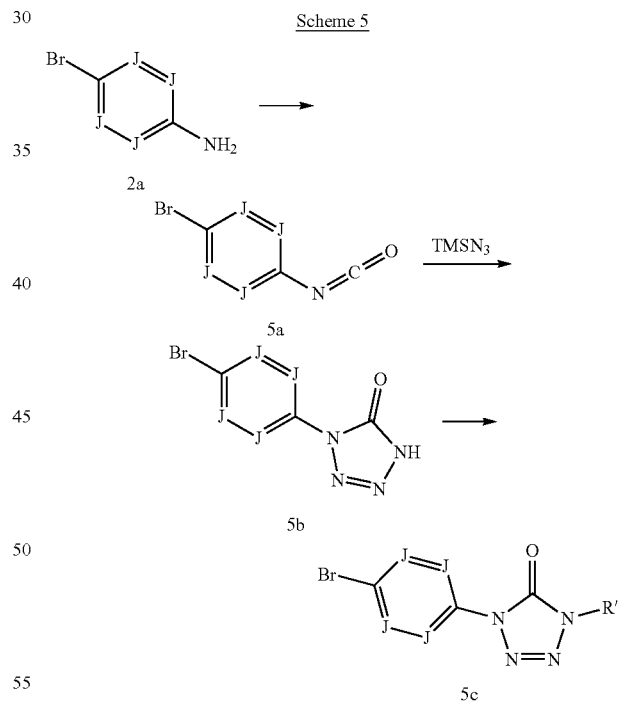

Scheme 5 shows the synthesis of tetrazolone 5c from aniline or heteroarylamine 2a. This starting material is either commercially available or is prepared via known methods.

Reaction of 2a with triphosgene or phosgene in the presence of a base such as TEA or DIEA affords isocyanate 5a. Treatment of 5a with azidotrimethylsilane and trimethylsilylchloride affords tetrazolone 5b. Treatment of intermediate 5b with a base, such as K$_2$CO$_3$ or NaH, followed by addition of an electrophile R′—X affords intermeidate 5c.

Scheme 6

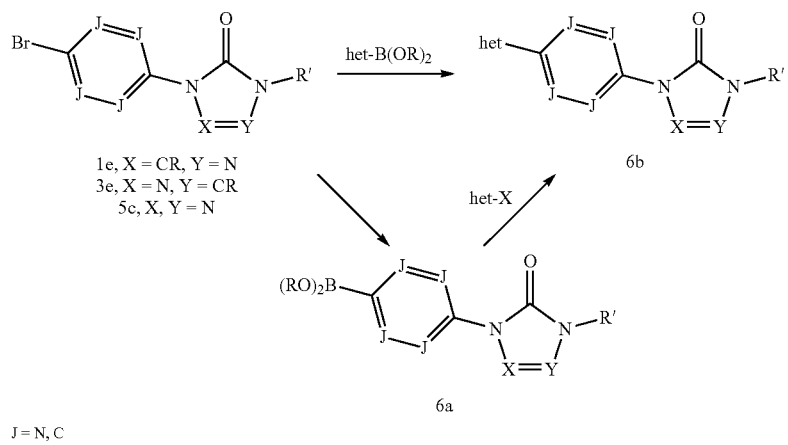

1e, X = CR, Y = N
3e, X = N, Y = CR
5c, X, Y = N

J = N, C

Scheme 6 shows the synthesis of compound 6b, where "het" is a heteraryl group, via two synthtic routes from compounds 1e, 3e and 5c. The starting aryl or heteroaryl halide is coupled with a heteroaryl boronic acid or boronate ester to afford 6b. This reaction proceeds via Suzuki coupling, using a reagent such as Pd(Ph$_3$)$_4$ or 2$^{nd}$ generation Xphos catalyst and a base such as sodium carbonate or potassium phosphate. Alternatively, compounds 1e, 3e and 5c are converted to boronic acid or boronate ester 6a, using a boron reagent, such as Bis(pinacolato)diboron, and a catalyst such as PdCl$_2$(dppf). 6a is then coupled with a heteroaryl halide (het-X) via Suzuki cross-coupling to afford compound 6b.

Purification of intermediates and final products was carried out via either normal or reverse phase chromatography. Normal phase chromatography was carried out using pre-packed SiO$_2$ cartridges eluting with either gradients of hexanes and EtOAc, DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm) (or) Sunfire Prep C18 OBD 5u 30×100 mm, 25 min gradient from 0-100% B. A=H$_2$O/ACN/TFA 90:10:0.1. B=ACN/H$_2$O/TFA 90:10:0.1

Unless otherwise stated, analysis of final products was carried out by reverse phase analytical HPLC.

Method A: Ascentis Express C18 (50×2.1 mm, 2.7 μm), A: 5% ACN- 95% H$_2$O -10 mM NH$_4$OAC; B: 95% ACN- 5% H$_2$O- 10 mM NH$_4$OAC; wavelength 220 nm; flow rate 1.1 mL/min; gradient time 0-3 min; 0 to 100% B, T=50° C.

Method B: Ascentis Express C18 (50×2.1 mm, 2.7 μm), A: 5% ACN- 95% H$_2$O- 0.05% TFA; B: 95% ACN- 5% H$_2$O- 0.05% TFA; wavelength 220 nm; flow rate 1.1 mL/min; gradient time 0-3 min; 0 to 100% B, T=50° C.

Intermediate 1

4-(4-bromophenyl)-1H-1,2,4-triazol-5(H)-one

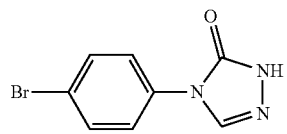 [SMILES: O=c1[nH]ncn1-c1ccc(Br)cc1]

Intermediate 1a

Preparation of phenyl (4-bromophenyl)carbamate

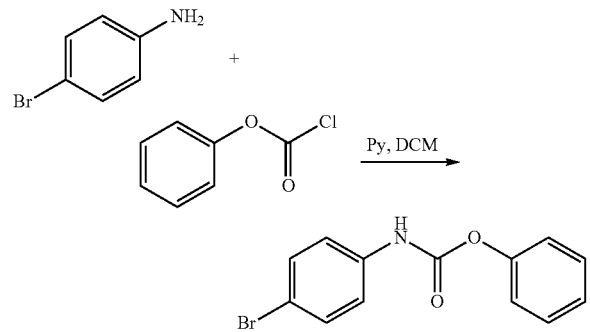

To a solution of 4-bromoaniline (200 mg, 1.16 mmol) and pyridine (0.094 mL, 1.16 mmol) in DCM (10 mL) at 0° C., was added phenyl chloroformate (218 mg, 1.40 mmol). The reaction mixture was stirred for 3 h at rt. The reaction mixture was diluted with DCM (100 mL), washed with water and brine. The organic layer was dried over Na$_2$SO$_4$, filtered and concentrated to give phenyl (4-bromophenyl) carbamate (320 mg, 91% yield) as a colorless solid. MS(ESI) m/z: 294.3 (M+H)$^+$; $^1$H NMR (400 MHz, CHLOROFORM-d) δ ppm 7.31-7.49 (m, 5H) 7.22-7.29 (m, 2H) 7.14-7.21 (m, 2H) 6.92 (br. S, 1H).

Intermediate 1b

Preparation of N-(4-bromophenyl)hydrazinecarboxamide

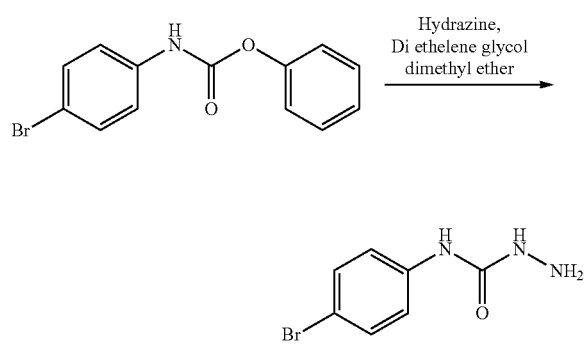 [SMILES: O=C(Nc1ccc(Br)cc1)Oc1ccccc1 ; NNC(=O)Nc1ccc(Br)cc1]

A solution of phenyl (4-bromophenyl) carbonate (300 mg, 1.027 mmol) and hydrazine (0.035 mL, 1.130 mmol) in diethylene glycol dimethyl ether (3 mL) was stirred at rt for 24 h. Reaction mixture was diluted with DCM (100 mL) and washed with water and brine. The organic layer was dried over $Na_2SO_4$, filtered and concentrated. The residue was washed with ether (20 mL) to give N-(4-bromophenyl) hydrazinecarboxamide (55 mg, 23% yield) as a colorless solid. MS(ESI) m/z: 232.4 $(M+H)^+$; $^1$H NMR (400 MHz, DMSO-$d_6$) δ ppm 8.76 (s, 1H) 7.44-7.62 (m, 3H) 7.31-7.43 (m, 3H) 4.36 (br. s, 2H).

Intermediate 1

Preparation of 4-(4-bromophenyl)-1H-1,2,4-triazol-5(4H)-one

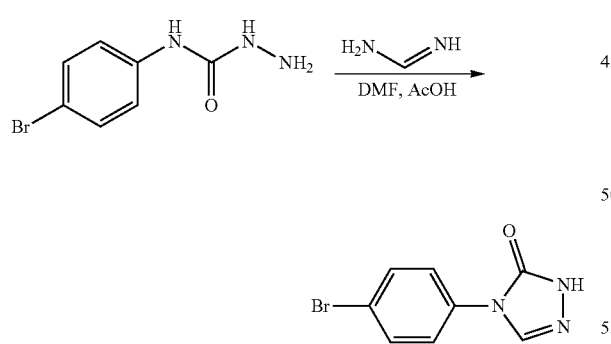

A mixture of N-(4-bromophenyl)hydrazinecarboxamide (50 mg, 0.217 mmol), formamidine acetate (67.9 mg, 0.652 mmol), and acetic acid (1 mL) in DMF (2 mL) was stirred overnight. The mixture was concentrated to give a residue which was diluted with cold water (30 mL) and stirred for 20 min to give a colorless precipitate, which was collected by filtration and dried to give 4-(4-bromophenyl)-1H-1,2,4-triazol-5(4H)-one (41 mg, 79% yield) as a colorless solid. MS(ESI) m/z: 239.9 $(M+H)^+$; $^1$H NMR (400 MHz, DMSO-$d_6$) δ ppm 11.99 (br, s 1H)) 8.41 (s, 1H) 7.70 (s, 4H)

Intermediate 2

Preparation of 4-(4-bromo-3-methoxyphenyl)-1H-1,2,4-triazol-5(4H)-one

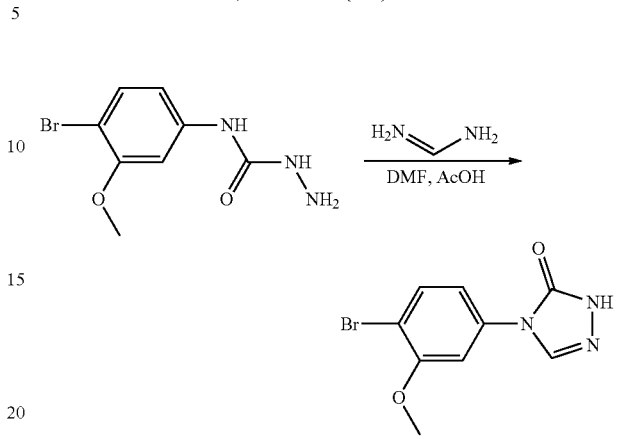

A solution of N-(4-bromo-3-methoxyphenyl)hydrazinecarboxamide (200 mg, 0.769 mmol), formamidine acetate (240 mg, 2.307 mmol), and acetic acid (3 mL) in DMF (5 mL) was stirred overnight. The mixture was concentrated. The resultant residue was diluted with cold water (30 mL) and stirred for 20 min to give a white precipitate. The precipitate was collected and dried to give 4-(4-bromo-3-methoxyphenyl)-1H-1,2,4-triazol-5(4H)-one (180 mg, 65% yield) as a colorless solid. MS(ESI) m/z: 269.9 $(M+H)^+$; $^1$H NMR (400 MHz, DMSO-$d_6$) δ ppm 12.05 (br, s 1H)) 8.45 (s, 1H) 7.70-7.68 (d, J=8.4 Hz, 1H) 7.49-7.48 (d, J=2.4 Hz, 1H) 7.30-7.27 (m, 1H) 3.90 (s, 3H).

Intermediate 3

Preparation of 4-(4-bromo-2-methoxyphenyl)-1H-1,2,4-triazol-5(4H)-one

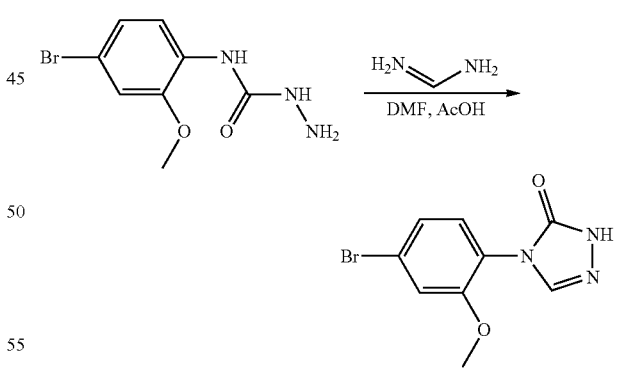

A solution of N-(4-bromo-2-methoxyphenyl)hydrazinecarboxamide (200 mg, 0.769 mmol), formamidine acetate (240 mg, 2.31 mmol), and acetic acid (3 mL) in DMF (5 mL) was stirred overnight. The mixture was concentrated. The resultant residue was diluted with cold water (30 mL) and stirred for 20 min to give a white precipitate. The precipitate was collected by filtration and dried to give 4-(4-bromo-2-methoxyphenyl)-1H-1,2,4-triazol-5(4H)-one (190 mg, 69% yield) as a colorless solid. MS(ESI) m/z: 271.9 $(M+H)^+$; $^1$H NMR (400 MHz, DMSO-$d_6$) δ ppm 11.82 (br, s 1H)) 7.99

(s, 1H) 7.44-7.43 (d, J=2.0 Hz, 1H) 7.39-7.37 (d, J=8.4 Hz, 1H) 7.28-7.26 (m, 1H) 3.86 (s, 3H).

Intermediate 4

1-(4-(1H-pyrazol-4-yl)phenyl)-1H-1,2,4-triazol-5(4H)-one

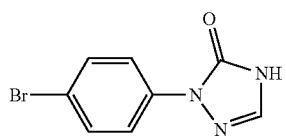 [SMILES: O=c1[nH]cnn1-c1ccc(Br)cc1]

Intermediate 4a

Preparation of (E)-2-(2-(4-bromophenyl)hydrazono)acetic acid

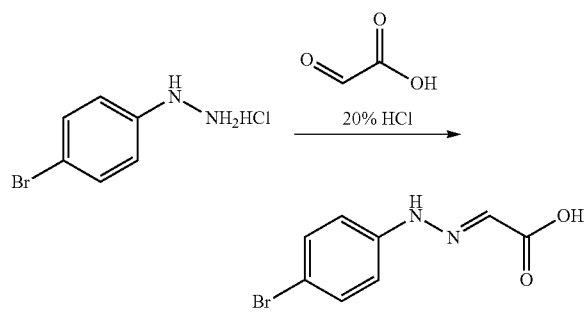

A solution of (4-bromophenyl)hydrazine hydrochloride (2.0 g, 8.95 mmol) and 2-oxoacetic acid (0.795 g, 10.7 mmol) in 20% HCl (30 mL) was stirred at rt for 3 h. The resultant yellow solid was collected by filtration, washed with water (20 mL) and dried to give the desired compound as an off-white solid. MS(ESI) m/z: 244.8 (M+H)$^+$; $^1$H NMR (400 MHz, DMSO-d$_6$) δ ppm 11.255 (s, 1H) 7.46-7.41 (m, 2H) 7.14-7.13 (d, J=1.2, 1H) 7.08-7.04 (m, 2H)

Intermediate 4

Preparation of 1-(4-bromophenyl)-1H-1,2,4-triazol-5(4H)-one

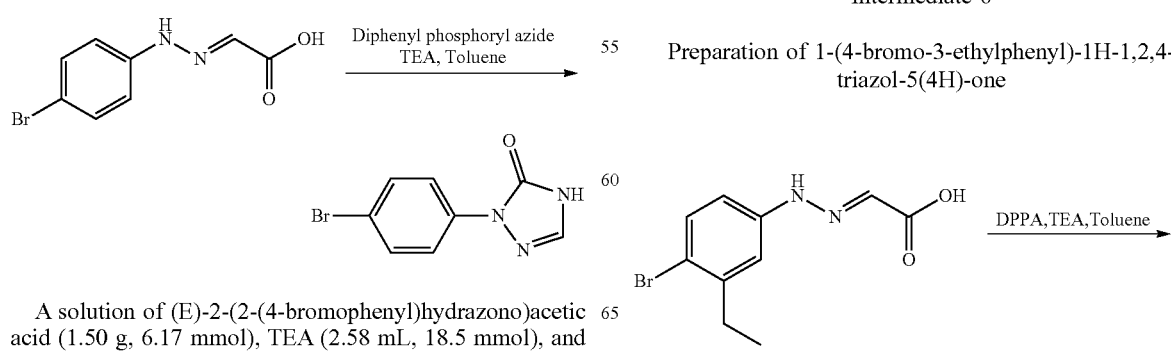

A solution of (E)-2-(2-(4-bromophenyl)hydrazono)acetic acid (1.50 g, 6.17 mmol), TEA (2.58 mL, 18.5 mmol), and diphenylphosphoryl azide (1.99 mL, 9.26 mmol) in toluene (10 mL) was stirred at 120° C. for 1 hr. The mixture was cooled to rt and evaporated. The resultant reddish residue was diluted with ethyl acetate (300 mL). The solution was washed with satd. aq. NH$_4$C$_1$ and brine, dried over Na$_2$SO$_4$, and concentrated. The resulting solid was washed with hexane (100 mL) and ether (100 mL) to give 1-(4-bromophenyl)-1H-1,2,4-triazol-5(4H)-one (1.1 g), which was used in the following step without further purification. MS(ESI) m/z: 241.9 (M+H)$^+$; $^1$H NMR (400 MHz, DMSO-d$_6$) δ ppm 12.05 (s, 1H) 8.14 (s, 1H) 7.90-7.85 (m, 2H) 7.65-7.60 (m, 2H).

Intermediate 5

Preparation of 1-(4-bromo-3-methoxyphenyl)-1H-1,2,4-triazol-5(4H)-one

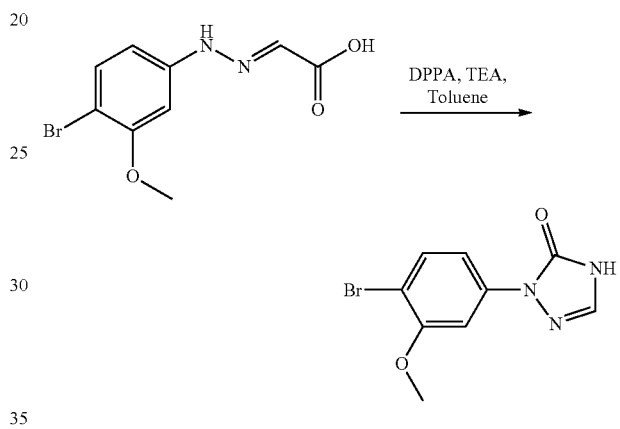

A solution of (E)-2-(2-(4-bromo-3-methoxyphenyl)hydrazono)acetic acid (1.20 g, 4.39 mmol), TEA (1.84 mL, 13.2 mmol), and diphenylphosphoryl azide (1.42 mL, 6.59 mmol) in toluene (10 mL) was stirred at 120° C. for 1 hr. The mixture was cooled to rt and evaporated. The resultant reddish residue was diluted with ethyl acetate (300 mL). The solution was washed with satd. aq. NH$_4$C$_1$ and brine, dried over Na$_2$SO$_4$, and concentrated. The resulting solid was washed with hexane (100 mL) and ether (100 mL) to give 0.8 g of 1-(4-bromo-3-methoxyphenyl)-1H-1,2,4-triazol-5(4H)-one, which was used without further purification. MS(ESI) m/z: 272.0 (M+H)$^+$; $^1$H NMR (400 MHz, DMSO-d$_6$) δ ppm 12.08 (br, s 1H)) 8.15 (s, 1H) 7.70-7.68 (d, J=8.4 Hz, 1H) 7,49-7.48 (d, J=2.4 Hz, 1H) 7.30-7.27 (m, 1H) 3.90 (s, 3H).

Intermediate 6

Preparation of 1-(4-bromo-3-ethylphenyl)-1H-1,2,4-triazol-5(4H)-one

-continued

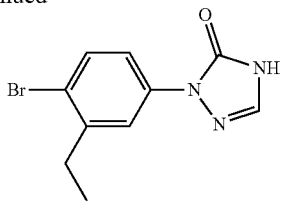

A solution of (E)-2-(2-(4-bromo-3-methoxyphenyl)hydrazono)acetic acid (1.20 g, 4.39 mmol), TEA (1.84 mL, 13.2 mmol), and diphenylphosphoryl azide (1.42 mL, 6.59 mmol) in toluene (10 mL) was stirred at 120° C. for 1 hr. The mixture was cooled to rt and evaporated. The resultant reddish residue was diluted with ethyl acetate (300 mL). The solution was washed with satd. aq. $NH_4C_1$ and brine, dried over $Na_2SO_4$, and concentrated. The resulting solid was washed with hexane (100 mL) and ether (100 mL) to give 0.8 g of 1-(4-bromo-3-methoxyphenyl)-1H-1,2,4-triazol-5 (4H)-one, which was used without further purification. MS(ESI) m/z: 272.0 (M+H)+; $^1$H NMR (400 MHz, DMSO-d$_6$) δ ppm 12.08 (br, s 1H)) 8.15 (s, 1H) 7.70-7.68 (d, J=8.4 Hz, 1H) 7.49-7.48 (d, J=2.4 Hz, 1H) 7.30-7.27 (m, 1H) 3.90 (s, 3H).

Intermediate 7

Preparation of 4-(4-bromophenyl)-3-methyl-1H-1,2,4-triazol-5(4H)-one

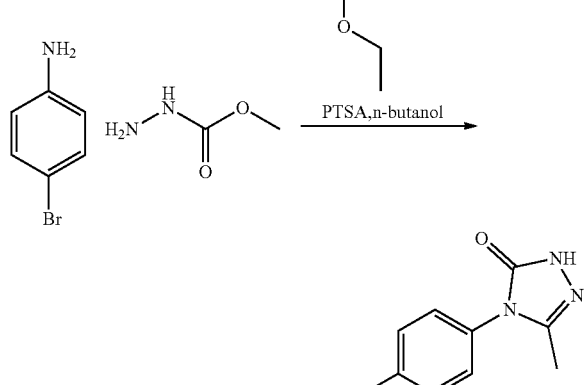

A solution of 4-bromoaniline (3.0 g, 17.4 mmol), methyl hydrazinecarboxylate (1.89 g, 20.93 mmol), 1,1,1-triethoxyethane (3.39 g, 20.9 mmol), and p-TsOH (0.20 g, 1.05 mmol) in n-butanol (30 mL) was refluxed for 24 h. The mixture was cooled to rt and concentrated. The resultant residue was partitioned with ethyl acetate and cold water. The aqueous layer was extracted with ethyl acetate (3×50 mL). The combined organic layer was washed with brine (20 mL), dried over $Na_2SO_4$, filtered and concentrated. The resultant yellow solid was stirred in pet. ether (50 mL) for 20 min. The solid product was collected by filtration and dried to give 4-(4-bromophenyl)-3-methyl-1H-1,2,4-triazol-5(4H)-one (2.5 g, 40% yield) as a white solid. MS(ESI) m/z: 256.4 (M+H)+

Intermediate 8

Preparation of 4-(4-bromo-2-methoxyphenyl)-3-methyl-1H-1,2,4-triazol-5(4H)-one

A solution of 4-bromo-2-methoxy aniline (1.0 g, 4.95 mmol), methyl hydrazinecarboxylate (0.535 g, 5.94 mmol), 1,1,1-triethoxy ethane (0.963 g, 5.94 mmol), and p-TsOH (0.10 g, 0.526 mmol) in n-butanol (15 mL) was refluxed for 24 h. The mixture was cooled to rt and concentrated. The resultant residue was partitioned with ethyl acetate and cold water. The aqueous layer was extracted with ethyl acetate (3×50 mL). The combined organic layer was washed with brine (20 mL), dried over $Na_2SO_4$, filtered and concentrated. The resultant yellow solid was stirred in pet. ether (50 mL) for 20 min. The solid product was collected by filtration and dried to give 4-(4-bromo-2-methoxyphenyl)-3-methyl-1H-1,2,4-triazol-5(4H)-one (250 mg, 16% yield) as an off-white solid. MS(ESI) m/z: 285.9 (M+H)+; $^1$H NMR (400 MHz, DMSO-d$_6$) δ ppm 11.45 (s, 1H) 7.44 (s, 1H) 7.286-7.282 (d, J=1.6, 2H) 3.82 (s, 3H) 1.89 (s, 3H).

Intermediate 9

Preparation of 4-(4-bromo-3-methoxyphenyl)-3-methyl-1H-1,2,4-triazol-5(4H)-one

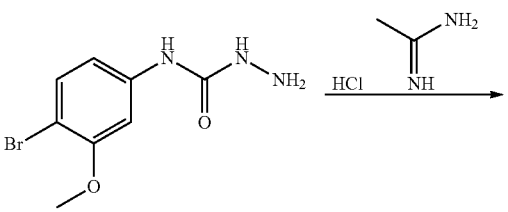

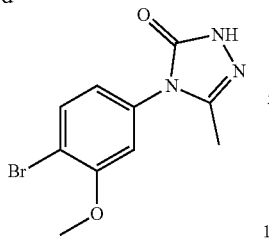

A solution of acetamidine hydrochloride (0.727 g, 7.69 mmol), sodium acetate (0.631 g, 7.69 mmol) in n-butanol (7 mL) was stirred for 30 min. to give a heterogeneous mixture, which was filtered through a pad of celite. The filtrate was added to a solution of N-(4-bromo-3-methoxyphenyl)hydrazinecarboxamide (1.0 g, 3.84 mmol) in DMF (10 mL), and the reaction mixture heated at 130° C. overnight. The reaction mixture was cooled to rt and concentrated. The resultant residue was partitioned with ethyl acetate and cold water. The aqueous layer was extracted with ethyl acetate (3×50 mL). The combined the organic layer was washed with brine, dried over Na$_2$SO$_4$, filtered and concentrated. The resultant yellow solid was stirred in pet. ether (50 mL) for 20 min. The solid product was collected by filtration and dried to give 4-(4-bromo-3-methoxyphenyl)-3-methyl-1H-1,2,4-triazol-5(4H)-one (600 mg, 52% yield) as an off-white solid. MS(ESI) m/z: 284.0 (M+H)$^+$; $^1$H NMR (400 MHz, DMSO-d$_6$) δ ppm 11.63 (s, 1H) 7.73-7.70 (d, J=11.2, 1H) 7.20-7.19 (d, J=3.2, 1H) 7.10-7.07 (d, J=11.2, 1H) 6.97-6.93 (m, 1H) 3.87 (s, 3H) 2.04 (s, 3H).

Intermediate 10

1-(4-bromophenyl)-3-methyl-1H-1,2,4-triazol-5(4H)-one

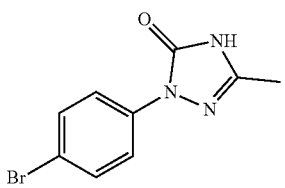

Intermediate 10a

Preparation of (E)-2-(2-(4-bromophenyl)hydrazono)propanoic acid

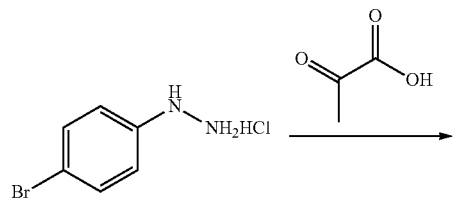

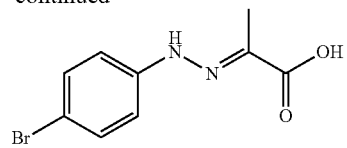

A solution of (4-bromophenyl)hydrazine hydrochloride (2.0 g, 8.95 mmol), 2-oxopropanoic acid (0.946 g, 10.7 mmol), in 20% HCl (30 mL) was stirred at rt for 3 h to give a yellow suspension. The solid was collected by filtration, washed with water (20 mL), and dried to afford (E)-2-(2-(4-bromophenyl)hydrazono)propanoic acid (2.0 g, 84% yield). MS(ESI) m/z: 256.9 (M+H)$^+$; $^1$H NMR (400 MHz, DMSO-d$_6$) δ ppm 12.04 (br, s. 1H) 9.85 (s, 1H) 7.43-7.39 (m, 2H) 7.32-7.28 (m, 2H) 2.02 (s, 3H).

Intermediate 10

Preparation of 1-(4-bromophenyl)-3-methyl-1H-1,2,4-triazol-5(4H)-one

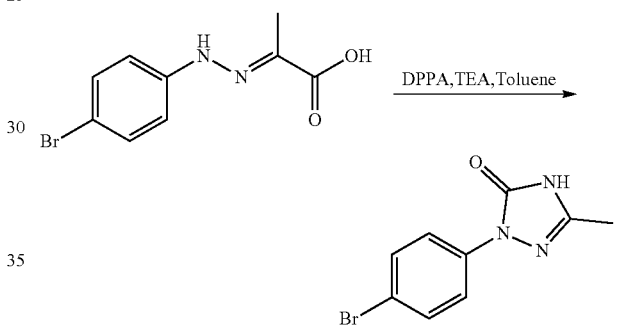

A solution of (E)-2-(2-(4-bromophenyl)hydrazono)propanoic acid (1.5 g, 5.83 mmol), TEA (2.44 mL, 17.5 mmol), and diphenylphosphoryl azide (1.88 mL, 8.75 mmol) in toluene (10 mL) was stirred at 120° C. for 1 h. The reaction mixture was cooled to rt and evaporated. The residue was dissolved in ethyl acetate (300 mL), washed with sat. aq. NH$_4$C$_1$ and brine, dried over Na$_2$SO$_4$, and concentrated. The resultant solid was washed with hexane (100 mL) and ether (100 mL) to give 1-(4-bromophenyl)-3-methyl-1H-1,2,4-triazol-5(4H)-one (1.4 g, 89% yield). MS(ESI) m/z: 255.9 (M+H)$^+$; $^1$H NMR (400 MHz, DMSO-d$_6$) δ ppm 11.87 (br, s. 1H) 7.86-7.82 (m, 2H) 7.61-7.58 (m, 2H) 2.17 (s, 3H).

Intermediate 11

Preparation of 1-(4-bromo-3-methoxyphenyl)-3-methyl-1H-1,2,4-triazol-5(4H)-one

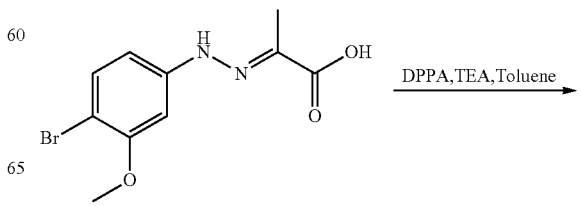

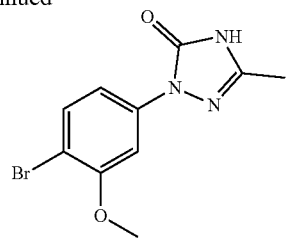

A solution of (E)-2-(2-(4-bromo-3-methoxyphenyl)hydrazono)propanoic acid (2.0 g, 6.97 mmol), TEA (2.91 mL, 20.9 mmol), and diphenylphosphoryl azide (2.25 mL, 10.5 mmol) in toluene (10 mL) was stirred at 120° C. for 1 h. The reaction mixture was cooled to rt and evaporated. The residue was dissolved in ethyl acetate (300 mL), washed with sat. aq. $NH_4C_1$ and brine, dried over $Na_2SO_4$, and concentrated. The resultant solid was washed with hexane (100 mL) and ether (100 mL) to give 1-(4-bromo-3-methoxyphenyl)-3-methyl-1H-1,2,4-triazol-5(4H)-one (1.5 g, 74% yield). MS(ESI) m/z: 286.0 (M+H)$^+$; $^1$H NMR (400 MHz, DMSO-d$_6$) δ ppm 11.92 (br, s. 1H) 7.63-7.58 (m, 2H) 7.48-7.45 (m, 1H) 3.87 (s, 3H) 2.18 (s, 3H).

Intermediate 12

Preparation of 1-(4-bromo-3-ethylphenyl)-3-methyl-1H-1,2,4-triazol-5(4H)-one

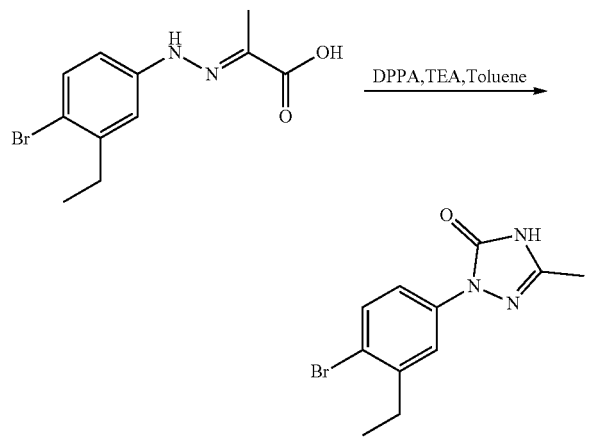

A solution of (E)-2-(2-(4-bromo-3-ethylphenyl)hydrazono)propanoic acid (3.0 g, 10.5 mmol), TEA (4.40 mL, 31.6 mmol), and diphenylphosphoryl azide (3.39 mL, 15.8 mmol) in toluene (10 mL) was stirred at 120° C. for 1 h. The reaction mixture was cooled to rt and evaporated. The residue was dissolved in ethyl acetate (300 mL), washed with sat. aq. $NH_4Cl$ and brine, dried over $Na_2SO_4$, and concentrated. The resultant solid was washed with hexane (100 mL) and ether (100 mL) to give 1-(4-bromo-3-ethylphenyl)-3-methyl-1H-1,2,4-triazol-5(4H)-one (2.5 g, 76% yield). MS(ESI) m/z: 282.0 (M+H)$^+$; $^1$H NMR (400 MHz, DMSO-d$_6$) δ ppm 11.88 (br, s. 1H) 7.85-7.84 (d, J=2.4 Hz 1H) 7.70-7.67 (m, 1H) 7.61-7.58 (d, J=8.8 Hz, 1H) 2.76-2.68 (q, J=10 Hz, 2H) 2.17 (s, 3H) 1.20-1.18 (t, J=5.2 Hz, 3H).

Intermediate 13

Ethyl 1-(4-bromophenyl)-5-oxo-4,5-dihydro-1H-1,2,4-triazole-3-carboxylate

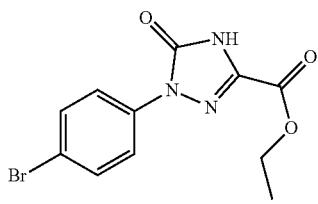 [SMILES: CCOC(=O)c1nn(-c2ccc(Br)cc2)c(=O)[nH]1]

Intermediate 13a

Preparation of (E)-ethyl 2-(2-(4-bromophenyl)hydrazono)-2-chloroacetate

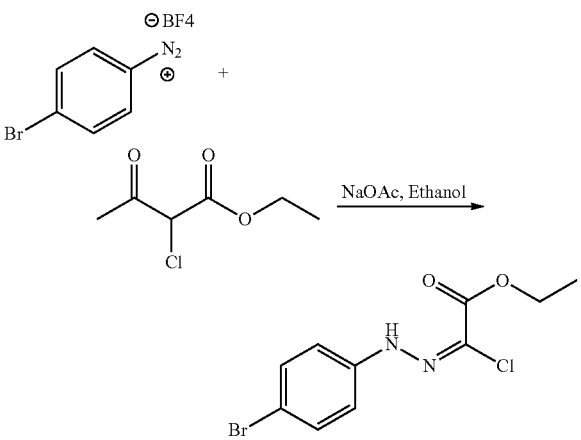

To a solution of 4-Bromo benzenediazonium tetrafluoroborate (2.0 g, 10.9 mmol) in water (10 mL) at 0° C., was added ethyl 2-chloro-3-oxobutanoate (1.97 g, 12.0 mmol) and sodium acetate (1.78 g, 21.7 mmol) in ethanol (5 mL). After stirring for 30 min, the resultant suspension was filtered, and the collected solid was dried to afford (E)-ethyl 2-(2-(4-bromophenyl)hydrazono)-2-chloroacetate (2.2 g, 66% yield). MS(ESI) m/z: 304.9 (M+H)$^+$; $^1$H NMR (400 MHz, DMSO-d$_6$) δ ppm 10.66 (s, 1H) 7.52.7.49 (d. J=11.6 Hz, 2H) 7.31-7.28 (d, J=12 Hz 2H) 4.32-4.27 (q, J=9.2 Hz, 2H) 1.31-1.27 (t, J=9.6 Hz, 3H).

Intermediate 13

Preparation of ethyl 1-(4-bromophenyl)-5-oxo-4,5-dihydro-1H-1,2,4-triazole-3-carboxylate

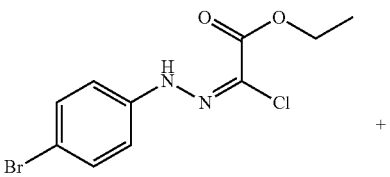

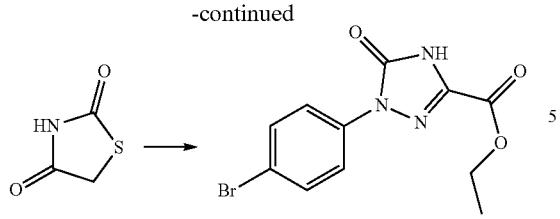

To a solution of (E)-ethyl 2-(2-(4-bromophenyl)hydrazono)-2-chloroacetate (2.0 g, 6.55 mmol), thiazolidine-2,4-dione (0.92 g, 7.85 mmol) in ethanol (20 mL), was added KOH (0.734 g, 13.1 mmol). The yellow solution formed was heated at 77° C. for 2 h. Reaction mixture was cooled to rt and evaporated. The residue was acidified with 1.5 N HCl (20 mL) to give yellow solid which was collected by filtration. The crude was purified by flash chromatography (20% ethyl acetate in pet. Ether) to give 1-(4-bromophenyl)-5-oxo-4,5-dihydro-1H-1,2,4-triazole-3-carboxylate (500 mg, 24% yield) as a brown solid. MS(ESI) m/z: 311.9 (M+H)$^+$; $^1$H NMR (400 MHz, DMSO-d$_6$) δ ppm 13.07 (s, 1H) 7.52.7.49 (d. J=11.6 Hz, 2H) 7.31-7.28 (d, J=12 Hz 2H) 4.32-4.27 (q, J=9.2 Hz, 2H) 1.31-1.27 (t, J=9.6 Hz, 3H).

Intermediate 14

1-(4-bromophenyl)-3-(hydroxymethyl)-4-(3-methoxybenzyl)-1H-1,2,4-triazol-5(4H)-one

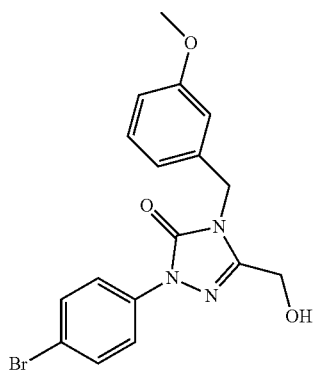 [SMILES: COc1cccc(Cn2c(CO)nn(-c3ccc(Br)cc3)c2=O)c1]

Intermediate 14a

Preparation of Ethyl 1-(4-bromophenyl)-4-(3-methoxybenzyl)-5-oxo-4,5-dihydro-1H-1,2,4-triazole-3-carboxylate

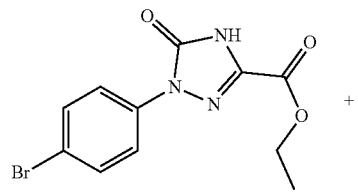 +

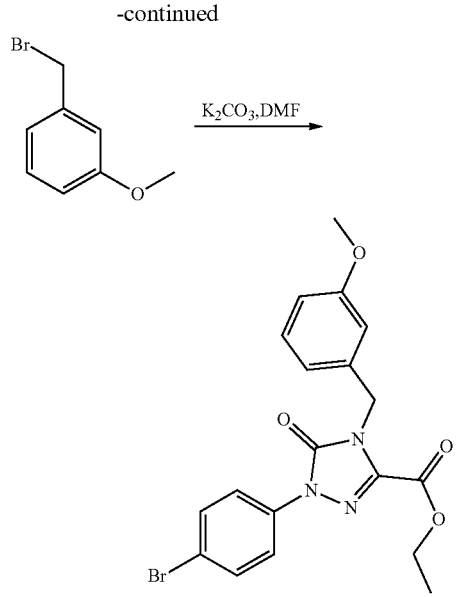

To a solution of ethyl 1-(4-bromophenyl)-5-oxo-4,5-dihydro-1H-1,2,4-triazole-3-carboxylate (200 mg, 0.641 mmol) and K$_2$CO$_3$ (177 mg, 1.28 mmol) in DMF (3 mL) at rt, was added 1-(bromomethyl)-3-methoxybenzene (142 mg, 0.705 mmol). The mixture was stirred for 2 h, then was diluted with DCM (200 mL). The solution was washed with sat. aq. NH$_4$Cl and brine, dried over Na$_2$SO$_4$, filtered and concentrated. The crude was purified by flash chromatography [15% ethyl acetate in pet. ether] to give Ethyl 1-(4-bromophenyl)-4-(3-methoxybenzyl)-5-oxo-4,5-dihydro-1H-1,2,4-triazole-3-carboxylate (170 mg, 60% yield) as a yellow solid. MS(ESI) m/z: 432.0 (M+H)$^+$; $^1$H NMR (400 MHz, DMSO-d$_6$) δ ppm 7.97.7.94 (m, 2H) 7.59-7.56 (m, 2H) 7.28-7.26 (m, 1H) 7.01-7.98 (m, 2H) 6.87-6.83 (m, 1H) 5.29 (s, 2H) 4.47-4.44 (q, J=9.2 Hz, 2H) 3.80 (s, 3H) 1.43-1.39 (t, J=9.6 Hz, 3H).

Intermediate 14

Preparation of 1-(4-bromophenyl)-3-(hydroxymethyl)-4-(3-methoxybenzyl)-1H-1,2,4-triazol-5(4H)-one

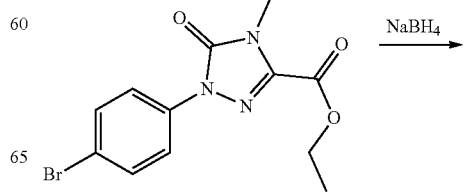

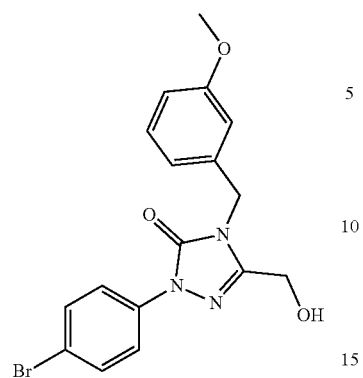

To a solution of ethyl 1-(4-bromophenyl)-4-(3-methoxybenzyl)-5-oxo-4,5-dihydro-1H-1,2,4-triazole-3-carboxylate (50 mg, 0.116 mmol) in THF (7 mL) and MeOH (3 mL) at 0° C., was added NaBH$_4$ (4.4 mg, 0.116 mmol). The reaction mixture was allowed to warm to RT and stirred at RT for 2 h. Reaction mixture was concentrated at reduced pressure to give yellow solid which was partitioned between DCM and 10% NH$_4$Cl solution. The aqueous layer was extracted with DCM (3×20 mL). Combined organic layers were washed with brine, dried over Na$_2$SO$_4$, filtered and concentrated at reduced pressure to give 1-(4-bromophenyl)-3-(hydroxymethyl)-4-(3-methoxybenzyl)-1H-1,2,4-triazol-5(4H)-one (40 mg, 84% yield) as a yellow solid. MS(ESI) m/z: 390.0 (M+H)$^+$; $^1$H NMR (400 MHz, DMSO-d$_6$) δ ppm 7.92.7.89 (d, J=12 Hz, 2H) 7.55-7.52 (d, J=11.6 Hz, 2H) 7.30-7.26 (m, 1H) 6.94-6.84 (m, 3H) 4.99 (s, 2H) 4.51-4.49 (d, J=8.4 Hz, 2H) 3.79 (s, 3H).

To a solution of Ethyl 1-(4-bromophenyl)-4-(3-fluoro-5-methoxybenzyl)-5-oxo-4,5-dihydro-1H-1,2,4-triazole-3-carboxylate (100 mg, 0.222 mmol) in THF (5 mL) at 0° C., was added dropwise a solution of methylmagnesium bromide (3M in THF) (0.222 mL, 0.666 mmol). The reaction mixture was quenched with 30 mL of 10% aq. NH$_4$Cl. The layers were separated and the aqueous layer was extracted with ethyl acetate (3×50 mL). Combined organic layers were washed with brine (25 mL), dried over Na$_2$SO$_4$, filtered and concentrated. The crude product was purified by flash chromatography [5%-30% of ethyl acetate in pet. ether] to give 1-(4-bromophenyl)-4-(3-fluoro-5-methoxybenzyl)-3-(2-hydroxypropan-2-yl)-1H-1,2,4-triazol-5(4H)-one (60 mg, 62% yield) as yellow gummy solid, which was used without further purification. MS(ESI) m/z: 436.2 (M+H)$^+$; $^1$H NMR (400 MHz, DMSO-d$_6$) δ ppm 7.96.7.93 (m, 2H) 7.57-7.53 (m, 2H) 6.66-6.51 (m, 3H) 5.19 (s, 2H) 3.83 (s, 3H) 1.52 (s, 6H).

Intermediate 15

Preparation of 1-(4-bromophenyl)-4-(3-fluoro-5-methoxybenzyl)-3-(2-hydroxypropan-2-yl)-1H-1,2,4-triazol-5(4H)-one Intermediate 16

1-(4-bromophenyl)-3-((dimethylamino)methyl)-4-(3-methoxybenzyl)-1H-1,2,4-triazol-5(4H)-one

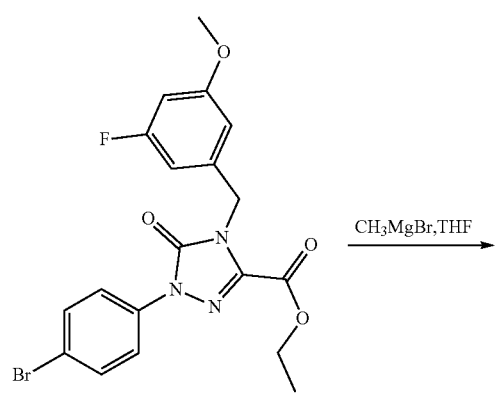

CH$_3$MgBr, THF

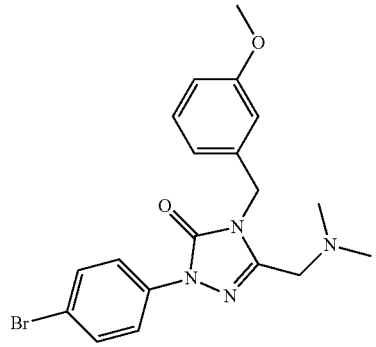 [SMILES: COc1cccc(Cn2c(CN(C)C)nn(-c3ccc(Br)cc3)c2=O)c1]

Intermediate 16a

Preparation of 1-(4-bromophenyl)-3-(chloromethyl)-4-(3-methoxybenzyl)-1H-1,2,4-triazol-5(4H)-one

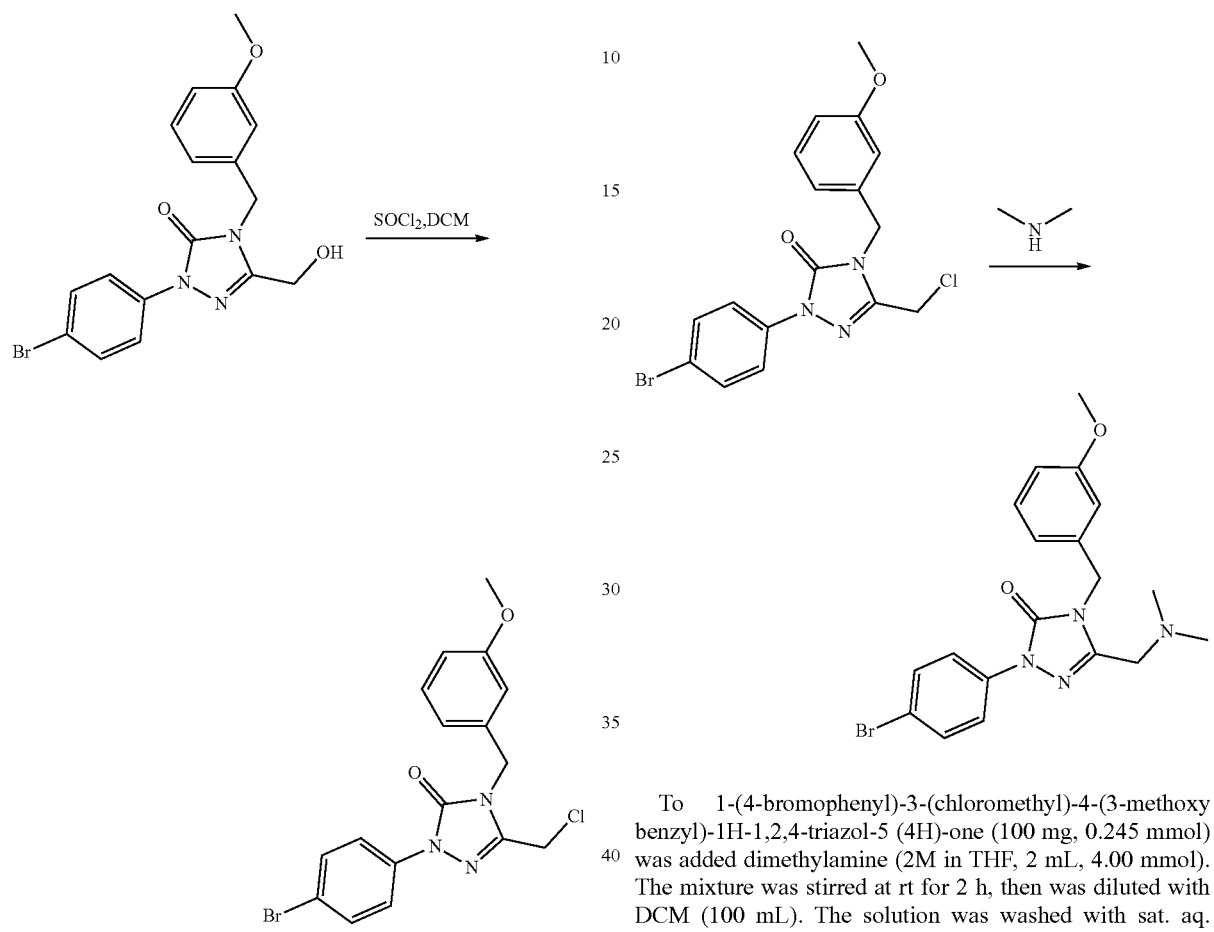

To a solution of 1-(4-bromophenyl)-3-(hydroxymethyl)-4-(3-methoxybenzyl)-1H-1,2,4-triazol-5(4H)-one (420 mg, 1.08 mmol) in DCM (10 mL) and one drop of DMF at 0° C., was added $SOCl_2$ (0.079 mL, 1.08 mmol). The reaction mixture was allowed to warm to rt and was stirred for 3 h. The mixture was diluted with DCM (100 mL), washed with sat. aq. $NaHCO_3$, sat. aq. $NH_4Cl$, and brine. The organic layer was dried over $Na_2SO_4$, filtered and concentrated to give 1-(4-bromophenyl)-3-(chloromethyl)-4-(3-methoxybenzyl)-1H-1,2,4-triazol-5(4H)-one (400 mg, 91% yield) as a yellow solid. MS(ESI) m/z: 408 (M+H)$^+$; $^1$H NMR (400 MHz, DMSO-$d_6$) δ ppm 7.92.7.88 (m, 2H) 7.57-7.53 (m, 2H) 7.31-7.26 (m, 1H) 6.93-6.86 (m, 3H) 5.036 (s, 2H) 4.28 (s, 2H) 3.82 (s, 3H).

Intermediate 16

Preparation of 1-(4-bromophenyl)-3-((dimethylamino)methyl)-4-(3-methoxybenzyl)-1H-1,2,4-triazol-5(4H)-one To 1-(4-bromophenyl)-3-(chloromethyl)-4-(3-methoxy benzyl)-1H-1,2,4-triazol-5 (4H)-one (100 mg, 0.245 mmol) was added dimethylamine (2M in THF, 2 mL, 4.00 mmol). The mixture was stirred at rt for 2 h, then was diluted with DCM (100 mL). The solution was washed with sat. aq. $NH_4Cl$ and brine, dried over $Na_2SO_4$, filtered and concentrated to give 1-(4-bromophenyl)-3-((dimethylamino)methyl)-4-(3-methoxybenzyl)-1H-1,2,4-triazol-5(4H)-one (85 mg, 83% yield) as yellow gummy solid. MS(ESI) m/z: 417.3 (M+H)$^+$; $^1$H NMR (400 MHz, DMSO-$d_6$) δ ppm 7.92.7.88 (m, 2H) 7.57-7.53 (m, 2H) 7.31-7.26 (m, 1H) 6.93-6.86 (m, 3H) 5.299 (s, 2H) 3.80 (s, 3H) 3.23 (s, 2H) 2.26 (s, 6H).

Intermediate 17

1-(4-bromophenyl)-4-(3-methoxybenzyl)-1H-tetrazol-5(4H)-one

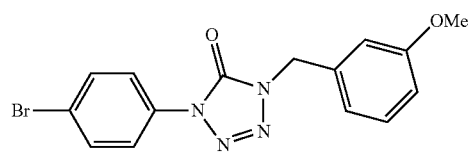 [SMILES: COc1cccc(Cn2nnn(-c3ccc(Br)cc3)c2=O)c1]

Intermediate 17a

Preparation of 1-(4-bromophenyl)-1H-tetrazol-5(4H)-one

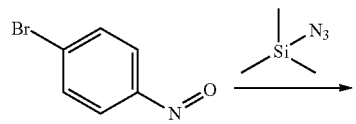

A solution of 1-bromo-4-isocyanatobenzene (2.0 g, 10.1 mmol) and azidotrimethylsilane (1.28 g, 11.1 mmol) in dry toluene (20 mL) was heated at 60° C. for 24 h. The solvent was evaporated, and the resultant solid was dissolved in toluene (30 mL) and cooled to 0° C. TMS-Cl (1.55 mL, 12.1 mmol) was added dropwise, followed by TEA (1.69 mL, 12.1 mmol) over a period of 30 min. The reaction mixture was heated at 100° C. for 6 h. The reaction mixture was cooled to rt and filtered, rinsing with toluene (20 mL). The filtrate was concentrated. The resultant solid was stirred in pet. ether (70 mL) for 30 min to give 1-(4-bromophenyl)-1H-tetrazol-5(4H)-one as (1.6 g, 80%) as a white solid. The compound was carried forward to the next step without further purification. MS (ESI) m/z: 241 (M+H)+; 1H NMR (300 MHz, DMSO-$d_6$) δ 7.94-7.90 (m, 2H), 7.70-7.66 (m, 2H).

Intermediate 17

Preparation of 1-(4-bromophenyl)-4-(3-methoxybenzyl)-1H-tetrazol-5(4H)-one

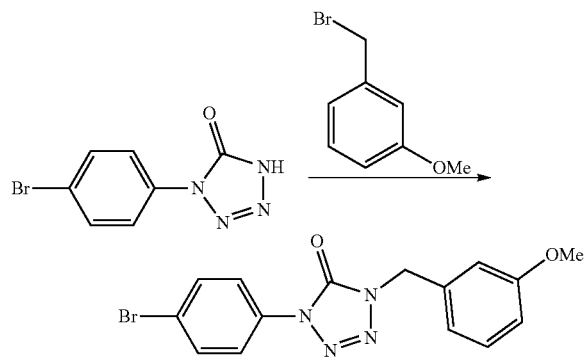

To a solution of 1-(4-bromophenyl)-1H-tetrazol-5(4H)-one (100 mg, 0.415 mmol) and K$_2$CO$_3$ (172 mg, 1.25 mmol) in DMF (3 mL), was added 1-(bromomethyl)-3-methoxybenzene (100 mg, 0.498 mmol). The reaction mixture was stirred at rt for 1 h. The reaction mixture was diluted with DCM (200 mL), washed with sat aq. NH$_4$Cl and brine, dried over Na$_2$SO$_4$, filtered and concentrated. The resultant solid was washed with pet. ether (2×30 mL) to afford 1-(4-bromophenyl)-4-(3-methoxybenzyl)-1H-tetrazol-5(4H)-one (0.060 g, 40% yield) as a white solid. The compound was carried forward to the next step without further purification. MS (ESI) m/z: 361.5 (M+H)+; 1H NMR (300 MHz, DMSO-$d_6$) δ 7.88-7.83 (m, 2H), 7.81-7.75 (m, 2H), 7.35-7.26 (m, 1H), 7.00-6.89 (m, 3H), 5.19 (s, 2H), 3.75 (s, 3H).

Intermediate 18

Preparation of 1-(4-bromophenyl)-4-(1-phenylethyl)-1H-tetrazol-5(4H)-one

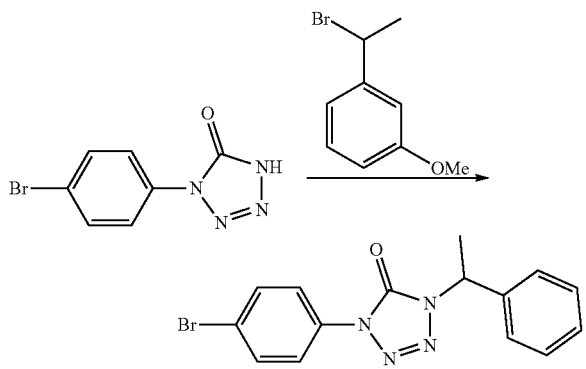

To a solution of 1-(4-bromophenyl)-1H-tetrazol-5(4H)-one (100 mg, 0.415 mmol) and K$_2$CO$_3$ (172 mg, 1.25 mmol) in DMF (3 mL), was added (1-bromoethyl)benzene (92 mg, 0.498 mmol). The reaction mixture was stirred at rt for 1 h. The reaction mixture was diluted with DCM (200 mL), washed with sat aq. NH$_4$Cl and brine, dried over Na$_2$SO$_4$, filtered and concentrated. The crude was washed with pet. ether (2×30 mL) to afford 1-(4-bromophenyl)-4-(1-phenylethyl)-1H-tetrazol-5(4H)-one (0.050 g, 35%). The compound was carried forward to the next step without further purification. MS (ESI) m/z: 345.0 (M+H)+.

Intermediate 19

Preparation of 1-(4-bromo-3-methoxyphenyl)-1H-tetrazol-5(4H)-one

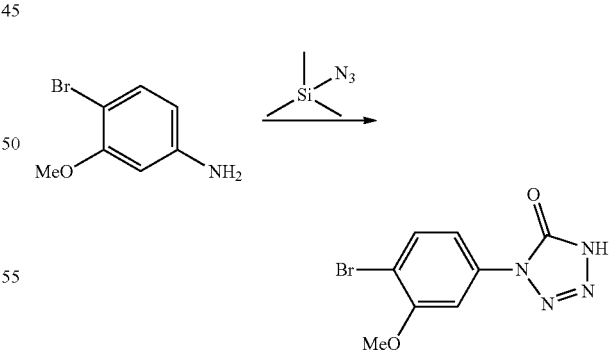

To a solution of 4-bromo-3-methoxyaniline (2.0 g, 9.90 mmol) and triphosgene (2.94 g, 9.90 mmol) in DCM (20 mL) at 0° C., was added TEA (1.66 mL, 11.9 mmol) dropwise over 20 min. The reaction mixture was stirred at rt for 2 h, then was concentrated. The crude compound was dissolved in toluene (20 mL). Azidotrimethylsilane (1.44 mL, 10.9 mmol) was added to the reaction mixture, which was stirred at rt for 24 h. The reaction was concentrated, and the resultant solid was dissolved in toluene (30 mL) and cooled 0° C. TMS-Cl (1.52 mL, 11.9 mmol) was added, followed by TEA (1.66 mL, 11.9 mmol) over 30 min. The reaction mixture heated at 100° C. for 6 h, then was cooled to rt and filtered, rinsing with toluene (20 mL). The filtrate was concentrated and the resultant solid was stirred with pet. ether (70 mL) for 30 min. The solid was collected by filtration and dried to give 1-(4-bromo-3-methoxyphenyl)-1H-tetrazol-5(4H)-one as (2.0 g, 97% yield) as a white solid. The compound was carried forward to the next step without further purification. MS (ESI) m/z: 271.2 (M+H)+; 1H NMR (300 MHz, DMSO-d6) δ 14.85 (br. s., 1H), 7.77 (d, J=8.7 Hz, 1H), 7.60 (d, J=2.3 Hz, 1H), 7.43 (dd, 2.5 Hz, 1H).

Example 1

4-(4-(1H-pyrazol-4-yl)phenyl)-1-(3-fluorobenzyl)-1H-1,2,4-triazol-5(4H)-one

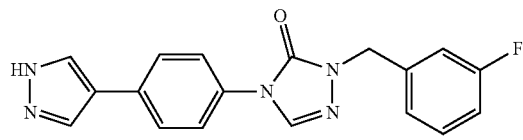 [SMILES: O=c1n(-c2ccc(-c3cn[nH]c3)cc2)cnn1Cc1cccc(F)c1]

Example 1A

Preparation of 4-(4-bromophenyl)-1-(3-fluorobenzyl)-1H-1,2,4-triazol-5(4H)-one

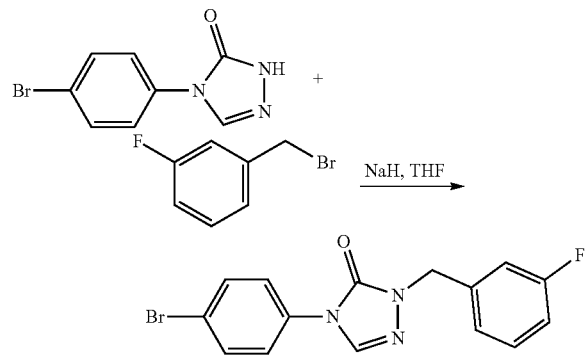

To a solution of 4-(4-bromophenyl)-1H-1,2,4-triazol-5(4H)-one (100 mg, 0.417 mmol) in THF (5 mL) at 0° C., was added NaH (20.0 mg, 0.833 mmol) to give a brown suspension. 1-(bromomethyl)-3-fluorobenzene (94 mg, 0.500 mmol) was added to the reaction mixture at 0° C., then the reaction mixture was stirred at rt overnight. The reaction mixture was quenched with methanol (5 mL) and concentrated. The residue was diluted with DCM (200 mL), washed with sat aq. NH4Cl and brine, dried over Na2SO4, filtered and concentrated. The resultant solid was washed with pet. ether (20 mL) to give 45 mg (21% yield) of an off-white solid, which was used in the following step without further purification. MS(ESI) m/z: 348.0 (M+H)+; 1H NMR (400 MHz, DMSO-d6) δ ppm 8.55 (s, 1H)) 7.30 (s, 4H) 7.43-7.38 (m, 1H) 7.16-7.12 (m, 4H) 4.99 (s, 2H).

Example 1

Preparation of 4-(4-(1H-pyrazol-4-yl)phenyl)-1-(3-fluorobenzyl)-1H-1,2,4-triazol-5(4H)-one

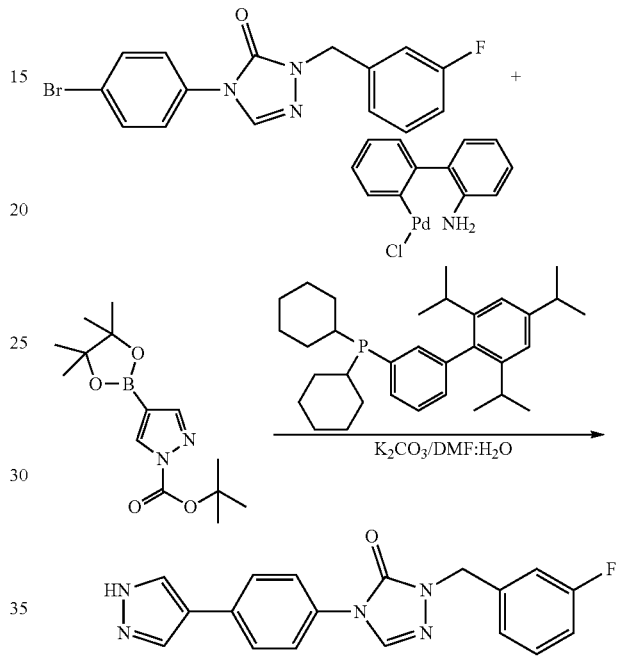

A solution of 4-(4-bromophenyl)-1-(3-fluorobenzyl)-1H-1,2,4-triazol-5(4H)-one (50 mg, 0.144 mmol), K2CO3 (59.5 mg, 0.431 mmol), and tert-butyl 4-(4,4,5,5-tetramethyl-1,3,2-dioxaborolan-2-yl)-1H-pyrazole-1-carboxylate (50.7 mg, 0.172 mmol) in DMF (2 mL) and water (0.2 mL) was flushed with nitrogen for 10 min. 2nd generation XPHOS precatalyst (3.3 mg, 4.3 μmol) was added and the reaction mixture heated at 80° C. for 6 h. Solvent was evaporated, and the resultant residue was diluted with DCM (100 mL) and washed with brine, dried over Na2SO4, filtered and concentrated. The product was purified by preparative HPLC to afford 4-(4-(1H-pyrazol-4-yl)phenyl)-1-(3-fluorobenzyl)-1H-1,2,4-triazol-5(4H)-one. MS(ESI) m/z: 336.2 (M+H)+; 1H NMR (400 MHz, DMSO-d6) δ ppm 12.94 (s, 1H) 8.53 (s, 1H) 8.25 (s, 1H) 7.98 (s, 1H) 7.73-7.79 (m, 2H) 7.66-7.72 (m, 2H) 7.36-7.47 (m, 1H) 7.09-7.20 (m, 3H) 5.01 (s, 2H); 19F NMR (377 MHz, DMSO-d6) δ ppm: −113.26; HPLC method A: RT=1.27 min, 98.8% purity, method B: RT=1.24 min, 98.9% purity.

The following Examples in Table 1 were made by using the same procedure as shown in Example 1.

TABLE 1

| Example | Structure | Name | LCMS (M + H)+ | HPLC Method, RT (min.) & Purity | NMR |
|---|---|---|---|---|---|
| 2 | 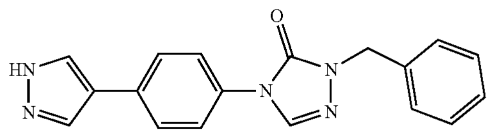 [SMILES: O=c1n(-c2ccc(-c3cn[nH]c3)cc2)cnn1Cc1ccccc1] | 4-(4-(1H-pyrazol-4-yl)phenyl)-1-benzyl-1H-1,2,4-triazol-5(4H)-one | 318.2 | A: 1.22, 98.2% B: 1.19, 97.7% | $^1$H NMR (400 MHz, DMSO-d$_6$) δ ppm 12.94 (s, 1 H) 8.51 (s, 1 H) 8.11 (s, 2 H) 7.73-7.79 (m, 2 H) 7.65-7.72 (m, 2 H) 7.36-7.41 (m, 2 H) 7.26-7.35 (m, 3 H) 4.98 (s, 2 H) |
| 3 | 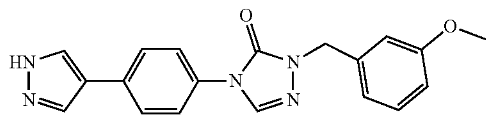 [SMILES: COc1cccc(Cn2ncn(-c3ccc(-c4cn[nH]c4)cc3)c2=O)c1] | 4-(4-(1H-pyrazol-4-yl)phenyl)-1-(3-methoxybenzyl)-1H-1,2,4-triazol-5(4H)-one | 348.2 | A: 1.24, 98.1% B: 1.21, 98.2% | $^1$H NMR (400 MHz, DMSO-d$_6$) δ ppm 8.51 (s, 1 H) 8.13 (br. s., 2 H) 7.73-7.81 (m, 2 H) 7.65-7.72 (m, 2 H) 7.25-7.33 (m, 1 H) 6.83-6.93 (m, 3 H) 4.94 (s, 2 H) 3.76 (s, 3 H) |
| 4 | 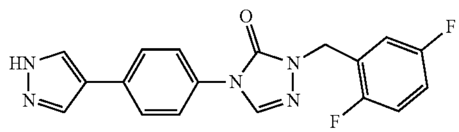 [SMILES: O=c1n(-c2ccc(-c3cn[nH]c3)cc2)cnn1Cc1cc(F)ccc1F] | 4-(4-(1H-pyrazol-4-yl)phenyl)-1-(2,5-difluorobenzyl)-1H-1,2,4-triazol-5(4H)-one | 354.2 | A: 1.30, 94.6% B: 1.26, 96.6% | $^1$H NMR (400 MHz, DMSO-d$_6$) δ ppm 12.99 (s, 1 H) 8.52 (s, 1 H) 8.51 (s, 1 H) 8.24 (s, 1 H) 7.73-7.79 (m, 2 H) 7.65-7.71 (m, 2 H) 7.15-7.37 (m, 3 H) 5.02 (s, 2 H); $^{19}$F NMR (377 MHz, DMSO-d$_6$) δ ppm −73.677, −118.659, −124.076 |
| 5 | 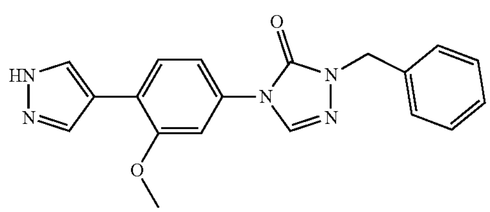 [SMILES: COc1cc(-n2cnn(Cc3ccccc3)c2=O)ccc1-c1cn[nH]c1] | 1-benzyl-4-(3-methoxy-4-(1H-pyrazol-4-yl)phenyl)-1H-1,2,4-triazol-5(4H)-one | 348.2 | A: 1.29, 96.6% B: 1.27, 97.4% | $^1$H NMR (400 MHz, DMSO-d$_6$) δ ppm 12.92 (s, 1 H) 8.55 (s, 1 H) 8.16 (s, 1 H) 8.00 (s, 1 H) 7.74 (d, J = 8.35 Hz, 1 H) 7.44 (d, J = 2.07 Hz, 1 H) 7.27-7.40 (m, 6 H) 4.97 (s, 2 H) 3.92 (s, 3 H) |
| 6 | 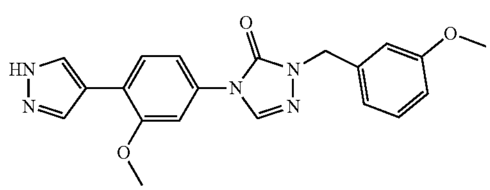 [SMILES: COc1cccc(Cn2ncn(-c3ccc(-c4cn[nH]c4)c(OC)c3)c2=O)c1] | 4-(3-methoxy-4-(1H-pyrazol-4-yl)phenyl)-1-(3-methoxybenzyl)-1H-1,2,4-triazol-5(4H)-one | 378.2 | A: 1.30, 97.6% B: 1.29, 96.0% | $^1$H NMR (400 MHz, DMSO-d$_6$) δ ppm 8.55 (s, 1 H) 8.08 (s, 2 H) 7.74 (d, J = 8.35 Hz, 1 H) 7.44 (d, J = 2.07 Hz, 1 H) 7.24-7.34 (m, 2 H) 6.85-6.91 (m, 3 H) 4.94 (s, 2 H) 3.92 (s, 3 H) 3.75 (s, 3 H) |
| 7 | 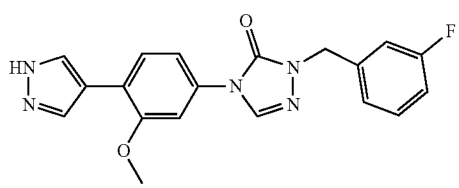 [SMILES: COc1cc(-n2cnn(Cc3cccc(F)c3)c2=O)ccc1-c1cn[nH]c1] | 1-(3-fluorobenzyl)-4-(3-methoxy-4-(1H-pyrazol-4-yl)phenyl)-1H-1,2,4-triazol-5(4H)-one | 366.2 | A: 1.33, 96.6% B: 1.32, 97.1% | $^1$H NMR (400 MHz, DMSO-d$_6$) δ ppm 12.92 (s, 1 H) 8.57 (s, 1 H) 8.08 (br. s., 2 H) 7.74 (d, J = 8.35 Hz, 1 H) 7.39-7.47 (m, 2 H) 7.32 (dd, J = 8.35, 2.13 Hz, 1 H) 7.08-7.20 (m, 3 H) 5.00 (s, 2 H) 3.92 (s, 3 H); $^{19}$F NMR (377 MHz, DMSO-d$_6$) δ ppm −113.010. |
| 8 | 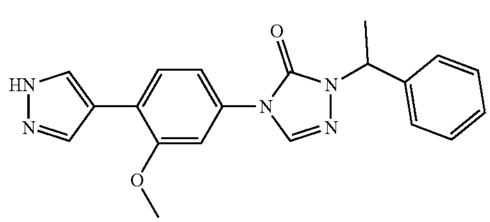 [SMILES: COc1cc(-n2cnn(C(C)c3ccccc3)c2=O)ccc1-c1cn[nH]c1] | 4-(3-methoxy-4-(1H-pyrazol-4-yl)phenyl)-1-(1-phenylethyl)-1H-1,2,4-triazol-5(4H)-one | 362.2 | A: 1.43, 98.9% B: 1.41, 98.7% | $^1$H NMR (400 MHz, DMSO-d$_6$) δ ppm 12.98 (s, 1 H) 8.47-8.60 (s, 1 H) 8.07 (s, 2 H) 7.73 (d, J = 8.35 Hz, 1 H) 7.42 (d, J = 2.07 Hz, 1 H) 7.23-7.40 (m, 6 H) 5.45 (d, J = 7.15 Hz, 1 H) 3.92 (s., 3 H) 1.72 (d, J = 7.15 Hz, 3H) |
| 9 | 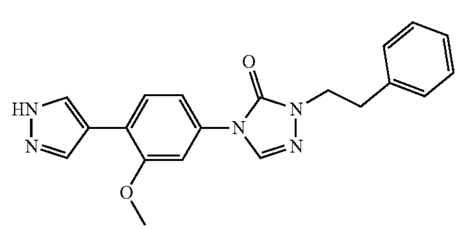 [SMILES: COc1cc(-n2cnn(CCc3ccccc3)c2=O)ccc1-c1cn[nH]c1] | 4-(3-methoxy-4-(1H-pyrazol-4-yl)phenyl)-1-phenethyl-1H-1,2,4-triazol-5(4H)-one | 362.2 | A: 1.36, 97.7% B: 1.34, 96.2% | $^1$H NMR (400 MHz, DMSO-d$_6$) δ ppm 8.52 (s, 1 H) 8.15 (s, 1 H) 7.99 (s, 1 H) 7.72 (d, J = 8.34 Hz, 1 H) 7.37 (d, J = 2.07 Hz, 1 H) 7.16-7.32 (m, 6 H) 3.99 (t, J = 7.28 Hz, 2 H) 3.91 (s, 3 H) 3.03 (t, J = 7.28 Hz, 2 H) |

TABLE 1-continued

| Example | Structure | Name | LCMS (M + H)+ | HPLC Method, RT (min.) & Purity | NMR |
|---|---|---|---|---|---|
| 10 | 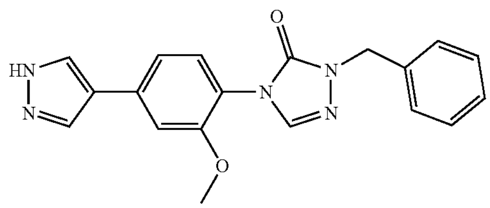 [SMILES: COc1cc(-c2cn[nH]c2)ccc1-n1cnn(Cc2ccccc2)c1=O] | 1-benzyl-4-(2-methoxy-4-(1H-pyrazol-4-yl)phenyl)-1H-1,2,4-triazol-5(4H)-one | 348.2 | A: 1.25, 96.4% B: 1.25, 95.3% | $^1$H NMR (400 MHz, DMSO-$d_6$) δ ppm 8.17 (s, 2 H) 8.10 (s, 1 H) 7.42 (d, J = 1.69 Hz, 1 H) 7.38 (t, J = 7.37 Hz, 3 H) 7.28-7.34 (m, 4 H) 4.94 (s, 2 H) 3.87 (s, 3 H) |
| 11 | 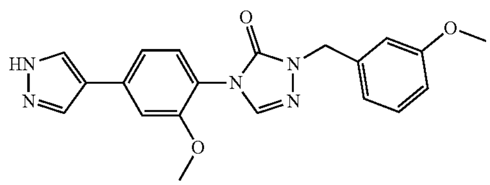 [SMILES: COc1cccc(Cn2ncn(-c3ccc(-c4cn[nH]c4)cc3OC)c2=O)c1] | 4-(2-methoxy-4-(1H-pyrazol-4-yl)phenyl)-1-(3-methoxybenzyl)-1H-1,2,4-triazol-5(4H)-one | 378.2 | A: 1.26, 97.3% B: 1.26, 97.2% | $^1$H NMR (400 MHz, DMSO-$d_6$) δ ppm 13.01 (br. s., 1 H) 8.31 (br. s., 1 H) 8.10 (s, 1 H) 7.98-8.05 (s, 1 H) 7.36-7.45 (m, 2 H) 7.21-7.33 (m, 2 H) 6.83-6.94 (m, 3 H) 4.91 (s, 2 H) 3.87 (s, 3 H) 3.75 (s, 3 H) |
| 12 | 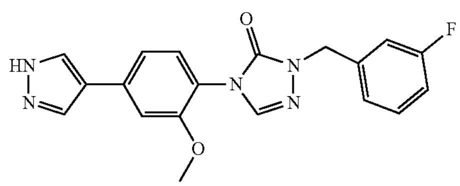 [SMILES: COc1cc(-c2cn[nH]c2)ccc1-n1cnn(Cc2cccc(F)c2)c1=O] | 1-(3-fluorobenzyl)-4-(2-methoxy-4-(1H-pyrazol-4-yl)phenyl)-1H-1,2,4-triazol-5(4H)-one | 366.2 | A: 1.30, 97.6% B: 1.30, 97.4% | $^1$H NMR (400 MHz, DMSO-$d_6$) δ ppm 8.17 (s, 2 H) 8.12 (s, 1 H) 7.37-7.48 (m, 3 H) 7.31 (dd, J = 8.13, 1.73 Hz, 1 H) 7.09-7.18 (m, 3 H) 4.98 (s, 2 H) 3.88 (s, 3 H); $^{19}$F NMR (377 MHz, DMSO-$d_6$) δ ppm -113.032 |
| 13 | 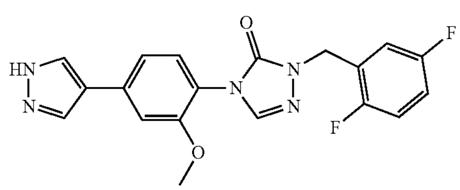 [SMILES: COc1cc(-c2cn[nH]c2)ccc1-n1cnn(Cc2cc(F)ccc2F)c1=O] | 1-(2,5-difluorobenzyl)-4-(2-methoxy-4-(1H-pyrazol-4-yl)phenyl)-1H-1,2,4-triazol-5(4H)-one | 384.2 | A: 1.32, 96.7% B: 1.32, 97.8% | $^1$H NMR (400 MHz, DMSO-$d_6$) δ ppm 8.17 (s, 2 H) 8.12 (s, 1 H) 7.38-7.43 (m, 2 H) 7.32 (s, 2 H) 7.20-7.27 (m, 1 H) 7.13 (ddd, J = 8.82, 5.68, 3.20 Hz, 1 H) 4.99 (s, 2 H) 3.87 (s, 3 H); $^{19}$F NMR (377 MHz, DMSO-$d_6$) δ ppm -118.423, -123.811 |
| 14 | 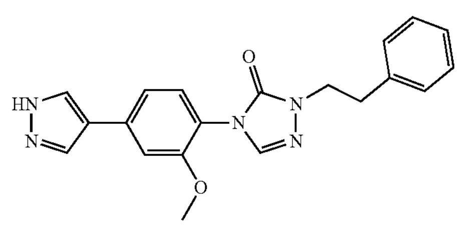 [SMILES: COc1cc(-c2cn[nH]c2)ccc1-n1cnn(CCc2ccccc2)c1=O] | 4-(2-methoxy-4-(1H-pyrazol-4-yl)phenyl)-1-phenethyl-1H-1,2,4-triazol-5(4H)-one | 362.2 | A: 1.33, 98.0% B: 1.33, 98.9% | $^1$H NMR (400 MHz, DMSO-$d_6$) δ ppm 13.01 (brs., 1 H) 8.30 (br. s., 1 H) 8.05-8.08 (s, 1 H) 8.02 (s, 1 H) 7.41 (s, 1 H) 7.26-7.36 (m, 4 H) 7.17-7.24 (m, 3 H) 3.91-3.99 (m, 2 H) 3.86 (s, 3 H) 2.97-3.04 (m, 2 H) |
| 15 | 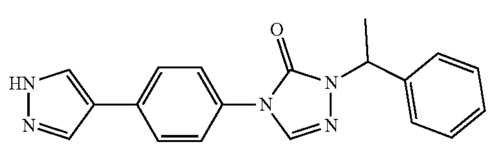 [SMILES: CC(c1ccccc1)n1ncn(-c2ccc(-c3cn[nH]c3)cc2)c1=O] | 4-(4-(1H-pyrazol-4-yl)phenyl)-1-(1-phenylethyl)-1H-1,2,4-triazol-5(4H)-one | 332.2 | A: 1.37, 91.5% B: 1.34, 90.6% | $^1$H NMR (400 MHz, DMSO-$d_6$) δ ppm 8.52 (s, 1 H) 8.12 (s, 2 H) 7.72-7.77 (m, 2 H) 7.64-7.71 (m, 2 H) 7.34-7.41 (m, 4 H) 7.27-7.33 (m, 1 H) 5.46 (q, J = 7.03 Hz, 1 H) 1.73 (d, J = 6.4 Hz 3 H) |
| 16 | 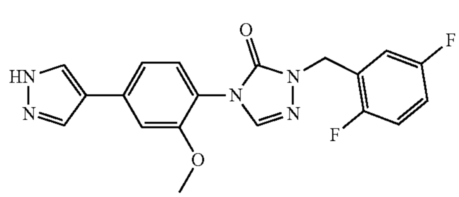 [SMILES: COc1cc(-c2cn[nH]c2)ccc1-n1cnn(Cc2cc(F)ccc2F)c1=O] | 1-(2,5-difluorobenzyl)-4-(2-methoxy-4-(1H-pyrazol-4-yl)phenyl)-1H-1,2,4-triazol-5(4H)-one | 384.2 | A: 1.36, 94.4% B: 1.34, 94.3% | $^1$H NMR (400 MHz, DMSO-$d_6$) δ ppm 12.92 (s, 1 H) 8.56 (s, 1 H) 8.08 (br. s, 2 H) 7.73-7.75 (d, J = 8.35 Hz, 1 H) 7.52-7.55 (t, J = 4.0 Hz, 1 H) 7.28-7.33 (m, 2 H) 7.19-7.26 (m, 2 H) 5.02 (s, 2 H) 3.92 (s, 3 H); $^{19}$F NMR (377 MHz, DMSO-$d_6$) δ ppm -118.39 and -123.803 |

Example 17

1-(4-(1H-pyrazol-4-yl)phenyl)-4-benzyl-1H-1,2,4-triazol-5(4H)-one

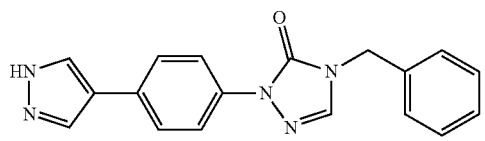 [SMILES: O=c1n(Cc2ccccc2)cnn1-c1ccc(-c2cn[nH]c2)cc1]

Example 17A

Preparation of 4-benzyl-1-(4-bromophenyl)-1H-1,2,4-triazol-5(4H)-one

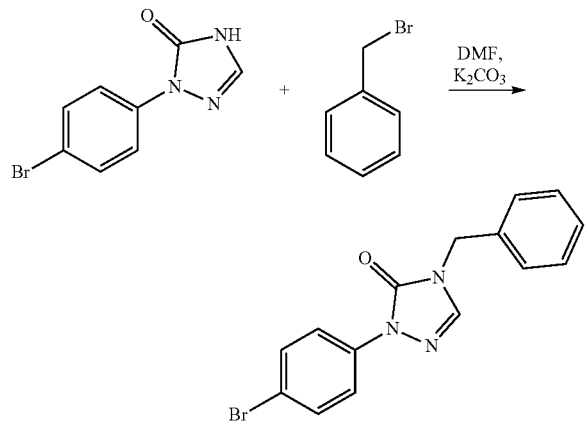

To a mixture of 1-(4-bromophenyl)-1H-1,2,4-triazol-5(4H)-one (100 mg, 0.417 mmol) and $K_2CO_3$ (173 mg, 1.25 mmol) in DMF (3 mL), was added benzyl bromide (85 mg, 0.500 mmol). The mixture was stirred at rt for 1 h. Reaction mixture was diluted with DCM (200 mL), washed with sat $NH_4Cl$, water and brine, dried over $Na_2SO_4$, filtered and concentrated. The residue was washed with pet. ether (2×30 mL) to afford 30 mg (21% yield) of the desired product as an off-white solid. MS(ESI) m/z: 330.0 (M+H)$^+$; $^1$H NMR (400 MHz, DMSO-$d_6$) δ ppm 8.39 (s, 1H) 8.89-7.86 (d, J=12 Hz, 2H) 7.67-7.64 (d, J=12, 2H) 4.88 (s, 2H).

Preparation of 1-(4-(1H-pyrazol-4-yl)phenyl)-4-benzyl-1H-1,2,4-triazol-5(4H)-one

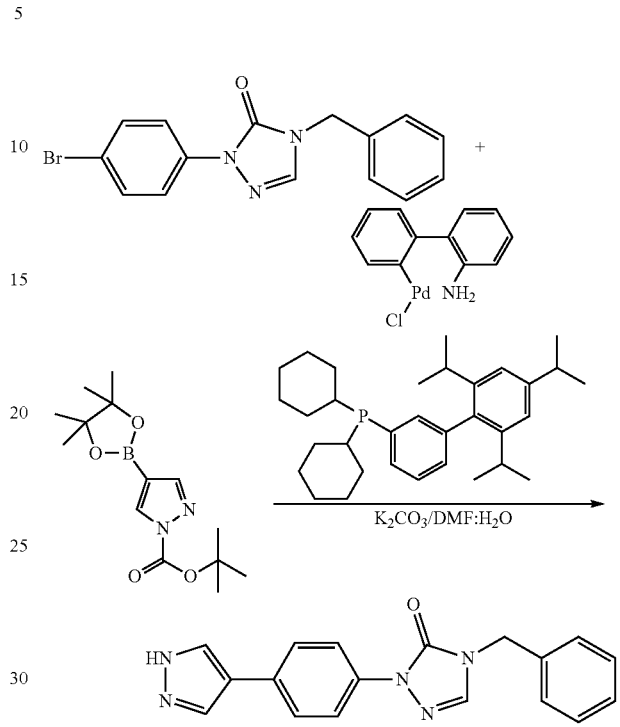

A mixture of 4-benzyl-1-(4-bromophenyl)-1H-1,2,4-triazol-5(4H)-one (30 mg, 0.091 mmol), $K_2CO_3$ (37.7 mg, 0.273 mmol), and tert-butyl 4-(4,4,5,5-tetramethyl-1,3,2-dioxaborolan-2-yl)-1H-pyrazole-1-carboxylate (32.1 mg, 0.109 mmol) in DMF (2 mL) and water (0.2 mL) was flushed with nitrogen for 10 min. 2$^{nd}$ generation XPHOS precatalyst (2.1 mg, 2.7 µmol) was added to the reaction mixture and the reaction mixture heated for 6 hrs at 80° C. The reaction mixture was cooled to RT and evaporated. The residue was diluted with DCM (100 mL), washed with brine, dried over $Na_2SO_4$, filtered and concentrated. The crude was purified by preparative HPLC to afford 1-(4-(1H-pyrazol-4-yl)phenyl)-4-benzyl-1H-1,2,4-triazol-5(4H)-one (5 mg, 17% yield) as an off-white solid. MS(ESI) m/z: 318.2 (M+H)$^+$; $^1$H NMR (400 MHz, DMSO-$d_6$) δ ppm 12.94 (s, 1H) 8.36 (s, 1H) 8.19 (br. s., 1H) 7.93 (br. s., 1H) 7.82-7.90 (m, 2H) 7.64-7.74 (m, 2H) 7.24-7.45 (m, 5H) 4.89 (s, 2H); HPLC method A: RT=1.28 min, 99.6% purity, method B: RT=1.25 min, 98.9% purity.

The following Examples in Table 2 were made by using the same procedure as shown in Example 17.

TABLE 2

| Example | Structure | Name | LCMS (M + H)$^+$ | HPLC Method, RT (min.) & urity | NMR |
|---|---|---|---|---|---|
| 18 | 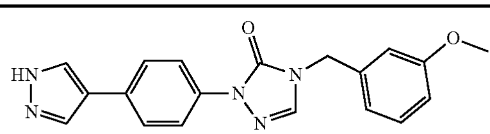 | 1-(4-(1H-pyrazol-4-yl)phenyl)-4-(3-methoxy-benzyl)-1H-1,2,4-triazol-5(4H)-one | 348.2 | A: 1.31, 99.9% B: 1.29, 100% | $^1$H NMR (400 MHz, DMSO-$d_6$) δ ppm 12.94 (br. s., 1 H) 8.35 (s, 1 H) 8.13-8.26 (m, 1 H) 7.92-7.98 (m, 1 H) 7.87 (d, J = 4.77 Hz, 2 H) 7.63-7.73 (m, 2 H) 7.23-7.35 (m, 1 H) 6.80-7.00 (m, 3 H) 4.85 (s, 2 H) 3.75 (s, 3 H) |

TABLE 2-continued

| Example | Structure | Name | LCMS (M + H)⁺ | HPLC Method, RT (min.) & urity | NMR |
|---|---|---|---|---|---|
| 19 | 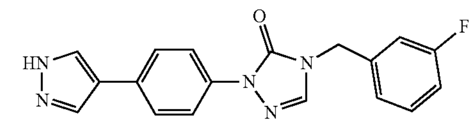 [SMILES: O=c1n(Cc2cccc(F)c2)cnn1-c1ccc(-c2cn[nH]c2)cc1] | 1-(4-(1H-pyrazol-4-yl)phenyl)-4-(3-fluoro-benzyl)-1H-1,2,4-triazol-5(4H)-one | 336.2 | A: 1.32, 100% B: 1.29, 99.7% | $^1$H NMR (400 MHz, DMSO-$d_6$) δ ppm 12.94 (br. s., 1 H) 8.37 (s, 1 H) 8.20 (br. s., 1 H) 7.93 (br. s., 1 H) 7.87 (q, J = 4.45 Hz, 2 H) 7.65-7.73 (m, 2 H) 7.44 (td, J = 7.94, 6.09 Hz, 1 H) 7.10-7.27 (m, 3 H) 4.91 (s, 2 H); $^{19}$F NMR (377 MHz, DMSO-$d_6$) δ ppm −112.749 |
| 20 | 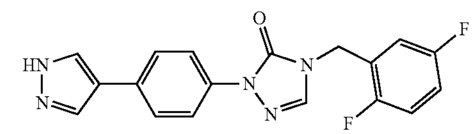 [SMILES: O=c1n(Cc2cc(F)ccc2F)cnn1-c1ccc(-c2cn[nH]c2)cc1] | 1-(4-(1H-pyrazol-4-yl)phenyl)-4-(2,5-difluoro-benzyl)-1H-1,2,4-triazol-5(4H)-one | 354.2 | A: 1.34, 100% B: 1.31, 99.4% | $^1$H NMR (400 MHz, DMSO-$d_6$) δ ppm 12.94 (br. s., 1 H) 8.32 (s, 1 H) 8.20 (br. s., 1 H) 7.93 (br. s., 1 H) 7.80-7.89 (m, 2 H) 7.63-7.75 (m, 2 H) 7.18-7.40 (m, 3 H) 4.95 (s, 2 H); $^{19}$F NMR (377 MHz, DMSO-$d_6$) δ ppm −118.181, −123.377 |
| 21 | 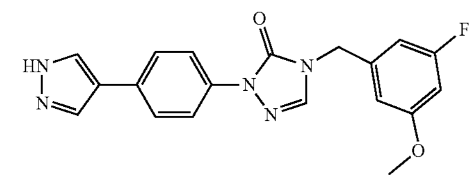 [SMILES: COc1cc(F)cc(Cn2cnn(-c3ccc(-c4cn[nH]c4)cc3)c2=O)c1] | 1-(4-(1H-pyrazol-4-yl)phenyl)-4-(3-fluoro-5-methoxy-benzyl)-1H-1,2,4-triazol-5(4H)-one | 366.2 | A: 1.40, 98.5% B: 1.37, 99.1% | $^1$H NMR (400 MHz, DMSO-$d_6$) δ ppm 12.95 (br. s., 1 H) 8.36 (s, 1 H) 8.08 (br. s, 2 H) 7.83-7.91 (m, 2 H) 7.64-7.74 (m, 2 H) 6.69-6.87 (m, 3 H) 4.86 (s, 2 H) 3.77 (s, 3 H); $^{19}$F NMR (377 MHz, DMSO-$d_6$) δ ppm −111.045 |
| 22 | 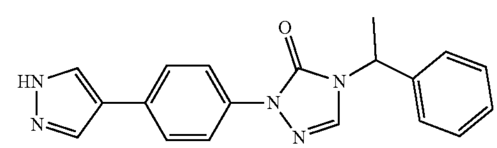 [SMILES: CC(c1ccccc1)n1cnn(-c2ccc(-c3cn[nH]c3)cc2)c1=O] | 1-(4-(1H-pyrazol-4-yl)phenyl)-4-(1-phenylethyl)-1H-1,2,4-triazol-5(4H)-one | 332.2 | A: 1.39, 99.2% B: 1.36, 97.8% | $^1$H NMR (400 MHz, DMSO-$d_6$) δ ppm 12.94 (br. s., 1 H) 8.54 (s, 1 H) 8.10 (br. s, 2 H) 7.82-7.92 (m, 2 H) 7.65-7.74 (m, 2 H) 7.36-7.43 (m, 4 H) 7.26-7.35 (m, 1 H) 5.29 (q, J = 7.26 Hz, 1 H) 1.78 (d, J = 7.28 Hz, 3 H) |
| 23 | 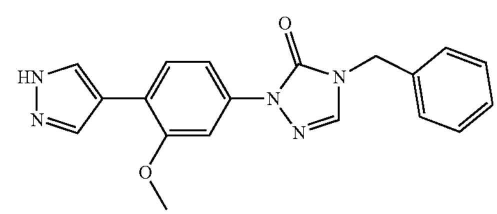 [SMILES: COc1cc(-n2ncn(Cc3ccccc3)c2=O)ccc1-c1cn[nH]c1] | 4-benzyl-1-(3-methoxy-4-(1H-pyrazol-4-yl)phenyl)-1H-1,2,4-triazol-5(4H)-one | 348.2 | A: 1.34, 96.6% B: 1.27, 97.8% | $^1$H NMR (400 MHz, DMSO-$d_6$) δ ppm 12.88 (br. s., 1 H) 8.38 (s, 1 H) 8.11 (br. s., 1 H) 8.08 (br. s., 1 H) 7.69 (d, J = 8.47 Hz, 1 H) 7.64 (d, J = 2.07 Hz, 1 H) 7.52 (dd, J = 8.47, 2.07 Hz, 1 H) 7.29-7.43 (m, 5 H) 4.90 (s, 2 H) 3.89 (s, 3 H) |
| 24 | 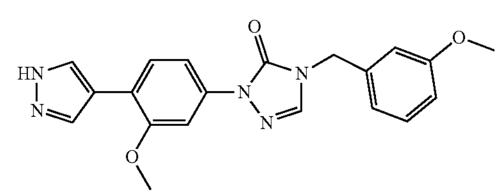 [SMILES: COc1cccc(Cn2cnn(-c3ccc(-c4cn[nH]c4)c(OC)c3)c2=O)c1] | 1-(3-methoxy-4-(1H-pyrazol-4-yl)phenyl)-4-(3-methoxy-benzyl)-1H-1,2,4-triazol-5(4H)-one | 378.2 | A: 1.35, 99.8% B: 1.29, 99.4% | $^1$H NMR (400 MHz, DMSO-$d_6$) δ ppm 8.38 (s, 1 H) 8.06 (s, 2 H) 7.71 (d, J = 8.47 Hz, 1 H) 7.65 (d, J = 2.01 Hz, 1 H) 7.53 (dd, J = 8.44, 2.10 Hz, 1 H) 7.32 (t, J = 7.91 Hz, 1 H) 6.86-6.99 (m, 3 H) 4.87 (s, 2 H) 3.90 (s, 3 H) 3.76 (s, 3 H) |
| 25 | 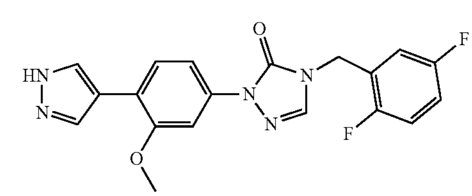 [SMILES: COc1cc(-n2ncn(Cc3cc(F)ccc3F)c2=O)ccc1-c1cn[nH]c1] | 4-(2,5-difluoro-benzyl)-1-(3-methoxy-4-(1H-pyrazol-4-yl)phenyl)-1H-1,2,4-triazol-5(4H)-one | 384.2 | A: 1.37, 99.4% B: 1.32, 96.8% | $^1$H NMR (400 MHz, DMSO-$d_6$) δ ppm 12.89 (s, 1 H) 8.35 (d, J = 0.31 Hz, 1 H) 8.13 (br. s., 1 H) 8.13 (br. s., 1 H) 7.72 (s, 1 H) 7.64 (s, 1 H) 7.49-7.54 (m, 1 H) 7.22-7.38 (m, 3 H) 4.96 (s, 2 H) 3.90 (s, 3 H); $^{19}$F NMR (377 MHz, DMSO-$d_6$) δ ppm −118.423, −123.613 |

TABLE 2-continued

| Example | Structure | Name | LCMS (M + H)+ | HPLC Method, RT (min.) & urity | NMR |
|---|---|---|---|---|---|
| 26 | 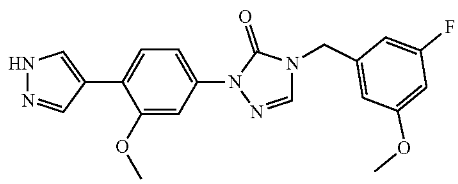 [SMILES: COc1cc(F)cc(Cn2cnn(-c3ccc(-c4cn[nH]c4)c(OC)c3)c2=O)c1] | 4-(3-fluoro-5-methoxy-benzyl)-1-(3-methoxy-4-(1H-pyrazol-4-yl)phenyl)-1H-1,2,4-triazol-5(4H)-one | 396.2 | A: 1.44, 98.4% B: 1.37, 97.9% | $^1$H NMR (400 MHz, METHANOL-$d_4$) δ ppm 12.89 (s, br, 1 H) 9.19 (s, 1 H) 8.86 (s, 2 H) 8.51 (d, J = 8.47 Hz, 1 H) 8.44 (d, J = 2.01 Hz, 1 H) 8.33 (dd, J = 8.41, 2.07 Hz, 1 H) 7.55-7.67 (m, 3 H) 5.67 (s, 2 H) 4.71 (s, 3 H) 4.59 (s, 3 H); $^{19}$F NMR (377 MHz, DMSO-$d_6$) δ ppm −110.230 |
| 27 | 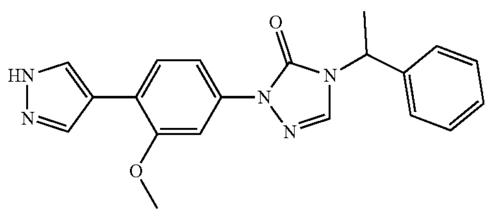 [SMILES: COc1cc(-n2ncn(C(C)c3ccccc3)c2=O)ccc1-c1cn[nH]c1] | 1-(3-methoxy-4-(1H-pyrazol-4-yl)phenyl)-4-(1-phenylethyl)-1H-1,2,4-triazol-5(4H)-one | 362.2 | A: 1.43, 98.3% B: 1.38, 98.5% | $^1$H NMR (400 MHz, DMSO-$d_6$) δ ppm 8.57 (s, 1 H) 8.06 (s, 2 H) 7.70 (d, J = 8.47 Hz, 1 H) 7.64 (d, J = 2.07 Hz, 1 H) 7.51 (dd, J = 8.44, 2.04 Hz, 1 H) 7.38-7.43 (m, 4 H) 7.31-7.37 (m, 1 H) 5.30 (q, J = 7.26 Hz, 1 H) 3.89 (s, 3 H) 1.79 (d, J = 7.22 Hz, 3 H) |
| 28 | 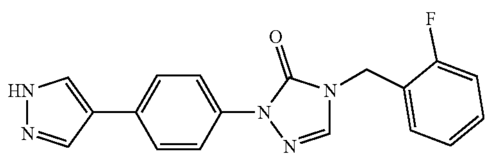 [SMILES: O=c1n(Cc2ccccc2F)cnn1-c1ccc(-c2cn[nH]c2)cc1] | 1-(4-(1H-pyrazol-4-yl)phenyl)-4-(2-fluorobenzyl)-1H-1,2,4-triazol-5(4H)-one | 336.2 | A: 1.27, 98.6% B: 1.25, 96.7% | $^1$H NMR (400 MHz, DMSO-$d_6$) δ ppm 12.89 (s, 1 H) 8.13 (br. s., 2 H) 8.31 (d, J = 0.44 Hz, 1 H) 7.82-7.91 (m, 2 H) 7.65-7.72 (m, 2 H) 7.35-7.46 (m, 2 H) 7.16-7.30 (m, 2 H) 4.96 (s, 2 H); $^{19}$F NMR (377 MHz, DMSO-$d_6$) δ ppm −118.118 |
| 29 | 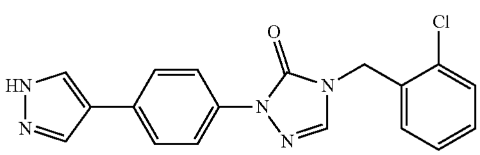 [SMILES: O=c1n(Cc2ccccc2Cl)cnn1-c1ccc(-c2cn[nH]c2)cc1] | 1-(4-(1H-pyrazol-4-yl)phenyl)-4-(2-chlorobenzyl)-1H-1,2,4-triazol-5(4H)-one | 352.2 | A: 1.40, 99.6% B: 1.38, 98.8% | $^1$H NMR (400 MHz, DMSO-$d_6$) δ ppm 12.94 (s, 1 H) 8.30 (s, 1 H) 8.23 (br, s, 1 H) 7.93 (br, s, 1 H) 7.83-7.91 (m, 2 H) 7.66-7.74 (m, 2 H) 7.51-7.57 (m, 1 H) 7.37-7.42 (m, 2 H) 7.30-7.34 (m, 1 H) 4.99 (s, 2 H) |
| 30 | 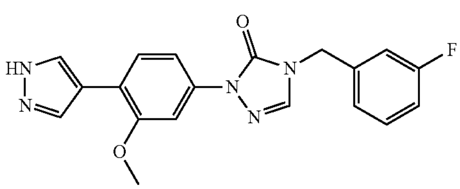 [SMILES: COc1cc(-n2ncn(Cc3cccc(F)c3)c2=O)ccc1-c1cn[nH]c1] | 4-(3-fluoro-benzyl)-1-(3-methoxy-4-(1H-pyrazol-4-yl)phenyl)-1H-1,2,4-triazol-5(4H)-one | 366.2 | A: 1.34, 100% B: 1.34, 100% | $^1$H NMR (400 MHz, DMSO-$d_6$) δ ppm 8.39 (s, 1 H) 8.04 (br. s., 2 H) 7.71-7.68 (d, J = 8.47 Hz, 1 H) 7.63-7.62 (d, J = 2.07 Hz, 1 H) 7.52-7.50 (dd, J = 8.47, 2.07 Hz, 1 H) 7.47-7.41 (td, J = 7.92, 6.05 Hz, 1 H) 7.25-7.15 (m, 3 H) 4.91 (s, 2 H) 3.89 (s, 3 H) $^{19}$F NMR (377 MHz, DMSO-$d_6$) δ ppm −112.998 |
| 31 | 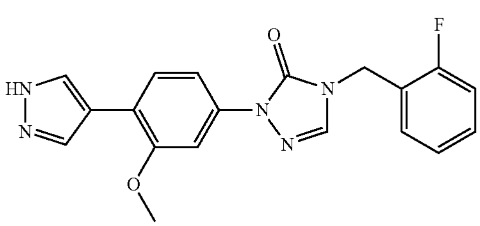 [SMILES: COc1cc(-n2ncn(Cc3ccccc3F)c2=O)ccc1-c1cn[nH]c1] | 4-(2-fluoro-benzyl)-1-(3-methoxy-4-(1H-pyrazol-4-yl)phenyl)-1H-1,2,4-triazol-5(4H)-one | 366.2 | A: 1.34, 100% B: 1.32, 99.5% | $^1$H NMR (400 MHz, DMSO-$d_6$) δ ppm 8.33 (s, 1 H) 8.06 (s, 2 H) 7.70 (d, J = 8.47 Hz, 1 H) 7.64 (d, J = 2.01 Hz, 1 H) 7.51 (dd, J = 8.44, 2.10 Hz, 1 H) 7.37-7.45 (m, 2 H) 7.18-7.31 (m, 2 H) 4.97 (s, 2 H) 3.90 (s, 3 H); $^{19}$F NMR (377 MHz, DMSO-$d_6$) δ ppm −118.360 |
| 32 | 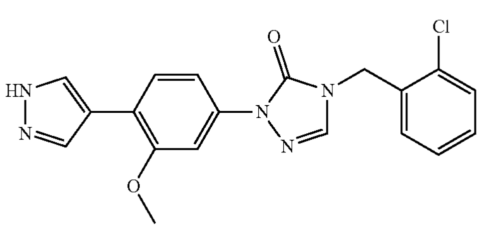 [SMILES: COc1cc(-n2ncn(Cc3ccccc3Cl)c2=O)ccc1-c1cn[nH]c1] | 4-(2-chloro-benzyl)-1-(3-methoxy-4-(1H-pyrazol-4-yl)phenyl)-1H-1,2,4-triazol-5(4H)-one | 382.2 | A: 1.47, 94.9% B: 1.45, 96.4% | $^1$H NMR (400 MHz, DMSO-$d_6$) δ ppm 12.89 (br. s., 1 H) 8.33 (s, 1 H) 8.13 (br. s., 1 H) 7.96 (br. s., 1 H) 7.71 (d, J = 8.41 Hz, 1 H) 7.65 (d, J = 2.01 Hz, 1 H) 7.49-7.57 (m, 2 H) 7.37-7.44 (m, 2 H) 7.31-7.36 (m, 1 H) 5.00 (s, 2 H) 3.90 (s, 3 H) |

TABLE 2-continued

| Example | Structure | Name | LCMS (M + H)+ | HPLC Method, RT (min.) & urity | NMR |
|---|---|---|---|---|---|
| 33 | 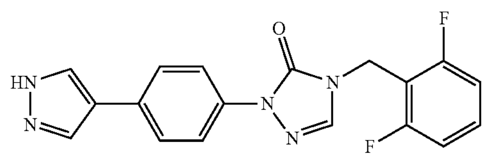 [SMILES: O=c1n(Cc2c(F)cccc2F)cnn1-c1ccc(-c2cn[nH]c2)cc1] | 1-(4-(1H-pyrazol-4-yl)phenyl)-4-(2,6-difluorobenzyl)-1H-1,2,4-triazol-5(4H)-one | 354.2 | A: 1.36, 97.3% B: 1.34, 97.1% | $^1$H NMR (400 MHz, DMSO-d$_6$) δ ppm 12.97 (s, 1 H) 8.30 (s, 1 H) 8.07 (br. s., 1 H) 7.81-7.86 (m, 2 H) 7.65-7.71 (m, 2 H) 7.50 (tt, J = 8.43, 6.66 Hz, 1 H) 7.09-7.23 (m, 2 H) 4.99 (s, 2 H); $^{19}$F NMR (377 MHz, DMSO-d$_6$) δ ppm −114.467 |
| 34 | 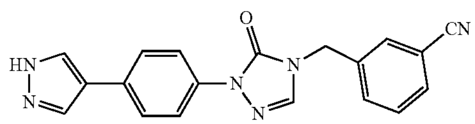 [SMILES: N#Cc1cccc(Cn2cnn(-c3ccc(-c4cn[nH]c4)cc3)c2=O)c1] | 3-((1-(4-(1H-pyrazol-4-yl)phenyl)-5-oxo-1H-1,2,4-triazol-4(5H)-yl)methyl)benzonitrile | 343.2 | A: 1.25, 100% B: 1.23, 100% | $^1$H NMR (400 MHz, DMSO-d$_6$) δ ppm 8.38 (s, 1 H) 8.07 (br. s., 2 H) 7.85-7.91 (m, 3 H) 7.83 (dt, J = 7.69, 1.36 Hz, 1 H) 7.68-7.75 (m, 3 H) 7.58-7.65 (m, 1 H) 4.97 (s, 2 H) |
| 35 | 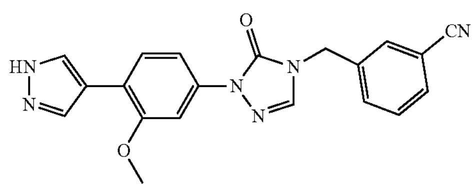 [SMILES: COc1cc(-n2ncn(Cc3cccc(C#N)c3)c2=O)ccc1-c1cn[nH]c1] | 3-((1-(3-methoxy-4-(1H-pyrazol-4-yl)phenyl)-5-oxo-1H-1,2,4-triazol-4(5H)-yl)methyl)benzonitrile | 373.2 | A: 1.21, 99.8% B: 1.16, 99.9% | $^1$H NMR (400 MHz, DMSO-d$_6$) δ ppm 8.39 (s, 1 H) 8.06 (s, 2 H) 7.89 (t, J = 1.41 Hz, 1 H) 7.82 (dt, J = 7.66, 1.41 Hz, 1 H) 7.68-7.75 (m, 2 H) 7.58-7.65 (m, 1 H) 7.51 (dd, J = 8.47, 2.07 Hz, 1 H) 4.97 (s, 2 H) 3.98 (s, 3 H) |
| 36 | 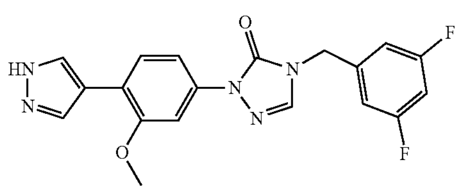 [SMILES: COc1cc(-n2ncn(Cc3cc(F)cc(F)c3)c2=O)ccc1-c1cn[nH]c1] | 4-(3,5-difluorobenzyl)-1-(3-methoxy-4-(1H-pyrazol-4-yl)phenyl)-1H-1,2,4-triazol-5(4H)-one | 384.2 | A: 1.42, 99.0% B: 1.38, 98.3% | $^1$H NMR (400 MHz, DMSO-d$_6$) δ ppm 8.38 (s, 1 H) 8.06 (s, 2 H) 7.70 (d, J = 8.47 Hz, 1 H) 7.63 (d, J = 2.07 Hz, 1 H) 7.51 (dd, J = 8.41, 2.07 Hz, 1 H) 7.19-7.27 (m, 1 H) 7.10-7.17 (m, 2 H) 4.93 (s, 2 H) 3.90 (s, 3 H); $^{19}$F NMR (377 MHz, DMSO-d$_6$) δ ppm −109.202 |
| 37 | 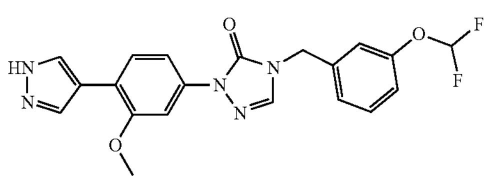 [SMILES: COc1cc(-n2ncn(Cc3cccc(OC(F)F)c3)c2=O)ccc1-c1cn[nH]c1] | 4-(3-(difluoromethoxy)benzyl)-1-(3-methoxy-4-(1H-pyrazol-4-yl)phenyl)-1H-1,2,4-triazol-5(4H)-one | 414.2 | A: 1.46, 99.3% B: 1.41, 99.1% | $^1$H NMR (400 MHz, DMSO-d$_6$) δ ppm 8.39 (s, 1 H) 8.05 (s, 2 H) 7.70 (d, J = 8.47 Hz, 1 H) 7.63 (d, J = 2.01 Hz, 1 H) 7.52 (dd, J = 8.41, 2.07 Hz, 1 H) 7.45 (d, J = 8.16 Hz, 1 H) 7.20-7.26 (m, 2 H) 7.15 (dd, J = 8.03, 2.20 Hz, 1 H) 7.07-7.44 (t, J = 73.6, 1 H) 4.92 (s, 2 H) 3.90 (s, 3 H); $^{19}$F NMR (377 MHz, DMSO-d$_6$) δ ppm −81.944 |
| 38 | 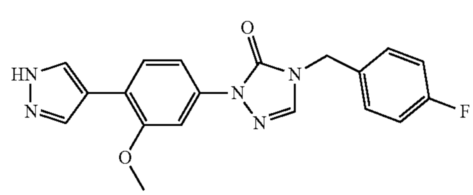 [SMILES: COc1cc(-n2ncn(Cc3ccc(F)cc3)c2=O)ccc1-c1cn[nH]c1] | 4-(4-fluorobenzyl)-1-(3-methoxy-4-(1H-pyrazol-4-yl)phenyl)-1H-1,2,4-triazol-5(4H)-one | 366.2 | A: 1.37, 96.8% B: 1.32, 96.6% | $^1$H NMR (400 MHz, DMSO-d$_6$) δ ppm 8.38 (s, 1 H) 8.06 (s, 2 H) 7.70 (d, J = 8.41 Hz, 1 H) 7.63 (d, J = 2.07 Hz, 1 H) 7.51 (dd, J = 8.47, 2.07 Hz, 1 H) 7.40-7.47 (m, 2 H) 7.19-7.27 (m, 2 H) 4.89 (s, 2 H) 3.89 (s, 3 H); $^{19}$F NMR (377 MHz, DMSO-d$_6$) δ ppm −74.800, −114.418 |
| 39 | 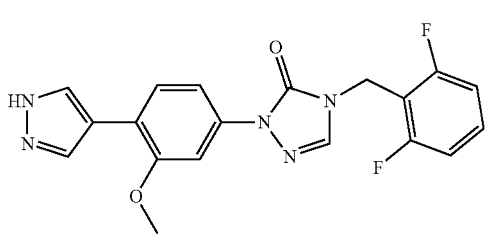 [SMILES: COc1cc(-n2ncn(Cc3c(F)cccc3F)c2=O)ccc1-c1cn[nH]c1] | 4-(2,6-difluorobenzyl)-1-(3-methoxy-4-(1H-pyrazol-4-yl)phenyl)-1H-1,2,4-triazol-5(4H)-one | 384.2 | A: 1.37, 99.0% B: 1.31, 97.6% | $^1$H NMR (400 MHz, DMSO-d$_6$) δ ppm 8.32 (s, 1 H) 8.04 (s, 2 H) 7.68 (d, J = 8.47 Hz, 1 H) 7.60 (d, J = 2.07 Hz, 1 H) 7.42-7.50 (m, 2 H) 7.17 (t, J = 8.13 Hz, 2 H) 4.99 (s, 2 H) 3.88 (s, 3 H); $^{19}$F NMR (377 MHz, DMSO-d$_6$) δ ppm −114.201 |

TABLE 2-continued

| Example | Structure | Name | LCMS (M + H)+ | HPLC Method, RT (min.) & urity | NMR |
|---|---|---|---|---|---|
| 40 | 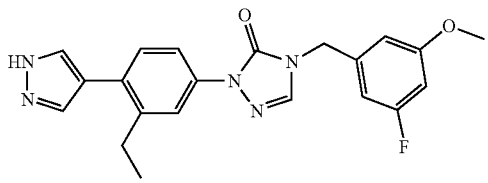 [SMILES: CCc1cc(-n2ncn(Cc3cc(F)cc(OC)c3)c2=O)ccc1-c1cn[nH]c1] | 1-(3-ethyl-4-(1H-pyrazol-4-yl)phenyl)-4-(3-fluoro-5-methoxybenzyl)-1H-1,2,4-triazol-5(4H)-one | 394.2 | A: 1.53, 100% B: 1.49, 99.9% | $^1$H NMR (400 MHz, DMSO-d$_6$) δ ppm 12.98 (br. s., 1 H) 8.36 (s, 1 H) 7.92 (s, 1 H) 7.82 (d, J = 2.26 Hz, 1 H) 7.73 (dd, J = 8.41, 2.32 Hz, 1 H) 7.66 (s, 1 H) 7.39 (d, J = 8.41 Hz, 1 H) 6.73-6.87 (m, 3 H) 4.86 (s, 2 H) 3.77 (s, 3 H) 2.73 (q, J = 7.42 Hz, 2 H) 1.14 (t, J = 7.50 Hz, 3 H); $^{19}$F NMR (377 MHz, DMSO-d$_6$) δ ppm −111.041 |
| 41 | 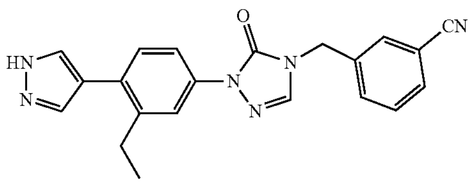 [SMILES: CCc1cc(-n2ncn(Cc3cccc(C#N)c3)c2=O)ccc1-c1cn[nH]c1] | 3-((1-(3-ethyl-4-(1H-pyrazol-4-yl)phenyl)-5-oxo-1H-1,2,4-triazol-4(5H)-yl)methyl)benzonitrile | 371.2 | A: 1.30, 99.7% B: 1.27, 99.4% | $^1$H NMR (400 MHz, DMSO-d$_6$) δ ppm 8.38 (s, 1 H) 7.87-7.90 (m, 1 H) 7.80-7.84 (m, 2 H) 7.79 (br. s., 2 H) 7.69-7.75 (m, 2 H) 7.58-7.65 (m, 1 H) 7.39 (d, J = 8.41 Hz, 1 H) 4.96 (s, 2 H) 2.73 (q, J = 7.47 Hz, 2 H) 1.14 (t, J = 7.50 Hz, 3 H) |
| 42 | 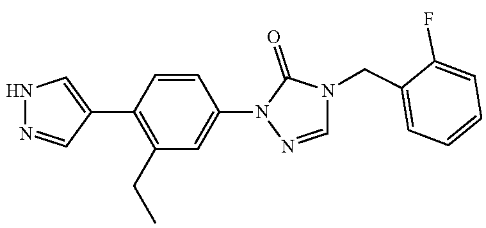 [SMILES: CCc1cc(-n2ncn(Cc3ccccc3F)c2=O)ccc1-c1cn[nH]c1] | 1-(3-ethyl-4-(1H-pyrazol-4-yl)phenyl)-4-(2-fluorobenzyl)-1H-1,2,4-triazol-5(4H)-one | 364.2 | A: 1.46, 97.9% B: 1.43, 99.3% | $^1$H NMR (400 MHz, DMSO-d$_6$) δ ppm 12.99 (br. s., 1 H) 8.32 (s, 1 H) 7.91 (s, 1 H) 7.82 (d, J = 2.26 Hz, 1 H) 7.72 (dd, J = 8.44, 2.35 Hz, 1 H) 7.66 (s, 1 H) 7.36-7.45 (m, 3 H) 7.21-7.30 (m, 2 H) 4.96 (s, 2 H) 2.73 (q, J = 7.53 Hz, 2 H) 1.14 (t, J = 7.50 Hz, 3 H); $^{19}$F NMR (377 MHz, DMSO-d$_6$) δ ppm −118.118 |
| 43 | 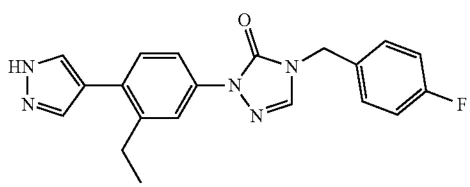 [SMILES: CCc1cc(-n2ncn(Cc3ccc(F)cc3)c2=O)ccc1-c1cn[nH]c1] | 1-(3-ethyl-4-(1H-pyrazol-4-yl)phenyl)-4-(4-fluorobenzyl)-1H-1,2,4-triazol-5(4H)-one | 364.2 | A: 1.46, 98.5% B: 1.43, 99.7% | $^1$H NMR (400 MHz, DMSO-d$_6$) δ ppm 12.99 (br. s., 1 H) 8.36 (s, 1 H) 7.91 (s, 1 H) 7.82 (d, J = 2.26 Hz, 1 H) 7.72 (dd, J = 8.44, 2.35 Hz, 1 H) 7.66 (s, 1 H) 7.41-7.47 (m, 2 H) 7.39 (d, J = 8.41 Hz, 1 H) 7.17-7.27 (m, 2 H) 4.88 (s, 2 H) 2.73 (q, J = 7.47 Hz, 2 H) 1.14 (t, J = 7.50 Hz, 3 H); $^{19}$F NMR (377 MHz, DMSO-d$_6$) δ ppm −114.432 |
| 44 | 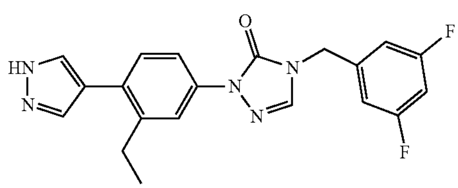 [SMILES: CCc1cc(-n2ncn(Cc3cc(F)cc(F)c3)c2=O)ccc1-c1cn[nH]c1] | 4-(3,5-difluorobenzyl)-1-(3-ethyl-4-(1H-pyrazol-4-yl)phenyl)-1H-1,2,4-triazol-5(4H)-one | 382.2 | A: 1.52, 98.0% B: 1.49, 97.7% | $^1$H NMR (400 MHz, DMSO-d$_6$) δ ppm 8.37 (s, 1 H) 7.82 (d, J = 2.26 Hz, 1 H) 7.79 (br. s., 2 H) 7.73 (dd, J = 8.41, 2.32 Hz, 1 H) 7.40 (d, J = 8.41 Hz, 1 H) 7.23 (tt, J = 9.39, 2.35 Hz, 1 H) 7.13 (dd, J = 8.35, 2.26 Hz, 2 H) 4.92 (s, 2 H) 2.73 (q, J = 7.42 Hz, 2 H) 1.14 (t, J = 7.53 Hz, 3 H); $^{19}$F NMR (377 MHz, DMSO-d$_6$) δ ppm −109.203 |
| 45 | 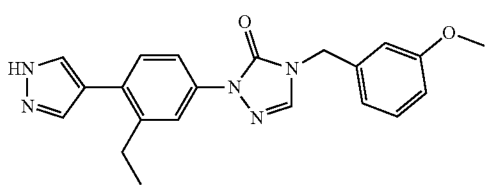 [SMILES: CCc1cc(-n2ncn(Cc3cccc(OC)c3)c2=O)ccc1-c1cn[nH]c1] | 1-(3-ethyl-4-(1H-pyrazol-4-yl)phenyl)-4-(3-methoxybenzyl)-1H-1,2,4-triazol-5(4H)-one | 376.2 | A: 1.44, 94.9% B: 1.42, 94.5% | $^1$H NMR (400 MHz, DMSO-d$_6$) δ ppm 12.98 (br. s., 1 H) 8.36 (s, 1 H) 7.91 (br. s., 1 H) 7.83 (d, J = 2.32 Hz, 1 H) 7.73 (dd, J = 8.41, 2.32 Hz, 1 H) 7.66 (br. s., 1 H) 7.37-7.42 (m, 1 H) 7.31 (t, J = 7.91 Hz, 1 H) 6.86-6.98 (m, 3 H) 4.85 (s, 2 H) 3.76 (s, 3 H) 2.73 (q, J = 7.47 Hz, 2 H) 1.14 (t, J = 7.53 Hz, 3 H) |

TABLE 2-continued

| Example | Structure | Name | LCMS (M + H)+ | HPLC Method, RT (min.) & urity | NMR |
|---|---|---|---|---|---|
| 46 | 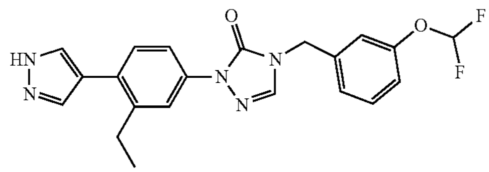 [SMILES: CCc1cc(-n2ncn(Cc3cccc(OC(F)F)c3)c2=O)ccc1-c1cn[nH]c1] | 4-(3-(difluoromethoxy)benzyl)-1-(3-ethyl-4-(1H-pyrazol-4-yl)phenyl)-1H-1,2,4-triazol-5(4H)-one | 412.2 | A: 1.55, 98.4% B: 1.52, 100% | $^1$H NMR (400 MHz, DMSO-d$_6$) δ ppm 12.97 (br. s., 1 H) 8.38 (s, 1 H) 7.91 (s, 1 H) 7.83 (d, J = 2.26 Hz, 1 H) 7.73 (dd, J = 8.41, 2.32 Hz, 1 H) 7.66 (s, 1 H) 7.36-7.49 (m, 2 H) 7.20-7.27 (m, 3 H) 7.05-7.17 (m, 1 H) 4.91 (s, 2 H) 2.73 (q, J = 7.47 Hz, 2 H) 1.14 (t, J = 7.53 Hz, 3 H); $^{19}$F NMR (377 MHz, DMSO-d$_6$) δ ppm −81.934 |
| 47 | 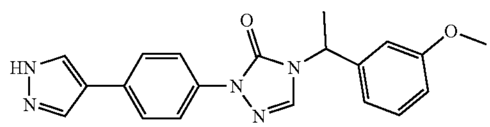 [SMILES: COc1cccc(C(C)n2cnn(-c3ccc(-c4cn[nH]c4)cc3)c2=O)c1] | 1-(4-(1H-pyrazol-4-yl)phenyl)-4-(1-(3-methoxyphenyl)ethyl)-1H-1,2,4-triazol-5(4H)-one (enantiomer 1) | 362.2 | A: 1.37, 99.5% B: 1.27, 98.3% | $^1$H NMR (400 MHz, DMSO-d$_6$) δ ppm 12.90 (br. s., 1 H) 8.55 (s, 1 H) 8.20 (s, 1 H) 7.93 (s, 1 H) 7.81-7.88 (m, 2 H) 7.63-7.73 (m, 2 H) 7.30 (t, J = 7.91 Hz, 1 H) 6.83-6.98 (m, 3 H) 5.25 (q, J = 7.17 Hz, 1 H) 3.76 (s, 3 H) 1.76 (d, J = 7.28 Hz, 3 H); [α]$^{24.9}_D$ = −108° (c 0.1, MeOH) |
| 48 | 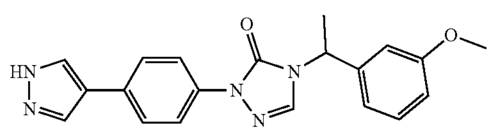 | 1-(4-(1H-pyrazol-4-yl)phenyl)-4-(1-(3-methoxyphenyl)ethyl)-1H-1,2,4-triazol-5(4H)-one (enantiomer 2) | 362.2 | A: 1.47, 99.3% B: 1.42, 98.5% | $^1$H NMR (400 MHz, DMSO-d$_6$) δ ppm 12.90 (br. s., 1 H) 8.55 (s, 1 H) 8.20 (s, 1 H) 7.93 (s, 1 H) 7.81-7.88 (m, 2 H) 7.63-7.73 (m, 2 H) 7.30 (t, J = 7.91 Hz, 1 H) 6.83-6.98 (m, 3 H) 5.25 (q, J = 7.17 Hz, 1 H) 3.76 (s, 3 H) 1.76 (d, J = 7.28 Hz, 3 H); [α]$^{24.9}_D$ = +88° (c 0.1, MeOH) |
| 49 | 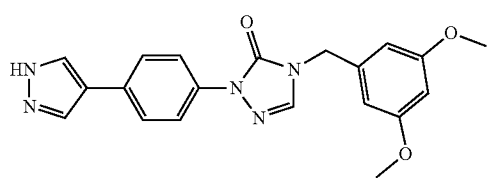 [SMILES: COc1cc(Cn2cnn(-c3ccc(-c4cn[nH]c4)cc3)c2=O)cc(OC)c1] | 1-(4-(1H-pyrazol-4-yl)phenyl)-4-(3,5-dimethoxybenzyl)-1H-1,2,4-triazol-5(4H)-one | 378.2 | A: 1.39, 99.5% B: 1.39, 97.1% | $^1$H NMR (400 MHz, DMSO-d$_6$) δ ppm 12.94 (s, 1 H), 8.35 (s, 1H), 7.93 (br. s., 1H), 7.89 (br. s., 1H), 7.90-7.81 (m, 2H), 7.74-7.65 (m, 2H), 6.53 (d, J = 2.3 Hz, 2H), 6.48-6.44 (m, 1H), 4.80 (s, 2H), 3.74 (s, 6H) |
| 50 | 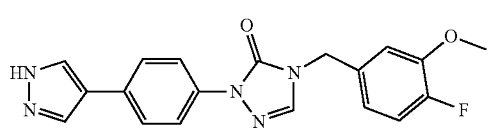 [SMILES: COc1cc(Cn2cnn(-c3ccc(-c4cn[nH]c4)cc3)c2=O)ccc1F] | 4-[(4-fluoro-3-methoxyphenyl)methyl]-1-[4-(1H-pyrazol-4-yl)phenyl]-4,5-dihydro-1H-1,2,4-triazol-5-one | 366.2 | A: 1.42, 96.9% B: 1.40, 98.0% | $^1$H NMR (400 MHz, DMSO-d$_6$) δ ppm 12.94 (s, 1H) 8.35 (s, 1H), 8.20 (s, 1H), 7.93 (s, 1H), 7.89-7.84 (m, 2H), 7.72-7.67 (m, 2H), 7.29-7.18 (m, 2H), 6.92 (ddd, J = 2.0, 4.3, 8.3 Hz, 1H), 4.85 (s, 2H), 3.85 (s, 3H); $^{19}$F NMR (377 MHz, DMSO-d$_6$) δ ppm −136.428 |
| 51 | 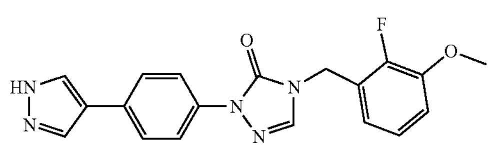 [SMILES: COc1cccc(Cn2cnn(-c3ccc(-c4cn[nH]c4)cc3)c2=O)c1F] | 1-(4-(1H-pyrazol-4-yl)phenyl)-4-(2-fluoro-3-methoxybenzyl)-1H-1,2,4-triazol-5(4H)-one | 366.2 | A: 1.36, 99.4% B: 1.34, 99.2% | $^1$H NMR (400 MHz, DMSO-d$_6$) δ ppm 12.94 (s, 1H), 8.30 (s, 1H), 8.20 (s, 1H), 7.93 (s, 1H), 7.86 (d, J = 8.6 Hz, 2H), 7.69 (d, J = 8.6 Hz, 2H), 7.20-7.07 (m, 2H), 6.94-6.81 (m, 1H), 4.94 (s, 2H), 3.84 (s, 3H); $^{19}$F NMR (377 MHz, DMSO-d$_6$) δ ppm −140.812 |
| 52 | 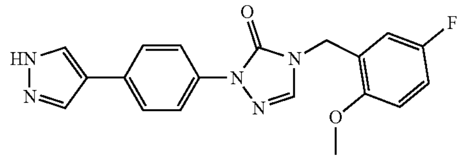 [SMILES: COc1ccc(F)cc1Cn1cnn(-c2ccc(-c3cn[nH]c3)cc2)c1=O] | 1-(4-(1H-pyrazol-4-yl)phenyl)-4-(5-fluoro-2-methoxybenzyl)-1H-1,2,4-triazol-5(4H)-one | 366.2 | A: 1.40, 99.7% B: 1.43, 99.7% | $^1$H NMR (400 MHz, DMSO-d$_6$) δ ppm 12.94 (s, 1H), 8.23 (s, 1H), 8.20 (s, 1H), 7.93 (s, 1H), 7.85 (d, J = 8.7 Hz, 2H), 7.68 (d, J = 8.7 Hz, 2H), 7.15-7.20 (m, 1H), 7.05-7.09 (m, 2H), 4.81 (s, 2H), 3.84 (s, 3H); $^{19}$F NMR (377 MHz, DMSO-d$_6$) δ ppm −123.816 |

TABLE 2-continued

| Example | Structure | Name | LCMS (M + H)+ | HPLC Method, RT (min.) & urity | NMR |
|---|---|---|---|---|---|
| 53 | 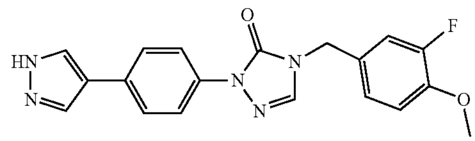 [SMILES: COc1ccc(Cn2cnn(-c3ccc(-c4cn[nH]c4)cc3)c2=O)cc1F] | 1-(4-(1H-pyrazol-4-yl)phenyl)-4-(3-fluoro-4-methoxy-benzyl)-1H-1,2,4-triazol-5(4H)-one | 366.2 | A: 1.32, 100% B: 1.30, 100% | $^1$H NMR (400 MHz, DMSO-d$_6$) δ ppm = 12.96 (s, 1 H), 8.32 (s, 1H), 8.05 (s, 2H), 7.84 (d, J = 8.7 Hz, 2H), 7.67 (d, J = 8.7 Hz, 2H), 7.27-7.30 (m, 1H), 7.15-7.20 (m, 2H), 4.81 (s, 2H), 3.82 (s, 3H); $^{19}$F NMR (377 MHz, DMSO-d$_6$) δ ppm −134.876 |
| 54 | 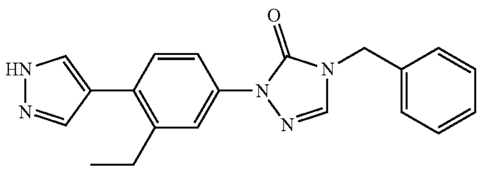 [SMILES: CCc1cc(-n2ncn(Cc3ccccc3)c2=O)ccc1-c1cn[nH]c1] | 4-benzyl-1-(3-ethyl-4-(1H-pyrazol-4-yl)phenyl)-1H-1,2,4-triazol-5(4H)-one | 346.2 | A: 1.43, 97.0% B: 1.40, 99.1% | $^1$H NMR (400 MHz, DMSO-d$_6$) δ ppm 12.98 (br. s., 1 H) 8.37 (s, 1 H) 7.91 (br. s., 1 H) 7.83 (d, J = 2.26 Hz, 1 H) 7.73 (dd, J = 8.44, 2.35 Hz, 1 H) 7.66 (br. s., 1 H) 7.30-7.43 (m, 6 H) 4.89 (s, 2 H) 2.73 (q, J = 7.47 Hz, 2 H) 1.14 (t, J = 7.53 Hz, 3 H) |
| 55 | 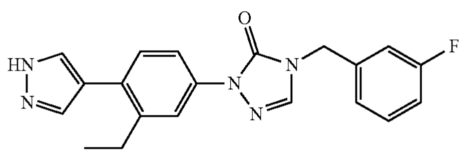 [SMILES: CCc1cc(-n2ncn(Cc3cccc(F)c3)c2=O)ccc1-c1cn[nH]c1] | 1-(3-ethyl-4-(1H-pyrazol-4-yl)phenyl)-4-(3-fluoro-benzyl)-1H-1,2,4-triazol-5(4H)-one | 364.2 | A: 1.46, 99.3% B: 1.43, 99.7% | $^1$H NMR (400 MHz, DMSO-d$_6$) δ ppm 12.98 (br. s., 1 H) 8.38 (s, 1 H) 7.92 (s, 1 H) 7.83 (d, J = 2.26 Hz, 1 H) 7.73 (dd, J = 8.41, 2.32 Hz, 1 H) 7.66 (s, 1 H) 7.36-7.49 (m, 2 H) 7.09-7.27 (m, 3 H) 4.91 (s, 2 H) 2.73 (q, J = 7.42 Hz, 2 H) 1.14 (t, J = 7.53 Hz, 3 H); $^{19}$F NMR (377 MHz, DMSO-d$_6$) δ ppm −112.749 |
| 57 | 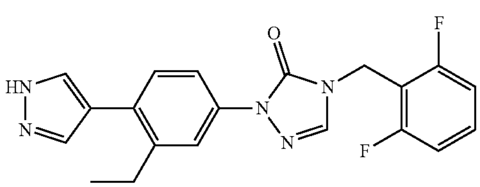 [SMILES: CCc1cc(-n2ncn(Cc3c(F)cccc3F)c2=O)ccc1-c1cn[nH]c1] | 4-(2,6-difluoro-benzyl)-1-(3-ethyl-4-(1H-pyrazol-4-yl)phenyl)-1H-1,2,4-triazol-5(4H)-one | 382.2 | A: 1.45, 99.4% B: 1.42, 99.9% | $^1$H NMR (400 MHz, DMSO-d$_6$) δ ppm 12.98 (br. s., 1 H) 8.30 (s, 1 H) 7.91 (br. s., 1 H) 7.80 (d, J = 2.26 Hz, 1 H) 7.68 (dd, J = 8.41, 2.32 Hz, 1 H) 7.66 (br. s., 1 H) 7.49 (tt, J = 8.42, 6.67 Hz, 1 H) 7.38 (d, J = 8.41 Hz, 1 H) 7.11-7.22 (m, 2 H) 4.98 (s, 2 H) 2.73 (q, J = 7.42 Hz, 2 H) 1.14 (t, J = 7.53 Hz, 3 H); $^{19}$F NMR (377 MHz, DMSO-d$_6$) δ ppm −114.220 |
| 58 | 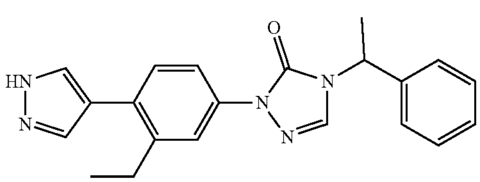 [SMILES: CCc1cc(-n2ncn(C(C)c3ccccc3)c2=O)ccc1-c1cn[nH]c1] | 1-(3-ethyl-4-(1H-pyrazol-4-yl)phenyl)-4-(1-phenylethyl)-1H-1,2,4-triazol-5(4H)-one | 360.2 | A: 1.54, 98.4% B: 1.50, 99.9% | $^1$H NMR (400 MHz, DMSO-d$_6$) δ ppm 8.55 (s, 1 H) 7.82 (d, J = 2.26 Hz, 1 H) 7.78 (s, 2 H) 7.71 (dd, J = 8.41, 2.32 Hz, 1 H) 7.36-7.43 (m, 5 H) 7.27-7.35 (m, 1 H) 5.29 (q, J = 7.28 Hz, 1 H) 2.73 (q, J = 7.42 Hz, 2 H) 1.78 (d, J = 7.28 Hz, 3 H) 1.14 (t, J = 7.53 Hz, 3 H) |

Example 59

4-(4-(1H-pyrazol-4-yl)phenyl)-1-benzyl-3-methyl-1H-1,2,4-triazol-5(4H)-one

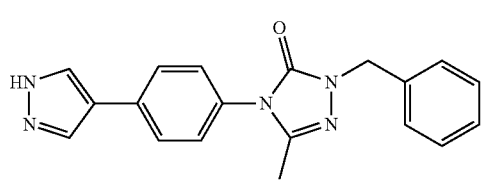 [SMILES: Cc1nn(Cc2ccccc2)c(=O)n1-c1ccc(-c2cn[nH]c2)cc1]

Example 59A

Preparation of 1-benzyl-4-(4-bromophenyl)-3-methyl-1H-1,2,4-triazol-5(4H)-one

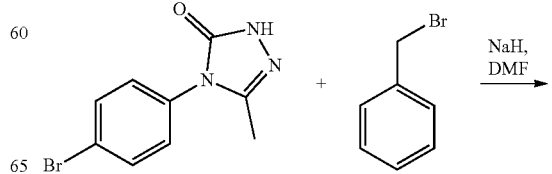

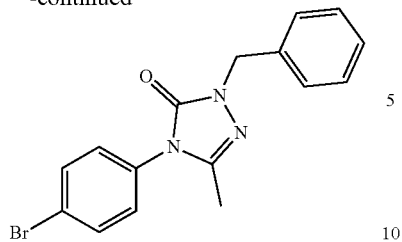

To a solution of 4-(4-bromophenyl)-3-methyl-1H-1,2,4-triazol-5(4H)-one (100 mg, 0.394 mmol) in DMF (3 mL) at 0° C., was added NaH (31.5 mg, 0.787 mmol) to give a brown suspension. Benzyl bromide (81 mg, 0.472 mmol) was added to reaction mixture at 0° C. The reaction mixture was warmed to rt and stirred for 1 h. The mixture was diluted with DCM (200 mL), washed with sat. aq. NH$_4$Cl and brine, dried over Na$_2$SO$_4$, filtered and concentrated. The residue was washed with pet ether (2×30 mL) to give 1-benzyl-4-(4-bromophenyl)-3-methyl-1H-1,2,4-triazol-5(4H)-one (60 mg, 44% yield) as a yellow solid. MS(ESI) m/z: 344.5 (M+H)$^+$; $^1$H NMR (400 MHz, DMSO-d$_6$) δ ppm 7.76-7.73 (d, J=11.6, 1H) 7.46-7.43 (d, J=11.6, 1H) 7.39-7.33 (m, 5H) 4.90 (s, 2H) 2.08 (s, 3H).

Example 59

Preparation of 4-(4-(1H-pyrazol-4-yl)phenyl)-1-benzyl-3-methyl-1H-1,2,4-triazol-5(4H)-one

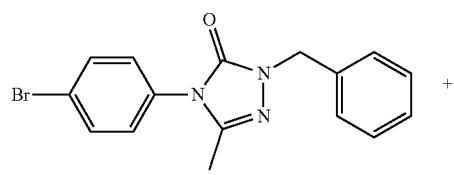

A mixture of 1-benzyl-4-(4-bromophenyl)-3-methyl-1H-1,2,4-triazol-5(4H)-one (60 mg, 0.174 mmol), K$_2$CO$_3$ (72.3 mg, 0.523 mmol), and tert-butyl 4-(4,4,5,5-tetramethyl-1,3,2-dioxaborolan-2-yl)-1H-pyrazole-1-carboxylate (61.5 mg, 0.209 mmol) in DMF (2 mL) and water (0.2 mL) was bubbled with nitrogen for 10 min. 2$^{nd}$ generation XPHOS precatalyst (4.1 mg, 5.2 μmol) was added and the reaction mixture heated at 80° C. for 6 h. Solvent was evaporated. The resultant residue was diluted with DCM (100 mL) and washed with brine, dried over Na$_2$SO$_4$, filtered and concentrated. The crude product was purified by preparative HPLC to afford 4-(4-(1H-pyrazol-4-yl)phenyl)-1-benzyl-3-methyl-1H-1,2,4-triazol-5(4H)-one (24 mg, 41% yield). MS(ESI) m/z: 332.2 (M+H)$^+$; $^1$H NMR (400 MHz, DMSO-d$_6$) δ ppm 12.95 (br. s., 1H) 8.28 (br. s., 1H) 8.00 (br. s., 1H) 7.75-7.77 (dd, J=1.6 Hz, J=1.6 Hz 2H) 7.29-7.46 (m, 7H) 4.91 (s, 2H) 2.09 (s, 3H); HPLC method A: RT=1.20 min, 99.7% purity, method B: RT=1.19 min, 99.7% purity.

The following Examples in Table 3 were made by using the same procedure as shown in Example 59.

TABLE 3

| Example | Structure | Name | LCMS (M + H)$^+$ | LC\MS Method, RT (min.), & Purity | NMR |
|---------|-----------|------|------------------|-----------------------------------|-----|
| 60 | 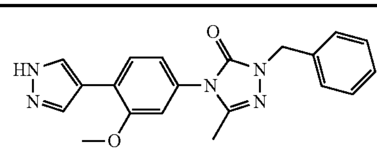 | 1-benzyl-4-(3-methoxy-4-(1H-pyrazol-4-yl)phenyl)-3-methyl-1H-1,2,4-triazol-5(4H)-one | 362.2 | A: 1.26, 99.9% B: 1.24, 99.9% | $^1$H NMR (400 MHz, DMSO-d$_6$) δ ppm 8.10 (s, 2 H) 7.75 (d, J = 8.22 Hz, 1 H) 7.27-7.41 (m, 5 H) 7.15 (d, J = 2.01 Hz, 1 H) 7.02 (dd, J = 8.16, 2.01 Hz, 1 H) 4.91 (s, 2 H) 3.90 (s, 3 H) 2.11 (s, 3 H) |
| 61 | 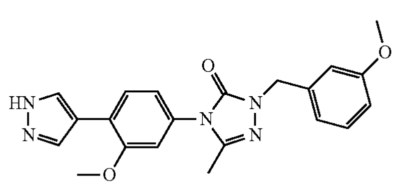 [SMILES: COc1cccc(Cn2nc(C)n(-c3ccc(-c4cn[nH]c4)c(OC)c3)c2=O)c1] | 4-(3-methoxy-4-(1H-pyrazol-4-yl)phenyl)-1-(3-methoxy-benzyl)-3-methyl-1H-1,2,4-triazol-5(4H)-one | 392.3 | A: 1.28, 97.3% B: 1.26, 99.2% | $^1$H NMR (400 MHz, DMSO-d$_6$) δ ppm 8.10 (s, 2 H) 7.75 (d, J = 8.16 Hz, 1 H) 7.29 (t, J = 8.06 Hz, 1 H) 7.15 (d, J = 1.95 Hz, 1 H) 7.02 (dd, J = 8.16, 2.01 Hz, 1 H) 6.85-6.93 (m, 3 H) 4.87 (s, 2 H) 3.90 (s, 3 H) 3.89 (s, 3 H) 2.11 (s, 3 H) |

TABLE 3-continued

| Example | Structure | Name | LCMS (M + H)+ | LC\MS Method, RT (min.), & Purity | NMR |
|---|---|---|---|---|---|
| 62 | 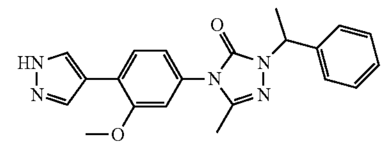 [SMILES: COc1cc(-n2c(C)nn(C(C)c3ccccc3)c2=O)ccc1-c1cn[nH]c1] | 4-(3-methoxy-4-(1H-pyrazol-4-yl)phenyl)-3-methyl-1-(1-phenylethyl)-1H-1,2,4-triazol-5(4H)-one | 376.3 | A: 1.40, 98.8% B: 1.38, 98.3% | $^1$H NMR (400 MHz, DMSO-$d_6$) δ ppm 8.10 (s, 2 H) 7.74 (d, J = 8.16 Hz, 1 H) 7.34-7.44 (m, 4 H) 7.25-7.32 (m, 1 H) 7.12 (d, J = 2.01 Hz, 1 H) 7.00 (dd, J = 8.19, 2.04 Hz, 1 H) 5.41 (q, J = 7.07 Hz, 1 H) 3.90 (s, 3 H) 2.14 (s, 3 H) 1.70 (d, J = 7.15 Hz, 3 H) |
| 63 | 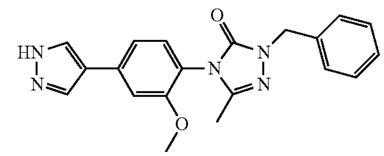 [SMILES: COc1cc(-c2cn[nH]c2)ccc1-n1c(C)nn(Cc2ccccc2)c1=O] | 1-benzyl-4-(2-methoxy-4-(1H-pyrazol-4-yl)phenyl)-3-methyl-1H-1,2,4-triazol-5(4H)-one | 362.2 | A: 1.25, 98.6% B: 1.25, 98.9% | $^1$H NMR (400 MHz, DMSO-$d_6$) δ ppm 8.18 (s, 2 H) 7.43 (s, 1 H) 7.35-7.40 (m, 2 H) 7.27-7.33 (m, 5 H) 4.89 (s, 2 H) 3.90 (s, 3 H) 1.93 (s, 3 H) |
| 64 | 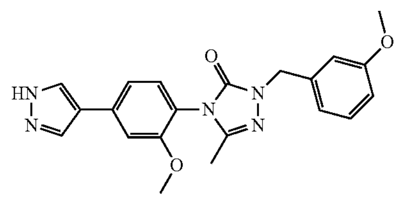 [SMILES: COc1cccc(Cn2nc(C)n(-c3ccc(-c4cn[nH]c4)cc3OC)c2=O)c1] | 4-(2-methoxy-4-(1H-pyrazol-4-yl)phenyl)-1-(3-methoxybenzyl)-3-methyl-1H-1,2,4-triazol-5(4H)-one | 392.2 | A: 1.27, 96.4% B: 1.27, 97.8% | $^1$H NMR (400 MHz, DMSO-$d_6$) δ ppm 8.19 (s, 2 H) 7.43 (s, 1 H) 7.25-7.34 (m, 3 H) 6.83-6.90 (m, 3 H) 4.86 (s, 2 H) 3.86 (s, 3 H) 3.76 (s, 3 H) 1.94 (s, 3 H) |
| 65 | 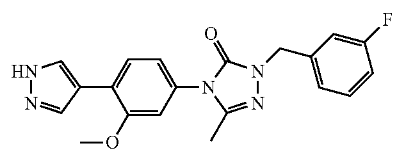 [SMILES: COc1cc(-n2c(C)nn(Cc3cccc(F)c3)c2=O)ccc1-c1cn[nH]c1] | 1-(3-fluorobenzyl)-4-(3-methoxy-4-(1H-pyrazol-4-yl)phenyl)-3-methyl-1H-1,2,4-triazol-5(4H)-one | 380.2 | A: 1.32, 97.1% B: 1.30, 97.0% | $^1$H NMR (400 MHz, DMSO-$d_6$) δ ppm 12.95 (s, 1 H) 8.18 (s, 1 H) 8.01 (s, 1 H) 7.75 (d, J = 8.16 Hz, 1 H) 7.37-7.47 (m, 1 H) 7.11-7.21 (m, 4H) 7.03 (dd, J = 8.16, 2.01 Hz, 1 H) 4.94 (s, 2 H) 3.90 (s, 3 H) 2.12 (s, 3 H); $^{19}$F NMR (377 MHz, DMSO-$d_6$) δ ppm −113.052 |
| 66 | 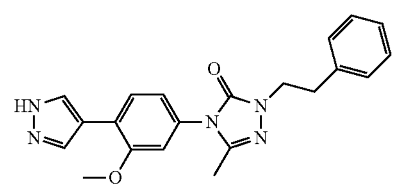 [SMILES: COc1cc(-n2c(C)nn(CCc3ccccc3)c2=O)ccc1-c1cn[nH]c1] | 4-(3-methoxy-4-(1H-pyrazol-4-yl)phenyl)-3-methyl-1-phenethyl-1H-1,2,4-triazol-5(4H)-one | 376.3 | A: 1.34, 95.4% B: 1.32, 95.5% | $^1$H NMR (400 MHz, DMSO-$d_6$) δ ppm 12.95 (br. s., 1 H) 8.18 (br. s., 1 H) 8.00 (br. s., 1 H) 7.73 (d, J = 8.16 Hz, 1 H) 7.29-7.35 (m, 2 H) 7.20-7.27 (m, 3 H) 7.04 (s, 1 H) 6.94 (dd, J = 8.16, 2.01 Hz, 1 H) 3.89-3.95 (t, J = 7.44 Hz, 2 H) 3.88 (s, 3 H) 3.01 (t, J = 7.44 Hz, 2 H) 2.13 (s, 3 H) |
| 67 | 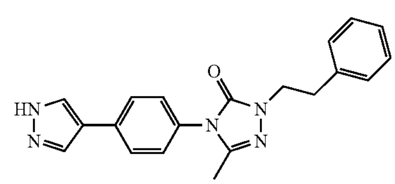 [SMILES: Cc1nn(CCc2ccccc2)c(=O)n1-c1ccc(-c2cn[nH]c2)cc1] | 4-(4-(1H-pyrazol-4-yl)phenyl)-3-methyl-1-phenethyl-1H-1,2,4-triazol-5(4H)-one | 346.2 | A: 1.28, 97.2% B: 1.27, 97.9% | $^1$H NMR (400 MHz, DMSO-$d_6$) δ ppm 8.13 (br. s., 2 H) 8.00 (br. s., 1 H) 7.73-7.75 (d, J = 8.4 Hz, 1 H) 7.29-7.34 (m, 3 H) 7.20-7.24 (m, 4 H) 3.90-3.93 (t, J = 7.2 Hz, 2 H) 2.99-3.03 (t, J = 7.6 Hz, 2 H) 2.11 (s, 3 H) |
| 68 | 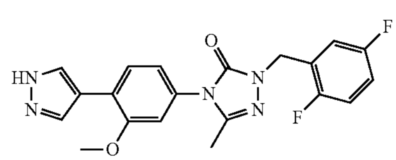 [SMILES: COc1cc(-n2c(C)nn(Cc3cc(F)ccc3F)c2=O)ccc1-c1cn[nH]c1] | 1-(2,5-difluorobenzyl)-4-(3-methoxy-4-(1H-pyrazol-4-yl)phenyl)-3-methyl-1H-1,2,4-triazol-5(4H)-one | 398.2 | A: 1.34, 96.3% B: 1.32, 95.7% | $^1$H NMR (400 MHz, DMSO-$d_6$) δ ppm 12.95 (br. s., 1 H) 8.18 (s, 1 H) 8.02 (s, 1 H) 7.75 (d, J = 8.22 Hz, 1 H) 7.27-7.36 (m, 1 H) 7.19-7.27 (m, 2 H) 7.16 (d, J = 1.94 Hz, 1 H) 7.03 (dd, J = 8.16, 2.01 Hz, 1 H) 4.96 (s, 2 H) 3.89 (s, 3 H) 2.11 (s, 3 H); $^{19}$F NMR (377 MHz, DMSO-$d_6$) δ ppm −118.379 and −123.811 |

TABLE 3-continued

| Example | Structure | Name | LCMS (M + H)+ | LC\MS Method, RT (min.), & Purity | NMR |
|---|---|---|---|---|---|
| 69 | 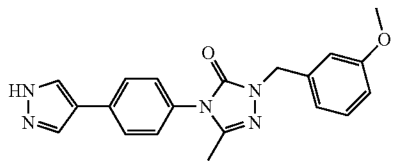 [SMILES: COc1cccc(Cn2nc(C)n(-c3ccc(-c4cn[nH]c4)cc3)c2=O)c1] | 4-(4-(1H-pyrazol-4-yl)phenyl)-1-(3-methoxybenzyl)-3-methyl-1H-1,2,4-triazol-5(4H)-one | 362.2 | A: 1.22, 99.0% B: 1.21, 98.7% | $^1$H NMR (400 MHz, DMSO-d$_6$) δ ppm 8.14 (s, 2 H) 7.71-7.80 (m, 2 H) 7.39-7.47 (m, 2 H) 7.25-7.31 (m, 1 H) 6.84-6.92 (m, 3 H) 4.87 (s, 2 H) 3.75 (s, 3 H) 2.09 (s, 3 H) |
| 70 | 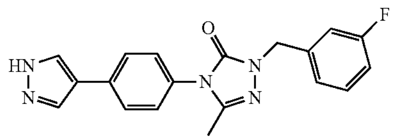 [SMILES: Cc1nn(Cc2cccc(F)c2)c(=O)n1-c1ccc(-c2cn[nH]c2)cc1] | 4-(4-(1H-pyrazol-4-yl)phenyl)-1-(3-fluorobenzyl)-3-methyl-1H-1,2,4-triazol-5(4H)-one | 350.2 | A: 1.26, 100% B: 1.25, 100% | $^1$H NMR (400 MHz, DMSO-d$_6$) δ ppm 8.15 (s, 2 H) 7.70-7.80 (m, 2 H) 7.36-7.49 (m, 3 H) 7.09-7.21 (m, 3 H) 4.94 (s, 2 H) 2.10 (s, 3 H); $^{19}$F NMR (377 MHz, DMSO-d$_6$) δ ppm: −113.048 |
| 71 | 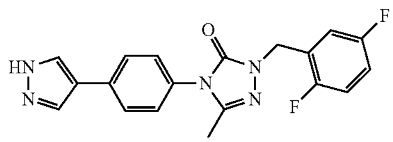 [SMILES: Cc1nn(Cc2cc(F)ccc2F)c(=O)n1-c1ccc(-c2cn[nH]c2)cc1] | 4-(4-(1H-pyrazol-4-yl)phenyl)-1-(2,5-difluorobenzyl)-3-methyl-1H-1,2,4-triazol-5(4H)-one | 368.2 | A: 1.28, 100% B: 1.27, 100% | $^1$H NMR (400 MHz, DMSO-d$_6$) δ ppm 8.14 (s, 2 H) 7.71-7.82 (m, 2 H) 7.40-7.46 (m, 2 H) 7.17-7.35 (m, 3 H) 4.95 (s, 2 H) 2.09 (s, 3 H); $^{19}$F NMR (377 MHz, DMSO-d$_6$) δ ppm −74.539, −118.395, −123.874 |
| 72 | 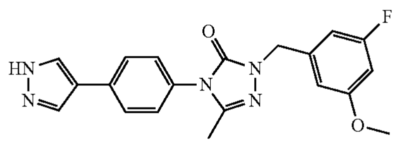 [SMILES: COc1cc(F)cc(Cn2nc(C)n(-c3ccc(-c4cn[nH]c4)cc3)c2=O)c1] | 4-(4-(1H-pyrazol-4-yl)phenyl)-1-(3-fluoro-5-methoxybenzyl)-3-methyl-1H-1,2,4-triazol-5(4H)-one | 380.2 | A: 1.33, 99.9% B: 1.32, 99.8% | $^1$H NMR (400 MHz, DMSO-d$_6$) δ ppm 8.14 (s, 2 H) 7.72-7.80 (m, 2 H) 7.40-7.47 (m, 2 H) 6.62-6.81 (m, 3 H) 4.89 (s, 2 H) 3.77 (s, 3 H) 2.10 (s, 3 H); $^{19}$F NMR (377 MHz, DMSO-d$_6$) δ ppm −111.398 |
| 73 | 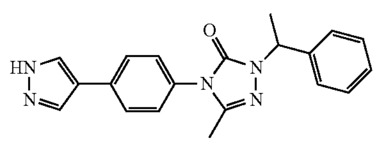 [SMILES: Cc1nn(C(C)c2ccccc2)c(=O)n1-c1ccc(-c2cn[nH]c2)cc1] | 4-(4-(1H-pyrazol-4-yl)phenyl)-3-methyl-1-(1-phenylethyl)-1H-1,2,4-triazol-5(4H)-one | 346.2 | A: 1.35, 100% B: 1.33, 100% | $^1$H NMR (400 MHz, DMSO-d$_6$) δ ppm 8.13 (s, 2 H) 7.71-7.78 (m, 2 H) 7.33-7.44 (m, 6 H) 7.23-7.32 (m, 1 H) 5.40 (q, J = 7.09 Hz, 1 H) 2.12 (s, 3 H) 1.70 (d, J = 7.15 Hz, 3 H) |
| 74 | 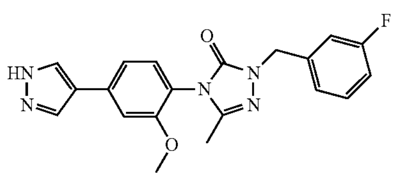 [SMILES: COc1cc(-c2cn[nH]c2)ccc1-n1c(C)nn(Cc2cccc(F)c2)c1=O] | 1-(3-fluorobenzyl)-4-(2-methoxy-4-(1H-pyrazol-4-yl)phenyl)-3-methyl-1H-1,2,4-triazol-5(4H)-one | 380.2 | A: 1.31, 100% B: 1.31, 100% | $^1$H NMR (400 MHz, DMSO-d$_6$) δ ppm 13.03 (s, 1 H) 8.33 (s, 1 H) 8.04 (s, 1 H) 7.40-7.44 (m, 2 H) 7.31-7.35 (m, 2 H) 7.08-7.17 (m, 3 H) 4.93 (s, 2 H) 3.87 (s, 3 H) 1.95 (s, 3 H); $^{19}$F NMR (377 MHz, DMSO-d$_6$) δ ppm −113.067 |
| 75 | 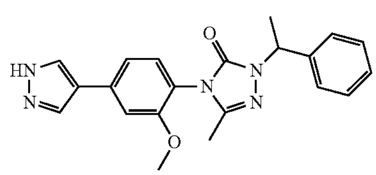 [SMILES: COc1cc(-c2cn[nH]c2)ccc1-n1c(C)nn(C(C)c2ccccc2)c1=O] | 4-(2-methoxy-4-(1H-pyrazol-4-yl)phenyl)-3-methyl-1-(1-phenylethyl)-1H-1,2,4-triazol-5(4H)-one | 376.2 | A: 1.40, 96.6% B: 1.39, 96.7% | $^1$H NMR (400 MHz, DMSO-d$_6$) δ ppm 8.18 (br. s., 2 H) 7.16-7.49 (m, 8 H) 5.37 (q, J = 7.09 Hz, 1 H) 3.82 (s, 3 H) 1.97 (s, 3 H) 1.70 (d, J = 7.15 Hz, 3 H) |
| 76 | 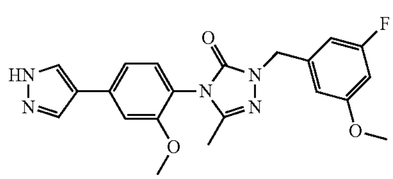 [SMILES: COc1cc(F)cc(Cn2nc(C)n(-c3ccc(-c4cn[nH]c4)cc3OC)c2=O)c1] | 1-(3-fluoro-5-methoxybenzyl)-4-(2-methoxy-4-(1H-pyrazol-4-yl)phenyl)-3-methyl-1H-1,2,4-triazol-5(4H)-one | 410.2 | A: 1.37, 99.4% B: 1.37, 99.7% | $^1$H NMR (400 MHz, DMSO-d$_6$) δ ppm 8.19 (s, 2 H) 7.43 (s, 1 H) 7.32 (s, 2H) 6.77 (dt, J = 11.09, 2.30 Hz, 1 H) 6.71 (s, 1 H) 6.62-6.68 (m, 1 H) 4.88 (s, 2 H) 3.86 (s, 3 H) 3.77 (s, 3 H) 1.95 (s, 3 H); $^{19}$F NMR (377 MHz, DMSO-d$_6$) δ ppm −74.707 and −111.441 |
| 77 | 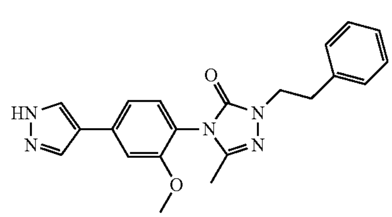 [SMILES: COc1cc(-c2cn[nH]c2)ccc1-n1c(C)nn(CCc2ccccc2)c1=O] | 4-(2-methoxy-4-(1H-pyrazol-4-yl)phenyl)-3-methyl-1-phenethyl-1H-1,2,4-triazol-5(4H)-one | 376.2 | A: 1.33, 95.5% B: 1.34, 98.5% | $^1$H NMR (400 MHz, DMSO-d$_6$) δ ppm 13.00 (s, 1 H) 8.25 (br. s., 1 H) 8.16 (br. s., 1 H) 7.40-7.41 (d, J = 1.6 Hz, 1 H) 7.28-7.32 (m, 3 H) 7.18-7.23 (m, 4 H) 3.87-3.90 (t, J = 7.2 Hz, 2 H) 3.84 (s, 3 H) 2.97-3.01 (t, J = 7.6 Hz, 2 H) 1.95 (s, 3 H) |

TABLE 3-continued

| Example | Structure | Name | LCMS (M + H)+ | LC\MS Method, RT (min.), & Purity | NMR |
|---|---|---|---|---|---|
| 78 | 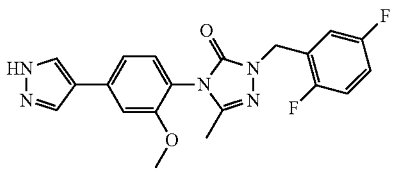 | 1-(2,5-difluorobenzyl)-4-(2-methoxy-4-(1H-pyrazol-4-yl)phenyl)-3-methyl-1H-1,2,4-triazol-5(4H)-one | 398.2 | A: 1.34, 99.3% B: 1.31, 99.5% | $^1$H NMR (400 MHz, DMSO-d$_6$) δ ppm 8.20 (s, 2 H) 7.44 (s, 1 H) 7.29-7.36 (m, 3 H) 7.20-7.28 (m, 1 H) 7.11 (ddd, J = 8.75, 5.62, 3.01 Hz, 1 H) 4.96 (s, 2 H) 3.87 (, 3 H) 1.95 (s, 3 H); $^{19}$F NMR (377 MHz, DMSO-d$_6$) δ ppm −118.654 and −124.129 |

Example 79

1-(4-(1H-pyrazol-4-yl)phenyl)-4-benzyl-3-methyl-1H-1,2,4-triazol-5(4H)-one

Example 79

Preparation 1-(4-(1H-pyrazol-4-yl)phenyl)-4-benzyl-3-methyl-1H-1,2,4-triazol-5(4H)-one

Example 79a

Preparation of 4-benzyl-1-(4-bromophenyl)-3-methyl-1H-1,2,4-triazol-5(4H)-one

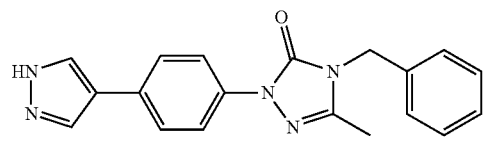 [SMILES: Cc1nn(-c2ccc(-c3cn[nH]c3)cc2)c(=O)n1Cc1ccccc1]

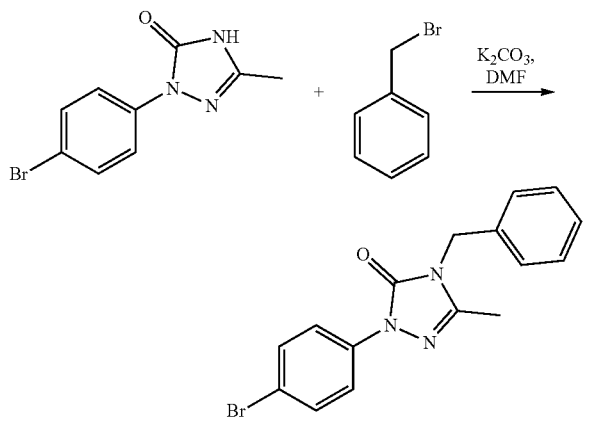

To a suspension of 1-(4-bromophenyl)-3-methyl-1H-1,2,4-triazol-5(4H)-one (100 mg, 0.394 mmol) and K$_2$CO$_3$ (163 mg, 1.18 mmol) in DMF (3 mL) was added benzyl bromide (81 mg, 0.47 mmol). The mixture was stirred at rt for 3 h. The reaction mixture was diluted with DCM (200 mL), washed with sat. aq. NH$_4$Cl and brine, dried over Na$_2$SO$_4$, filtered and concentrated. The resultant residue was washed with pet. ether (2×30 mL) to afford 4-benzyl-1-(4-bromophenyl)-3-methyl-1H-1,2,4-triazol-5(4H)-one (55 mg, 41% yield) as white solid. MS(ESI) m/z: 344.0 (M+H)+; $^1$H NMR (400 MHz, DMSO-d$_6$) δ ppm 7.91-7.89 (m, 2H) 7.66-7.64 (m, 2H) 7.39-7.31 (m, 3H) 4.92 (s, 2H) 2.22 (s, 3H).

A mixture of 4-benzyl-1-(4-bromophenyl)-3-methyl-1H-1,2,4-triazol-5(4H)-one (55 mg, 0.160 mmol), K$_2$CO$_3$ (66.3 mg, 0.479 mmol), and tert-butyl 4-(4,4,5,5-tetramethyl-1,3,2-dioxaborolan-2-yl)-1H-pyrazole-1-carboxylate (56.4 mg, 0.192 mmol) in DMF (2 mL) and water (0.2 mL) was flushed with nitrogen for 10 min. 2$^{nd}$ generation XPHOS precatalyst (3.8 mg, 4.8 µmol) was added and the reaction mixture heated at 80° C. for 6 h. Solvent was evaporated to afford a residue, which was diluted with DCM (100 mL) and washed with brine. The organic layer was dried over Na$_2$SO$_4$, filtered and concentrated. The crude compound was purified by preparative HPLC to afford 1-(4-(1H-pyrazol-4-yl)phenyl)-4-benzyl-3-methyl-1H-1,2,4-triazol-5(4H)-one (10 mg, 19% yield). MS(ESI) m/z: 332.2 (M+H)+; $^1$H NMR (400 MHz, DMSO-d$_6$) δ ppm 12.93 (br. s., 1H) 8.19 (br. s., 1H) 7.92 (br. s., 1H) 7.84-7.90 (m, 2H) 7.65-7.72 (m, 2H) 7.36-7.42 (m, 2H) 7.27-7.35 (m, 3H) 4.92 (s, 2H) 2.22 (s, 3H); HPLC method A: RT=1.37 min, 99.8% purity, method B: RT=1.31 min, 100% purity.

The following Examples in Table 4 were made by using the same procedure as shown in Example 79.

TABLE 4

| Example | Structure | Name | LCMS (M + H)+ | LC\MS Method, RT (min.), & Purity | NMR |
|---|---|---|---|---|---|
| 80 | 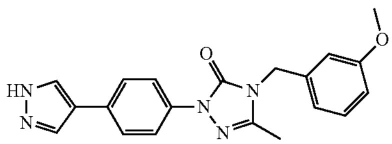 [SMILES: COc1cccc(Cn2c(C)nn(-c3ccc(-c4cn[nH]c4)cc3)c2=O)c1] | 1-(4-(1H-pyrazol-4-yl)phenyl)-4-(3-methoxybenzyl)-3-methyl-1H-1,2,4-triazol-5(4H)-one | 362.2 | A: 1.39, 99.2% B: 1.33, 99.2% | $^1$H NMR (400 MHz, DMSO-$d_6$) δ ppm 12.94 (br. s., 1 H) 8.19 (s, 1 H) 7.92 (s, 1 H) 7.84-7.90 (m, 2 H) 7.65-7.73 (m, 2 H) 7.26-7.33 (m, 1 H) 6.87-6.92 (m, 2 H) 6.85 (d, J = 7.84 Hz, 1 H) 4.88 (s, 2 H) 3.32 (s, 3 H) 2.22 (s, 3 H) |
| 81 | 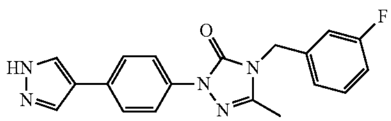 [SMILES: Cc1nn(-c2ccc(-c3cn[nH]c3)cc2)c(=O)n1Cc1cccc(F)c1] | 1-(4-(1H-pyrazol-4-yl)phenyl)-4-(3-fluorobenzyl)-3-methyl-1H-1,2,4-triazol-5(4H)-one | 350.2 | A: 1.40, 94.7% B: 1.35, 95.1% | $^1$H NMR (400 MHz, DMSO-$d_6$) δ ppm 12.94 (br. s., 1 H) 8.19 (br. s., 1 H) 7.93 (br. s., 1 H) 7.84-7.90 (m, 2 H) 7.63-7.73 (m, 2 H) 7.38-7.47 (m, 1 H) 7.11-7.22 (m, 3 H) 4.93 (s, 2H) 2.24 (s, 3 H); $^{19}$F NMR (377 MHz, DMSO-$d_6$) δ ppm −112.613 |
| 82 | 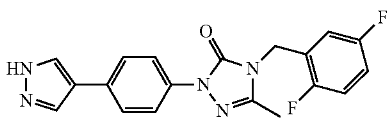 [SMILES: Cc1nn(-c2ccc(-c3cn[nH]c3)cc2)c(=O)n1Cc1cc(F)ccc1F] | 1-(4-(1H-pyrazol-4-yl)phenyl)-4-(2,5-difluorobenzyl)-3-methyl-1H-1,2,4-triazol-5(4H)-one | 368.2 | A: 1.43, 98.9% B: 1.37, 98.9% | $^1$H NMR (400 MHz, DMSO-$d_6$) δ ppm 12.93 (br. s., 1 H) 8.19 (br. s., 1 H) 7.92 (br. s., 1 H) 7.83-7.89 (m, 2 H) 7.65-7.71 (m, 2 H) 7.29-7.37 (m, 1 H) 7.17-7.28 (m, 2 H) 4.95 (s, 2 H) 2.26 (s, 3 H); $^{19}$F NMR (377 MHz, DMSO-$d_6$) δ ppm −118.032 and −123.478 |
| 83 | 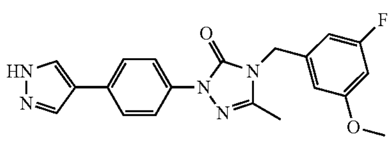 [SMILES: COc1cc(F)cc(Cn2c(C)nn(-c3ccc(-c4cn[nH]c4)cc3)c2=O)c1] | 1-(4-(1H-pyrazol-4-yl)phenyl)-4-(3-fluoro-5-methoxybenzyl)-3-methyl-1H-1,2,4-triazol-5(4H)-one | 380.2 | A: 1.46, 98.9% B: 1.41, 98.8% | $^1$H NMR (400 MHz, DMSO-$d_6$) δ ppm 12.94 (br. s., 1 H) 8.19 (br. s., 1 H) 7.92 (br. s., 1 H) 7.84-7.90 (m, 2 H) 7.66-7.71 (m, 2 H) 6.77-6.83 (m, 1 H) 6.68-6.75 (m, 2 H) 4.88 (s, 2 H) 3.76 (s, 3 H) 2.23 (s, 3 H); $^{19}$F NMR (377 MHz, DMSO-$d_6$) δ ppm −110.848 |
| 84 | 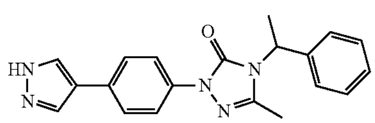 [SMILES: Cc1nn(-c2ccc(-c3cn[nH]c3)cc2)c(=O)n1C(C)c1ccccc1] | 1-(4-(1H-pyrazol-4-yl)phenyl)-3-methyl-4-(1-phenylethyl)-1H-1,2,4-triazol-5(4H)-one | 346.2 | A: 1.49, 99.2% B: 1.44, 98.6% | $^1$H NMR (400 MHz, DMSO-$d_6$) δ ppm 12.90 (br. s., 1 H) 8.05 (br. s., 2 H) 7.83-7.90 (m, 2 H) 7.64-7.71 (m, 2 H) 7.36-7.43 (m, 4 H) 7.28-7.36 (m, 1 H) 5.43 (q, J = 7.19 Hz, 1 H) 2.16 (s, 3 H) 1.85 (d, J = 7.22 Hz, 3 H) |
| 85 | 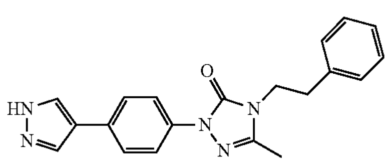 [SMILES: Cc1nn(-c2ccc(-c3cn[nH]c3)cc2)c(=O)n1CCc1ccccc1] | 1-(4-(1H-pyrazol-4-yl)phenyl)-3-methyl-4-phenethyl-1H-1,2,4-triazol-5(4H)-one | 346.2 | A: 1.41, 100% B: 1.37, 99.8% | $^1$H NMR (400 MHz, DMSO-$d_6$) δ ppm 8.07 (s, 2 H) 7.82-7.90 (m, 2 H) 7.65-7.71 (m, 2 H) 7.30-7.36 (m, 2 H) 7.19-7.28 (m, 3 H) 3.88 (t, J = 7.09 Hz, 2H) 2.96 (t, J = 7.03 Hz, 2 H) 1.96 (s, 3 H) |
| 86 | 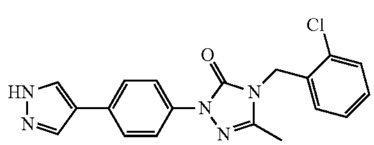 | 1-(4-(1H-pyrazol-4-yl)phenyl)-4-(2-chlorobenzyl)-3-methyl-1H-1,2,4-triazol-5(4H)-one | 366.2 | A: 1.52, 97.6% B: 1.49, 95.1% | $^1$H NMR (400 MHz, DMSO-$d_6$) δ ppm 12.94 (s, 1 H) 8.17 (br. s., 2 H) 7.83-7.93 (m, 2 H) 7.64-7.73 (m, 2 H) 7.47-7.58 (m, 1 H) 7.29-7.41 (m, 2 H) 7.06-7.19 (m, 1 H) 4.99 (s, 2 H) 2.21 (s, 3 H) |
| 87 | 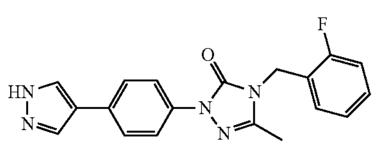 [SMILES: Cc1nn(-c2ccc(-c3cn[nH]c3)cc2)c(=O)n1Cc1ccccc1F] | 2-(4-(1H-pyrazol-4-yl)phenyl)-4-(2-fluorobenzyl)-5-methyl-2,4-dihydro-3H-1,2,4-triazol-3-one | 350.2 | A: 1.38, 98.9% B: 1.37, 100% | $^1$H NMR (400 MHz, DMSO-$d_6$) d ppm 12.93 (br. s., 1 H) 8.19 (s, 1 H) 7.92 (s, 1 H) 7.83-7.89 (m, 2 H) 7.65-7.71 (m, 2 H) 7.36-7.43 (m, 1 H) 7.17-7.34 (m, 3 H) 4.96 (s, 2 H) 2.24 (s, 3 H) |
| 88 | 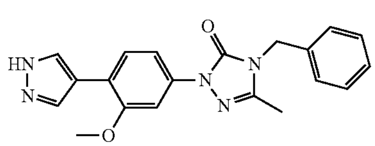 [SMILES: COc1cc(-n2nc(C)n(Cc3ccccc3)c2=O)ccc1-c1cn[nH]c1] | 4-benzyl-1-(3-methoxy-4-(1H-pyrazol-4-yl)phenyl)-3-methyl-1H-1,2,4-triazol-5(4H)-one | 362.2 | A: 1.39, 99.5% B: 1.39, 99.5% | $^1$H NMR (400 MHz, DMSO-$d_6$) δ ppm 8.06 (s, 2 H) 7.70 (d, J = 8.47 Hz, 1 H) 7.65 (d, J = 2.01 Hz, 1 H) 7.55 (dd, J = 8.41, 2.07 Hz, 1 H) 7.37-7.43 (m, 2 H) 7.30-7.36 (m, 3 H) 4.93 (s, 2 H) 3.91 (s, 3 H) 2.25 (s, 3 H) |

TABLE 4-continued

| Example | Structure | Name | LCMS (M + H)+ | LC\MS Method, RT (min.), & Purity | NMR |
|---|---|---|---|---|---|
| 89 | 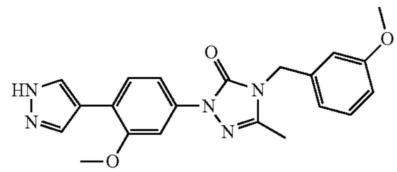 [SMILES: COc1cccc(Cn2c(C)nn(-c3ccc(-c4cn[nH]c4)c(OC)c3)c2=O)c1] | 1-(3-methoxy-4-(1H-pyrazol-4-yl)phenyl)-4-(3-methoxybenzyl)-3-methyl-1H-1,2,4-triazol-5(4H)-one | 392.2 | A: 1.41, 99.3% B: 1.40, 99.3% | $^1$H NMR (400 MHz, DMSO-d$_6$) δ ppm 8.05 (s, 2 H) 7.70 (d, J = 8.41 Hz, 1 H) 7.64 (d, J = 2.07 Hz, 1 H) 7.55 (dd, J = 8.41, 2.07 Hz, 1 H) 7.27-7.35 (m, 1 H) 6.89-6.93 (m, 2 H) 6.86 (d, J = 7.91 Hz, 1 H) 4.90 (s, 2 H) 3.91 (s, 3 H) 3.74 (s, 3 H) 2.25 (s, 3 H) |
| 90 | 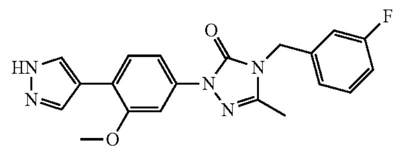 [SMILES: COc1cc(-n2nc(C)n(Cc3cccc(F)c3)c2=O)ccc1-c1cn[nH]c1] | 4-(3-fluorobenzyl)-1-(3-methoxy-4-(1H-pyrazol-4-yl)phenyl)-3-methyl-1H-1,2,4-triazol-5(4H)-one | 380.2 | A: 1.42, 98.9% B: 1.41, 99.7% | $^1$H NMR (400 MHz, DMSO-d$_6$) δ ppm 12.79 (br. s., 1 H) 8.05 (s, 2 H) 7.70 (d, J = 8.47 Hz, 1 H) 7.65 (d, J = 2.07 Hz, 1 H) 7.55 (dd, J = 8.44, 2.04 Hz, 1 H) 7.41-7.49 (m, 1 H) 7.13-7.22 (m, 3 H) 4.95 (s, 2 H) 3.91 (s, 3 H) 2.26 (s, 3 H); $^{19}$F NMR (377 MHz, DMSO-d$_6$) δ ppm −112.862 |
| 91 | 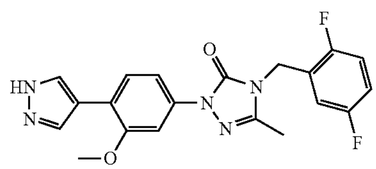 [SMILES: COc1cc(-n2nc(C)n(Cc3cc(F)ccc3F)c2=O)ccc1-c1cn[nH]c1] | 4-(2,5-difluorobenzyl)-1-(3-methoxy-4-(1H-pyrazol-4-yl)phenyl)-3-methyl-1H-1,2,4-triazol-5(4H)-one | 398.2 | A: 1.45, 98.8% B: 1.43, 99.0% | $^1$H NMR (400 MHz, DMSO-d$_6$) δ ppm 12.79 (br. s., 1 H) 8.05 (br. s., 2 H) 7.69 (d, J = 8.47 Hz, 1 H) 7.63 (d, J = 2.07 Hz, 1 H) 7.52 (dd, J = 8.47, 2.07 Hz, 1 H) 7.30-7.38 (m, 1 H) 7.19-7.29 (m, 2 H) 4.97 (s, 2 H) 3.90 (s, 3 H) 2.29 (s, 3 H); $^{19}$F NMR (377 MHz, DMSO-d$_6$) δ ppm −118.274, −123.711 |
| 92 | 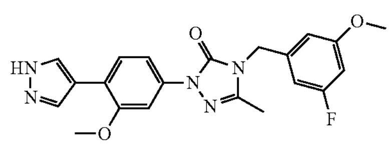 [SMILES: COc1cc(F)cc(Cn2c(C)nn(-c3ccc(-c4cn[nH]c4)c(OC)c3)c2=O)c1] | 4-(3-fluoro-5-methoxybenzyl)-1-(3-methoxy-4-(1H-pyrazol-4-yl)phenyl)-3-methyl-1H-1,2,4-triazol-5(4H)-one | 410.2 | A: 1.48, 98.3% B: 1.47, 98.6% | $^1$H NMR (400 MHz, DMSO-d$_6$) δ ppm 12.79 (br. s., 1 H) 8.05 (s, 2 H) 7.70 (d, J = 8.47 Hz, 1 H) 7.64 (d, J = 2.01 Hz, 1 H) 7.55 (dd, J = 8.44, 2.04 Hz, 1 H) 6.81 (dt, J = 11.06, 2.28 Hz, 1 H) 6.69-6.76 (m, 2 H) 4.90 (s, 2 H) 3.91 (s, 3 H) 3.76 (s, 3 H) 2.26 (s, 3 H); $^{19}$F NMR (377 MHz, DMSO-d$_6$) δ ppm −111.087 |
| 93 | 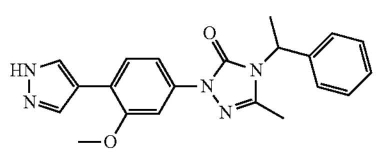 [SMILES: COc1cc(-n2nc(C)n(C(C)c3ccccc3)c2=O)ccc1-c1cn[nH]c1] | 1-(3-methoxy-4-(1H-pyrazol-4-yl)phenyl)-3-methyl-4-(1-phenylethyl)-1H-1,2,4-triazol-5(4H)-one | 376.2 | A: 1.52, 95.0% B: 1.50, 95.8% | $^1$H NMR (400 MHz, DMSO-d$_6$) δ ppm 8.05 (s, 2 H) 7.68 (d, J = 8.47 Hz, 1 H) 7.64 (d, J = 2.01 Hz, 1 H) 7.52 (dd, J = 8.41, 2.07 Hz, 1 H) 7.42 (s, 4 H) 7.31-7.37 (m, 1 H) 5.45 (q, J = 7.17 Hz, 1 H) ) 3.88 (s, 3 H) 2.19 (s, 3 H) 1.88 (s, 3 H) |
| 94 | 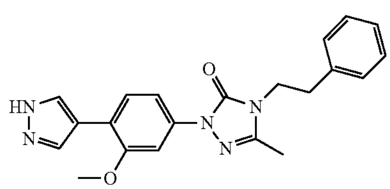 [SMILES: COc1cc(-n2nc(C)n(CCc3ccccc3)c2=O)ccc1-c1cn[nH]c1] | 1-(3-methoxy-4-(1H-pyrazol-4-yl)phenyl)-3-methyl-4-phenethyl-1H-1,2,4-triazol-5(4H)-one | 376.2 | A: 1.45, 94.8% B: 1.43, 97.8% | $^1$H NMR (400 MHz, DMSO-d$_6$) δ ppm 8.05 (s, 2 H) 7.69 (s, 1 H) 7.63 (d, J = 2.01 Hz, 1 H) 7.53 (dd, J = 8.47, 2.07 Hz, 1 H) 7.30-7.36 (m, 2 H) 7.21-7.28 (m, 3 H) 3.85-3.93 (m, 5 H) 2.97 (t, J = 7.06 Hz, 2 H) 1.97 (s, 3 H) |
| 95 | 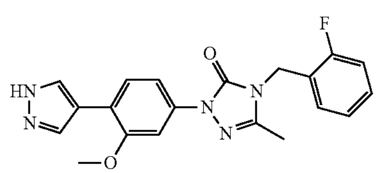 [SMILES: COc1cc(-n2nc(C)n(Cc3ccccc3F)c2=O)ccc1-c1cn[nH]c1] | 4-(2-fluorobenzyl)-1-(3-methoxy-4-(1H-pyrazol-4-yl)phenyl)-3-methyl-1H-1,2,4-triazol-5(4H)-one | 380.2 | A: 1.43, 95.8% B: 1.42, 94.9% | $^1$H NMR (400 MHz, DMSO-d$_6$) δ ppm 12.79 (br. s., 1 H) 8.05 (s, 2 H) 7.67-7.71 (m, 1 H) 7.64 (d, J = 2.07 Hz, 1 H) 7.53 (dd, J = 8.47, 2.07 Hz, 1 H) 7.38-7.45 (m, 1 H) 7.33 (td, J = 7.70, 1.66 Hz, 1 H) 7.26-7.30 (m, 1 H) 7.20-7.26 (m, 1 H) 4.98 (s, 2 H) 3.90 (s, 3 H) 2.27 (s, 3 H); $^{19}$F NMR (377 MHz, DMSO-d$_6$) δ ppm −111.087 |
| 96 | 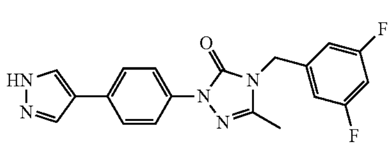 [SMILES: Cc1nn(-c2ccc(-c3cn[nH]c3)cc2)c(=O)n1Cc1cc(F)cc(F)c1] | 1-(4-(1H-pyrazol-4-yl)phenyl)-4-(3,5-difluorobenzyl)-3-methyl-1H-1,2,4-triazol-5(4H)-one | 368.2 | A: 1.45, 99.0% B: 1.41, 99.2% | $^1$H NMR (400 MHz, DMSO-d$_6$) δ ppm 12.90 (br. s., 1 H) 8.15 (br. s., 2 H) 7.84-7.92 (m, 2 H) 7.64-7.72 (m, 2 H) 7.21 (tt, J = 9.39, 2.35 Hz, 1 H) 7.02-7.11 (m, 2 H) 4.94 (s, 2 H) 2.25 (s, 3 H); $^{19}$F NMR (377 MHz, DMSO-d$_6$) δ ppm −109.048 |

TABLE 4-continued

| Example | Structure | Name | LCMS (M + H)+ | LC\MS Method, RT (min.), & Purity | NMR |
|---|---|---|---|---|---|
| 97 | 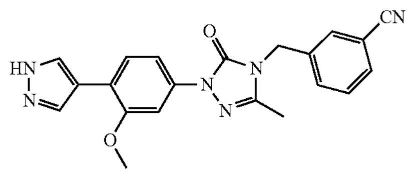 [SMILES: COc1cc(-n2nc(C)n(Cc3cccc(C#N)c3)c2=O)ccc1-c1cn[nH]c1] | 3-((1-(3-methoxy-4-(1H-pyrazol-4-yl)phenyl)-3-methyl-5-oxo-1H-1,2,4-triazol-4(5H)-yl)methyl)benzonitrile | 387.2 | A: 1.28, 98.2% B: 1.22, 98.5% | $^1$H NMR (400 MHz, DMSO-d$_6$) δ ppm 12.88 (br. s., 1 H) 8.081 (br. s., 1 H) 8.04 (br. s., 1 H) 7.79-7.86 (m, 2 H) 7.66-7.72 (m, 2H) 7.57-7.64 (m, 2 H) 7.53 (dd, J = 8.44, 2.10 Hz, 1 H) 4.98 (s, 2 H) 3.89 (s, 3 H) 2.26 (s, 3 H) |
| 98 | 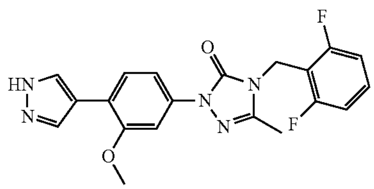 [SMILES: COc1cc(-n2nc(C)n(Cc3c(F)cccc3F)c2=O)ccc1-c1cn[nH]c1] | 4-(2,6-difluorobenzyl)-1-(3-methoxy-4-(1H-pyrazol-4-yl)phenyl)-3-methyl-1H-1,2,4-triazol-5(4H)-one | 398.2 | A: 1.43, 96.1% B: 1.38, 96.2% | $^1$H NMR (400 MHz, DMSO-d$_6$) δ ppm 12.85 (br. s., 1 H) 8.13 (br. s., 1 H) 7.96 (br. s., 1 H) 7.66 (d, J = 8.47 Hz, 1 H) 7.59 (d, J = 2.07 Hz, 1 H) 7.44-7.51 (m, 2 H) 7.11-7.21 (m, 2 H) 4.98 (s, 2 H) 3.88 (s, 3 H) 2.29 (s, 3 H); $^{19}$F NMR (377 MHz, DMSO-d$_6$) δ ppm −114.249 |
| 99 | 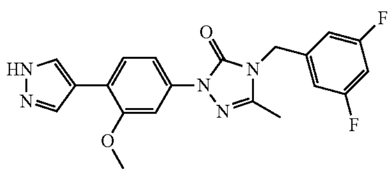 [SMILES: COc1cc(-n2nc(C)n(Cc3cc(F)cc(F)c3)c2=O)ccc1-c1cn[nH]c1] | 4-(3,5-difluorobenzyl)-1-(3-methoxy-4-(1H-pyrazol-4-yl)phenyl)-3-methyl-1H-1,2,4-triazol-5(4H)-one | 398.2 | A: 1.50, 98.6% B: 1.45, 100% | $^1$H NMR (400 MHz, DMSO-d$_6$) δ ppm 8.05 (s, 2 H) 7.69 (d, J = 8.47 Hz, 1 H) 7.63 (d, J = 2.07 Hz, 1 H) 7.53 (dd, J = 8 47, 2 07 Hz, 1 H) 7.17-7.26 (m, 1 H) 7.08 (dd, J = 8.35, 2.20 Hz, 2 H) 4.94 (s, 2 H) 3.89 (s, 3 H) 2.26 (s, 3 H); $^{19}$F NMR (377 MHz, DMSO-d$_6$) δ ppm −109.039 |
| 100 | 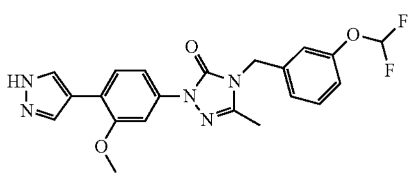 [SMILES: COc1cc(-n2nc(C)n(Cc3cccc(OC(F)F)c3)c2=O)ccc1-c1cn[nH]c1] | 4-(3-(difluoromethoxy)benzyl)-1-(3-methoxy-4-(1H-pyrazol-4-yl)phenyl)-3-methyl-1H-1,2,4-triazol-5(4H)-one | 428.2 | A: 1.52, 96.6% B: 1.48, 96.9% | $^1$H NMR (400 MHz, DMSO-d$_6$) δ ppm 8.05 (s, 2 H) 7.69 (d, J = 8.47 Hz, 1 H) 7.63 (d, J = 2.01 Hz, 1 H) 7.54 (dd, J = 8.47, 2.07 Hz, 1 H) 7.41-7.48 (m, 1 H) 7.12-7.21 (m, 3 H) 7.06-7.44 (t, J = 73.6, 1 H) 4.94 (s, 2 H) 3.89 (s, 3 H) 2.25 (s, 3 H); $^{19}$F NMR (377 MHz, DMSO-d$_6$) δ ppm −82.026 |
| 101 | 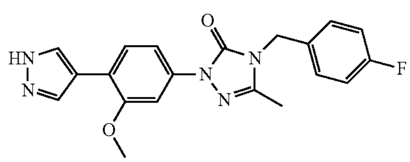 [SMILES: COc1cc(-n2nc(C)n(Cc3ccc(F)cc3)c2=O)ccc1-c1cn[nH]c1] | 4-(4-fluorobenzyl)-1-(3-methoxy-4-(1H-pyrazol-4-yl)phenyl)-3-methyl-1H-1,2,4-triazol-5(4H)-one | 380.2 | A: 1.45, 99.8% B: 1.40, 99.8% | $^1$H NMR (400 MHz, DMSO-d$_6$) δ ppm 12.88 (br. s., 1 H) 8.12 (br. s., 1 H) 7.96 (br. s., 1 H) 7.70 (s, 1 H) 7.63 (s, 1 H) 7.53 (dd, J = 8.47, 2.07 Hz, 1 H) 7.36-7.42 (m, 2 H) 7.18-7.27 (m, 2 H) 4.91 (s, 2 H) 3.89 (s, 3 H) 2.25 (s, 3 H); $^{19}$F NMR (377 MHz, DMSO-d$_6$) δ ppm −114.628 |
| 102 | 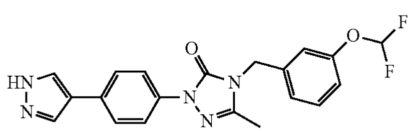 [SMILES: Cc1nn(-c2ccc(-c3cn[nH]c3)cc2)c(=O)n1Cc1cccc(OC(F)F)c1] | 1-(4-(1H-pyrazol-4-yl)phenyl)-4-(3-(difluoromethoxy)benzyl)-3-methyl-1H-1,2,4-triazol-5(4H)-one | 398.2 | A: 1.49, 99.4% B: 1.46, 98.6% | $^1$H NMR (400 MHz, DMSO-d$_6$) δ ppm 12.90 (br. s., 1 H) 8.19 (br. s., 1 H) 7.95 (br. s., 1 H) 7.89 (m, 2 H) 7.63-7.73 (m, 2 H) 7.41-7.48 (m, 1 H) 7.10-7.21 (m, 3 H) 7.06-7.44 (t, J = 73.6, 1 H) 4.94 (s, 2 H) 2.24 (s, 3 H); $^{19}$F NMR (377 MHz, DMSO-d$_6$) δ ppm −81.572 |
| 103 | 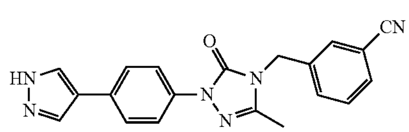 [SMILES: Cc1nn(-c2ccc(-c3cn[nH]c3)cc2)c(=O)n1Cc1cccc(C#N)c1] | 3-((1-(4-(1H-pyrazol-4-yl)phenyl)-3-methyl-5-oxo-1H-1,2,4-triazol-4(5H)-yl)methyl)benzonitrile | 357.2 | A: 1.24, 99.2% B: 1.20, 100% | $^1$H NMR (400 MHz, DMSO-d$_6$) δ ppm 12.94 (br. s., 1 H) 8.20 (s, 1 H) 7.93 (s, 1 H) 7.89 (s, 2 H) 7.84 (s, 1 H) 7.81 (d, J = 7.59 Hz, 1 H) 7.65-7.71 (m, 3 H) 7.56-7.63 (m, 1 H) 4.98 (s, 2 H) 2.25 (s, 3 H) |
| 104 | 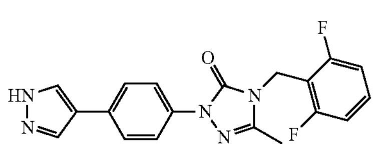 [SMILES: Cc1nn(-c2ccc(-c3cn[nH]c3)cc2)c(=O)n1Cc1c(F)cccc1F] | 1-(4-(1H-pyrazol-4-yl)phenyl)-4-(2,6-difluorobenzyl)-3-methyl-1H-1,2,4-triazol-5(4H)-one | 368.2 | A: 1.37, 100% B: 1.34, 100% | $^1$H NMR (400 MHz, DMSO-d$_6$) δ ppm 12.92 (br. s., 1 H) 8.18 (br. s., 1 H) 7.92 (br. s., 1 H) 7.78-7.86 (m, 2 H) 7.61-7.70 (m, 2 H) 7.47 (tt, J = 8.42, 6.64 Hz, 1 H) 7.09-7.20 (m, 2 H) 4.98 (s, 2 H) 2.27 (s, 3 H); $^{19}$F NMR (377 MHz, DMSO-d$_6$) δ ppm −114.244 |

TABLE 4-continued

| Example | Structure | Name | LCMS (M + H)⁺ | LC\MS Method, RT (min.), & Purity | NMR |
|---|---|---|---|---|---|
| 105 | 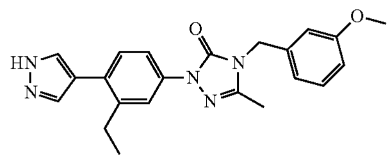 [SMILES: CCc1cc(-n2nc(C)n(Cc3cccc(OC)c3)c2=O)ccc1-c1cn[nH]c1] | 1-(3-ethyl-4-(1H-pyrazol-4-yl)phenyl)-4-(3-methoxybenzyl)-3-methyl-1H-1,2,4-triazol-5(4H)-one | 390.3 | A: 1.54, 99.6% B: 1.50, 100% | $^1$H NMR (400 MHz, DMSO-d$_6$) δ ppm 7.90 (br. s., 1 H) 7.83 (d, J = 2.32 Hz, 1 H) 7.82 (dd, J = 8.41, 2.32 Hz, 1 H) 7.77 (br. s., 1 H) 7.38 (d, J = 8.41 Hz, 1 H) 7.26-7.33 (m, 1 H) 6.88-6.92 (m, 2 H) 6.83-6.87 (m, 1 H) 4.88 (s, 2 H) 3.75 (s, 3 H) 2.73 (q, J = 7.47 Hz, 2 H) 2.23 (s, 3 H) 1.14 (t, J = 7.53 Hz, 3 H) |
| 106 | 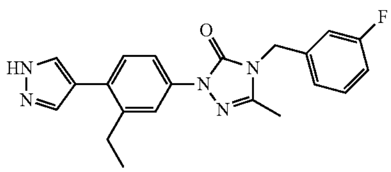 [SMILES: CCc1cc(-n2nc(C)n(Cc3cccc(F)c3)c2=O)ccc1-c1cn[nH]c1] | 1-(3-ethyl-4-(1H-pyrazol-4-yl)phenyl)-4-(3-fluorobenzyl)-3-methyl-1H-1,2,4-triazol-5(4H)-one | 378.2 | A: 1.56, 98.8% B: 1.52, 99.8% | $^1$H NMR (400 MHz, DMSO-d$_6$) δ ppm 12.94 (br. s., 1 H) 7.83 (d, J = 2.26 Hz, 1 H) 7.78 (br. s., 2 H) 7.75 (dd, J = 8.41, 2.32 Hz, 1 H) 7.41-7.47 (m, 1 H) 7.38 (d, J = 8.41 Hz, 1 H) 7.12-7.22 (m, 3 H) 4.94 (s, 2 H) 2.73 (q, J = 7.49 Hz, 2 H) 2.24 (s, 3 H) 1.14 (t, J = 7.53 Hz, 3 H); $^{19}$F NMR (377 MHz, DMSO-d$_6$) δ ppm −112.604 |
| 107 | 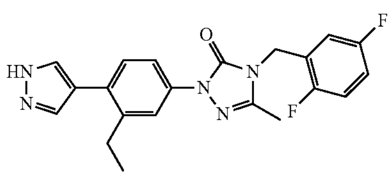 [SMILES: CCc1cc(-n2nc(C)n(Cc3cc(F)ccc3F)c2=O)ccc1-c1cn[nH]c1] | 4-(2,5-difluorobenzyl)-1-(3-ethyl-4-(1H-pyrazol-4-yl)phenyl)-3-methyl-1H-1,2,4-triazol-5(4H)-one | 396.2 | A: 1.59, 99.7% B: 1.55, 99.6% | $^1$H NMR (400 MHz, DMSO-d$_6$) δ ppm 12.96 (br. s., 1 H) 7.82 (d, J = 2.26 Hz, 1 H) 7.80 (br. s., 2 H) 7.73 (dd, J = 8.44, 2.35 Hz, 1 H) 7.29-7.40 (m, 2 H) 7.16-7.28 (m, 2 H) 4.95 (s, 2 H) 2.73 (q, J = 7.53 Hz, 2 H) 2.27 (s, 3 H) 1.10-1.17 (t, J = 7.53 Hz, 3 H); $^{19}$F NMR (377 MHz, DMSO-d$_6$) δ ppm −118.026, −123.469 |
| 108 | 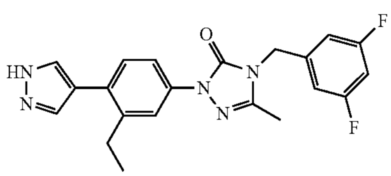 [SMILES: CCc1cc(-n2nc(C)n(Cc3cc(F)cc(F)c3)c2=O)ccc1-c1cn[nH]c1] | 4-(3,5-difluorobenzyl)-1-(3-ethyl-4-(1H-pyrazol-4-yl)phenyl)-3-methyl-1H-1,2,4-triazol-5(4H)-one | 396.2 | A: 1.61, 97.9% B: 1.57, 98.3% | $^1$H NMR (400 MHz, DMSO-d$_6$) δ ppm 12.98 (br. s., 1 H) 7.83 (d, J = 2.26 Hz, 1 H) 7.80 (br. s., 2 H) 7.75 (dd, J = 8.41, 2.32 Hz, 1 H) 7.40 (s, 1 H) 7.21 (tt, J = 9.40, 2.34 Hz, 1 H) 7.00-7.12 (m, 2 H) 4.94 (s, 2 H) 2.69-2.79 (q, J = 7.53 Hz, 2 H) 2.25 (s, 3 H) 1.10-1.18 (t, J = 7.53 Hz, 3 H); $^{19}$F NMR (377 MHz, DMSO-d$_6$) δ ppm −109.034 |
| 109 | 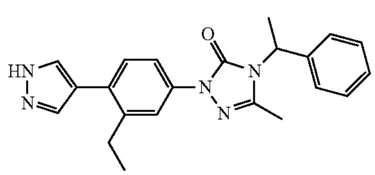 [SMILES: CCc1cc(-n2nc(C)n(C(C)c3ccccc3)c2=O)ccc1-c1cn[nH]c1] | 1-(3-ethyl-4-(1H-pyrazol-4-yl)phenyl)-3-methyl-4-(1-phenylethyl)-1H-1,2,4-triazol-5(4H)-one | 374.3 | A: 1.66, 97.7% B: 1.62, 91.7% | $^1$H NMR (400 MHz, DMSO-d$_6$) δ ppm 12.97 (br. s., 1 H) 7.82 (d, J = 2.26 Hz, 1 H) 7.78 (s, 2 H) 7.72 (dd, J = 8.47, 2.32 Hz, 1 H) 7.27-7.42 (m, 6 H) 5.43 (q, J = 7.17 Hz, 1 H) 2.72 (q, J = 7.47 Hz, 2 H) 2.17 (s, 3 H) 1.85 (d, J = 7.2 Hz, 3 H) 1.14 (t, J = 7.53 Hz, 3 H) |
| 110 | 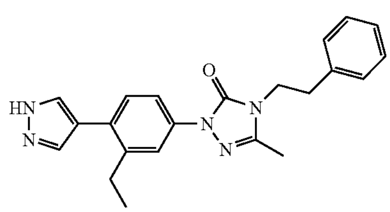 [SMILES: CCc1cc(-n2nc(C)n(CCc3ccccc3)c2=O)ccc1-c1cn[nH]c1] | 1-(3-ethyl-4-(1H-pyrazol-4-yl)phenyl)-3-methyl-4-phenethyl-1H-1,2,4-triazol-5(4H)-one | 374.3 | A: 1.58, 96.8% B: 1.55, 97.1% | $^1$H NMR (400 MHz, DMSO-d$_6$) δ ppm 12.97 (br. s., 1 H) 7.80 (d, J = 2.26 Hz, 1 H) .80 (br. s., 2 H) 7.73 (dd, J = 8.41, 2.32 Hz, 1 H) 7.38 (s, 1 H) 7.29-7.34 (m, 2 H) 7.24-7.27 (m, 1 H) 7.21 (d, J = 6.71 Hz, 2 H) 3.87 (t, J = 7.09 Hz, 2 H) 2.96 (t, J = 7.03 Hz, 2 H) 2.72 (q, J = 7.53 Hz, 2 H) 1.95 (s, 3 H) 1.12 (t, J = 7.53 Hz, 3 H) |
| 111 | 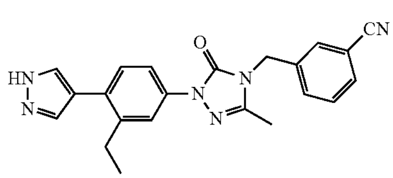 | 3-((1-(3-ethyl-4-(1H-pyrazol-4-yl)phenyl)-3-methyl-5-oxo-1H-1,2,4-triazol-4(5H)-yl)methyl)benzonitrile | 385.2 | A: 1.38, 99.8% B: 1.34, 98.0% | $^1$H NMR (400 MHz, DMSO-d$_6$) δ ppm 12.98 (br. s., 1 H) 7.79-7.86 (m, 4 H) 7.75 (dd, J = 8.41, 2.32 Hz, 1 H) 7.57-7.70 (m, 3 H) 7.39 (s, 1 H) 4.98 (s, 2 H) 2.73 (q, J = 7.53 Hz, 2 H) 2.26 (s, 3 H) 1.11-1.17 (t, J = 7.53 Hz, 3 H) |

TABLE 4-continued

| Example | Structure | Name | LCMS (M + H)+ | LC\MS Method, RT (min.), & Purity | NMR |
|---|---|---|---|---|---|
| 112 | 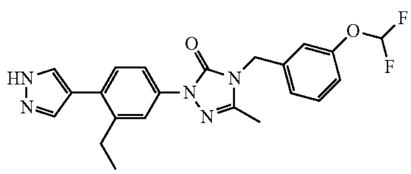 [SMILES: CCc1cc(-n2nc(C)n(Cc3cccc(OC(F)F)c3)c2=O)ccc1-c1cn[nH]c1] | 4-(3-(difluoromethoxy)benzyl)-1-(3-ethyl-4-(1H-pyrazol-4-yl)phenyl)-3-methyl-1H-1,2,4-triazol-5(4H)-one | 426.2 | A: 1.63, 99.7% B: 1.58, 100% | $^1$H NMR (400 MHz, DMSO-d$_6$) δ ppm 12.97 (br. s., 1 H) 7.90 (br. s., 1 H) 7.83 (d, J = 2.26 Hz, 1 H) 7.77 (br. s., 1 H) 7.76 (dd, J = 8.41, 2.32 Hz, 1 H) 7.42-7.48 (m, 1 H) 7.39 (d, J = 8.41 Hz, 1 H) 7.12-7.20 (m, 3 H) 7.06-7.48 (t, J = 74 Hz, 1 H) 4.94 (s, 2 H) 2.73 (q, J = 7.47 Hz, 2 H) 2.24 (s, 3 H) 1.12-1.18 (t, J = 7.53 Hz, 3 H); $^{19}$F NMR (377 MHz, DMSO-d$_6$) δ ppm −82.016 |
| 113 | 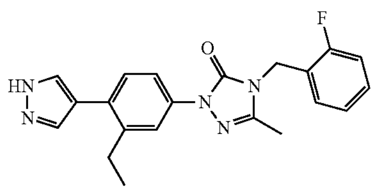 [SMILES: CCc1cc(-n2nc(C)n(Cc3ccccc3F)c2=O)ccc1-c1cn[nH]c1] | 1-(3-ethyl-4-(1H-pyrazol-4-yl)phenyl)-4-(2-fluorobenzyl)-3-methyl-1H-1,2,4-triazol-5(4H)-one | 378.2 | A: 1.58, 99.8% B: 1.53, 99.8% | $^1$H NMR (400 MHz, DMSO-d$_6$) δ ppm 12.98 (br. s., 1 H) 7.83 (d, J = 2.26 Hz, 1 H) 7.78 (br. s., 2 H) 7.74 (dd, J = 8.44, 2.35 Hz, 1 H) 7.35-7.44 (m, 2 H) 7.14-7.35 (m, 3 H) 4.96 (s, 2 H) 2.73 (q, J = 7.47 Hz, 2 H) 2.25 (s, 3 H) 1.11-1.17 (t, J = 7.53 Hz, 3 H); $^{19}$F NMR (377 MHz, DMSO-d$_6$) δ ppm −118.191 |
| 114 | 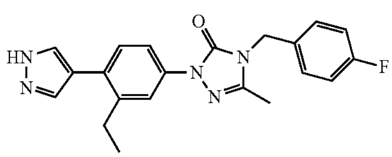 | 1-(3-ethyl-4-(1H-pyrazol-4-yl)phenyl)-4-(4-fluorobenzyl)-3-methyl-1H-1,2,4-triazol-5(4H)-one | 378.2 | A: 1.57, 99.8% B: 1.52, 100% | $^1$H NMR (400 MHz, DMSO-d$_6$) δ ppm 12.98 (br. s., 1 H) 7.83 (d, J = 2.26 Hz, 1 H) 7.78 (br. s., 2 H) 7.75 (dd, J = 8.47, 2.32 Hz, 1 H) 7.36-7.42 (m, 3 H) 7.21 (t, J = 8.91 Hz, 2 H) 4.90 (s, 2 H) 2.73 (q, J = 7.53 Hz, 2 H) 2.24 (s, 3 H) 1.10-1.18 (t, J = 7.53 Hz, 3 H); $^{19}$F NMR (377 MHz, DMSO-d$_6$) δ ppm −114.625 |
| 115 | 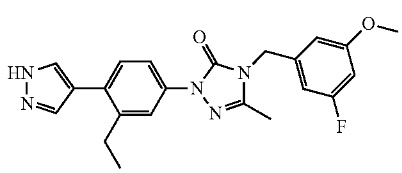 [SMILES: CCc1cc(-n2nc(C)n(Cc3cc(F)cc(OC)c3)c2=O)ccc1-c1cn[nH]c1] | 1-(3-ethyl-4-(1H-pyrazol-4-yl)phenyl)-4-(3-fluoro-5-methoxybenzyl)-3-methyl-1H-1,2,4-triazol-5(4H)-one | 408.3 | A: 1.61, 95.4% B: 1.57, 97.9% | $^1$H NMR (400 MHz, DMSO-d$_6$) δ ppm 12.86 (br. s., 1 H) 7.83 (d, J = 2.26 Hz, 1 H) 7.78 (br. s., 2 H) 7.76 (dd, J = 8.44, 2.35 Hz, 1 H) 7.38 (d, J = 8.41 Hz, 1 H) 6.80 (dt, J = 11.07, 2.27 Hz, 1 H) 6.68-6.75 (m, 2 H) 4.88 (s, 2 H) 3.76 (s, 3 H) 2.73 (q, J = 7.53 Hz, 2 H) 2.24 (s, 3 H) 1.14 (t, J = 7.53 Hz, 3 H); $^{19}$F NMR (377 MHz, DMSO-d$_6$) δ ppm −110.833 |
| 116 | 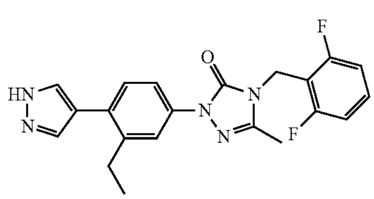 [SMILES: CCc1cc(-n2nc(C)n(Cc3c(F)cccc3F)c2=O)ccc1-c1cn[nH]c1] | 4-(2,6-difluorobenzyl)-1-(3-ethyl-4-(1H-pyrazol-4-yl)phenyl)-3-methyl-1H-1,2,4-triazol-5(4H)-one | 396.2 | A: 1.54, 99.4% B: 1.49, 100% | $^1$H NMR (400 MHz, DMSO-d$_6$) δ ppm 12.96 (br. s., 1 H) 7.90 (s, 1 H) 7.79 (s, 1 H) 7.69 (dd, J = 8.44, 2.35 Hz, 1 H) 7.64 (s, 1 H) 7.47 (tt, J = 8.40, 6.72 Hz, 1 H) 7.37 (s, 1 H) 7.15 (t, J = 8.22 Hz, 2 H) 4.98 (s, 2 H) 2.73 (q, J = 7.47 Hz, 2 H) 2.28 (s, 3 H) 1.14 (t, J = 7.50 Hz, 3 H); $^{19}$F NMR (377 MHz, DMSO-d$_6$) δ ppm −114.255 |
| 117 | 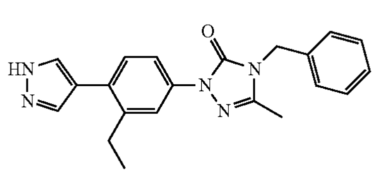 [SMILES: CCc1cc(-n2nc(C)n(Cc3ccccc3)c2=O)ccc1-c1cn[nH]c1] | 4-benzyl-1-(3-ethyl-4-(1H-pyrazol-4-yl)phenyl)-3-methyl-1H-1,2,4-triazol-5(4H)-one | 360.2 | A: 1.53, 98.9% B: 1.49, 99.5% | $^1$H NMR (400 MHz, DMSO-d$_6$) δ ppm 12.99 (br. s., 1 H) 7.91 (s, 1 H) 7.83 (d, J = 2.26 Hz, 1 H) 7.76 (dd, J = 8.44, 2.35 Hz, 1 H) 7.66 (s, 1 H) 7.36-7.43 (m, 3 H) 7.27-7.35 (m, 3 H) 4.92 (s, 2 H) 2.73 (q, J = 7.47 Hz, 2 H) 2.23 (s, 3 H) 1.14 (t, J = 7.50 Hz, 3 H) |
| 118 | 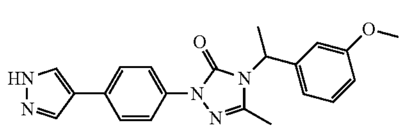 [SMILES: COc1cccc(C(C)n2c(C)nn(-c3ccc(-c4cn[nH]c4)cc3)c2=O)c1] | 1-(4-(1H-pyrazol-4-yl)phenyl)-4-(1-(3-methoxyphethyl)ethyl)-3-methyl-1H-1,2,4-triazol-5(4H)-one (enantiomer 1) | 376.3 | A: 1.49, 100% B: 1.57, 99.0% | $^1$H NMR (400 MHz, DMSO-d$_6$) δ ppm 12.94 (br. s., 1 H) 8.19 (br. s., 1 H) 7.93 (br. s., 1 H) 7.87 (m, 2 H) 7.58-7.71 (m, 2 H) 7.24-7.36 (m, 1 H) 6.86-7.00 (m, 3 H) 5.39 (q, J = 7.15 Hz, 1 H) 3.72 (s, 3 H) 2.17 (s, 3 H) 1.85 (d, J = 7.28 Hz, 3 H); [α]$^{25}$ D = +42 (c 0.1, MeOH) |

TABLE 4-continued

| Example | Structure | Name | LCMS (M + H)⁺ | LC\MS Method, RT (min.), & Purity | NMR |
|---|---|---|---|---|---|
| 119 | 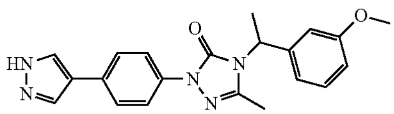 [SMILES: COc1cccc(C(C)n2c(C)nn(-c3ccc(-c4cn[nH]c4)cc3)c2=O)c1] | 1-(4-(1H-pyrazol-4-yl)phenyl)-4-(1-(3-methoxyphenyl)ethyl)-3-methyl-1H-1,2,4-triazol-5(4H)-one (enantiomer 2) | 376.3 | A: 1.52, 99.6% B: 1.58, 99.3% | $^1$H NMR (400 MHz, DMSO-$d_6$) δ ppm 12.94 (br. s., 1 H) 8.19 (br. s., 1 H) 7.93 (br. s., 1 H) 7.87 (m, 2 H) 7.58-7.71 (m, 2 H) 7.24-7.36 (m, 1 H) 6.86-7.00 (m, 3 H) 5.39 (q, J = 7.15 Hz, 1 H) 3.72 (s, 3 H) 2.17 (s, 3 H) 1.85 (d, J = 7.28 Hz, 3 H); [α]$^{25}$ D = −40 (c 0.1, MeOH) |
| 120 | 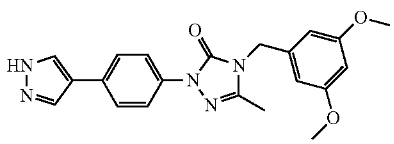 [SMILES: COc1cc(Cn2c(C)nn(-c3ccc(-c4cn[nH]c4)cc3)c2=O)cc(OC)c1] | 1-(4-(1H-pyrazol-4-yl)phenyl)-4-(3,5-dimethoxybenzyl)-3-methyl-1H-1,2,4-triazol-5(4H)-one | 378.2 | A: 1.39, 99.5% B: 1.38, 97.1% | $^1$H NMR (400 MHz, DMSO-$d_6$) δ ppm 12.94 (s, 1 H), 8.35 (s, 1H), 7.93 (br. s., 1H), 7.89 (br. s., 1H), 7.90-7.81 (m, 2H), 7.74-7.65 (m, 2H), 6.53 (d, J = 2.3 Hz, 2H), 6.48-6.44 (m, 1H), 4.80 (s, 2H), 3.74 (s, 6H) |
| 121 | 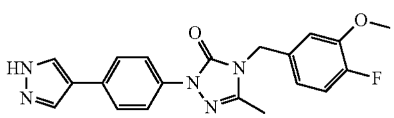 [SMILES: COc1cc(Cn2c(C)nn(-c3ccc(-c4cn[nH]c4)cc3)c2=O)ccc1F] | 1-(4-(1H-pyrazol-4-yl)phenyl)-4-(4-fluoro-3-methoxybenzyl)-3-methyl-1H-1,2,4-triazol-5(4H)-one | 380.2 | A: 1.49, 99.0% B: 1.47, 99.1% | $^1$H NMR (400 MHz, DMSO-$d_6$) δ ppm 12.93 (s, 1 H) 8.19 (s, 1H), 7.93 (s, 1H), 7.90-7.85 (m, 2H), 7.72-7.66 (m, 2H), 7.24-7.16 (m, 2H), 6.84 (ddd, J = 2.1, 4.3, 8.3 Hz, 1H), 4.88 (s, 2H), 3.84 (s, 3H), 2.25 (s, 3H); $^{19}$F $^1$H NMR (377 MHz, DMSO-$d_6$) δ ppm −136.659 |
| 122 | 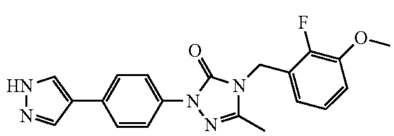 [SMILES: COc1cccc(Cn2c(C)nn(-c3ccc(-c4cn[nH]c4)cc3)c2=O)c1F] | 1-(4-(1H-pyrazol-4-yl)phenyl)-4-(2-fluoro-3-methoxybenzyl)-3-methyl-1H-1,2,4-triazol-5(4H)-one | 380.2 | A: 1.42, 100% B: 1.43, 99.2% | $^1$H NMR (400 MHz, DMSO-$d_6$) δ ppm 12.94 (s, 1 H) 8.30 (s, 1H), 8.17 (s, 1H), 8.06 (s, 1H), 7.87 (d, J = 8.6 Hz, 2H), 7.68 (d, J = 8.6 Hz, 2H), 7.21-7.08 (m, 2H), 6.88-6.74 (m, 1H), 4.95 (s, 2H), 3.84 (s, 3H) 2.24 (s, 3 H); $^{19}$F NMR (377 MHz, DMSO-$d_6$) δ ppm −140.982 |
| 123 | 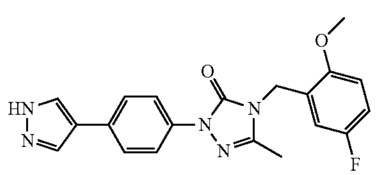 [SMILES: COc1ccc(F)cc1Cn1c(C)nn(-c2ccc(-c3cn[nH]c3)cc2)c1=O] | 1-(4-(1H-pyrazol-4-yl)phenyl)-4-(5-fluoro-2-methoxybenzyl)-3-methyl-1H-1,2,4-triazol-5(4H)-one | 380.2 | A: 1.49, 100% B: 1.50, 100% | $^1$H NMR (400 MHz, DMSO-$d_6$) δ ppm 12.93 (s, 1 H), 8.19 (s, 1H), 7.92 (s, 1H), 7.85 (d, J = 8.7 Hz, 2H), 7.66 (d, J = 8.7 Hz, 2H), 7.13-7.18 (m, 1H), 7.05-7.08 (m, 1H), 6.95-6.98 (m, 1H), 4.82 (s, 2H), 3.83 (s, 3H), 2.25 (s, 3H); $^{19}$F NMR (377 MHz, DMSO-$d_6$) δ ppm −123.604 |
| 124 | 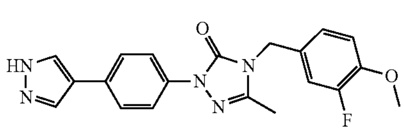 [SMILES: COc1ccc(Cn2c(C)nn(-c3ccc(-c4cn[nH]c4)cc3)c2=O)cc1F] | 1-(4-(1H-pyrazol-4-yl)phenyl)-4-(3-fluoro-4-methoxybenzyl)-3-methyl-1H-1,2,4-triazol-5(4H)-one | 380.2 | A: 1.42, 99.8% B: 1.40, 99.8% | $^1$H NMR (400 MHz, DMSO-$d_6$) δ ppm 8.06 (s, 2H), 7.86 (d, J = 8.7 Hz, 2H), 7.67 (d, J = 8.7 Hz, 2H), 7.10-7.24 (m, 3H), 4.83 (s, 2H), 3.82 (s, 3H), 2.23 (s, 3H); $^{19}$F NMR (377 MHz, DMSO-$d_6$) δ ppm −74.692 and −134.711 |

Example 125

1-(4-(1H-pyrazol-4-yl)phenyl)-3-(hydroxymethyl)-4-(3-methoxybenzyl)-1H-1,2,4-triazol-5(4H)-one

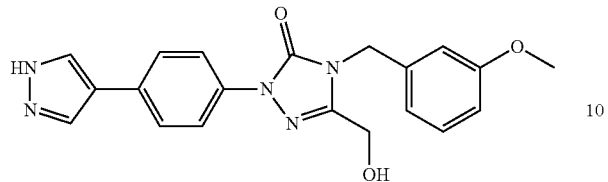

Preparation of 1-(4-(1H-pyrazol-4-yl)phenyl)-3-(hydroxymethyl)-4-(3-methoxybenzyl)-1H-1,2,4-triazol-5(4H)-one

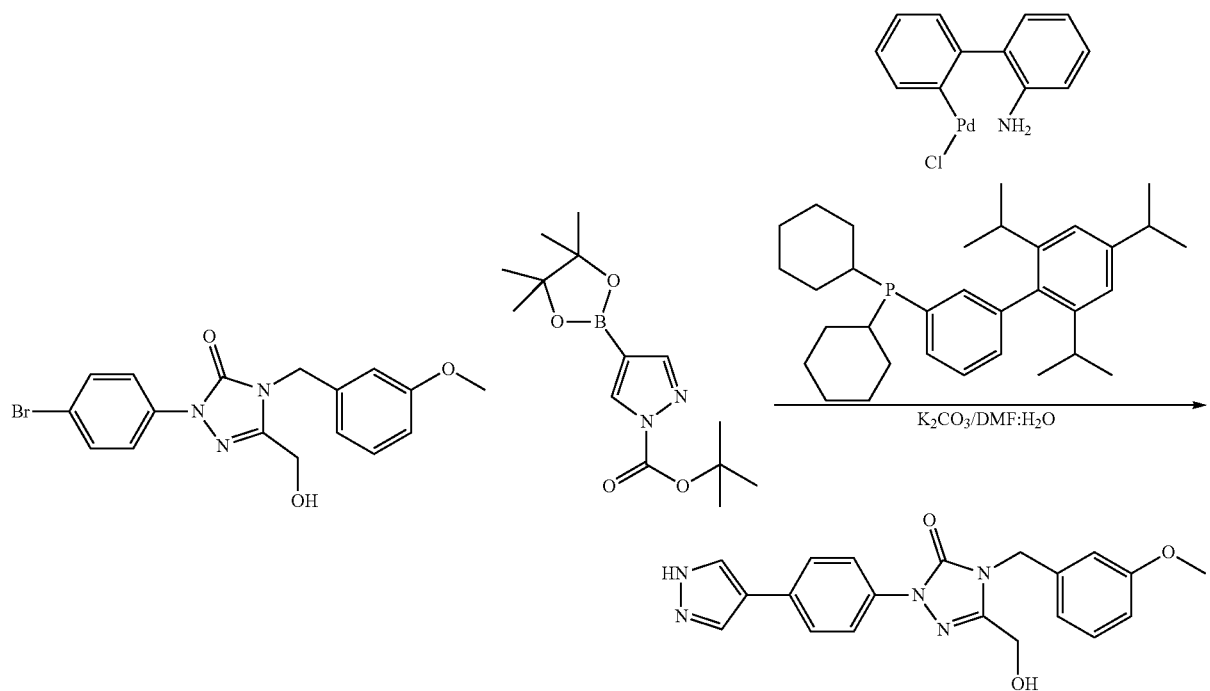

A mixture of 1-(4-bromophenyl)-3-(hydroxymethyl)-4-(3-methoxybenzyl)-1H-1,2,4-triazol-5(4H)-one (50 mg, 0.128 mmol), $K_2CO_3$ (53.1 mg, 0.384 mmol), and tert-butyl 4-(4,4,5,5-tetramethyl-1,3,2-dioxaborolan-2-yl)-1H-pyrazole-1-carboxylate (45.2 mg, 0.154 mmol) in DMF (2 mL) and water (0.2 mL) was flushed with nitrogen for 10 min. $2^{nd}$ generation XPHOS precatalyst (3.0 mg, 3.8 µmol) was added and the reaction mixture at 95° C. for 2 h. The reaction mixture was cooled to rt and evaporated. The residue was diluted with DCM (100 mL), washed with brine, dried over $Na_2SO_4$, filtered and concentrated. The crude product was purified by preparative HPLC to afford 1-(4-(1H-pyrazol-4-yl)phenyl)-3-(hydroxymethyl)-4-(3-methoxybenzyl)-1H-1,2,4-triazol-5(4H)-one (14 mg, 29% yield) as a white solid. MS(ESI) m/z: 378.2 $(M+H)^+$; $^1$H NMR (400 MHz, DMSO-$d_6$) dδ ppm 12.95 (br. s., 1H) 8.20 (s, 1H) 7.93 (s, 1H) 7.84-7.91 (m, 2H) 7.65-7.73 (m, 2H) 7.28 (t, J=7.91 Hz, 1H) 6.81-6.96 (m, 3H) 5.80 (t, J=5.6 Hz, 1H) 4.95 (s, 2H) 4.43 (d, J=5.84 Hz, 2H) 3.73 (s, 3H); HPLC RT=1.16 min, 99.4% (Method A); RT=1.23 min, 99.0% (Method B).

The following Examples in Table 5 were made by using the same procedure as shown in Example 125.

TABLE 5

| Example | Structure | Name | LCMS (M + H)+ | LC\MS Method, RT (min.), & Purity | NMR |
|---|---|---|---|---|---|
| 126 | 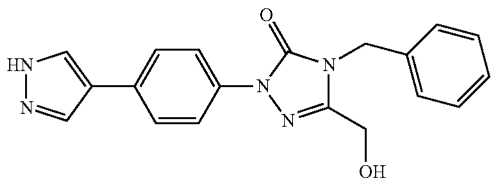 [SMILES: O=c1n(-c2ccc(-c3cn[nH]c3)cc2)nc(CO)n1Cc1ccccc1] | 1-(4-(1H-pyrazol-4-yl)phenyl)-4-benzyl-3-(hydroxymethyl)-1H-1,2,4-triazol-5(4H)-one | 348.2 | A: 1.12, 99.7% B: 1.20, 98.7% | $^1$H NMR (400 MHz, DMSO-d$_6$) δ ppm 12.95 (br. s., 1 H) 8.20 (s, 1 H) 7.93 (s, 1 H) 7.88 (d, J = 8.78 Hz, 2 H) 7.70 (d, J = 8.78 Hz, 2 H) 7.34-7.40 (m, 4 H) 7.28-7.33 (m, 1 H) 5.80 (t, J = 5.6 Hz, 1 H) 4.98 (s, 2 H) 4.42 (d, J = 5.84 Hz, 2 H) |
| 127 | 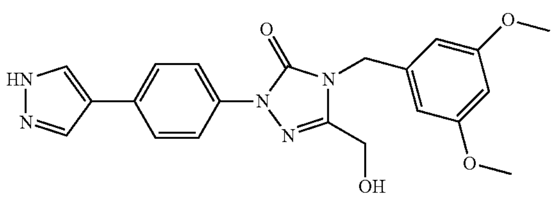 [SMILES: COc1cc(Cn2c(CO)nn(-c3ccc(-c4cn[nH]c4)cc3)c2=O)cc(OC)c1] | 1-(4-(1H-pyrazol-4-yl)phenyl)-4-(3,5-dimethoxybenzyl)-3-(hydroxy methyl)-1H-1,2,4-triazol-5(4H)-one | 408.3 | A: 1.26, 94.0% B: 1.31, 96.0% | $^1$H NMR (400 MHz, DMSO-d$_6$) δ ppm 12.94 (br. s., 1 H) 8.20 (s, 1 H) 7.93 (s, 1 H) 7.84-7.90 (m, 2 H) 7.67-7.73 (m, 2 H) 6.50 (d, J = 2.20 Hz, 2 H) 6.42-6.46 (m, 1 H) 5.80 (t, J = 5.80 Hz, 1 H) 4.90 (s, 2 H) 4.43 (d, J = 5.84 Hz, 2 H) 3.72 (s, 6 H) |
| 128 | 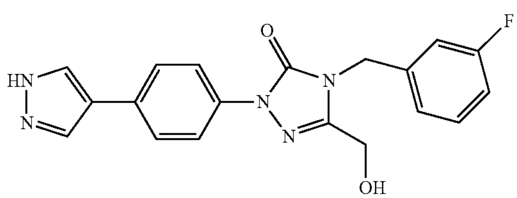 [SMILES: O=c1n(-c2ccc(-c3cn[nH]c3)cc2)nc(CO)n1Cc1cccc(F)c1] | 1-(4-(1H-pyrazol-4-yl)phenyl)-4-(3-fluorobenzyl)-3-(hydroxymethyl)-1H-1,2,4-triazol-5(4H)-one | 366.2 | A: 1.24, 100% B: 1.29, 100% | $^1$H NMR (400 MHz, DMSO-d$_6$) δ ppm 12.94 (br. s., 1 H) 8.20 (s, 1 H) 7.93 (s, 1 H) 77.83-7.90 (m, 2 H) 7.66-7.73 (m, 2 H) 7.42 (td, J = 8.09, 6.21 Hz, 1 H) 7.18-7.24 (m, 2 H) 7.10-7.18 (m, 1 H) 5.80 (t, J = 5.80 Hz, 1 H) 4.99 (s, 2 H) 4.45 (d, J = 5.84 Hz, 2 H); $^{19}$F NMR (377 MHz, DMSO-d$_6$) δ ppm -118.277 |
| 129 | 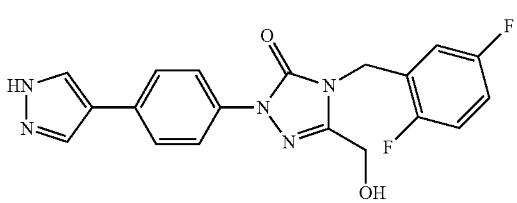 [SMILES: O=c1n(-c2ccc(-c3cn[nH]c3)cc2)nc(CO)n1Cc1cc(F)ccc1F] | 1-(4-(1H-pyrazol-4-yl)phenyl)-4-(2,5-difluorobenzyl)-3-(hydroxymethyl)-1H-1,2,4-triazol-5(4H)-one | 384.2 | A: 1.25, 100% B: 1.30, 100% | $^1$H NMR (400 MHz, DMSO-d$_6$) δ ppm 12.94 (br. s., 1 H) 8.20 (s, 1 H) 7.93 (s, 1 H) 7.83-7.89 (m, 2 H) 7.67-7.73 (m, 2 H) 7.28-7.36 (m, 1 H) 7.12-7.26 (m, 2 H) 5.80 (t, J = 5.80 Hz, 1 H) 5.03 (s, 2 H) 4.45 (d, J = 5.84 Hz, 2 H); $^{19}$F NMR (377 MHz, DMSO-d$_6$) δ ppm -118.273, -123.748 |

TABLE 5-continued

| Example | Structure | Name | LCMS (M + H)+ | LC\MS Method, RT (min.), & Purity | NMR |
|---|---|---|---|---|---|
| 130 | 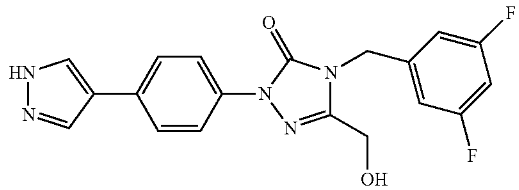 [SMILES: O=c1n(-c2ccc(-c3cn[nH]c3)cc2)nc(CO)n1Cc1cc(F)cc(F)c1] | 1-(4-(1H-pyrazol-4-yl)phenyl)-4-(3,5-difluorobenzyl)-3-(hydroxymethyl)-1H-1,2,4-triazol-5(4H)-one | 384.2 | A: 1.30, 100% B: 1.33, 97.1% | $^1$H NMR (400 MHz, DMSO-d$_6$) δ ppm 12.94 (br. s., 1 H) 8.20 (s, 1 H) 7.93 (s, 1 H) 7.83-7.90 (m, 2 H) 7.66-7.74 (m, 2 H) 7.19 (tt, J = 9.40, 2.34 Hz, 1 H) 7.07-7.14 (m, 2 H) 5.79 (t, J = 5.84 Hz, 1 H) 4.99 (s, 2 H) 4.45 (d, J = 5.84 Hz, 2 H); $^{19}$F NMR (377 MHz, DMSO-d$_6$) δ ppm −109.550 |
| 131 | 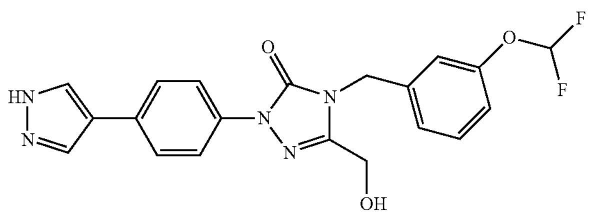 [SMILES: O=c1n(-c2ccc(-c3cn[nH]c3)cc2)nc(CO)n1Cc1cccc(OC(F)F)c1] | 1-(4-(1H-pyrazol-4-yl)phenyl)-4-(3-(difluoromethoxy)benzyl)-3-(hydroxymethyl)-1H-1,2,4-triazol-5(4H)-one | 414.2 | A: 1.34, 97.1% B: 1.39, 97.4% | $^1$H NMR (400 MHz, DMSO-d$_6$) δ ppm 12.94 (br. s., 1 H) 8.20 (s, 1 H) 7.93 (s, 1 H) 7.84-7.91 (m, 2 H) 7.66-7.73 (m, 2 H) 7.39-7.46 (m, 2 H) 7.18-7.26 (m, 2 H) 7.03-7.15 (m, 1 H) 5.79 (t, J = 5.84 Hz, 1 H) 4.99 (s, 2 H) 4.45 (d, J = 5.84 Hz, 2 H); $^{19}$F NMR (377 MHz, DMSO-d$_6$) δ ppm −81.910 |
| 132 | 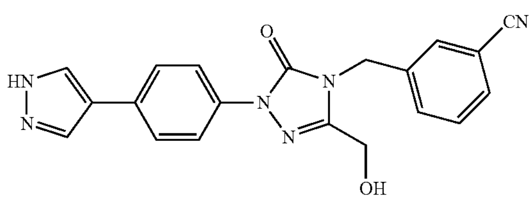 [SMILES: N#Cc1cccc(Cn2c(CO)nn(-c3ccc(-c4cn[nH]c4)cc3)c2=O)c1] | 3-((1-(4-(1H-pyrazol-4-yl)phenyl)-3-(hydroxymethyl)-5-oxo-1H-1,2,4-triazol-4(5H)-yl)methyl)benzonitrile | 373.2 | A: 1.13, 98.1% B: 1.17, 98.2% | $^1$H NMR (400 MHz, DMSO-d$_6$) δ ppm 12.95 (br. s., 1 H) 8.20 (s, 1 H) 7.93 (s, 1 H) 7.83-7.89 (m, 3 H) 7.77-7.81 (m, 1 H) 7.66-7.74 (m, 3 H) 7.56-7.62 (m, 1 H) 5.79 (t, J = 5.77 Hz, 1 H) 5.03 (s, 2 H) 4.47 (d, J = 5.77 Hz, 2 H) |
| 133 | 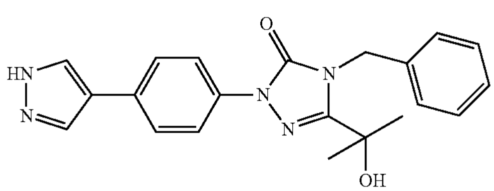 [SMILES: CC(C)(O)c1nn(-c2ccc(-c3cn[nH]c3)cc2)c(=O)n1Cc1ccccc1] | 1-(4-(1H-pyrazol-4-yl)phenyl)-4-benzyl-3-(2-hydroxypropan-2-yl)-1H-1,2,4-triazol-5(4H)-one | 376.2 | A: 1.44, 96.6% B: 1.49, 94.4% | $^1$H NMR (400 MHz, DMSO-d$_6$) δ ppm 12.95 (br. s., 1 H) 8.20 (s, 1 H) 7.93 (s, 1 H) 7.86-7.91 (m, 2 H) 7.67-7.72 (m, 2 H) 7.32-7.38 (m, 2 H) 7.24-7.31 (m, 3 H) 5.78 (s, 1 H) 5.23 (s, 2 H) 1.45 (s, 6H) |

TABLE 5-continued

| Example | Structure | Name | LCMS (M + H)+ | LC\MS Method, RT (min.), & Purity | NMR |
|---|---|---|---|---|---|
| 134 | 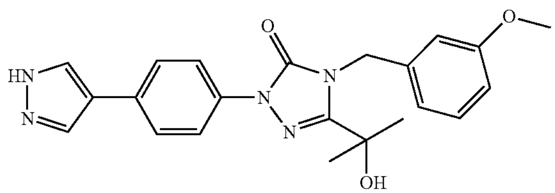 [SMILES: COc1cccc(Cn2c(C(C)(C)O)nn(-c3ccc(-c4cn[nH]c4)cc3)c2=O)c1] | 1-(4-(1H-pyrazol-4-yl)phenyl)-3-(2-hydroxypropan-2-yl)-4-(3-methoxybenzyl)-1H-1,2,4-triazol-5(4H)-one | 406.2 | A: 1.44, 96.4% B: 1.50, 97.9% | ¹H NMR (400 MHz, DMSO-d₆) δ ppm 12.95 (br. s., 1 H) 8.20 (s, 1 H) 7.93 (s, 1 H) 7.84-7.92 (m, 2 H) 7.65-7.73 (m, 2 H) 7.27 (dd, J = 8.97, 7.59 Hz, 1 H) 6.77-6.89 (m, 3 H) 5.79 (s, 1 H) 5.19 (s, 2 H) 3.73 (s, 3 H) 1.46 (s, 6H) |
| 135 | 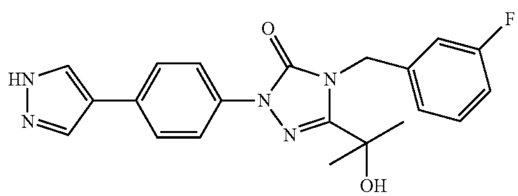 [SMILES: CC(C)(O)c1nn(-c2ccc(-c3cn[nH]c3)cc2)c(=O)n1Cc1cccc(F)c1] | 1-(4-(1H-pyrazol-4-yl)phenyl)-4-(3-fluorobenzyl)-3-(2-hydroxypropan-2-yl)-1H-1,2,4-triazol-5(4H)-one | 394.2 | A: 1.44, 93.8% B: 1.48, 93.7% | ¹H NMR (400 MHz, DMSO-d₆) δ = 12.94 (br. s., 1H) 8.20 (br. s., 1H), 7.93 (br. s., 1H), 7.89 (d, J = 8.7 Hz, 2H), 7.70 (d, J = 8.7 Hz, 2H), 7.44-7.35 (m, 1H), 7.16-7.06 (m, 3H), 5.80 (s, 1H), 5.22 (s, 2H), 1.48 (s, 6H); ¹⁹F NMR (377 MHz, DMSO-d6) δ ppm −113.235 |
| 136 | 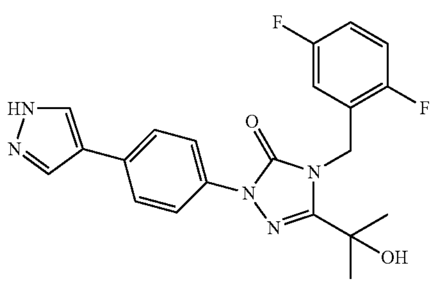 [SMILES: CC(C)(O)c1nn(-c2ccc(-c3cn[nH]c3)cc2)c(=O)n1Cc1cc(F)ccc1F] | 1-(4-(1H-pyrazol-4-yl)phenyl)-4-(2,5-difluorobenzyl)-3-(2-hydroxypropan-2-yl)-1H-1,2,4-triazol-5(4H)-one | 412.2 | A: 1.46, 100% B: 1.49, 99.2% | ¹H NMR (400 MHz, DMSO-d₆) δ ppm 12.95 (br. s., 1H) 8.20 (br. s., 1H), 7.93 (br. s., 1H), 7.88 (d, J = 8.7 Hz, 2H), 7.71 (d, J = 8.7 Hz, 2H), 7.31 (dt, J = 4.5, 9.3 Hz, 1H), 7.23-7.15 (m, 1H), 7.01 (ddd, J = 3.0, 5.7, 8.9 Hz, 1H), 5.79 (s, 1H), 5.24 (s, 2H), 1.49 (s, 6H); ¹⁹F NMR (377 MHz, DMSO-d₆) δ ppm −118.235, −124.101 |
| 137 | 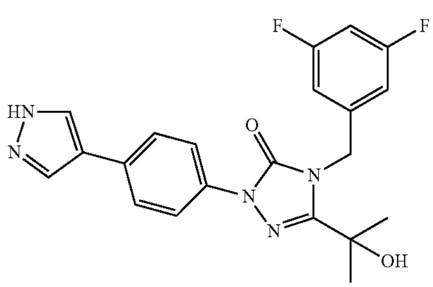 [SMILES: CC(C)(O)c1nn(-c2ccc(-c3cn[nH]c3)cc2)c(=O)n1Cc1cc(F)cc(F)c1] | 1-(4-(1H-pyrazol-4-yl)phenyl)-4-(3,5-difluorobenzyl)-3-(2-hydroxypropan-2-yl)-1H-1,2,4-triazol-5(4H)-one | 412.2 | A: 1.51, 100% B: 1.55, 99.9% | ¹H NMR (400 MHz, DMSO-d₆) δ ppm 12.94 (br. s., 1H) 8.20 (s, 1H), 7.93 (s, 1H), 7.88 (d, J = 8.7 Hz, 2H), 7.70 (d, J = 8.7 Hz, 2H), 7.20-7.11 (m, 1H), 7.04 (d, J = 6.6 Hz, 2H), 5.81 (s, 1H), 5.21 (s, 2H), 1.50 (s, 6H); ¹⁹F NMR (377 MHz, DMSO-d₆) δ ppm −109.747 |

TABLE 5-continued

| Example | Structure | Name | LCMS (M + H)+ | LC\MS Method, RT (min.), & Purity | NMR |
|---|---|---|---|---|---|
| 138 | 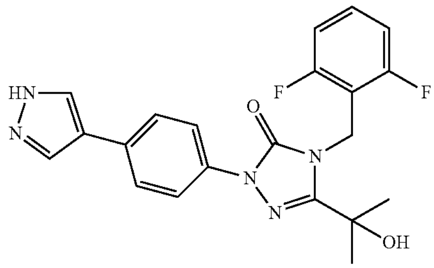 [SMILES: CC(C)(O)c1nn(-c2ccc(-c3cn[nH]c3)cc2)c(=O)n1Cc1c(F)cccc1F] | 1-(4-(1H-pyrazol-4-yl)phenyl)-4-(2,6-difluorobenzyl)-3-(2-hydroxypropan-2-yl)-1H-1,2,4-triazol-5(4H)-one | 412.2 | A: 1.40, 98.3% B: 1.44, 98.5% | $^1$H NMR (400 MHz, DMSO-d$_6$) δ ppm 12.94 (br. s., 1H) 8.20 (br. s., 1H), 7.93 (br. s., 1H), 7.85 (d, J = 8.7 Hz, 2H), 7.68 (d, J = 8.7 Hz, 2H), 7.46-7.30 (m, 1H), 7.13-7.00 (m, 2H), 5.81 (s, 1H), 5.29 (s, 2H), 1.44 (s, 6H); $^{19}$F NMR (377 MHz, DMSO-d$_6$) δ ppm −115.308 |
| 139 | 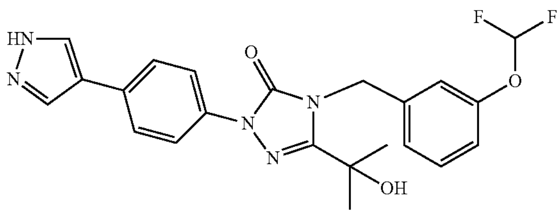 [SMILES: CC(C)(O)c1nn(-c2ccc(-c3cn[nH]c3)cc2)c(=O)n1Cc1cccc(OC(F)F)c1] | 1-(4-(1H-pyrazol-4-yl)phenyl)-4-(3-(difluoromethoxy)benzyl)-3-(2-hydroxypropan-2-yl)-1H-1,2,4-triazol-5(4H)-one | 442.3 | A: 1.53, 98.8% B: 1.56, 97.8% | $^1$H NMR (400 MHz, DMSO-d$_6$) δ ppm 12.94 (br. s., 1H) 8.20 (br. s., 1H), 7.93 (br. s., 1H), 7.85 (d, J = 8.7 Hz, 2H), 7.68 (d, J = 8.7 Hz, 2H), 7.42-7.38 (t, J = 15.6 Hz, 1 H), 7.22-7.03 (m, 4H), 5.81 (s, 1H), 5.29 (s, 2H), 1.44 (s, 6H); $^{19}$F NMR (377 MHz, DMSO-d$_6$) δ ppm −81.596 |
| 140 | 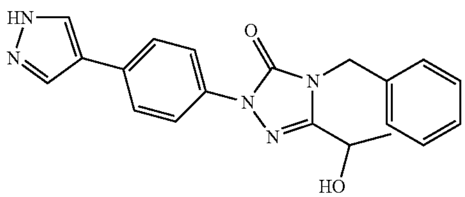 [SMILES: CC(O)c1nn(-c2ccc(-c3cn[nH]c3)cc2)c(=O)n1Cc1ccccc1] | 1-(4-(1H-pyrazol-4-yl)phenyl)-4-benzyl-3-(1-hydroxyethyl)-1H-1,2,4-triazol-5(4H)-one (nantiomer 1) | 362.2 | A: 1.33, 100% B: 1.31, 100% | $^1$H NMR (400 MHz, DMSO-d$_6$) δ ppm = 12.94 (s, 1 H) 8.07 (s, 2 H) 7.92-7.85 (m, 2H), 7.73-7.67 (m, 2H), 7.41-7.26 (m, 5H), 5.85 (d, J = 6.1 Hz, 1H), 5.04 (q, J = 16 Hz, 2 H), 4.68 (t, J = 6.3 Hz, 1H), 1.42 (d, J = 6.5 Hz, 3H); [α]$^{25}$D = −130° (c 0.1, MeOH) |
| 141 | 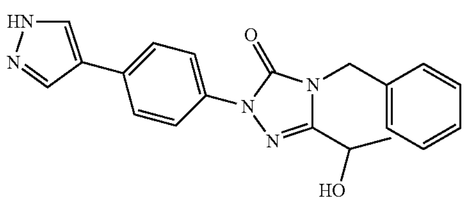 [SMILES: CC(O)c1nn(-c2ccc(-c3cn[nH]c3)cc2)c(=O)n1Cc1ccccc1] | 1-(4-(1H-pyrazol-4-yl)phenyl)-4-benzyl-3-(1-hydroxyethyl)-1H-1,2,4-triazol-5(4H)-one (enantiomer 2) | 362.2 | A: 1.33, 96.1% B: 1.31, 96.5% | $^1$H NMR (400 MHz, DMSO-d$_6$) δ ppm = 12.94 (s, 1 H) 8.07 (s, 2 H) 7.92-7.85 (m, 2H), 7.73-7.67 (m, 2H), 7.41-7.26 (m, 5H), 5.85 (d, J = 6.1 Hz, 1H), 5.04 (q, J = 16 Hz, 2 H), 4.68 (t, J = 6.3 Hz, 1H), 1.42 (d, J = 6.5 Hz, 3H) |
| 142 | 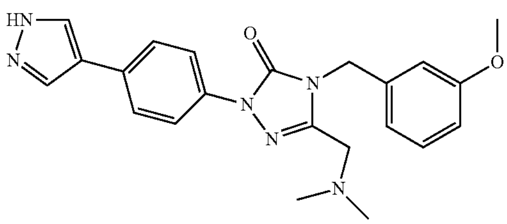 [SMILES: COc1cccc(Cn2c(CN(C)C)nn(-c3ccc(-c4cn[nH]c4)cc3)c2=O)c1] | 1-(4-(1H-pyrazol-4-yl)phenyl)-3-((dimethylamino)methyl)-4-(3-methoxybenzyl)-1H-1,2,4-triazol-5(4H)-one | 405.3 | A: 1.67, 98.5% B: 1.02, 96.9% | $^1$H NMR (400 MHz, DMSO-d$_6$) δ ppm 12.94 (s, 1 H) 8.20 (br. s, 1H), 7.93 (br. s., 1H), 7.90-7.85 (m, 2H), 7.72-7.67 (m, 2H), 7.28 (t, J = 7.9 Hz, 1H), 6.94-6.85 (m, 3H), 4.97 (s, |

TABLE 5-continued

| Example | Structure | Name | LCMS (M + H)+ | LC\MS Method, RT (min.), & Purity | NMR |
|---|---|---|---|---|---|
| | | | | | 2H), 3.74 (s, 3H), 3.36 (s, 2H), 2.21 (s, 6H) |
| 143 | 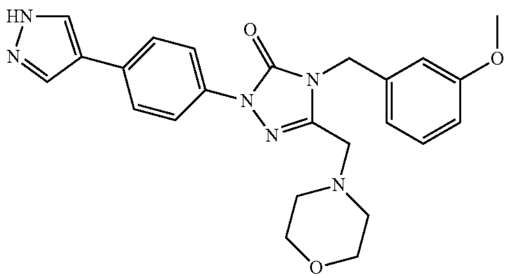 [SMILES: COc1cccc(Cn2c(CN3CCOCC3)nn(-c3ccc(-c4cn[nH]c4)cc3)c2=O)c1] | 1-(4-(1H-pyrazol-4-yl)phenyl)-4-(3-methoxybenzyl)-3-(morpholinomethyl)-1H-1,2,4-triazol-5(4H)-one | 447.3 | A: 1.55, 98.9% B: 1.17, 98.9% | $^1$H NMR (400 MHz, DMSO-d$_6$) δ ppm 12.94 (s, 1 H) 8.20 (s, 1H), 7.93 (s, 1H), 7.90-7.84 (m, 2H), 7.73-7.66 (m, 2H), 7.31-7.24 (m, 1H), 6.91-6.84 (m, 3H), 4.98 (s, 2H), 3.74 (s, 3H), 3.44 (s, 2H), 3.40 (br. s., 4H), 2.37 (br. s., 4H) |
| 144 | 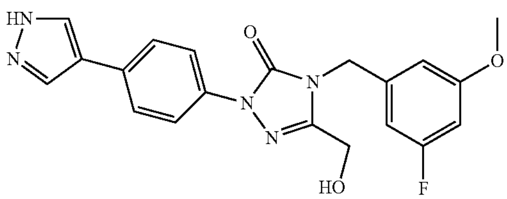 [SMILES: COc1cc(F)cc(Cn2c(CO)nn(-c3ccc(-c4cn[nH]c4)cc3)c2=O)c1] | 1-(4-(1H-pyrazol-4-yl)phenyl)-4-(3-fluoro-5-methoxybenzyl)-3-(hydroxymethyl)-1H-1,2,4-triazol-5(4H)-one | 396.2 | A: 1.32, 97.1% B: 1.31, 98.9% | $^1$H NMR (400 MHz, DMSO-d$_6$) δ ppm 12.95 (s, 1 H) 8.20 (br. s, 1H), 7.93 (br. s., 1H), 7.90-7.84 (m, 2H), 7.74-7.67 (m, 2H), 6.82-6.71 (m, 3H), 5.80 (t, J = 5.8 Hz, 1H), 4.94 (s, 2H), 4.45 (d, J = 5.8 Hz, 2H), 3.76 (s, 3H); $^{19}$F NMR (377 MHz, DMSO-d$_6$) δ ppm −111.306 |
| 145 | 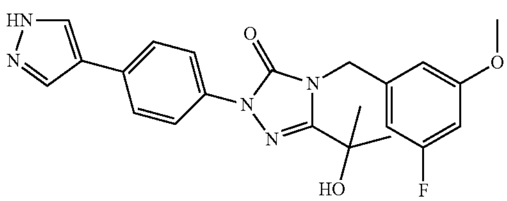 [SMILES: COc1cc(F)cc(Cn2c(C(C)(C)O)nn(-c3ccc(-c4cn[nH]c4)cc3)c2=O)c1] | 1-(4-(1H-pyrazol-4-yl)phenyl)-4-(3-fluoro-5-methoxybenzyl)-3-(2-hydroxypropan-2-yl)-1H-1,2,4-triazol-5(4H)-one | 424.3 | A: 1.49, 98.4% B: 1.53, 98.4% | $^1$H NMR (400 MHz, DMSO-d$_6$) δ ppm = 12.99 (s, 1 H) 8.20 (br. s, 1H), 7.93 (br. s., 1H), 7.90-7.84 (m, 2H), 7.74-7.67 (m, 2H), 6.82-6.71 (m, 3H), 5.80 (s, 1H), 5.18(s, 2H), 3.78(s, 3H), 1.49 (s, 6H); $^{19}$F NMR (377 MHz, DMSO-d$_6$) δ ppm −111.050 |
| 146 | 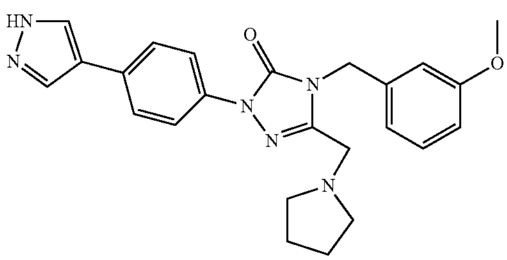 [SMILES: COc1cccc(Cn2c(CN3CCCC3)nn(-c3ccc(-c4cn[nH]c4)cc3)c2=O)c1] | 1-(4-(1H-pyrazol-4-yl)phenyl)-4-(3-methoxybenzyl)-3-(pyrrolidin-1-ylmethyl)-1H-1,2,4-triazol-5(4H)-one | 431.3 | A: 1.84, 100% B: 1.03, 99.1% | $^1$H NMR (400 MHz, DMSO-d$_6$) δ ppm 10.45 (s, 1 H), 8.09 (s, 2H), 7.91 (d, J = 8.7 Hz, 2H), 7.73 (d, J = 8.7 Hz, 2H), 7.32 (t, J = 8.3 Hz, 1H), 6.97-6.83 (m, 3H), 4.95 (s, 2H), 4.60 (br. s., 2H) 3.76 (s, 3 H), 3.59 (s, 2 H), 3.16 (s, 2 H), 2.04 (s, 2 H), 1.92 (s, 2 H) |

TABLE 5-continued

| Example | Structure | Name | LCMS (M + H)+ | LC\MS Method, RT (min.), & Purity | NMR |
|---|---|---|---|---|---|
| 147 | 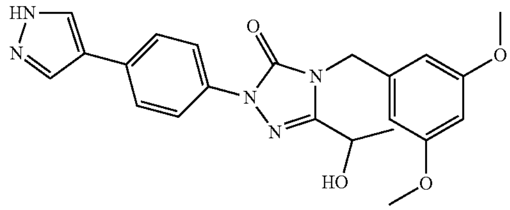 [SMILES: COc1cc(Cn2c(C(C)O)nn(-c3ccc(-c4cn[nH]c4)cc3)c2=O)cc(OC)c1] | 1-(4-(1H-pyrazol-4-yl)phenyl)-4-(3,5-dimethoxybenzyl)-3-(1-hydroxyethyl)-1H-1,2,4-triazol-5(4H)-one (enantiomer 1) | 422.3 | A: 1.34, 100% B: 1.36, 100% | $^1$H NMR (400 MHz, DMSO-d$_6$) δ 12.91 (s, 1 H) 8.08 (s, 2 H) 7.89-7.86 (m, 2H), 7.70-7.68 (m, 2H), 6.49-6.44 (m, 3H), 5.88 (d, J = 6.1 Hz, 1H), 4.93 (q, J = 16 Hz, 2 H), 4.72-4.65 (m, 1H), 3.73 (s, 6H) 1.42 (d, J = 6.5 Hz, 3H) |
| 148 | 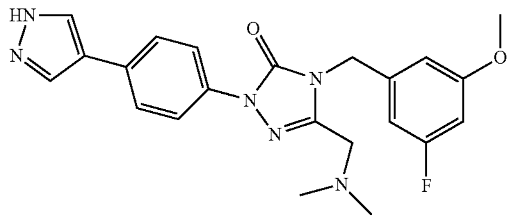 [SMILES: COc1cc(F)cc(Cn2c(CN(C)C)nn(-c3ccc(-c4cn[nH]c4)cc3)c2=O)c1] | 1-(4-(1H-pyrazol-4-yl)phenyl)-3-((dimethylamino)methyl)-4-(3-fluoro-5-methoxybenzyl)-1H-1,2,4-triazol-5(4H)-one | 423.3 | A: 1.68, 100% B: 1.01, 100% | $^1$H NMR (400 MHz, DMSO-d$_6$) δ ppm = 12.94 (s, 1 H), 8.19 (s, 1H), 8.06 (s, 1H), 7.86 (d, J = 8.7 Hz, 2H), 7.68 (d, J = 8.7 Hz, 2H), 6.73-6.78 (m, 3H), 4.95 (s, 2H), 3.75 (s, 3H), 3.39 (s, 2H), 2.20 (s, 6 H); $^{19}$F NMR (377 MHz, DMSO-d$_6$) δ ppm −111.383 |
| 149 | 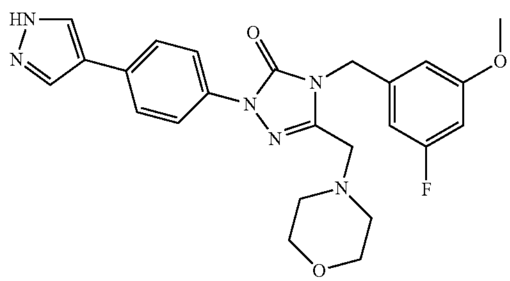 [SMILES: COc1cc(F)cc(Cn2c(CN3CCOCC3)nn(-c3ccc(-c4cn[nH]c4)cc3)c2=O)c1] | 1-(4-(1H-pyrazol-4-yl)phenyl)-4-(3-fluoro-5-methoxybenzyl)-3-(morpholinomethyl)-1H-1,2,4-triazol-5(4H)-one | 465.3 | A: 1.52, 100% B: 1.24, 100% | $^1$H NMR (400 MHz, DMSO-d$_6$) δ ppm 12.94 (s, 1 H), 8.18 (s, 1H), 7.93 (s, 1H), 7.86 (d, J = 8.7 Hz, 2H), 7.68 (d, J = 8.7 Hz, 2H), 6.73-6.80 (m, 3H), 4.95 (s, 2H), 3.75 (s, 3H), 3.47 (s, 2H), 3.34-3.37 (m, 4 H), 2.32-2.37 (m, 4 H); $^{19}$F NMR (377 MHz, DMSO-d$_6$) δ ppm −111.614 |
| 150 | 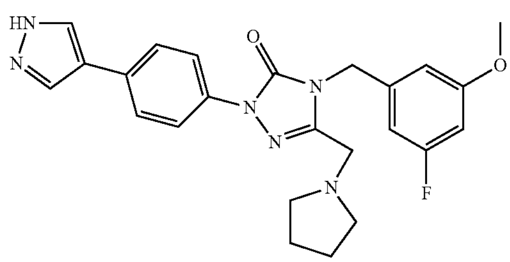 [SMILES: COc1cc(F)cc(Cn2c(CN3CCCC3)nn(-c3ccc(-c4cn[nH]c4)cc3)c2=O)c1] | 1-(4-(1H-pyrazol-4-yl)phenyl)-4-(3-fluoro-5-methoxybenzyl)-3-(pyrrolidin-1-ylmethyl)-1H-1,2,4-triazol-5(4H)-one | 449.3 | A: 1.86, 99.7% B: 1.08, 97.6% | $^1$H NMR (400 MHz, DMSO-d$_6$) δ ppm 12.95 (s, 1 H), 8.18 (s, 1H), 7.94 (s, 1H), 7.86 (d, J = 8.7 Hz, 2H), 7.68 (d, J = 8.7 Hz, 2H), 6.74-6.78 (m, 3H), 4.93 (s, 2H), 3.75 (s, 3H), 3.59 (s, 2H), 2.46-2.50 (m, 4 H), 1.62-1.69 (m, 4 H); $^{19}$F NMR (377 MHz, DMSO-d$_6$) δ ppm −111.610 |

TABLE 5-continued

| Example | Structure | Name | LCMS (M + H)+ | LC\MS Method, RT (min.), & Purity | NMR |
|---|---|---|---|---|---|
| 151 | 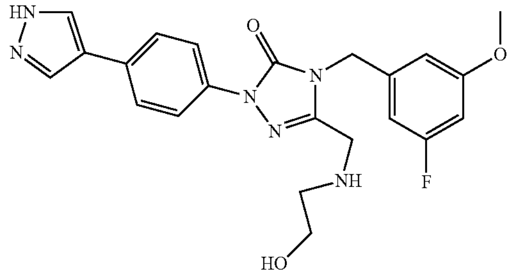 [SMILES: COc1cc(F)cc(Cn2c(CNCCO)nn(-c3ccc(-c4cn[nH]c4)cc3)c2=O)c1] | 1-(4-(1H-pyrazol-4-yl)phenyl)-4-(3-fluoro-5-methoxybenzyl)-3-(((2-hydroxyethyl)amino)methyl)-1H-1,2,4-triazol-5(4H)-one | 439.3 | A: 1.21, 96.0% B: 0.96, 98.1% | $^1$H NMR (400 MHz, DMSO-d$_6$) δ ppm 9.30 (s, 2 H), 8.08 (s, 2H), 7.89 (d, J = 8.7 Hz, 2H), 7.72 (d, J = 8.7 Hz, 2H), 6.75-6.84 (m, 3H), 4.95 (s, 3H), 4.34 (s, 2H), 3.75 (s, 3H), 3.70-3.73 (m, 2 H), 3.16-3.22 (m, 2 H); $^{19}$F NMR (377 MHz, DMSO-d$_6$) δ ppm −110.771 |
| 152 | 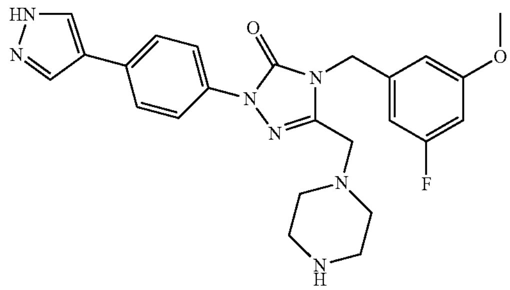 [SMILES: COc1cc(F)cc(Cn2c(CN3CCNCC3)nn(-c3ccc(-c4cn[nH]c4)cc3)c2=O)c1] | 1-(4-(1H-pyrazol-4-yl)phenyl)-4-(3-fluoro-5-methoxybenzyl)-3-(piperazin-1-ylmethyl)-1H-1,2,4-triazol-5(4H)-one | 464.3 | A: 1.01, 92.9% B: 1.00, 92.0% | $^1$H NMR (400 MHz, DMSO-d$_6$) δ ppm 8.06 (s, 2H), 7.86 (d, J = 8.7 Hz, 2H), 7.68 (d, J = 8.7 Hz, 2H), 6.73-6.78 (m, 3H), 4.94 (s, 2H), 3.71 (s, 3H), 3.41 (s, 2H), 2.52 (br. s., 4H), 2.30 (br. s., 4H) 1.89 (s, 1H); $^{19}$F NMR (377 MHz, DMSO-d$_6$) δ ppm −111.620 |
| 153 | 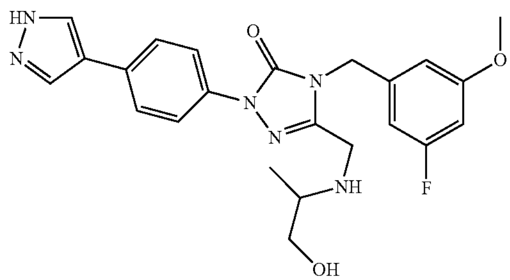 [SMILES: COc1cc(F)cc(Cn2c(CNC(C)CO)nn(-c3ccc(-c4cn[nH]c4)cc3)c2=O)c1] | 1-(4-(1H-pyrazol-4-yl)phenyl)-4-(3-fluoro-5-methoxybenzyl)-3-(((1-hydroxypropan-2-yl)amino)methyl)-1H-1,2,4-triazol-5(4H)-one | 453.3 | A: 1.32, 99.0% B: 1.00, 97.9% | $^1$H NMR (400 MHz, DMSO-d$_6$) δ ppm 12.94 (s, 1 H), 8.17 (s, 1H), 8.06 (s, 1H), 7.82-7.89 (m, 2H), 7.67-7.71 (m, 2H), 6.76-6.78 (m, 3H), 5.00 (s, 2H), 4.54 (t, J = 5.2 Hz, 1H) 3.76 (s, 3H) 3.71 (s, 2H) 3.23-3.26 (m, 2H) 2.60-2.67 (M, 1H) 2.12-2.19 (m, 1H) 0.89-0.91 (d, J = 6.4, 3H); $^{19}$F NMR (377 MHz, DMSO-d$_6$) δ ppm −111.248 |
| 155 | 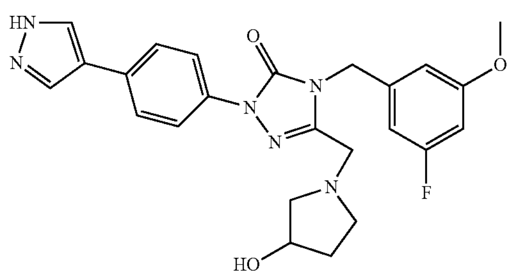 [SMILES: COc1cc(F)cc(Cn2c(CN3CCC(O)C3)nn(-c3ccc(-c4cn[nH]c4)cc3)c2=O)c1] | 1-(4-(1H-pyrazol-4-yl)phenyl)-4-(3-fluoro-5-methoxybenzyl)-3-((3-hydroxypyrrolidin-1-yl)methyl)-1H-1,2,4-triazol-5(4H)-one | 465.3 | A: 1.40, 100% B: 1.01, 98.0% | $^1$H NMR (400 MHz, DMSO-d$_6$) δ ppm 12.94 (s, 1H) 8.18 (s, 1H), 8.09 (s, 1H) 7.86 (d, J = 8.7 Hz, 2H), 7.68 (d, J = 8.7 Hz, 2H), 6.73-6.79 (m, 3H), 4.94 (s, 2H), 4.71 (d, J = 4.4 Hz, 1H), 4.11-4.12 (d, J = 2.4, 1 H) 3.75 (s, 3H), 3.56-(s., 2H) 2.74-2.78 m., 1H), 2.55-2.59 (m., 1H) 2.46-2.49(m, 1H), 2.34-2.35 (m, 1H) 1.85-1.90 (m, 1H), 1.52-1.54 (m, 1H); $^{19}$F NMR |

TABLE 5-continued

| Example | Structure | Name | LCMS (M + H)+ | LC\MS Method, RT (min.), & Purity | NMR |
|---|---|---|---|---|---|
| | | | | | (377 MHz, DMSO-d₆) δ ppm −111.412 |
| 156 | 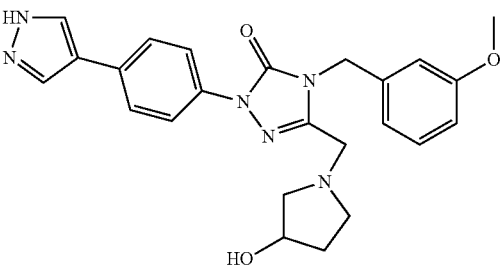 [SMILES: COc1cccc(Cn2c(CN3CCC(O)C3)nn(-c3ccc(-c4cn[nH]c4)cc3)c2=O)c1] | 1-(4-(1H-pyrazol-4-yl)phenyl)-3-((3-hydroxypyrrolidin-1-yl)methyl)-4-(3-methoxybenzyl)-1H-1,2,4-triazol-5(4H)-one | 447.3 | A: 1.32, 99.1% B: 0.94, 96.9% | ¹H NMR (400 MHz, DMSO-d₆) δ ppm 8.06 (s, 2H), 7.86 (d, J = 8.7 Hz, 2H), 7.68 (d, J = 8.7 Hz, 2H), 7.25 (t, J = 7.6, 1H), 6.73-6.79 (m, 3H), 4.94 (s, 2H), 4.71(d, J = 4.4 Hz, 1H), 4.11-4.12 (d, J = 2.4, 1 H) 3.75 (s, 3H), 3.56-(s., 2H) 2.74-2.78 m., 1H), 2.55-2.59 (m., 1H) 2.46-2.49(m, 1H), 2.34-2.35 (m, 1H) 1.85-1.90 (m, 1H), 1.52-1.54 (m, 1H) |
| 157 | 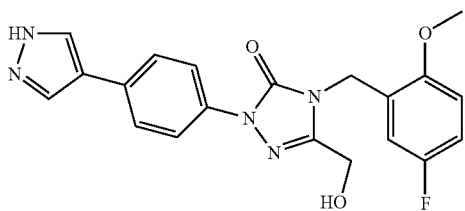 [SMILES: COc1ccc(F)cc1Cn1c(CO)nn(-c2ccc(-c3cn[nH]c3)cc2)c1=O] | 1-(4-(1H-pyrazol-4-yl)phenyl)-4-(5-fluoro-2-methoxybenzyl)-3-(hydroxymethyl)-1H-1,2,4-triazol-5(4H)-one | 396.2 | A: 1.91, 100% B: 1.25, 98.1% | ¹H NMR (400 MHz, DMSO-d₆) δ ppm 12.94 (s, 1H), 8.20 (s, 1H), 7.93 (s, 1H), 7.90-7.85 (m, 2H), 7.72-7.68 (m, 2H), 7.16-7.10 (m, 1H), 7.08-7.03 (m, 1H), 6.90 (dd, J = 3.0, 9.1 Hz, 1H), 5.84 (t, J = 5.4 Hz, 1H), 4.92 (s, 2H), 4.46 (d, J = 4.8 Hz, 2H), 3.84 (s, 3H); ¹⁹F NMR (377 MHz, DMSO-d₆) δ ppm −123.794 |
| 158 | 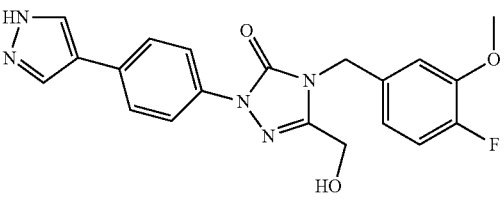 [SMILES: COc1cc(Cn2c(CO)nn(-c3ccc(-c4cn[nH]c4)cc3)c2=O)ccc1F] | 1-(4-(1H-pyrazol-4-yl)phenyl)-4-(4-fluoro-3-methoxybenzyl)-3-(hydroxymethyl)-1H-1,2,4-triazol-5(4H)-one | 396.2 | A: 1.17, 98.6% B: 1.23, 98.6% | ¹H NMR (400 MHz, DMSO-d₆) δ ppm 12.94 (s, 1H), 8.20 (s, 1H), 7.93 (s, 1H), 7.90-7.85 (m, 2H), 7.73-7.67 (m, 2H), 7.28-7.23 (m, 1H), 7.19 (dd, J = 8.3, 11.5 Hz, 1H), 6.91 (ddd, J = 2.0, 4.3, 8.3 Hz, 1H), 5.84 (t, J = 5.4 Hz, 1H), 4.94 (s, 2H), 4.46 (d, J = 4.8 Hz, 2H), 3.83 (s, 3H); ¹⁹F NMR (377 MHz, DMSO-d₆) δ ppm −136.838 |
| 159 | 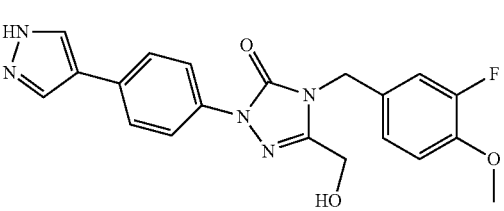 [SMILES: COc1ccc(Cn2c(CO)nn(-c3ccc(-c4cn[nH]c4)cc3)c2=O)cc1F] | 1-(4-(1H-pyrazol-4-yl)phenyl)-4-(3-fluoro-4-methoxybenzyl)-3-(hydroxymethyl)-1H-1,2,4-triazol-5(4H)-one | 396.2 | A: 1.12, 100% B: 1.23, 97.4% | ¹H NMR (400 MHz, DMSO-d₆) δ ppm 12.94 (s, 1H), 8.20 (s, 1H), 7.93 (s, 1H), 7.90-7.84 (m, 2H), 7.72-7.66 (m, 2H), 7.30-7.24 (m, 1H), 7.19-7.10 (m, 2H), 5.82 (t, J = 5.8 |

TABLE 5-continued

| Example | Structure | Name | LCMS (M + H)+ | LC\MS Method, RT (min.), & Purity | NMR |
|---|---|---|---|---|---|
| | | | | | Hz, 1H), 4.90 (s, 2H), 4.46 (d, J = 4.8 Hz, 2H), 3.82 (s, 3H); 19F NMR (377 MHz, DMSO-d6) δ ppm −135.115 |
| 160 | 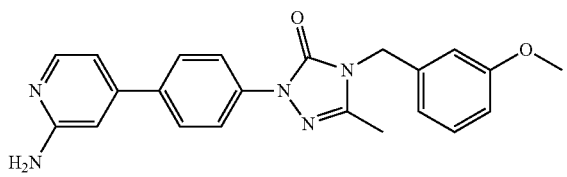 [SMILES: COc1cccc(Cn2c(C)nn(-c3ccc(-c4ccnc(N)c4)cc3)c2=O)c1] | 1-(4-(1H-pyrazol-4-yl)phenyl)-4-(2-fluoro-3-methoxybenzyl)-3-(hydroxymethyl)-1H-1,2,4-triazol-5(4H)-one | 396.2 | A: 1.12, 100% B: 1.18, 100% | 1H NMR (400 MHz, DMSO-d6) δ ppm 12.94 (s, 1H), 8.20 (s, 1H), 7.93 (s, 1H), 7.90-7.85 (m, 2H), 7.73-7.67 (m, 2H), 7.17-7.08 (m, 2H), 6.86-6.78 (m, 1H), 5.75 (t, J = 5.7 Hz, 1H), 5.03 (s, 2H), 4.46 (d, J = 4.8 Hz, 2H), 3.84 (s, 3H); 19F NMR (377 MHz, DMSO-d6) δ ppm −141.141 |

Example 161

1-(4-(2-aminopyridin-4-yl)phenyl)-4-(3-methoxybenzyl)-3-methyl-1H-1,2,4-triazol-5(4H)-one

Example 161a

Preparation of 4-(3-methoxybenzyl)-3-methyl-1-(4-(4,4,5,5-tetramethyl-1,3,2-dioxaborolan-2-yl)phenyl)-1H-1,2,4-triazol-5(4H)-one

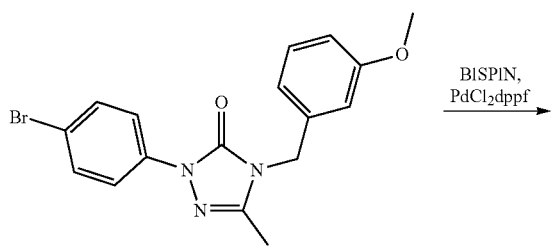

BISPIN, PdCl2dppf

-continued

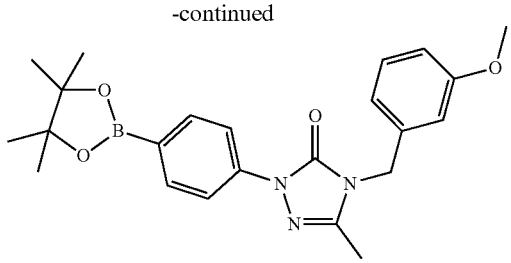

A mixture of 1-(4-bromophenyl)-4-(3-methoxybenzyl)-3-methyl-1H-1,2,4-triazol-5(4H)-one (200 mg, 0.534 mmol), potassium acetate (131 mg, 1.34 mmol) and bis(catecholato)diboron (147 mg, 0.615 mmol) in 1,4-Dioxane (10 mL) was flushed with nitrogen for 20 min. PdCl2(dppf) (11.73 mg, 0.016 mmol) was added to the reaction mixture and the reaction mixture heated at 80° C. for 8 h. The reaction mixture was cooled to RT and solvents were evaporated at reduced pressure to give black color residue. The residue was diluted with ethyl acetate (150 mL) and washed with satd aq. NH4Cl and brine. The ethyl acetate layer was dried over Na2SO4, filtered and concentrated to give the crude. Crude was purified by flash chromatography [5-20% ethyl acetate/pet. ether gradient] to afford 4-(3-methoxybenzyl)-3-methyl-1-(4-(4,4,5,5-tetramethyl-1,3,2-dioxaborolan-2-yl)phenyl)-1H-1,2,4-triazol-5(4H)-one (190 mg, 84% yield) as a white solid. MS(ESI) m/z: 422 (M+H)+; 1H NMR (400 MHz, DMSO-d6) δ ppm 7.98-7.93 (m, 2H) 7.76-7.73 (d, J=11.6 Hz, 2H) 7.32-7.27 (m, 1H) 6.90-6.83 (m, 3H) 3.92 (s, 2H) 3.74 (s, 3H) 1.99 (s, 3H) 1.07 (s, 12H).

Example 161

Preparation of 1-(4-(2-aminopyridin-4-yl)phenyl)-4-(3-methoxybenzyl)-3-methyl-1H-1,2,4-triazol-5(4H)-one

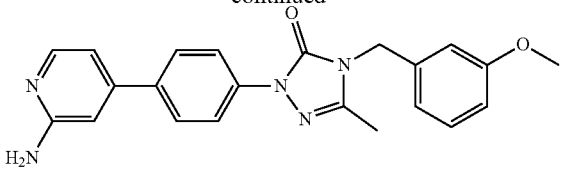

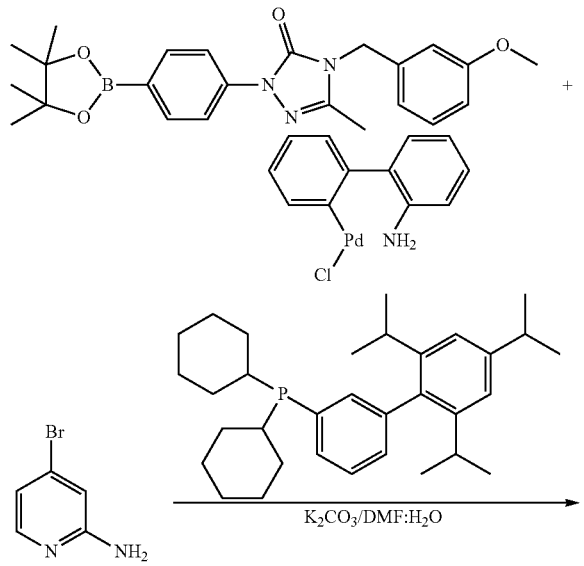

A mixture of 4-bromopyridin-2-amine (50 mg, 0.289 mmol), $K_2CO_3$ (120 mg, 0.867 mmol), and 4-(3-methoxybenzyl)-3-methyl-1-(4-(4,4,5,5-tetramethyl-1,3,2-dioxaborolan-2-yl)phenyl)-1H-1,2,4-triazol-5(4H)-one (146 mg, 0.347 mmol) in DMF (2 mL) and water (0.2 mL) was flushed with nitrogen for 10 min. $2^{nd}$ generation XPHOS precatalyst (6.8 mg, 8.7 µmol) was added and the reaction mixture was heated at at 95° C. for 2 h. The reaction mixture was cooled to rt and the solvent was evaporated. The residue was diluted with DCM (100 mL), washed with brine, dried over $Na_2SO_4$, filtered and concentrated. The crude was purified by preparative HPLC to afford 1-(4-(2-aminopyridin-4-yl)phenyl)-4-(3-methoxybenzyl)-3-methyl-1H-1,2,4-triazol-5(4H)-one (3 mg, 2% yield) as a white solid. MS(ESI) m/z: 388 (M+H)$^+$; $^1$H NMR (400 MHz, DMSO-$d_6$) δ=8.18-8.08 (m, 2H), 8.02 (d, J=6.7 Hz, 1H), 7.94-7.84 (m, 2H), 7.70 (s, 2H) 7.31 (dd, J=7.6, 9.0 Hz, 1H), 7.23 (dd, J=1.6, 6.8 Hz, 1H), 7.18 (s, 1H), 6.94-6.82 (m, 3H), 4.91 (s, 2H), 3.75 (s, 3H), 2.25 (s, 3H); HPLC RT=1.57, 99.5% (Method A); RT=1.27 min, 100% (Method B).

The following Examples in Table 6 were made by using the same procedure as shown in Example 161.

TABLE 6

| Table 6 Example | Structure | Name | LCMS (M + H)$^+$ | LC\MS Method, RT (min.), & Purity | NMR |
|---|---|---|---|---|---|
| 162 | 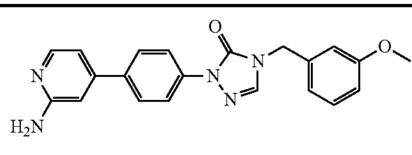 | 1-(4-(2-aminopyridin-4-yl)phenyl)-4-(3-methoxybenzyl)-1H-1,2,4-triazol-5(4H)-one | 374.3 | A: 1.47, 95.3% B: 1.16, 95.3% | $^1$H NMR (400 MHz, DMSO-$d_6$) δ ppm 8.40 (s, 1H), 8.02 (d, J = 8.7 Hz, 2H), 7.97 (d, J = 5.3 Hz, 1H), 7.75 (d, J = 8.7 Hz, 2H), 7.31 (t, J = 7.9 Hz, 1H), 6.98-6.88 (m, 3H), 6.80 (d, J = 5.3 Hz, 1H), 6.72 (s, 1H), 5.97 (s, 2H), 4.87 (s, 2H), 3.76 (s, 3H) |
| 163 | 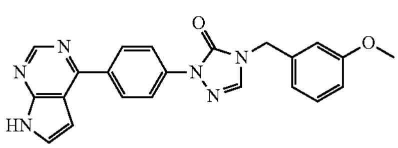 | 1-(4-(7H-pyrrolo[2,3-d]pyrimidin-4-yl)phenyl)-4-(3-methoxybenzyl)-1H-1,2,4-triazol-5(4H)-one | 399.2 | A: 1.47, 96.7% B: 1.31, 97.5% | $^1$H NMR (400 MHz, DMSO-$d_6$) δ ppm 12.25 (s, 1 H) 8.83 (s, 1H), 8.44 (s, 1H), 8.33 (d, J = 8.7 Hz, 2H), 8.15 (d, J = 28.7 Hz, 2H), 7.66 (d, J = 2.5 Hz, 1H), 7.32 (t, J = 7.9 Hz, 1H), 7.00-6.86 (m, 4H), 4.89 (s, 2H), 3.76 (s, 3H) |
| 164 | 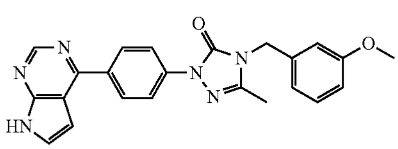 [SMILES: COc1cccc(Cn2c(C)nn(-c3ccc(-c4ncnc5[nH]ccc45)cc3)c2=O)c1] | 1-(4-(7H-pyrrolo[2,3-d]pyrimidin-4-yl)phenyl)-4-(3-methoxybenzyl)-3-methyl-1H-1,2,4-triazol-5(4H)-one | 413.3 | A: 1.56, 100% B: 1.25, 100% | $^1$H NMR (400 MHz, DMSO-$d_6$) δ ppm 12.25 (s, 1 H) 8.82 (s, 1H), 8.34-8.31 (m, 2H), 8.16-8.13 (m, 2H), 7.67-7.65 (m, 1H), 7.33-7.29 (m, 1H), 6.97-6.95 (m, 1H), 6.91-6.89 (m, 3H), 4.91 (s, 2H), 3.75 (s, 3H), 2.26 (s, 3H) |
| 165 | 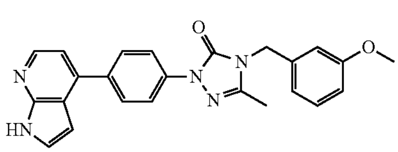 [SMILES: COc1cccc(Cn2c(C)nn(-c3ccc(-c4ccnc5[nH]ccc45)cc3)c2=O)c1] | 1-(4-(1H-pyrrolo[2,3-b]pyridin-4-yl)phenyl)-4-(3-methoxybenzyl)-3-methyl-1H-1,2,4-triazol-5(4H)-one | 412.3 | A: 1.75, 98.0% B: 1.36, 96.1% | $^1$H NMR (400 MHz, DMSO-$d_6$) δ ppm 11.84 (s, 1 H), 8.30 (d, J = 5.0 Hz, 1H), 8.12 (d, J = 8.7 Hz, 2H), 7.90 (d, J = 8.7 Hz, 2H), 7.57 (t, J = 2.8 Hz, 1H), 7.34-7.28 (m, 1H), 7.24 (d, J = 5.0 Hz, 1H), 6.94-6.85 (m, 3H), 6.68 (d, J = 1.5 Hz, 1H), 4.92 (s, 2H), 3.75 (s, 3 H), 2.26 (s, 3H) |

TABLE 6-continued

| Table 6 Example | Structure | Name | LCMS (M + H)+ | LC\MS Method, RT (min.), & Purity | NMR |
|---|---|---|---|---|---|
| 166 | 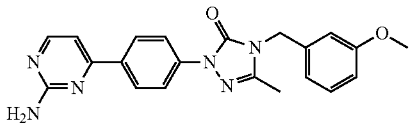 [SMILES: COc1cccc(Cn2c(C)nn(-c3ccc(-c4ccnc(N)n4)cc3)c2=O)c1] | 1-(4-(2-aminopyrimidin-4-yl)phenyl)-4-(3-methoxybenzyl)-3-methyl-1H-1,2,4-triazol-5(4H)-one | 389.3 | A: 1.52, 100% B: 1.22, 100% | $^1$H NMR (400 MHz, DMSO-$d_6$) δ ppm 8.38 (d, J = 6.0 Hz, 1H), 8.27 (d, J = 8.8 Hz, 2H), 8.12 (d, J = 8.8 Hz, 2H), 7.59 (s, 2 H) 7.38 (d, J = 5.9 Hz, 1H), 7.34-7.25 (m, 1H), 6.94-6.82 (m, 3H), 4.90 (s, 2H), 3.74 (s, 3 H), 2.25 (s, 3H) |
| 169 | 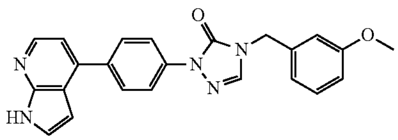 [SMILES: COc1cccc(Cn2cnn(-c3ccc(-c4ccnc5[nH]ccc45)cc3)c2=O)c1] | 1-(4-(1H-pyrrolo[2,3-b]pyridin-4-yl)phenyl)-4-(3-methoxybenzyl)-1H-1,2,4-triazol-5(4H)-one | 398.2 | A: 1.60, 98.2% B: 1.28, 98.3% | $^1$H NMR (400 MHz, DMSO-$d_6$) δ ppm 11.84 (s, 1H), 8.42 (s, 1H), 8.29 (d, J = 4.8 Hz, 1H), 8.10 (d, J = 8.7 Hz, 2H), 7.89 (d, J = 8.7 Hz, 2H), 7.56 (t, J = 2.8 Hz, 1H), 7.30 (t, J = 7.6 Hz, 1H), 7.23 (d, J = 5.0 Hz, 1H), 6.90-6.97 (m, 3H), 6.67-6.68 (m, 1H), 4.89 (s, 2H), 3.75 (s, 3 H) |
| 170 | 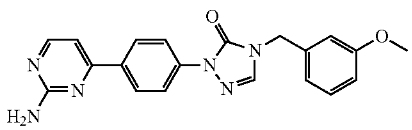 [SMILES: COc1cccc(Cn2cnn(-c3ccc(-c4ccnc(N)n4)cc3)c2=O)c1] | 1-(4-(2-aminopyrimidin-4-yl)phenyl)-4-(3-methoxybenzyl)-1H-1,2,4-triazol-5(4H)-one | 375.2 | A: 1.40, 99.8% B: 1.14, 99.3% | $^1$H NMR (400 MHz, DMSO-$d_6$) δ ppm 8.44 (s, 1H) 8.38 (d, J = 6.0 Hz, 1H), 8.26 (d, J = 8.8 Hz, 2H), 8.09 (d, J = 8.8 Hz, 2H), 7.65 (s, 2H), 7.37 (d, J = 5.6 Hz, 1H), 7.28 (t, J = 8 Hz, 1H), 6.89-6.96 (m, 3H), 4.86 (s, 2H), 3.75 (s, 3 H |

Example 172

Preparation 1-(4-(1H-pyrazol-4-yl)phenyl)-4-(3-methoxybenzyl)-1H-tetrazol-5(4H)-one

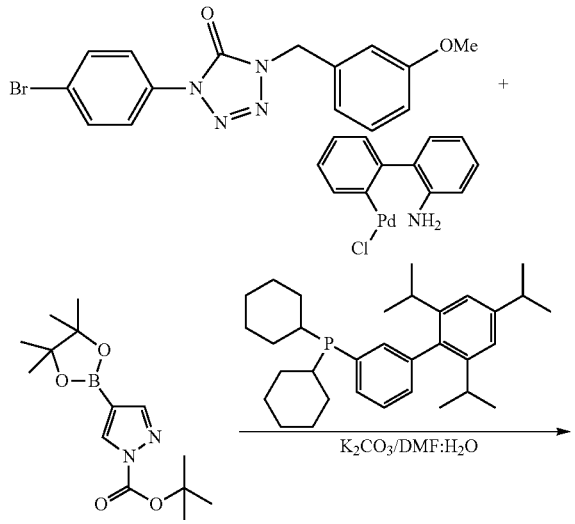

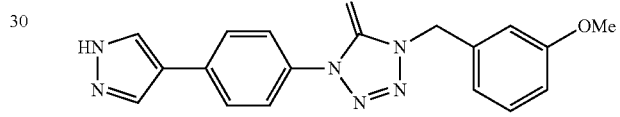

A solution of added 1-(4-bromophenyl)-4-(3-methoxybenzyl)-1H-tetrazol-5(4H)-one (60 mg, 0.166 mmol), $K_2CO_3$ (68.9 mg, 0.498 mmol), and tert-butyl 4-(4,4,5,5-tetramethyl-1,3,2-dioxaborolan-2-yl)-1H-pyrazole-1-carboxylate (58.6 mg, 0.199 mmol) in DMF (2 mL) and water (0.2 mL) was flushed with nitrogen for 10 min. $2^{nd}$ generation XPHOS precatalyst (3.9 mg, 5.0 μmol) was added to reaction mixture. The reaction mixture was heated at 80° C. for 6 h. The reaction mixture was cooled to RT and solvent was removed in vacuo to afford the residue which was diluted with DCM (100 mL), washed with brine. The DCM layer was dried over $Na_2SO_4$, filtered and concentrated. The crude material was purified via preparative HPLC to afford 1-(4-(1H-pyrazol-4-yl)phenyl)-4-(3-methoxybenzyl)-1H-tetrazol-5(4H)-one (0.051 g, 81%) as a white solid. MS (ESI) m/z: 349.2 (M+H)+; $^1$H NMR (400 MHz, DMSO-$d_6$) δ ppm 13.03 (br. s., 1H) 8.28 (br. s., 1H) 8.00 (br. s., 1H) 7.74-7.87 (m, 4H) 7.26-7.36 (m, 1H) 6.88-7.01 (m, 3H) 5.20 (s, 2H) 3.76 (s, 3H); HPLC RT=1.48, 99.3% (Method A); RT=1.50 min, 99.7% (Method B).

The following Examples in Table 7 were made by using the same procedure as shown in Example 172.

TABLE 7

| Example | Structure | Name | LCMS (M + H)+ | LC\MS Method, RT (min.), & Purity | NMR |
|---|---|---|---|---|---|
| 173 | 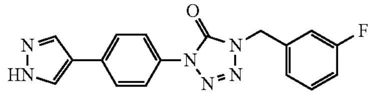 [SMILES: O=c1n(Cc2cccc(F)c2)nnn1-c1ccc(-c2cn[nH]c2)cc1] | 1-(4-(1H-pyrazol-4-yl)phenyl)-4-(3-fluorobenzyl)-1H-tetrazol-5(4H)-one | 337.2 | A: 1.50, 94.9% B: 1.52, 94.4% | $^1$H NMR (400 MHz, DMSO-$d_6$) δ ppm 13.02 (br. s., 1 H) 8.13 (br. s, 2 H) 7.76-7.87 (m, 4 H) 7.41-7.49 (m, 1 H) 7.16-7.31 (m, 3 H) 5.26 (s, 2 H) |

TABLE 7-continued

| Example | Structure | Name | LCMS (M + H)+ | LC\MS Method, RT (min.), & Purity | NMR |
|---|---|---|---|---|---|
| 174 | 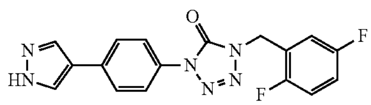 [SMILES: O=c1n(Cc2cc(F)ccc2F)nnn1-c1ccc(-c2cn[nH]c2)cc1] | 1-(4-(1H-pyrazol-4-yl)phenyl)-4-(2,5-difluorobenzyl)-1H-tetrazol-5(4H)-one | 355.2 | A: 1.51, 94.4% B: 1.52, 94.2% | $^1$H NMR (400 MHz, DMSO-$d_6$) δ ppm 13.03 (br. s., 1 H) 8.28 (br. s., 1 H) 8.00 (br. s., 1 H) 7.76-7.86 (m, 4 H) 7.23-7.47 (m, 3 H) 5.27 (s, 2 H) |
| 175 | 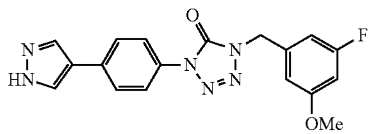 [SMILES: COc1cc(F)cc(Cn2nnn(-c3ccc(-c4cn[nH]c4)cc3)c2=O)c1] | 1-(4-(1H-pyrazol-4-yl)phenyl)-4-(3-fluoro-5-methoxybenzyl)-1H-tetrazol-5(4H)-one | 367.2 | A: 1.56, 100% B: 1.58, 100% | $^1$H NMR (400 MHz, DMSO-$d_6$) δ ppm 13.03 (br. s., 1 H) 8.28 (br. s., 1 H) 7.99 (br. s., 1 H) 7.75-7.87 (m, 4 H) 6.76-6.87 (m, 3 H) 5.21 (s, 2 H) 3.77 (s, 3 H) |
| 176 | 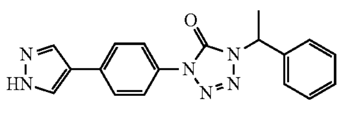 [SMILES: CC(c1ccccc1)n1nnn(-c2ccc(-c3cn[nH]c3)cc2)c1=O] | 1-(4-(1H-pyrazol-4-yl)phenyl)-4-(1-phenylethyl)-1H-tetrazol-5(4H)-one | 333.2 | A: 1.61, 100% B: 1.62, 99.1% | $^1$H NMR (400 MHz, DMSO-$d_6$) δ ppm 13.02 (br. s., 1 H) 8.27 (s, 1 H) 7.99 (s, 1 H) 7.76-7.84 (m, 4 H) 7.37-7.46 (m, 4 H) 7.31-7.36 (m, 1 H) 5.57 (q, J = 7.13 Hz, 1 H) 1.85 (d, J = 7.15 Hz, 3 H) |
| 177 | 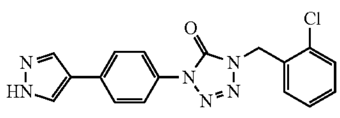 | 1-(4-(1H-pyrazol-4-yl)phenyl)-4-(2-chlorobenzyl)-1H-tetrazol-5(4H)-one( | 353.2 | A: 1.61, 97.5% B: 1.62, 96.0% | $^1$H NMR (400 MHz, DMSO-$d_6$) δ ppm 13.03 (br. s., 1 H) 8.28 (s, 1 H) 8.00 (s, 1 H) 7.82 (d, J = 1.00 Hz, 4 H) 7.53-7.57 (m, 1 H) 7.47-7.51 (m, 1 H) 7.37-7.45 (m, 2 H) 5.30 (s, 2 H) |
| 178 | 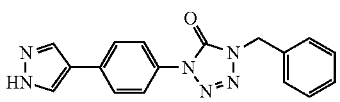 [SMILES: O=c1n(Cc2ccccc2)nnn1-c1ccc(-c2cn[nH]c2)cc1] | 1-(4-(1H-pyrazol-4-yl)phenyl)-4-benzyl-1H-tetrazol-5(4H)-one | 319.2 | A: 1.47, 99.7% B: 1.49, 99.7% | $^1$H NMR (400 MHz, DMSO-$d_6$) δ ppm 13.01 (br. s., 1 H) 8.29 (br. s., 1 H) 8.00 (br. s., 1 H) 7.76-7.87 (m, 4 H) 7.28-7.45 (m, 5 H) 5.24 (s, 2 H) |
| 179 | 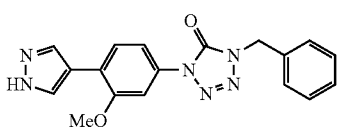 [SMILES: COc1cc(-n2nnn(Cc3ccccc3)c2=O)ccc1-c1cn[nH]c1] | 1-benzyl-4-(3-methoxy-4-(1H-pyrazol-4-yl)phenyl)-1H-tetrazol-5(4H)-one | 349.2 | A: 1.59, 98.7% B: 1.57, 100% | $^1$H NMR (400 MHz, DMSO-$d_6$) δ ppm 12.96 (s, 1 H) 8.21 (s, 1 H) 8.02 (s, 1 H) 7.83 (d, J = 8.41 Hz, 1 H) 7.56 (d, J = 2.07 Hz, 1 H) 7.47 (dd, J = 8.35, 2.07 Hz, 1 H) 7.41-7.44 (m, 4 H) 7.34-7.40 (m, 1 H) 5.25 (s, 2 H) 3.94 (s, 3 H) |
| 180 | 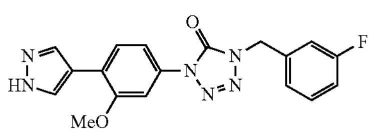 [SMILES: COc1cc(-n2nnn(Cc3cccc(F)c3)c2=O)ccc1-c1cn[nH]c1] | 1-(3-fluorobenzyl)-4-(3-methoxy-4-(1H-pyrazol-4-yl)phenyl)-1H-tetrazol-5(4H)-one | 367.2 | A: 1.62, 99.7% B: 1.59, 100% | $^1$H NMR (400 MHz, DMSO-$d_6$) δ ppm = 11.73 (s, 1H) 8.02 (d, J = 8.8 Hz, 2H), 7.67-7.73 (m, 3H), 7.57 (d, J = 5.2 Hz, 1H), 7.29-7.36 (m, 2 H) 6.85-6.91 (m, 3H), 4.91 (s, 2H), 3.75 (s, 3 H), 2.25 (s, 3H) |
| 181 | 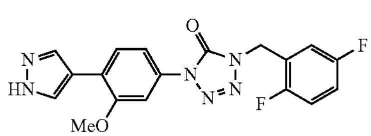 [SMILES: COc1cc(-n2nnn(Cc3cc(F)ccc3F)c2=O)ccc1-c1cn[nH]c1] | 1-(2,5-difluorobenzyl)-4-(3-methoxy-4-(1H-pyrazol-4-yl)phenyl)-1H-tetrazol-5(4H)-one | 385.2 | A: 1.62, 99.3% B: 1.60, 99.6% | $^1$H NMR (400 MHz, DMSO-$d_6$) δ ppm 12.96 (s, 1 H) 8.21 (s, 1 H) 8.02 (br. s., 1 H) 7.83 (d, J = 8.35 Hz, 1 H) 7.55 (d, J = 2.07 Hz, 1 H) 7.47 (dd, J = 8.38, 2.10 Hz, 1 H) 7.25-7.44 (m, 3 H) 5.29 (s, 2 H) 3.94 (s, 3 H); $^{19}$F NMR (377 MHz, DMSO-$d_6$) δ ppm −118.397, −123.498 |
| 182 | 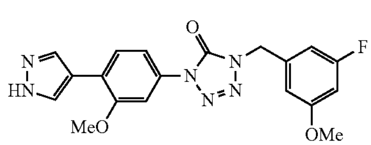 [SMILES: COc1cc(F)cc(Cn2nnn(-c3ccc(-c4cn[nH]c4)c(OC)c3)c2=O)c1] | 1-(3-fluoro-5-methoxybenzyl)-4-(3-methoxy-4-(1H-pyrazol-4-yl)phenyl)-1H-tetrazol-5(4H)-one | 397.2 | A: 1.66, 96.9% B: 1.64, 94.8% | $^1$H NMR (400 MHz, DMSO-$d_6$) δ ppm 12.97 (s, 1 H) 8.21 (s, 1 H) 8.03 (s, 1 H) 7.83 (d, J = 8.41 Hz, 1 H) 7.57 (d, J = 2.07 Hz, 1 H) 7.48 (dd, J = 8.41, 2.07 Hz, 1 H) 6.80-6.87 (m, 3 H) 5.22 (s, 2 H) 3.94 (s, 3 H) 3.79 (s, 3 H); $^{19}$F NMR (377 MHz, DMSO-$d_6$) δ ppm −111.240 |

TABLE 7-continued

| Example | Structure | Name | LCMS (M + H)+ | LC\MS Method, RT (min.), & Purity | NMR |
|---|---|---|---|---|---|
| 183 | 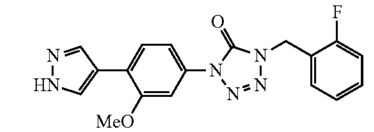 [SMILES: COc1cc(-n2nnn(Cc3ccccc3F)c2=O)ccc1-c1cn[nH]c1] | 1-(2-fluorobenzyl)-4-(3-methoxy-4-(1H-pyrazol-4-yl)phenyl)-1H-tetrazol-5(4H)-one | 367.2 | A: 1.60, 99.2% B: 1.57, 99.3% | $^1$H NMR (400 MHz, DMSO-d$_6$) δ ppm 12.97 (s, 1 H) 8.21 (s, 1 H) 8.02 (s, 1 H) 7.83 (d, J = 8.35 Hz, 1 H) 7.55 (d, J = 2.07 Hz, 1 H) 7.41-7.53 (m, 3 H) 7.23-7.32 (m, 2 H) 5.29 (s, 2 H) 3.94 (s, 3 H); $^{19}$F NMR (377 MHz, DMSO-d$_6$) δ ppm −118.168 |
| 184 | 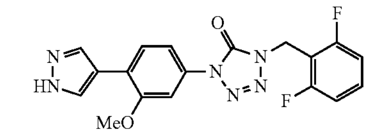 | 1-(2,6-difluorobenzyl)-4-(3-methoxy-4-(1H-pyrazol-4-yl)phenyl)-1H-tetrazol-5(4H)-one | 385.2 | A: 1.58, 98.1% B: 1.56, 98.5% | $^1$H NMR (400 MHz, DMSO-d$_6$) δ ppm 8.11 (s, 2 H) 7.82 (d, J = 8.35 Hz, 1 H) 7.52-7.57 (m, 2 H) 7.44 (dd, J = 8.38, 2.10 Hz, 1 H) 7.18-7.25 (m, 2 H) 5.29 (s, 2 H) 3.93 (s, 3 H); $^{19}$F NMR (377 MHz, DMSO-d$_6$) δ ppm −114.396 |
| 185 | 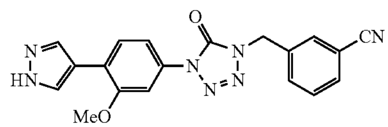 [SMILES: COc1cc(-n2nnn(Cc3cccc(C#N)c3)c2=O)ccc1-c1cn[nH]c1] | 3-((4-(3-methoxy-4-(1H-pyrazol-4-yl)phenyl)-5-oxo-4,5-dihydro-1H-tetrazol-1-yl)methyl)benzonitrile | 374.2 | A: 1.46, 98.5% B: 1.44, 98.1% | $^1$H NMR (400 MHz, DMSO-d$_6$) δ ppm 12.96 (s, 1 H) 8.19 (s, 1 H) 8.01 (s, 1 H) 7.93 (s, 1 H) 7.82-7.88 (m, 2 H) 7.78 (d, J = 7.97 Hz, 1 H) 7.61-7.67 (m, 1 H) 7.57 (d, J = 2.07 Hz, 1 H) 7.48 (dd, J = 8.41, 2.07 Hz, 1 H) 5.33 (s, 2 H) 3.94 (s, 3 H) |
| 186 | 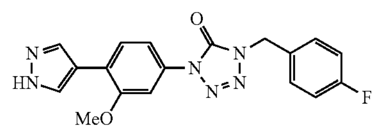 [SMILES: COc1cc(-n2nnn(Cc3ccc(F)cc3)c2=O)ccc1-c1cn[nH]c1] | 1-(4-fluorobenzyl)-4-(3-methoxy-4-(1H-pyrazol-4-yl)phenyl)-1H-tetrazol-5(4H)-one | 367.2 | A: 1.61, 94.7% B: 1.59, 94.8% | $^1$H NMR (400 MHz, DMSO-d$_6$) δ ppm 12.97 (s, 1 H) 8.21 (br. s., 1 H) 8.03 (br. s., 1 H) 7.83 (d, J = 8.41 Hz, 1 H) 7.56 (d, J = 2.07 Hz, 1 H) 7.43-7.52 (m, 3 H) 7.21-7.29 (m, 2 H) 5.24 (s, 2 H) 3.94 (s, 3 H); $^{19}$F NMR (377 MHz, DMSO-d$_6$) δ ppm −114.250 |
| 187 | 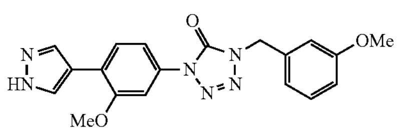 [SMILES: COc1cccc(Cn2nnn(-c3ccc(-c4cn[nH]c4)c(OC)c3)c2=O)c1] | 1-(3-methoxy-4-(1H-pyrazol-4-yl)phenyl)-4-(3-methoxybenzyl)-1H-tetrazol-5(4H)-one | 379.2 | A: 1.61, 100% B: 1.47, 100% | $^1$H NMR (400 MHz, DMSO-d$_6$) δ ppm 12.96 (s, 1 H) 8.19 (s, 1 H) 8.01 (s, 1 H) 7.83 (d, J = 8.35 Hz, 1 H) 7.56 (d, J = 2.01 Hz, 1 H) 7.48 (dd, J = 8.41, 2.07 Hz, 2 H) 7.28-7.36 (m, 1 H) 6.90-7.02 (m, 2 H) 5.21 (s, 2 H) 3.94 (s, 3 H) 3.75-3.80 (s, 3 H) |

What is claimed is:

1. A compound according to Formula (I):

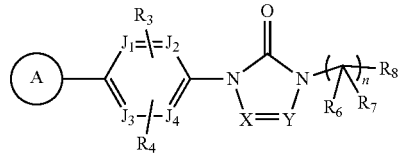

(I)

or an enantiomer, a diastereomer, a stereoisomer, a tautomer, a pharmaceutically acceptable salt thereof, wherein Ring A is independently selected from

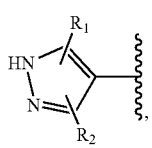,

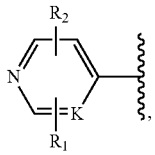,

-continued

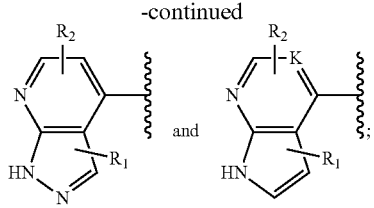

and;

$J_1$, $J_2$, $J_3$, and $J_4$ are independently selected from N, $CR_3$, and $CR_4$; provided no more than two of $J_1$, $J_2$, $J_3$, and $J_4$ are N;

K, at each occurrence, is independently selected from N, $CR_1$, and $CR_2$;

X and Y are independently selected from N and $CR_5$; provided X and Y are not both $CR_5$;

$R_1$, at each occurrence, is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$, at each occurrence, is independently selected from H, —$(CH_2)_rOR_b$, —$(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rC(=O)R_b$, —$(CH_2)_rNR_aC(=O)NR_aR_a$, —$(CH_2)_rNR_aC(=O)OR_b$, —$(CH_2)_rOC(=O)$ $NR_aR_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_3$ is independently selected from H, F, Cl, Br, CN, C$_{1-4}$ alkyl substituted with 0-3 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_4$ is independently selected from H, F, Cl, Br, OH, CN, OC$_{1-4}$ alkyl substituted with 0-3 R$_e$, NR$_a$R$_a$, and C$_{1-4}$ alkyl substituted with 0-3 R$_e$;

R$_5$ is independently selected from H, C$_{1-4}$alkyl substituted with 0-4 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$-C$_{3-6}$ carbocyclyl substituted with 0-3 R$_e$, and —(CH$_2$)$_r$-heterocyclyl substituted with 0-3 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_8$ is independently selected from C$_{3-6}$ cycloalkyl, heterocyclyl, aryl and heteroaryl, each substituted with 0-5 R$_9$;

R$_9$, at each occurrence, is independently selected from F, Cl, Br, C$_{1-4}$alkyl, C$_{2-4}$alkenyl, C$_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$ and —(CH$_2$)$_r$NR$_f$R$_f$;

R$_f$, at each occurrence, is independently selected from H, F, Cl, Br, CN, OH, C$_{1-5}$alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

n is independently selected from 1, 2, and 3;

p, at each occurrence, is independently selected from zero, 1, and 2; and r, at each occurrence, is independently selected from zero, 1, 2, 3, and 4.

2. The compound of claim 1 or an enantiomer, a diastereomer, a stereoisomer, a tautomer, a pharmaceutically acceptable salt thereof, wherein R$_1$, at each occurrence, is independently selected from H, F, Cl, Br, OH, CN, NR$_a$R$_a$, —OC$_{1-4}$ alkyl substituted with 0-3 R$_e$, and C$_{1-4}$ alkyl substituted with 0-3 R$_e$;

R$_2$, at each occurrence, is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$NR$_a$S(O)$_p$NR$_a$R$_a$, and —(CH$_2$)$_r$NR$_a$S(O)$_p$R$_c$;

R$_3$ is independently selected from H, F, Cl, Br, CN, C$_{1-4}$ alkyl substituted with 0-3 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$—C$_{3-6}$ carbocyclyl substituted with 0-3 R$_e$, and —(CH$_2$)$_r$-heterocyclyl substituted with 0-3 R$_e$;

R$_4$ is independently selected from H, F, Cl, Br, OH, CN, and C$_{1-4}$ alkyl substituted with 0-3 R$_e$;

R$_5$ is independently selected from H, C$_{1-4}$alkyl substituted with 0-4 R$_e$, —(CH$_2$)$_r$OR$_b$, —(CH$_2$)$_r$NR$_a$R$_a$, and —(CH$_2$)$_r$-heterocyclyl substituted with 0-3 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$C(=O)OR$_b$, (CH$_2$)$_r$—C$_{3-6}$ carbocyclyl substituted with 0-3 R$_e$, and —(CH$_2$)$_r$-heterocyclyl substituted with 0-3 R$_e$;

R$_8$ is independently selected from

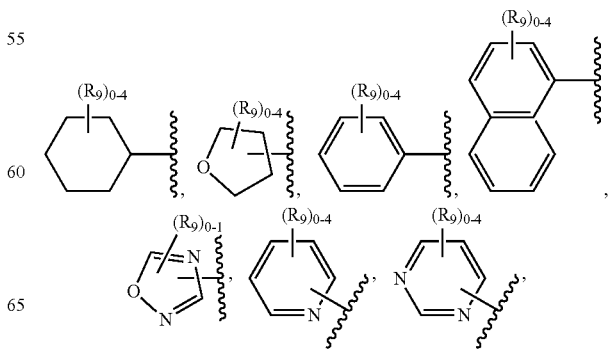

-continued

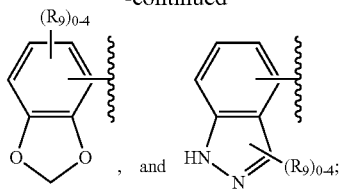
, and $R_9$, at each occurrence, is independently selected from F, Cl, Br, $C_{1-4}$alkyl, $C_{2-4}$alkenyl, $C_{2-4}$alkynyl, nitro, $-(CHR_d)_rS(O)_pR_c$, $-(CHR_d)_rS(O)_pNR_aR_a$, $-(CHR_d)_rNR_aS(O)_pR$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_rOC(=O)R_b$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$.

3. The compound of claim 2, having Formula (II):

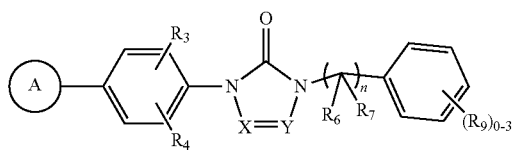

or an enantiomer, a diastereomer, a stereoisomer, a tautomer, a pharmaceutically acceptable salt thereof, wherein Ring A is independently selected from

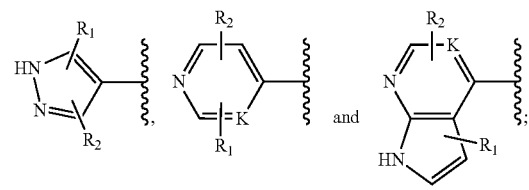

X and Y are independently selected from N and $CR_5$; provided X and Y are not both $CR_5$;

$R_1$, at each occurrence, is independently selected from H, F, Cl, Br, CN, $NR_aR_a$, and $C_{1-4}$alkyl substituted with 0-4 $R_e$;

$R_2$, at each occurrence, is independently selected from H, F, Cl, Br, OH, CN, $NR_aR_a$, and $C_{1-4}$alkyl substituted with 0-4 $R_e$;

$R_3$ is independently selected from H, F, Cl, Br, CN, $C_{1-4}$ alkyl substituted with 0-3 $R_e$, $-(CH_2)_rOR_b$, and $-C_{3-6}$ cycloalkyl;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, $C_{1-4}$alkyl substituted with 0-4 $R_e$, $-(CH_2)_rOR_b$, $-(CH_2)_rNR_aR_a$, and $-(CH_2)_r$-heterocyclyl substituted with 0-3 $R_e$;

$R_6$ and $R_7$ are independently selected from H, $C_{1-4}$alkyl substituted with 0-4 $R_e$, $-(CH_2)_rOR_b$, $-(CH_2)_rC(=O)R_b$, $-(CH_2)_rNR_aR_a$, $-(CH_2)_rC(=O)NR_aR_a$, $-(CH_2)_rNR_aC(=O)R_b$, $-(CH_2)_rC(=O)OR_b$, $-(CH_2)_r-C_{3-6}$ carbocyclyl substituted with 0-3 $R_e$, and $-(CH_2)_r$-heterocyclyl substituted with 0-3 $R_e$;

$R_9$, at each occurrence, is independently selected from F, Cl, Br, $C_{1-4}$ alkyl, nitro, $-(CH_2)_rS(O)_pR_c$, $-(CH_2)_rS(O)_pNR_aR_a$, $-(CH_2)_rNR_aS(O)_pR_c$, $-(CH_2)_rOR_b$, $-(CH_2)_rCN$, $-(CH_2)_rNR_aR_a$, $-(CH_2)_rNR_aC(=O)R_b$, $-(CH_2)_rNR_aC(=O)NR_aR_a$, $-(CH_2)_rC(=O)OR_b$, $-(CH_2)_rC(=O)R_b$, $-(CH_2)_rOC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r-C_{4-6}$ heterocyclyl, F, Cl, Br, CN, $NO_2$, $=O$, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

4. The compound of claim 3, having Formula (III):

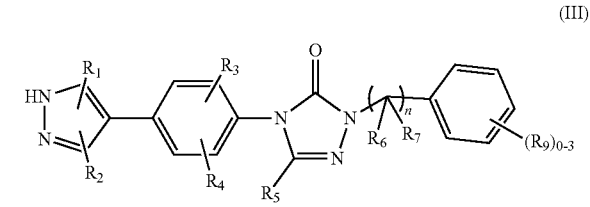

or an enantiomer, a diastereomer, a stereoisomer, a tautomer, a pharmaceutically acceptable salt thereof, wherein $R_1$ is independently selected from H, F, Cl, Br, CN, $NR_aR_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, $-(CH_2)_rOR_b$, and $-C_{3-6}$ cycloalkyl;

R₄ is independently selected from H, F, Cl, Br, OH, CN, OC$_{1-4}$ alkyl substituted with 0-3 R$_e$, and C$_{1-4}$ alkyl substituted with 0-3 R$_e$;

R₅ is independently selected from H and C$_{1-4}$alkyl substituted with 0-4 R$_e$;

R₆ is independently selected from H, C$_{1-4}$alkyl substituted with 0-4 R$_e$, —CH₂OR$_b$, —C(=O)R$_b$, NR$_a$C(=O)R$_b$, —CH₂NR$_a$R$_a$, —C(=O)NR$_a$R$_a$, —$_r$C(=O)OR$_b$, and heterocyclyl substituted with 0-3 R$_e$;

R₇ is independently selected from H and C$_{1-4}$alkyl;

R₉, at each occurrence, is independently selected from F, Cl, Br, C$_{1-4}$ alkyl, —(CH₂)$_r$OR$_b$, —(CH₂)$_r$CN, —(CH₂)$_r$NR$_a$R$_a$, —(CH₂)$_r$NR$_a$C(=O)R$_b$, —(CH₂)$_r$NR$_a$C(=O)NR$_a$R$_a$, —(CH₂)$_r$C(=O)OR$_b$, —(CH₂)$_r$C(=O)R$_b$, —(CH₂)$_r$OC(=O)R$_b$, —(CH₂)$_r$C(=O)NR$_a$R$_a$, —(CH₂)$_r$-cycloalkyl, —(CH₂)$_r$-heterocyclyl, —(CH₂)$_r$-aryl, and —(CH₂)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH₂)$_r$—C$_{3-10}$cycloalkyl substituted with 0-5 R$_e$, —(CH₂)$_r$-aryl substituted with 0-5 R$_e$, and —(CH₂)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH₂)$_r$—C$_{3-10}$carbocyclyl substituted with 0-5 R$_e$, and —(CH₂)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from C$_{1-6}$ alkyl substituted with 0-5 R$_f$, C$_{2-6}$ alkenyl, C$_{2-6}$ alkynyl, —(CH₂)$_r$—C$_{3-6}$ cycloalkyl, —(CH₂)$_r$—C$_{4-6}$ heterocyclyl, F, Cl, Br, CN, NO₂, =O, CO₂H, —(CH₂)$_r$OR$_f$, S(O)$_p$R$_f$, S(O)$_p$NR$_f$R$_f$, and —(CH₂)$_r$NR$_f$R$_f$;

R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

n is independently selected from 1 and 2;

p, at each occurrence, is independently selected from zero, 1, and 2; and r, at each occurrence, is independently selected from zero, 1, 2, 3, and 4.

5. The compound of claim 4, having Formula (IV):

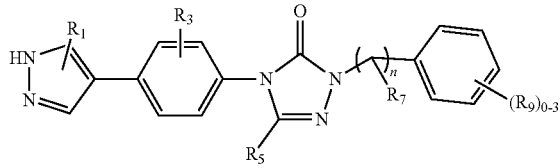

(IV)

or enantiomer, a diastereomer, a stereoisomer, a tautomer, a pharmaceutically acceptable salt thereof, wherein R₁ is independently selected from H and CF₃;

R₃ is independently selected from H, CN, C$_{1-4}$ alkyl, —OC$_{1-3}$ alkyl, and —C$_{3-6}$ cycloalkyl;

R₅ is independently selected from H and C$_{1-4}$alkyl;

R₇ is independently selected from H and C$_{1-4}$alkyl;

R₉, at each occurrence, is independently selected from F, Cl, C$_{1-4}$ alkyl substituted with 0-3 R$_e$, —OR$_b$, CN, and heterocyclyl substituted with 0-3 R$_e$;

R$_a$, at each occurrence, is independently selected from H, C$_{1-6}$ alkyl substituted with 0-5 R$_e$, —(CH₂)$_r$—C$_{3-6}$ cycloalkyl substituted with 0-5 R$_e$, —(CH₂)$_r$-aryl substituted with 0-5 R$_e$, and —(CH₂)$_r$-heterocyclyl substituted with 0-5 R$_e$;

R$_b$, at each occurrence, is independently selected from H, C$_{1-6}$ alkyl substituted with 0-5 R$_e$, —(CH₂)$_r$—C$_{3-10}$carbocyclyl substituted with 0-5 R$_e$, and —(CH₂)$_r$-heterocyclyl substituted with 0-5 R$_e$;

R$_e$, at each occurrence, is independently selected from C$_{1-6}$ alkyl substituted with 0-5 R$_f$, F, Cl, Br, CN, NO₂, =O, CO₂H, OH, and OC$_{1-4}$alkyl;

n is independently selected from 1 and 2; and r, at each occurrence, is independently selected from zero, 1, 2, and 3.

6. The compound of claim 3, having Formula (V):

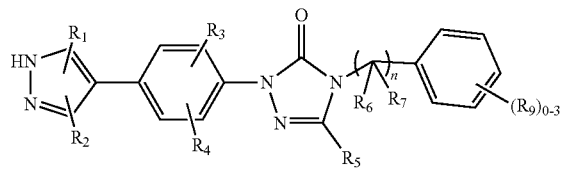

(V)

or an enantiomer, a diastereomer, a stereoisomer, a tautomer, a pharmaceutically acceptable salt thereof, wherein R₁ is independently selected from H, F, Cl, Br, CN, NR$_a$R$_a$, and C$_{1-4}$alkyl substituted with 0-4 R$_e$;

R₂ is independently selected from H and C$_{1-4}$alkyl substituted with 0-4 R$_e$;

R₃ is independently selected from H, F, Cl, Br, CN, C$_{1-4}$ alkyl substituted with 0-3 R$_e$, —(CH₂)$_r$OR$_b$, and —C$_{3-6}$ cycloalkyl;

R₄ is independently selected from H, F, Cl, Br, OH, CN, OC$_{1-4}$ alkyl substituted with 0-3 R$_e$, and C$_{1-4}$ alkyl substituted with 0-3 R$_e$;

R₅ is independently selected from H, C$_{1-4}$alkyl substituted with 0-4 R$_e$, —(CH₂)$_r$OR$_b$, —(CH₂)$_r$NR$_a$R$_a$, and —(CH₂)$_r$-heterocyclyl substituted with 0-3 R$_e$;

R₆ is independently selected from H, C$_{1-4}$alkyl substituted with 0-4 R$_e$, —CH₂OR$_b$, —C(=O)R$_b$, NR$_a$C(=O)R$_b$, —CH₂NR$_a$R$_a$, —C(=O)NR$_a$R$_a$, —$_r$C(=O)OR$_b$, and heterocyclyl substituted with 0-3 R$_e$;

R₇ is independently selected from H and C$_{1-4}$alkyl;

R₉, at each occurrence, is independently selected from F, Cl, Br, C$_{1-4}$ alkyl, —(CH₂)$_r$OR$_b$, —(CH₂)$_r$CN, —(CH₂)$_r$NR$_a$R$_a$, —(CH₂)$_r$NR$_a$C(=O)R$_b$, —(CH₂)$_r$NR$_a$C(=O)NR$_a$R$_a$, —(CH₂)$_r$C(=O)OR$_b$, —(CH₂)$_r$C(=O)R$_b$, —(CH₂)$_r$OC(=O)R$_b$, —(CH₂)$_r$C(=O)NR$_a$R$_a$, —(CH₂)$_r$-cycloalkyl, —(CH₂)$_r$-heterocyclyl, —(CH₂)$_r$-aryl, and —(CH₂)$_r$-heteroaryl, wherein said alkyl, cycloalkyl, heterocyclyl, aryl, or heteroaryl is substituted with 0-4 R$_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

7. The compound of claim 3, having Formula (VI):

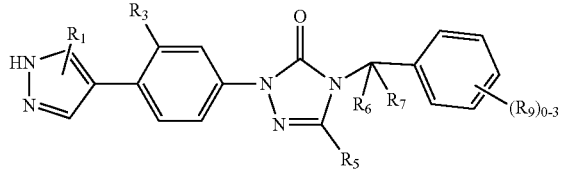

(VI)

or enantiomer, a diastereomer, a stereoisomer, a tautomer, a pharmaceutically acceptable salt thereof, wherein $R_1$ is independently selected from H and $CF_3$;

$R_3$ is independently selected from H, CN, $C_1$-4 alkyl, —$OC_{1-3}$ alkyl, and —$C_{3-6}$ cycloalkyl;

$R_5$ is independently selected from H, $C_{1-4}$alkyl substituted with 0-4 $R_e$, —$(CH_2)_rOR_b$, —$(CH_2)_rNR_aR_a$;

$R_6$ is independently selected from H and $C_{1-4}$alkyl substituted with 0-3 $R_e$;

$R_7$ is independently selected from H and $C_{1-4}$alkyl;

$R_9$, at each occurrence, is independently selected from F, Cl, $C_{1-4}$ alkyl substituted with 0-3 $R_e$, —$OR_b$, CN, and heterocyclyl substituted with 0-3 $R_e$;

$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$ or $R_a$ and $R_a$ together with the nitrogen atom to which they are both attached form a heterocyclic ring selected from

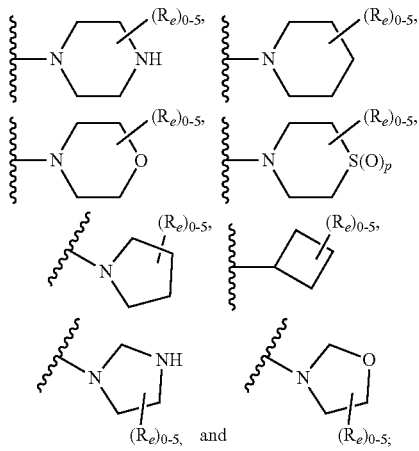

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl; and r, at each occurrence, is independently selected from zero, 1, 2, and 3.

8. The compound of claim 3, having Formula (VII):

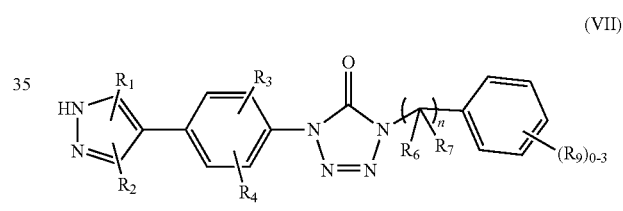

(VII)

or an enantiomer, a diastereomer, a stereoisomer, a tautomer, a pharmaceutically acceptable salt thereof, wherein $R_1$ is independently selected from H, F, Cl, Br, CN, $NR_aR_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, —$(CH_2)_rOR_b$, and —$C_{3-6}$ cycloalkyl;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_6$ is independently selected from H, $C_{1-4}$alkyl substituted with 0-4 $R_e$, —$CH_2OR_b$, —$C(=O)R_b$, $NR_aC(=O)R_b$, —$CH_2NR_aR_a$, —$C(=O)NR_aR_a$, —$_rC(=O)OR_b$, and heterocyclyl substituted with 0-3 $R_e$;

$R_7$ is independently selected from H and $C_{1-4}$alkyl;

$R_9$, at each occurrence, is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$- heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

9. The compound of claim 8, having Formula (VIII):

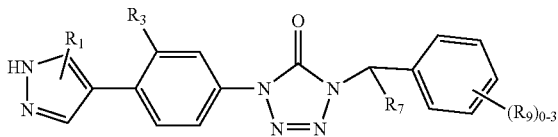

(VIII)

or enantiomer, a diastereomer, a stereoisomer, a tautomer, a pharmaceutically acceptable salt thereof, wherein $R_1$ is independently selected from H and $CF_3$;

$R_3$ is independently selected from H, CN, $C_{1-4}$ alkyl, —$OC_{1-3}$ alkyl, and —$C_{3-6}$ cycloalkyl;

$R_5$ is independently selected from H, $C_{1-4}$alkyl substituted with 0-4 $R_e$, —$CH_2OR_b$, C(=O)$R_b$, and —C(=O) $OR_b$;

$R_7$ is independently selected from H and $C_{1-4}$alkyl;

$R_9$, at each occurrence, is independently selected from F, Cl, $C_{1-4}$ alkyl substituted with 0-3 $R_e$, —$OR_b$, CN, and heterocyclyl substituted with 0-3 $R_e$;

$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;

and r, at each occurrence, is independently selected from zero, 1, 2, and 3.

10. The compound of claim 3, having Formula (IX):

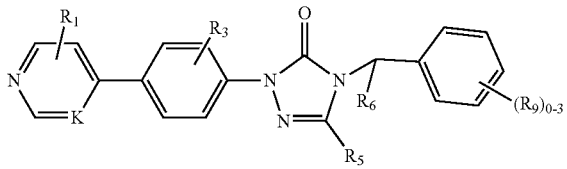

(IX)

or an enantiomer, a diastereomer, a stereoisomer, a tautomer, a pharmaceutically acceptable salt thereof, wherein K, at each occurrence, is independently selected from N and $CR_1$;

$R_1$ is independently selected from H, F, Cl, Br, CN, $NR_aR_a$, and $C_{1-4}$alkyl substituted with 0-4 $R_e$;

$R_3$ is independently selected from H, CN, $C_{1-4}$ alkyl substituted with 0-3 $R_e$, and —$OR_b$;

$R_5$ is independently selected from H, $C_{1-4}$alkyl substituted with 0-4 $R_e$, —$(CH_2)_rOR_b$, —$(CH_2)_rNR_aR_a$, and —$(CH_2)_r$-heterocyclyl substituted with 0-3 $R_e$;

$R_6$ is independently selected from H and $C_{1-4}$alkyl substituted with 0-4 $R_e$;

$R_9$, at each occurrence, is independently selected from F, Cl, Br, $C_{1-4}$ alkyl, nitro, —$S(O)_pR_c$, —$S(O)_pNR_aR_a$, —$OR_b$, CN, —$NR_aR_a$, —C(=O)$OR_b$, —$(CH_2)_rC$ (=O)$R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

11. The compound of claim 3, having Formula (X):

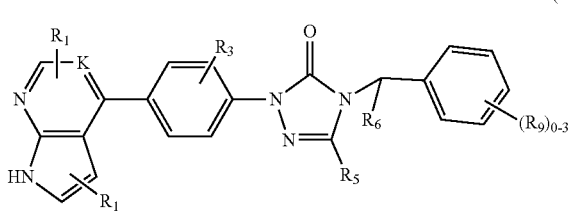

(X)

or an enantiomer, a diastereomer, a stereoisomer, a tautomer, a pharmaceutically acceptable salt thereof, wherein K is independently selected from N and $CR_2$;

$R_1$, at each occurrence, is independently selected from H, F, Cl, Br, CN, $NR_aR_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, CN, $C_{1-4}$ alkyl substituted with 0-3 $R_e$, and $-OR_b$;

$R_5$ is independently selected from H, $C_{1-4}$alkyl substituted with 0-4 $R_e$, $-(CH_2)_rOR_b$, $-(CH_2)_rNR_aR_a$, and $-(CH_2)_r$-heterocyclyl substituted with 0-3 $R_e$;

$R_6$ is independently selected from H and $C_{1-4}$alkyl substituted with 0-4 $R_e$;

$R_9$, at each occurrence, is independently selected from F, Cl, Br, $C_{1-4}$ alkyl, nitro, $-S(O)_pR_c$, $-S(O)_pNR_aR_a$, $-OR_b$, CN, $-NR_aR_a$, $-C(=O)OR_b$, $-(CH_2)_rC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $-(CH_2)_r-C_{3-6}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r-C_{4-6}$ heterocyclyl, F, Cl, Br, CN, $NO_2$, $=O$, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

12. The compound of claim 3, having Formula (XI):

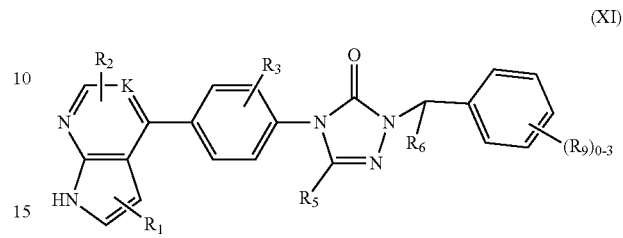

(XI)

or an enantiomer, a diastereomer, a stereoisomer, a tautomer, a pharmaceutically acceptable salt thereof, wherein K is independently selected from N and $CR_2$;

$R_1$, at each occurrence, is independently selected from H, F, Cl, Br, CN, $NR_aR_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, CN, $C_{1-4}$ alkyl substituted with 0-3 $R_e$, and $-OR_b$;

$R_5$ is independently selected from H, $C_{1-4}$alkyl substituted with 0-4 $R_e$, $-(CH_2)_rOR_b$, $-(CH_2)_rNR_aR_a$, and $-(CH_2)_r$-heterocyclyl substituted with 0-3 $R_e$;

$R_6$ is independently selected from H, $C_{1-4}$alkyl substituted with 0-4 $R_e$, $-(CH_2)_rOR_b$, $-(CH_2)_rC(=O)R_b$, $-(CH_2)_rNR_aC(=O)R_b$, $-(CH_2)_rC(=O)OR_b$, and heterocyclyl substituted with 0-3 $R_e$;

$R_9$, at each occurrence, is independently selected from F, Cl, Br, $C_{1-4}$ alkyl, nitro, $-S(O)_pR_c$, $-S(O)_pNR_aR_a$, $-OR_b$, CN, $-NR_aR_a$, $-C(=O)OR_b$, $-(CH_2)_rC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $-(CH_2)_r-C_{3-6}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_rC_{4-6}$ heterocyclyl, F, Cl, Br, CN, $NO_2$, $=O$, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

13. A compound selected from the group consisting of:
4-(4-(1H-pyrazol-4-yl)phenyl)-1-(3-fluorobenzyl)-1H-1,2,4-triazol-5(4H)-one;
4-(4-(1H-pyrazol-4-yl)phenyl)-1-benzyl-1H-1,2,4-triazol-5(4H)-one;
4-(4-(1H-pyrazol-4-yl)phenyl)-1-(3-methoxybenzyl)-1H-1,2,4-triazol-5(4H)-one;
4-(4-(1H-pyrazol-4-yl)phenyl)-1-(2,5-difluorobenzyl)-1H-1,2,4-triazol-5(4H)-one;
1-benzyl-4-(3-methoxy-4-(1H-pyrazol-4-yl)phenyl)-1H-1,2,4-triazol-5(4H)-one;
4-(3-methoxy-4-(1H-pyrazol-4-yl)phenyl)-1-(3-methoxybenzyl)-1H-1,2,4-triazol-5(4H)-one;
1-(3-fluorobenzyl)-4-(3-methoxy-4-(1H-pyrazol-4-yl)phenyl)-1H-1,2,4-triazol-5(4H)-one;
4-(3-methoxy-4-(1H-pyrazol-4-yl)phenyl)-1-(1-phenylethyl)-1H-1,2,4-triazol-5(4H)-one;
4-(3-methoxy-4-(1H-pyrazol-4-yl)phenyl)-1-phenethyl-1H-1,2,4-triazol-5(4H)-one;
1-benzyl-4-(2-methoxy-4-(1H-pyrazol-4-yl)phenyl)-1H-1,2,4-triazol-5(4H)-one;
4-(2-methoxy-4-(1H-pyrazol-4-yl)phenyl)-1-(3-methoxybenzyl)-1H-1,2,4-triazol-5(4H)-one;
1-(3-fluorobenzyl)-4-(2-methoxy-4-(1H-pyrazol-4-yl)phenyl)-1H-1,2,4-triazol-5(4H)-one;
1-(2,5-difluorobenzyl)-4-(2-methoxy-4-(1H-pyrazol-4-yl)phenyl)-1H-1,2,4-triazol-5(4H)-one;
4-(2-methoxy-4-(1H-pyrazol-4-yl)phenyl)-1-phenethyl-1H-1,2,4-triazol-5(4H)-one;
4-(4-(1H-pyrazol-4-yl)phenyl)-1-(1-phenylethyl)-1H-1,2,4-triazol-5(4H)-one;
1-(2,5-difluorobenzyl)-4-(2-methoxy-4-(1H-pyrazol-4-yl)phenyl)-1H-1,2,4-triazol-5(4H)-one;
1-(4-(1H-pyrazol-4-yl)phenyl)-4-benzyl-1H-1,2,4-triazol-5(4H)-one;
1-(4-(1H-pyrazol-4-yl)phenyl)-4-(3-methoxybenzyl)-1H-1,2,4-triazol-5(4H)-one;
1-(4-(1H-pyrazol-4-yl)phenyl)-4-(3-fluorobenzyl)-1H-1,2,4-triazol-5(4H)-one;
1-(4-(1H-pyrazol-4-yl)phenyl)-4-(2,5-difluorobenzyl)-1H-1,2,4-triazol-5(4H)-one;
1-(4-(1H-pyrazol-4-yl)phenyl)-4-(3-fluoro-5-methoxybenzyl)-1H-1,2,4-triazol-5(4H)-one;
1-(4-(1H-pyrazol-4-yl)phenyl)-4-(1-phenylethyl)-1H-1,2,4-triazol-5(4H)-one;
4-benzyl-1-(3-methoxy-4-(1H-pyrazol-4-yl)phenyl)-1H-1,2,4-triazol-5(4H)-one;
1-(3-methoxy-4-(1H-pyrazol-4-yl)phenyl)-4-(3-methoxybenzyl)-1H-1,2,4-triazol-5(4H)-one;
4-(2,5-difluorobenzyl)-1-(3-methoxy-4-(1H-pyrazol-4-yl)phenyl)-1H-1,2,4-triazol-5(4H)-one;
4-(3-fluoro-5-methoxybenzyl)-1-(3-methoxy-4-(1H-pyrazol-4-yl)phenyl)-1H-1,2,4-triazol-5(4H)-one;
1-(3-methoxy-4-(1H-pyrazol-4-yl)phenyl)-4-(1-phenylethyl)-1H-1,2,4-triazol-5(4H)-one;
1-(4-(1H-pyrazol-4-yl)phenyl)-4-(2-fluorobenzyl)-1H-1,2,4-triazol-5(4H)-one;
1-(4-(1H-pyrazol-4-yl)phenyl)-4-(2-chlorobenzyl)-1H-1,2,4-triazol-5(4H)-one;
4-(3-fluorobenzyl)-1-(3-methoxy-4-(1H-pyrazol-4-yl)phenyl)-1H-1,2,4-triazol-5(4H)-one;
4-(2-fluorobenzyl)-1-(3-methoxy-4-(1H-pyrazol-4-yl)phenyl)-1H-1,2,4-triazol-5(4H)-one;
4-(2-chlorobenzyl)-1-(3-methoxy-4-(1H-pyrazol-4-yl)phenyl)-1H-1,2,4-triazol-5(4H)-one;
1-(4-(1H-pyrazol-4-yl)phenyl)-4-(2,6-difluorobenzyl)-1H-1,2,4-triazol-5(4H)-one;
3-((1-(4-(1H-pyrazol-4-yl)phenyl)-5-oxo-1H-1,2,4-triazol-4(5H)-yl)methyl)benzonitrile;
3-((1-(3-methoxy-4-(1H-pyrazol-4-yl)phenyl)-5-oxo-1H-1,2,4-triazol-4(5H)-yl)methyl)benzonitrile;
4-(3,5-difluorobenzyl)-1-(3-methoxy-4-(1H-pyrazol-4-yl)phenyl)-1H-1,2,4-triazol-5(4H)-one;
4-(3-(difluoromethoxy)benzyl)-1-(3-methoxy-4-(1H-pyrazol-4-yl)phenyl)-1H-1,2,4-triazol-5(4H)-one;
4-(4-fluorobenzyl)-1-(3-methoxy-4-(1H-pyrazol-4-yl)phenyl)-1H-1,2,4-triazol-5(4H)-one;
4-(2,6-difluorobenzyl)-1-(3-methoxy-4-(1H-pyrazol-4-yl)phenyl)-1H-1,2,4-triazol-5(4H)-one;
1-(3-ethyl-4-(1H-pyrazol-4-yl)phenyl)-4-(3-fluoro-5-methoxybenzyl)-1H-1,2,4-triazol-5(4H)-one;
3-((1-(3-ethyl-4-(1H-pyrazol-4-yl)phenyl)-5-oxo-1H-1,2,4-triazol-4(5H)-yl)methyl)benzonitrile;
1-(3-ethyl-4-(1H-pyrazol-4-yl)phenyl)-4-(2-fluorobenzyl)-1H-1,2,4-triazol-5(4H)-one;
1-(3-ethyl-4-(1H-pyrazol-4-yl)phenyl)-4-(4-fluorobenzyl)-1H-1,2,4-triazol- 5(4H)-one;
4-(3,5-difluorobenzyl)-1-(3-ethyl-4-(1H-pyrazol-4-yl)phenyl)-1H-1,2,4-triazol-5(4H)-one;
1-(3-ethyl-4-(1H-pyrazol-4-yl)phenyl)-4-(3-methoxybenzyl)-1H-1,2,4-triazol-5(4H)-one;
4-(3-(difluoromethoxy)benzyl)-1-(3-ethyl-4-(1H-pyrazol-4-yl)phenyl)-1H-1,2,4-triazol-5(4H)-one;
1-(4-(1H-pyrazol-4-yl)phenyl)-4-(1-(3-methoxyphenyl)ethyl)-1H-1,2,4-triazol-5(4H)-one;
1-(4-(1H-pyrazol-4-yl)phenyl)-4-(3,5-dimethoxybenzyl)-1H-1,2,4-triazol-5(4H)-one;
4-[(4-fluoro-3-methoxyphenyl)methyl]-1-[4-(1H-pyrazol-4-yl)phenyl]-4,5-dihydro-1H-1,2,4-triazol-5-one;
1-(4-(1H-pyrazol-4-yl)phenyl)-4-(2-fluoro-3-methoxybenzyl)-1H-1,2,4-triazol-5(4H)-one;
1-(4-(1H-pyrazol-4-yl)phenyl)-4-(5-fluoro-2-methoxybenzyl)-1H-1,2,4-triazol-5(4H)-one;
1-(4-(1H-pyrazol-4-yl)phenyl)-4-(3-fluoro-4-methoxybenzyl)-1H-1,2,4-triazol-5(4H)-one;
4-benzyl-1-(3-ethyl-4-(1H-pyrazol-4-yl)phenyl)-1H-1,2,4-triazol-5(4H)-one;
1-(3-ethyl-4-(1H-pyrazol-4-yl)phenyl)-4-(3-fluorobenzyl)-1H-1,2,4-triazol-5(4H)-one;
4-(2,6-difluorobenzyl)-1-(3-ethyl-4-(1H-pyrazol-4-yl)phenyl)-1H-1,2,4-triazol-5(4H)-one;
1-(3-ethyl-4-(1H-pyrazol-4-yl)phenyl)-4-(1-phenylethyl)-1H-1,2,4-triazol-5(4H)-one;
4-(4-(1H-pyrazol-4-yl)phenyl)-1-benzyl-3-methyl-1H-1,2,4-triazol-5(4H)-one;
1-benzyl-4-(3-methoxy-4-(1H-pyrazol-4-yl)phenyl)-3-methyl-1H-1,2,4-triazol-5(4H)-one;
4-(3-methoxy-4-(1H-pyrazol-4-yl)phenyl)-1-(3-methoxybenzyl)-3-methyl-1H-1,2,4-triazol-5(4H)-one;
4-(3-methoxy-4-(1H-pyrazol-4-yl)phenyl)-3-methyl-1-(1-phenylethyl)-1H-1,2,4-triazol-5(4H)-one;
1-benzyl-4-(2-methoxy-4-(1H-pyrazol-4-yl)phenyl)-3-methyl-1H-1,2,4-triazol-5(4H)-one;
4-(2-methoxy-4-(1H-pyrazol-4-yl)phenyl)-1-(3-methoxybenzyl)-3-methyl-1H-1,2,4-triazol-5(4H)-one;
1-(3-fluorobenzyl)-4-(3-methoxy-4-(1H-pyrazol-4-yl)phenyl)-3-methyl-1H-1,2,4-triazol-5(4H)-one;

4-(3-methoxy-4-(1H-pyrazol-4-yl)phenyl)-3-methyl-1-phenethyl-1H-1,2,4-triazol-5(4H)-one;
4-(4-(1H-pyrazol-4-yl)phenyl)-3-methyl-1-phenethyl-1H-1,2,4-triazol-5(4H)-one;
1-(2,5-difluorobenzyl)-4-(3-methoxy-4-(1H-pyrazol-4-yl)phenyl)-3-methyl-1H-1,2,4-triazol-5(4H)-one;
4-(4-(1H-pyrazol-4-yl)phenyl)-1-(3-methoxybenzyl)-3-methyl-1H-1,2,4-triazol-5(4H)-one;
4-(4-(1H-pyrazol-4-yl)phenyl)-1-(3-fluorobenzyl)-3-methyl-1H-1,2,4-triazol-5(4H)-one;
4-(4-(1H-pyrazol-4-yl)phenyl)-1-(2,5-difluorobenzyl)-3-methyl-1H-1,2,4-triazol-5(4H)-one;
4-(4-(1H-pyrazol-4-yl)phenyl)-1-(3-fluoro-5-methoxybenzyl)-3-methyl-1H-1,2,4-triazol-5(4H)-one;
4-(4-(1H-pyrazol-4-yl)phenyl)-3-methyl-1-(1-phenylethyl)-1H-1,2,4-triazol-5(4H)-one;
1-(3-fluorobenzyl)-4-(2-methoxy-4-(1H-pyrazol-4-yl)phenyl)-3-methyl-1H-1,2,4-triazol-5(4H)-one;
4-(2-methoxy-4-(1H-pyrazol-4-yl)phenyl)-3-methyl-1-(1-phenylethyl)-1H-1,2,4-triazol-5(4H)-one;
1-(3-fluoro-5-methoxybenzyl)-4-(2-methoxy-4-(1H-pyrazol-4-yl)phenyl)-3-methyl-1H-1,2,4-triazol-5(4H)-one;
4-(2-methoxy-4-(1H-pyrazol-4-yl)phenyl)-3-methyl-1-phenethyl-1H-1,2,4-triazol-5(4H)-one;
1-(2,5-difluorobenzyl)-4-(2-methoxy-4-(1H-pyrazol-4-yl)phenyl)-3-methyl-1H-1,2,4-triazol-5(4H)-one;
1-(4-(1H-pyrazol-4-yl)phenyl)-4-benzyl-3-methyl-1H-1,2,4-triazol-5(4H)-one;
1-(4-(1H-pyrazol-4-yl)phenyl)-4-(3-methoxybenzyl)-3-methyl-1H-1,2,4-triazol-5(4H)-one;
1-(4-(1H-pyrazol-4-yl)phenyl)-4-(3-fluorobenzyl)-3-methyl-1H-1,2,4-triazol-5(4H)-one;
1-(4-(1H-pyrazol-4-yl)phenyl)-4-(2,5-difluorobenzyl)-3-methyl-1H-1,2,4-triazol-5(4H)-one;
1-(4-(1H-pyrazol-4-yl)phenyl)-4-(3-fluoro-5-methoxybenzyl)-3-methyl-1H-1,2,4-triazol-5(4H)-one;
1-(4-(1H-pyrazol-4-yl)phenyl)-3-methyl-4-(1-phenylethyl)-1H-1,2,4-triazol-5(4H)-one;
1-(4-(1H-pyrazol-4-yl)phenyl)-3-methyl-4-phenethyl-1H-1,2,4-triazol-5(4H)-one;
1-(4-(1H-pyrazol-4-yl)phenyl)-4-(2-chlorobenzyl)-3-methyl-1H-1,2,4-triazol-5(4H)-one;
2-(4-(1H-pyrazol-4-yl)phenyl)-4-(2-fluorobenzyl)-5-methyl-2,4-dihydro-3H-1,2,4-triazol-3-one;
4-benzyl-1-(3-methoxy-4-(1H-pyrazol-4-yl)phenyl)-3-methyl-1H-1,2,4-triazol-5(4H)-one;
1-(3-methoxy-4-(1H-pyrazol-4-yl)phenyl)-4-(3-methoxybenzyl)-3-methyl-1H-1,2,4-triazol-5(4H)-one;
4-(3-fluorobenzyl)-1-(3-methoxy-4-(1H-pyrazol-4-yl)phenyl)-3-methyl-1H-1,2,4-triazol-5(4H)-one;
4-(2,5-difluorobenzyl)-1-(3-methoxy-4-(1H-pyrazol-4-yl)phenyl)-3-methyl-1H-1,2,4-triazol-5(4H)-one;
4-(3-fluoro-5-methoxybenzyl)-1-(3-methoxy-4-(1H-pyrazol-4-yl)phenyl)-3-methyl-1H-1,2,4-triazol-5(4H)-one;
1-(3-methoxy-4-(1H-pyrazol-4-yl)phenyl)-3-methyl-4-(1-phenylethyl)-1H-1,2,4-triazol-5(4H)-one;
1-(3-methoxy-4-(1H-pyrazol-4-yl)phenyl)-3-methyl-4-phenethyl-1H-1,2,4-triazol-5(4H)-one;
4-(2-fluorobenzyl)-1-(3-methoxy-4-(1H-pyrazol-4-yl)phenyl)-3-methyl-1H-1,2,4-triazol-5(4H)-one;
1-(4-(1H-pyrazol-4-yl)phenyl)-4-(3,5-difluorobenzyl)-3-methyl-1H-1,2,4-triazol-5(4H)-one;
3-((1-(3-methoxy-4-(1H-pyrazol-4-yl)phenyl)-3-methyl-5-oxo-1H-1,2,4-triazol-4(5H)-yl)methyl)benzonitrile;
4-(2,6-difluorobenzyl)-1-(3-methoxy-4-(1H-pyrazol-4-yl)phenyl)-3-methyl-1H-1,2,4-triazol-5(4H)-one;
4-(3,5-difluorobenzyl)-1-(3-methoxy-4-(1H-pyrazol-4-yl)phenyl)-3-methyl-1H-1,2,4-triazol-5(4H)-one;
4-(3-(difluoromethoxy)benzyl)-1-(3-methoxy-4-(1H-pyrazol-4-yl)phenyl)-3-methyl-1H-1,2,4-triazol-5(4H)-one;
4-(4-fluorobenzyl)-1-(3-methoxy-4-(1H-pyrazol-4-yl)phenyl)-3-methyl-1H-1,2,4-triazol-5(4H)-one;
1-(4-(1H-pyrazol-4-yl)phenyl)-4-(3-(difluoromethoxy)benzyl)-3-methyl-1H-1,2,4-triazol-5(4H)-one;
3-((1-(4-(1H-pyrazol-4-yl)phenyl)-3-methyl-5-oxo-1H-1,2,4-triazol-4(5H)-yl)methyl)benzonitrile;
1-(4-(1H-pyrazol-4-yl)phenyl)-4-(2,6-difluorobenzyl)-3-methyl-1H-1,2,4-triazol-5(4H)-one;
1-(3-ethyl-4-(1H-pyrazol-4-yl)phenyl)-4-(3-methoxybenzyl)-3-methyl-1H-1,2,4-triazol-5(4H)-one;
1-(3-ethyl-4-(1H-pyrazol-4-yl)phenyl)-4-(3-fluorobenzyl)-3-methyl-1H-1,2,4-triazol-5(4H)-one;
4-(2,5-difluorobenzyl)-1-(3-ethyl-4-(1H-pyrazol-4-yl)phenyl)-3-methyl-1H-1,2,4-triazol-5(4H)-one;
4-(3,5-difluorobenzyl)-1-(3-ethyl-4-(1H-pyrazol-4-yl)phenyl)-3-methyl-1H-1,2,4-triazol-5(4H)-one;
1-(3-ethyl-4-(1H-pyrazol-4-yl)phenyl)-3-methyl-4-(1-phenylethyl)-1H-1,2,4-triazol-5(4H)-one;
1-(3-ethyl-4-(1H-pyrazol-4-yl)phenyl)-3-methyl-4-phenethyl-1H-1,2,4-triazol-5(4H)-one;
3-((1-(3-ethyl-4-(1H-pyrazol-4-yl)phenyl)-3-methyl-5-oxo-1H-1,2,4-triazol-4(5H)-yl)methyl)benzonitrile;
4-(3-(difluoromethoxy)benzyl)-1-(3-ethyl-4-(1H-pyrazol-4-yl)phenyl)-3-methyl-1H-1,2,4-triazol-5(4H)-one;
1-(3-ethyl-4-(1H-pyrazol-4-yl)phenyl)-4-(2-fluorobenzyl)-3-methyl-1H-1,2,4-triazol-5(4H)-one;
1-(3-ethyl-4-(1H-pyrazol-4-yl)phenyl)-4-(4-fluorobenzyl)-3-methyl-1H-1,2,4-triazol-5(4H)-one;
1-(3-ethyl-4-(1H-pyrazol-4-yl)phenyl)-4-(3-fluoro-5-methoxybenzyl)-3-methyl-1H-1,2,4-triazol-5(4H)-one;
4-(2,6-difluorobenzyl)-1-(3-ethyl-4-(1H-pyrazol-4-yl)phenyl)-3-methyl-1H-1,2,4-triazol-5(4H)-one;
4-benzyl-1-(3-ethyl-4-(1H-pyrazol-4-yl)phenyl)-3-methyl-1H-1,2,4-triazol-5(4H)-one;
1-(4-(1H-pyrazol-4-yl)phenyl)-4-(1-(3-methoxyphenyl)ethyl)-3-methyl-1H-1,2,4-triazol-5(4H)-one;
1-(4-(1H-pyrazol-4-yl)phenyl)-4-(3,5-dimethoxybenzyl)-3-methyl-1H-1,2,4-triazol-5(4H)-one;
1-(4-(1H-pyrazol-4-yl)phenyl)-4-(4-fluoro-3-methoxybenzyl)-3-methyl-1H-1,2,4-triazol-5(4H)-one;
1-(4-(1H-pyrazol-4-yl)phenyl)-4-(2-fluoro-3-methoxybenzyl)-3-methyl-1H-1,2,4-triazol-5(4H)-one;
1-(4-(1H-pyrazol-4-yl)phenyl)-4-(5-fluoro-2-methoxybenzyl)-3-methyl-1H-1,2,4-triazol-5(4H)-one;
1-(4-(1H-pyrazol-4-yl)phenyl)-4-(3-fluoro-4-methoxybenzyl)-3-methyl-1H-1,2,4-triazol-5(4H)-one;
1-(4-(1H-pyrazol-4-yl)phenyl)-3-(hydroxymethyl)-4-(3-methoxybenzyl)-1H-1,2,4-triazol-5(4H)-one;
1-(4-(1H-pyrazol-4-yl)phenyl)-4-benzyl-3-(hydroxymethyl)-1H-1,2,4-triazol-5(4H)-one;
1-(4-(1H-pyrazol-4-yl)phenyl)-4-(3,5-dimethoxybenzyl)-3-(hydroxymethyl)-1H-1,2,4-triazol-5(4H)-one;
1-(4-(1H-pyrazol-4-yl)phenyl)-4-(3-fluorobenzyl)-3-(hydroxymethyl)-1H-1,2,4-triazol-5(4H)-one;
1-(4-(1H-pyrazol-4-yl)phenyl)-4-(2,5-difluorobenzyl)-3-(hydroxymethyl)-1H-1,2,4-triazol-5(4H)-one;
1-(4-(1H-pyrazol-4-yl)phenyl)-4-(3,5-difluorobenzyl)-3-(hydroxymethyl)-1H-1,2,4-triazol-5 (4H)-one;

1-(4-(1H-pyrazol-4-yl)phenyl)-4-(3-(difluoromethoxy)benzyl)-3-(hydroxymethyl)-1H-1,2,4-triazol-5 (4H)-one;
3-((1-(4-(1H-pyrazol-4-yl)phenyl)-3-(hydroxymethyl)-5-oxo-1H-1,2,4-triazol-4(5H)-yl)methyl)benzonitrile;
1-(4-(1H-pyrazol-4-yl)phenyl)-4-benzyl-3-(2-hydroxypropan-2-yl)-1H-1,2,4-triazol-5(4H)-one;
1-(4-(1H-pyrazol-4-yl)phenyl)-3-(2-hydroxypropan-2-yl)-4-(3-methoxybenzyl)-1H-1,2,4-triazol-5(4H)-one;
1-(4-(1H-pyrazol-4-yl)phenyl)-4-(3-fluorobenzyl)-3-(2-hydroxypropan-2-yl)-1H-1,2,4-triazol-5(4H)-one;
1-(4-(1H-pyrazol-4-yl)phenyl)-4-(2,5-difluorobenzyl)-3-(2-hydroxypropan-2-yl)-1H-1,2,4-triazol-5(4H)-one;
1-(4-(1H-pyrazol-4-yl)phenyl)-4-(3,5-difluorobenzyl)-3-(2-hydroxypropan-2-yl)-1H-1,2,4-triazol-5(4H)-one;
1-(4-(1H-pyrazol-4-yl)phenyl)-4-(2,6-difluorobenzyl)-3-(2-hydroxypropan-2-yl)-1H-1,2,4-triazol-5(4H)-one;
1-(4-(1H-pyrazol-4-yl)phenyl)-4-(3-(difluoromethoxy)benzyl)-3-(2-hydroxypropan-2-yl)-1H-1,2,4-triazol-5(4H)-one;
1-(4-(1H-pyrazol-4-yl)phenyl)-4-benzyl-3-(1-hydroxyethyl)-1H-1,2,4-triazol-5(4H)-one;
1-(4-(1H-pyrazol-4-yl)phenyl)-3-((dimethylamino)methyl)-4-(3-methoxybenzyl)-1H-1,2,4-triazol-5(4H)-one;
1-(4-(1H-pyrazol-4-yl)phenyl)-4-(3-methoxybenzyl)-3-(morpholinomethyl)-1H-1,2,4-triazol-5(4H)-one;
1-(4-(1H-pyrazol-4-yl)phenyl)-4-(3-fluoro-5-methoxybenzyl)-3-(hydroxymethyl)-1H-1,2,4-triazol-5(4H)-one;
1-(4-(1H-pyrazol-4-yl)phenyl)-4-(3-fluoro-5-methoxybenzyl)-3-(2-hydroxypropan-2-yl)-1H-1,2,4-triazol-5(4H)-one;
1-(4-(1H-pyrazol-4-yl)phenyl)-4-(3-methoxybenzyl)-3-(pyrrolidin-1-ylmethyl)-1H-1,2,4-triazol-5(4H)-one;
1-(4-(1H-pyrazol-4-yl)phenyl)-4-(3,5-dimethoxybenzyl)-3-(1-hydroxyethyl)-1H-1,2,4-triazol-5(4H)-one;
1-(4-(1H-pyrazol-4-yl)phenyl)-3-((dimethylamino)methyl)-4-(3-fluoro-5-methoxybenzyl)-1H-1,2,4-triazol-5(4H)-one;
1-(4-(1H-pyrazol-4-yl)phenyl)-4-(3-fluoro-5-methoxybenzyl)-3-(morpholinomethyl)-1H-1,2,4-triazol-5(4H)-one;
1-(4-(1H-pyrazol-4-yl)phenyl)-4-(3-fluoro-5-methoxybenzyl)-3-(pyrrolidin-1-ylmethyl)-1H-1,2,4-triazol-5(4H)-one;
1-(4-(1H-pyrazol-4-yl)phenyl)-4-(3-fluoro-5-methoxybenzyl)-3-(((2-hydroxyethyl)amino)methyl)-1H-1,2,4-triazol-5(4H)-one;
1-(4-(1H-pyrazol-4-yl)phenyl)-4-(3-fluoro-5-methoxybenzyl)-3-(piperazin-1-ylmethyl)-1H-1,2,4-triazol-5(4H)-one;
1-(4-(1H-pyrazol-4-yl)phenyl)-4-(3-fluoro-5-methoxybenzyl)-3-(((1-hydroxypropan-2-yl)amino)methyl)-1H-1,2,4-triazol-5(4H)-one;
1-(4-(1H-pyrazol-4-yl)phenyl)-4-(3-fluoro-5-methoxybenzyl)-3-((3-hydroxypyrrolidin-1-yl)methyl)-1H-1,2,4-triazol-5(4H)-one;
1-(4-(1H-pyrazol-4-yl)phenyl)-3-((3-hydroxypyrrolidin-1-yl)methyl)-4-(3-methoxybenzyl)-1H-1,2,4-triazol-5(4H)-one;
1-(4-(1H-pyrazol-4-yl)phenyl)-4-(5-fluoro-2-methoxybenzyl)-3-(hydroxymethyl)-1H-1,2,4-triazol-5(4H)-one;
1-(4-(1H-pyrazol-4-yl)phenyl)-4-(4-fluoro-3-methoxybenzyl)-3-(hydroxymethyl)-1H-1,2,4-triazol-5(4H)-one;
1-(4-(1H-pyrazol-4-yl)phenyl)-4-(3-fluoro-4-methoxybenzyl)-3-(hydroxymethyl)-1H-1,2,4-triazol-5(4H)-one;
1-(4-(1H-pyrazol-4-yl)phenyl)-4-(2-fluoro-3-methoxybenzyl)-3-(hydroxymethyl)-1H-1,2,4-triazol-5(4H)-one;
1-(4-(2-aminopyridin-4-yl)phenyl)-4-(3-methoxybenzyl)-3-methyl-1H-1,2,4-triazol-5(4H)-one;
1-(4-(2-aminopyridin-4-yl)phenyl)-4-(3-methoxybenzyl)-3-methyl-1H-1,2,4-triazol-5(4H)-one;
1-(4-(2-aminopyridin-4-yl)phenyl)-4-(3-methoxybenzyl)-1H-1,2,4-triazol-5(4H)-one;
1-(4-(7H-pyrrolo[2,3-d]pyrimidin-4-yl)phenyl)-4-(3-methoxybenzyl)-1H-1,2,4-triazol-5(4H)-one;
1-(4-(7H-pyrrolo[2,3-d]pyrimidin-4-yl)phenyl)-4-(3-methoxybenzyl)-3-methyl-1H-1,2,4-triazol-5(4H)-one;
1-(4-(1H-pyrrolo[2,3-b]pyridin-4-yl)phenyl)-4-(3-methoxybenzyl)-3-methyl-1H-1,2,4-triazol-5(4H)-one;
1-(4-(2-aminopyrimidin-4-yl)phenyl)-4-(3-methoxybenzyl)-3-methyl-1H-1,2,4-triazol-5(4H)-one;
1-(4-(1H-pyrrolo[2,3-b]pyridin-4-yl)phenyl)-4-(3-methoxybenzyl)-1H-1,2,4-triazol-5(4H)-one;
1-(4-(2-aminopyrimidin-4-yl)phenyl)-4-(3-methoxybenzyl)-1H-1,2,4-triazol-5(4H)-one;
1-(4-(1H-pyrazol-4-yl)phenyl)-4-(3-methoxybenzyl)-1H-tetrazol-5(4H)-one;
1-(4-(1H-pyrazol-4-yl)phenyl)-4-(3-fluorobenzyl)-1H-tetrazol-5(4H)-one;
1-(4-(1H-pyrazol-4-yl)phenyl)-4-(2,5-difluorobenzyl)-1H-tetrazol-5(4H)-one;
1-(4-(1H-pyrazol-4-yl)phenyl)-4-(3-fluoro-5-methoxybenzyl)-1H-tetrazol-5(4H)-one;
1-(4-(1H-pyrazol-4-yl)phenyl)-4-(1-phenylethyl)-1H-tetrazol-5(4H)-one;
1-(4-(1H-pyrazol-4-yl)phenyl)-4-(2-chlorobenzyl)-1H-tetrazol-5(4H)-one;
1-(4-(1H-pyrazol-4-yl)phenyl)-4-benzyl-1H-tetrazol-5(4H)-one;
1-benzyl-4-(3-methoxy-4-(1H-pyrazol-4-yl)phenyl)-1H-tetrazol-5(4H)-one;
1-(3-fluorobenzyl)-4-(3-methoxy-4-(1H-pyrazol-4-yl)phenyl)-1H-tetrazol-5(4H)-one;
1-(2,5-difluorobenzyl)-4-(3-methoxy-4-(1H-pyrazol-4-yl)phenyl)-1H-tetrazol-5(4H)-one;
1-(3-fluoro-5-methoxybenzyl)-4-(3-methoxy-4-(1H-pyrazol-4-yl)phenyl)-1H-tetrazol-5(4H)-one;
1-(2-fluorobenzyl)-4-(3-methoxy-4-(1H-pyrazol-4-yl)phenyl)-1H-tetrazol-5(4H)-one;
1-(2,6-difluorobenzyl)-4-(3-methoxy-4-(1H-pyrazol-4-yl)phenyl)-1H-tetrazol-5(4H)-one;
3-((4-(3-methoxy-4-(1H-pyrazol-4-yl)phenyl)-5-oxo-4,5-dihydro-1H-tetrazol-1-yl)methyl)benzonitrile;
1-(4-fluorobenzyl)-4-(3-methoxy-4-(1H-pyrazol-4-yl)phenyl)-1H-tetrazol-5(4H)-one and
1-(3-methoxy-4-(1H-pyrazol-4-yl)phenyl)-4-(3-methoxybenzyl)-1H-tetrazol-5(4H)-one.

14. A pharmaceutical composition comprising one or more compounds according to claim 1 and a pharmaceutically acceptable carrier or diluent.

15. A method for treatment of a disorder associated with aberrant Rho kinase activity comprising administering to a patient in need thereof a therapeutically effective amount of a compound of claim 1.

16. The method of claim 15, wherein said disorder is selected from the group consisting of a cardiovascular disorder, a smooth muscle related disorder, a fibrotic disease, an inflammatory disease, a neuropathic disorder, an oncologic disorder, and an autoimmune disorder.

17. The method of claim 16, wherein said cardiovascular disorder is selected from the group consisting of angina, atherosclerosis, stroke, cerebrovascular disease, heart failure, coronary artery disease, myocardial infarction, peripheral vascular disease, stenosis, vasospasm, hypertension and pulmonary hypertension.

\* \* \* \* \*